United States Patent
Han et al.

(10) Patent No.: US 7,244,746 B2
(45) Date of Patent: Jul. 17, 2007

(54) IMIDAZOLYL DERIVATIVES AS CORTICOTROPIN RELEASING FACTOR INHIBITORS

(75) Inventors: Xiaojun Han, Cheshire, CT (US); Gene M. Dubowchik, Middlefield, CT (US); John E. Macor, Guilford, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 260 days.

(21) Appl. No.: 10/772,027

(22) Filed: Feb. 4, 2004

(65) Prior Publication Data

US 2004/0235924 A1 Nov. 25, 2004

Related U.S. Application Data

(62) Division of application No. 10/044,183, filed on Jan. 11, 2002, now Pat. No. 6,888,004.

(60) Provisional application No. 60/264,570, filed on Jan. 26, 2001.

(51) Int. Cl.
*A61K 31/4427* (2006.01)
*A61K 31/4188* (2006.01)
*C07D 487/04* (2006.01)
*C07D 403/04* (2006.01)
*C07D 471/04* (2006.01)
*C07D 471/14* (2006.01)

(52) U.S. Cl. ............ 514/338; 514/393; 514/394; 546/273.1; 548/320.1

(58) Field of Classification Search ............... 514/293, 514/338, 393, 394; 548/302.4, 302.1; 546/199, 546/273.1
See application file for complete search history.

(56) References Cited

U.S. PATENT DOCUMENTS

| | | | | |
|---|---|---|---|---|
| 4,873,244 A | * | 10/1989 | WaFrank et al. | 514/250 |
| 5,466,706 A | * | 11/1995 | George et al. | 514/394 |
| 5,639,756 A | * | 6/1997 | Anisimova et al. | 514/257 |
| 6,515,005 B2 | * | 2/2003 | Dubowchik et al. | 514/370 |
| 6,696,441 B1 | * | 2/2004 | Cottam et al. | 514/233.2 |
| 6,888,004 B2 | * | 5/2005 | Dubowchik et al. | 548/302.4 |

FOREIGN PATENT DOCUMENTS

| EP | 0 778 277 A1 | 6/1997 |
|---|---|---|
| EP | 0 812 831 A1 | 12/1997 |
| EP | 0 902 029 A1 | 3/1999 |
| EP | 0 970 958 A | 1/2000 |
| FR | 2722501 * | 1/1996 |
| JP | 05-107705 * | 4/1993 |
| WO | WO 97/29109 A | 8/1997 |
| WO | WO 98/35967 | 8/1998 |
| WO | WO 99/01454 | 1/1999 |
| WO | WO 99/10350 | 3/1999 |
| WO | WO 99/67247 | 12/1999 |
| WO | WO 00/01675 | 1/2000 |
| WO | WO 00/01697 | 1/2000 |
| WO | WO 00/39127 | 7/2000 |
| WO | WO 00/59907 | 10/2000 |
| WO | WO 00/59908 | 10/2000 |
| WO | WO 01-007440 A | 2/2001 |

OTHER PUBLICATIONS

Vippagunta, S.R. et. al., "Crystalline solids". Advanced Drug Delivery Reviews, 2001, vol. 48, pp. 3-26.*

Dunn et al., "Physiological and behavioral response to corticotropin-releasing factor administration: is CRF a mediator or anxiety or stress responses?", Brain Research Reviews, 15, 1990, pp. 71-100.

Gulyas, et al., "Potent, structurally constrained agonists and competitive antagonists of corticotropin-releasing factor," Prac. Natl. Acad. Sci. USA, 92, 1995, pp. 10575-10579.

McCarthy, et al., "Recent Advances with the CRF1 Receptor: Design of Small Molecule Inhibitors, Receptor Subtypes and Clinical Indications," Current Pharmaceutical Design, 5, 1999, pp. 289-315.

Holsboer, "The rationale for corticotropin-releasing hormone receptor (CRH-R) antagonists to treat depression and anxiety," Journal of Psychiatric Research, 33, 1999, pp. 181-214.

(Continued)

*Primary Examiner*—James O. Wilson
*Assistant Examiner*—Tamthom N. Truong
(74) *Attorney, Agent, or Firm*—Shah R. Makujina

(57) ABSTRACT

The present invention relates to novel heterocyclic antagonists of Formula (I) and pharmaceutical compositions comprising said antagonists of the corticotropin releasing factor receptor ("CRF receptor")

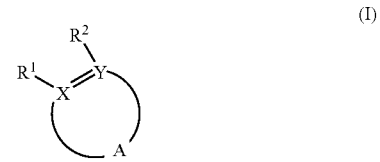

(I)

useful for the treatment of depression, anxiety, affective disorders, feeding disorders, post-traumatic stress disorder, headache, drug addiction, inflammatory disorders, drug or alcohol withdrawal symptoms and other conditions the treatment of which can be effected by the antagonism of the CRF-1 receptor.

16 Claims, No Drawings

OTHER PUBLICATIONS

Banki, et al., "CSF corticotropin-releaseing hormone and somatostatin in major depression: response to antidepressant treatment and relapse," European Neuropsychopharamacology, 2, 1992, pp. 107-113.

Zobel, et al., "Effects of the high-affinity corticotropin-releasing hormone receptor 1 antagonist R121919 in major depression, the first 20 patients treated," Journal of Psychiatric Research, 34, 2000, pp. 171-181.

Webster, et al., "Corticotropin-Releasing Hormone and Inflammation," Annals New York Academy of Sciences, 840, 1998, pp. 21-62.

Gilligan, et al., "Corticotropin Releasing Factor (CRF) Receptor Modulators: Progress and Opportunities for New Therapeutic Agents," Journal of Medicinal Chemistry, 43, 9, 2000, pp. 1641-1660.

McCarthy, et al., "Chapter 2. Recent Progress in Corticotropin-Releasing Factor Receptor Agents," Annual Reports in Medicinal Chemistry, 34, 1999, pp. 11-20.

* cited by examiner

IMIDAZOLYL DERIVATIVES AS CORTICOTROPIN RELEASING FACTOR INHIBITORS

CROSS-REFERENCE TO RELATED APPLICATION

This divisional application claims priority from non-provisional application Ser. No. 10/044,183 filed Jan. 11, 2002 now U.S. Pat. No. 6,888,004 which claims priority from provisional application U.S. Ser. No. 60/264,570 filed Jan. 26, 2001. The disclosures of these prior applications are incorporated herein by reference in their entirety.

FIELD OF THE INVENTION

The present invention relates to antagonists and pharmaceutical compositions comprising said antagonists of the corticotropin releasing factor receptor ("CRF receptor") useful for the treatment of depression, anxiety, affective disorders, feeding disorders, post-traumatic stress disorder, headache, drug addiction, inflammatory disorders, drug or alcohol withdrawal symptoms and other conditions the treatment of which can be effected by the antagonism of the CRF-1 receptor.

BACKGROUND OF THE INVENTION

It has been shown that the neuropeptide, corticotropin releasing factor ("CRF"), acting through its binding to the CRF-1 receptor, is a primary mediator of stress- and anxiety-related physiological responses in humans and other mammals by stimulating ACTH secretion from the anterior pituitary gland. See A. J. Dunn, et al., Brain Res. Rev., 15: 71-100 (1990). Antagonists of the CRF-1 receptor, both peptides (J. Gulyas, et al., Proc. Natl. Acad. Sci. U.S.A., 92: 10575-10579 (1995) and small molecules (J. R. McCarthy, et al., Curr. Pharm. Design, 5: 289-315 (1999), have demonstrated the ability to ameliorate the effects of stressful stimuli in several animal models. In addition, marked elevations of CRF in cerebrospinal fluid have been detected in a large portion of individuals diagnosed with major depression and anxiety disorders, and the levels correlate with severity of the disease. See F. Holsboer, J. Psychiatric Res., 33: 181-214 (1999). Following antidepressant treatment, the increased CRF levels observed in depressed patients were reduced. See C. M. Banki, et al., Eur. Neuropsychopharmacol., 2: 107-113 (1992); see also Effects of the high-affinity corticotropin-releasing hormone receptor 1 antagonist R121919 in major depression: the first 20 patients treated. Zobel A W, Nickel T, Kunzel H E, Ackl N, Sonntag A. Ising M, Holsboer F J Psychiatr Res 2000, 34, 171-181. CRF has also been shown to be a key mediator of several immune system functions through its effect on glucocorticoid plasma levels. See E. L. Webster, et al., Ann. N.Y. Acad. Sci., 840: 21-32 (1998). Recent reviews of the activity of CRF-1 antagonists include P. J. Gilligan, et al., J. Med. Chem., 43: 1641-1660 (2000) and J. R. McCarthy, et al., Ann. Rep. Med. Chem., 34: 11-20 (1999). There appears a need to discover novel small molecule CRF antagonists in order to treat a wide variety of human disorders including depression, anxiety, bipolar disorder, and other stress-related illnesses. See WO 98/35967, WO 99/01454, WO 99/10350, wo 99/67247, 00/01675, WO 00/01697, WO 00/39127, WO 00/59907, WO 00/59908, EP 778277, EP 812831.

SUMMARY OF THE INVENTION

Thus according to a first embodiment of the first aspect of the present invention are provided compounds of Formula (I)

and pharmaceutically acceptable salts and solvates thereof wherein $R^1$ is H, $C_{1-6}$alkyl, $C_{1-6}$haloalkyl, $C_{1-6}$alkoxy, $C_{1-6}$thioalkyl, cyano, halo, $C_{3-7}$cycloalkyl, —$C_{1-6}$alkylene-$C_{3-7}$cycloalkyl, $C_{2-6}$alkenyl or $C_{3-6}$alkynyl;

$R^2$ is $C(D)NR^3R^4$, D'—D"$(R^3)(R^4)$ or $CH_2N R^3R^4$

D' is $CH_2$ or a bond;

D" is C, C—OH or CH wherein
said C is attached to $R^3$ by a single or double bond;
said C is attached to $R^4$ by a single or double bond;
provided that
C is not attached to both $R^3$ and $R^4$ by double bonds;
said CH is attached to $R^3$ and $R^4$ by single bonds;
said C of C—OH is attached to $R^3$ and $R^4$ by single bonds;

D is O or S;

$R^3$ and $R^4$ are each independently selected from the group consisting of H, $C_{1-6}$alkyl, $C_{1-6}$haloalkyl, —$C_{1-6}$hydroxyalkyl, —$C_{1-4}$alkylene-O—$C_{1-4}$alkyl, —$C_{1-3}$alkylene-$C_{1-6}$thioalkyl, —$C_{2-6}$alkylidene-$(C_{1-4}$alkoxy$)_2$, $C_{3-7}$cycloalkyl, —$C_{1-6}$alkylene-$C_{3-7}$cycloalkyl, $C_{2-6}$alkenyl, $C_{3-6}$alkynyl, —$C_{1-6}$alkylene-CN, —$C_{1-6}$alkylene-heterocyclo and —$C_{1-6}$alkylene-aryl;

wherein said aryl of said —$C_{1-6}$alkylene-aryl is optionally substituted with one to three of the same or different substituents selected from the group consisting of fluoro, chloro, bromo, cyano, nitro, $C_{1-4}$alkyl and $C_{1-3}$alkoxy;

or $R^3$ and $R^4$ together with the nitrogen to which they are attached form a five or six-membered heterocycle, said heterocycle optionally containing one additional heteroatom selected from the group consisting of N, S and O; and said heterocycle optionally substituted with one or more groups selected from the group consisting of $C_{1-6}$alkyl, $C_{1-6}$alkoxy, aryl, —$C_{1-4}$alkylene-aryl, pyridyl and halogen;

wherein said aryl of said —$C_{1-4}$alkylene-aryl is optionally substituted with one to three of the same or different substituents selected from the group consisting of fluoro, chloro, bromo, cyano, nitro and $C_{1-3}$alkoxy;

X is C;

Y is C;

A is

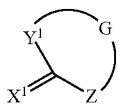

wherein
$X^1$ is N and is attached to X;
$Y^1$ is N and is attached to Y;
G is

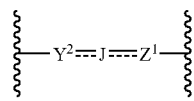

wherein
$Y^2$ is N, CH, $CH_2$, C(O), C(S), $CR^5$, $CHR^5$ or $CE^1$ and is attached to $Y^1$;
J is CH, $CH_2$, C(O), C(S), $CR^6$, $CHR^6$, a bond or $CE^2$;
$Z^1$ is CH, $CH_2$, C(O), C(S), $CR^7$, $CHR^7$ or $CE^3$ and is attached to Z;
wherein
$R^5$, $R^6$ and $R^7$ are each independently selected from the group consisting of —CN, —$C_{1-4}$alk(en)ylene-CN, halo, $C_{1-6}$alkyl, $C_{2-6}$alkenyl, $C_{3-6}$alkynyl, $C_{1-6}$haloalkyl, aryl, —$C_{1-4}$alk(en)ylene-aryl, —$C_{1-4}$alk(en)ylene-heterocyclo, heterocyclo, —$C_{1-4}$alk(en)ylene-amino, —$C_{1-4}$alkylene-amino-$C_{1-4}$alkyl, aryl-amino, -amino-($C_{1-6}$alk(en)yl)$_{1-2}$, -amino-aryl, -amino-heterocyclo, $C_{1-6}$alkoxy, —O-aryl and —O-heterocyclo;
$E^1$ and $E^2$ together form moieties selected from the group consisting of $C_4$-alk(en)lyene, $N(CH)_3$, $CHN(CH)_2$, $N(CH)_2N$, N=NCH=N and NCHNCH;
wherein said moieties are optionally substituted with halogen, —CN, $C_1$-$C_4$alkyl, $C_3$-$C_6$cycloalkyl, substituted or unsubstituted phenyl, hydroxy, $C_1$-$C_4$alkoxy, SH, $C_1$-$C_4$thioalkyl, $NH_2$, $NH(C_1$-$C_4$alkyl) or $N(C_1$-$C_4$alkyl)$_2$;
$E^2$ and $E^3$ together form moieties selected from the group consisting of $C_4$-alk(en)lyene, $N(CH)_3$, $CHN(CH)_2$, $N(CH)_2N$, N=NCH=N and NCHNCH;
wherein said moieties are optionally substituted with halogen, —CN, $C_1$-$C_4$alkyl, $C_3$-$C_6$cycloalkyl, substituted or unsubstituted phenyl, hydroxy, $C_1$-$C_4$alkoxy, SH, $C_1$-$C_4$thioalkyl, $NH_2$, $NH(C_1$-$C_4$alkyl) or $N(C_1$-$C_4$alkyl)$_2$;
$E^1$ and $E^3$ together form moieties selected from the group consisting of $C_4$-alk(en)lyene, $N(CH)_3$, $CHN(CH)_2$, $N(CH)_2N$, N=NCH=N and NCHNCH;
wherein said moieties are optionally substituted with halogen, —CN, $C_1$-$C_4$alkyl, $C_3$-$C_6$cycloalkyl, substituted or unsubstituted phenyl, hydroxy, $C_1$-$C_4$alkoxy, SH, $C_1$-$C_4$thioalkyl, $NH_2$, $NH(C_1$-$C_4$alkyl) or $N(C_1$-$C_4$alkyl)$_2$;

Z is N—V, wherein V is phenyl, 2-pyridyl or 3-pyridyl substituted with two to three of the same or different substitutents selected from the group consisting of $C_{1-4}$alkyl, $C_{1-4}$alkoxy, $C_{1-6}$thioalkyl, $C_{1-4}$haloalkyl, halogen, $N(C_1$-$C_4$alkyl)$_2$ and CN; and provided that
if $Y^2$ is N, then J is a bond and $Z^1$ is not $CE^3$;
if $y^2$ is $CE^1$ and $Z^1$ is $CE^3$, then J is a bond;
if $Y^2$ is not $CE^1$ and $Z^1$ is not $CE^3$, then J is not $CE^2$;
if J is $CE^2$,
then
$Y^2$ is $CE^1$ and $Z^1$ is not $CE^3$, $CR^7$ or $CHR^7$; or
$Z^1$ is $CE^2$ and $Y^2$ is not $CE^1$, $CR^5$ or $CHR^5$.

According to another embodiment of the first aspect of the present invention are provided compounds of Formula (I) according to the first embodiment of the first aspect wherein V is phenyl or 3-pyridyl and is substituted with two to three of the same or different substituents selected from the group consisting of $C_{1-4}$alkyl, $C_{1-4}$alkoxy, $C_{1-6}$thioalkyl, $C_{1-4}$haloalkyl, halogen, $N(C_1$-$C_4$alkyl)$_2$ and CN; said substituents attached at the 2, 4 or 6-positions of said phenyl or said 3-pyridyl.

According to another embodiment of the first aspect of the present invention are provided compounds of Formula (I) according to the first embodiment of the first aspect wherein V is 2-pyridyl and is substituted with two of the same or different substitutents selected from the group consisting of $C_{1-4}$alkyl, $C_{1-4}$alkoxy, $C_{1-6}$thioalkyl, $C_{1-4}$haloalkyl, halogen, $N(C_1$-$C_4$alkyl)$_2$ and CN; said substituents attached at the 3 and 5-positions of said 2-pyridyl.

According to another embodiment of the first aspect of the present invention are provided compounds of Formula (I) according to the first embodiment of the first aspect wherein $R^1$ is $C_{1-6}$alkyl or $C_{1-6}$haloalkyl.

According to another embodiment of the first aspect of the present invention are provided compounds of Formula (I) according to the first embodiment of the first aspect wherein $R^1$ is methyl or trifluoro methyl.

According to another embodiment of the first aspect of the present invention are provided compounds of Formula (I) according to the first embodiment of the first aspect wherein $R^2$ is $C(D)NR^3R^4$.

According to another embodiment of the first aspect of the present invention are provided compounds of Formula (I) according to the first embodiment of the first aspect wherein $R^2$ is $C(D)NR^3R^4$ and D is O.

According to another embodiment of the first aspect of the present invention are provided compounds of Formula (I) according to the first embodiment of the first aspect wherein $R^2$ is $C(D)NR^3R^4$ and D is S.

According to another embodiment of the first aspect of the present invention are provided compounds of Formula (I) according to the first embodiment of the first aspect wherein $R^2$ is $CH_2N R^3R^4$.

According to another embodiment of the first aspect of the present invention are provided compounds of Formula (I) according to the first embodiment of the first aspect wherein $R^2$ is D'-D"($R^3$)($R^4$), D is a bond and D" is C—OH.

According to another embodiment of the first aspect of the present invention are provided compounds of Formula (I) according to the first embodiment of the first aspect wherein $R^2$ is D'-D"($R^3$)($R^4$), D is a bond and D" is C or CH.

According to another embodiment of the first aspect of the present invention are provided compounds of Formula (I) according to the first embodiment of the first aspect wherein $R^2$ is D'-D"($R^3$)($R^4$), D is a $CH_2$ and D" is C—OH.

According to another embodiment of the first aspect of the present invention are provided compounds of Formula (I) according to the first embodiment of the first aspect wherein $R^2$ is D'-D''$(R^3)(R^4)$, D is $CH_2$ and D'' is C or CH.

According to another embodiment of the first aspect of the present invention are provided compounds of Formula (I) according to the first embodiment of the first aspect wherein $R^3$ and $R^4$ are each independently selected from the group consisting of H, $C_{1-6}$alkyl, $C_{1-6}$haloalkyl, —$C_{1-6}$hydroxyalkyl, —$C_{1-4}$alkylene-O—$C_{1-4}$alkyl, —$C_{1-3}$alkylene-$C_{1-6}$thioalkyl, —$C_{2-6}$alkylidene-$(C_{1-4}$alkoxy$)_2$, $C_{3-7}$cycloalkyl, —$C_{1-6}$alkylene-$C_{3-7}$cycloalkyl, $C_{2-6}$alkenyl, $C_{3-6}$alkynyl, —$C_{1-6}$alkylene-CN, —$C_{1-6}$alkylene-heterocyclo and —$C_{1-6}$alkylene-aryl; wherein said aryl of said —$C_{1-6}$alkylene-aryl is optionally substituted with one to three of the same or different substituents selected from the group consisting of fluoro, chloro, bromo, cyano, nitro, $C_{1-4}$alkyl and $C_{1-3}$alkoxy.

According to another embodiment of the first aspect of the present invention are provided compounds of Formula (I) according to the first embodiment of the first aspect wherein $R^3$ and $R^4$ are each independently selected from the group consisting of H, $C_{1-6}$alkyl, $C_{1-6}$haloalkyl, —$C_{1-6}$hydroxyalkyl, —$C_{1-4}$alkylene-O—$C_{1-4}$alkyl, —$C_{1-3}$alkylene-$C_{1-6}$thioalkyl, —$C_{2-6}$alkylidene-$(C_{1-4}$alkoxy$)_2$, $C_{3-7}$cycloalkyl, —$C_{1-6}$alkylene-$C_{3-7}$cycloalkyl, $C_{2-6}$alkenyl, $C_{3-6}$alkynyl and —$C_{1-6}$alkylene-CN.

According to another embodiment of the first aspect of the present invention are provided compounds of Formula (I) according to the first embodiment of the first aspect wherein $R^3$ and $R^4$ together with the nitrogen to which they are attached form a five or six-membered heterocycle, said heterocycle optionally containing one additional heteroatom selected from the group consisting of N, S and O; and said heterocycle optionally substituted with one or more groups selected from the group consisting of $C_{1-6}$alkyl, $C_{1-6}$alkoxy, aryl, —$C_{1-4}$alkylene-aryl, pyridyl and halogen; wherein said aryl of said —$C_{1-4}$alkylene-aryl is optionally substituted with one to three of the same or different substituents selected from the group consisting of fluoro, chloro, bromo, cyano, nitro and $C_{1-3}$alkoxy.

According to another embodiment of the first aspect of the present invention are provided compounds of Formula (I) according to the first embodiment of the first aspect wherein $R^3$ and $R^4$ together with the nitrogen to which they are attached form a five or six-membered heterocycle, said heterocycle optionally containing one additional heteroatom selected from the group consisting of N, S and O.

According to another embodiment of the first aspect of the present invention are provided compounds of Formula (I) according to the first embodiment of the first aspect wherein $R^3$ and $R^4$ together with the nitrogen to which they are attached form a five or six-membered heterocycle.

According to another embodiment of the first aspect of the present invention are provided compounds of Formula (I) according to the first embodiment of the first aspect wherein J is a bond.

According to another embodiment of the first aspect of the present invention are provided compounds of Formula (I) according to the first embodiment of the first aspect wherein $Y^2$ is $CE^1$ and $Z^1$ is $CE^3$.

According to another embodiment of the first aspect of the present invention are provided compounds of Formula (I) according to the first embodiment of the first aspect wherein $Y^2$ is $CE^1$ and $Z^1$ is $CE^3$.

According to another embodiment of the first aspect of the present invention are provided compounds of Formula (I) according to the first embodiment of the first aspect wherein J is $CE^2$.

According to another embodiment of the first aspect of the present invention are provided compounds of Formula (I) according to the first embodiment of the first aspect wherein V is substituted 3-pyridyl.

According to another embodiment of the first aspect of the present invention are provided compounds of Formula (I) according to the first embodiment of the first aspect wherein V is substituted phenyl.

According to another embodiment of the first aspect of the present invention are provided compounds of Formula (I) according to the first embodiment of the first aspect wherein V is 2,4,6-trimethylphenyl.

According to another embodiment of the first aspect of the present invention are provided compounds of Formula (I) according to the first embodiment of the first aspect wherein V is 2,4-dichlorophenyl.

According to another embodiment of the first aspect of the present invention are provided compounds of Formula (I) according to the first embodiment of the first aspect wherein $R^5$, $R^6$ and $R^7$ are each independently selected from the group consisting of halogen, $C_{1-6}$alkyl, $C_{1-6}$haloalkyl, benzyl, phenyl, $C_{1-3}$alkyl-imidazolyl, $C_{1-3}$allyl-indolyl and $C_{1-3}$alkyl-pyridyl.

According to another embodiment of the first aspect of the present invention are provided compounds of Formula (I) according to the first embodiment of the first aspect wherein $Y^2$ is $CH_2$, J is a bond and $Z^1$ is $CH_2$.

According to another embodiment of the first aspect of the present invention are provided compounds of Formula (I) according to the first embodiment of the first aspect wherein $Y^2$ is CH, J is a bond and $Z^1$ is CH.

According to another embodiment of the first aspect of the present invention are provided compounds of Formula (I) according to the first embodiment of the first aspect wherein $Y^2$ is $CR^5$, J is a bond and $Z^1$ is CH wherein said $R^5$ is halo.

According to another embodiment of the first aspect of the present invention are provided compounds of Formula (I) according to the first embodiment of the first aspect wherein $Y^2$ is CH, J is a bond and $Z^1$ is $CR^7$ wherein said $R^7$ is halo.

According to another embodiment of the first aspect of the present invention are provided compounds of Formula (I) according to the first embodiment of the first aspect wherein $Y^2$ is CH, J is a bond and $Z^1$ is $CR^7$ wherein said $R^7$ is halo, cyano or $C_{1-6}$alkyl.

According to another embodiment of the first aspect of the present invention are provided compounds of Formula (I) according to the first embodiment of the first aspect wherein $Y^2$ is C(O), J is a bond and $Z^1$ is $CH_2$.

According to another embodiment of the first aspect of the present invention are provided compounds of Formula (I) according to the first embodiment of the first aspect wherein $Y^2$ is $CH_2$, J is a bond and $Z^1$ is C(O).

According to another embodiment of the first aspect of the present invention is provided a compound of Formula (I) wherein $R^1$ is methyl, $R^2$ is C(O)$NR^3R^4$, $R^3$ is propyl, $R^4$ is —$CH_2$-cyclopropyl, $Y^2$ is $CH_2$, J is a bond, $Z^1$ is $CH_2$, Z is N—V and V is 2,4,6-trimethyl-phenyl.

According to another embodiment of the first aspect of the present invention is provided a compound of Formula (I) wherein $R^1$ is ethyl, $R^2$ is C(O)$NR^3R^4$, $R^3$ is propyl, $R^4$ is —$CH_2$-cyclopropyl, $Y^2$ is $CH_2$, J is a bond, $Z^1$ is $CH_2$, Z is N—V and V is 2,4,6-trimethyl-phenyl.

According to another embodiment of the first aspect of the present invention is provided a compound of Formula (I) wherein $R^1$ is methyl, $R^2$ is $CH_2NR^3R^4$, $R^3$ is propyl, $R^4$ is —$CH_2$-cyclopropyl, $Y^2$ is $CH_2$, J is a bond, $Z^1$ is $CH_2$, Z is N—V and V is 2,4,6-trimethyl-phenyl.

According to another embodiment of the first aspect of the present invention is provided a compound of Formula (I) wherein $R^1$ is ethyl, $R^2$ is $CH_2NR^3R^4$, $R^3$ is propyl, $R^4$ is —$CH_2$-cyclopropyl, $Y^2$ is $CH_2$, J is a bond, $Z^1$ is $CH_2$, Z is N—V and V is 2,4,6-trimethyl-phenyl.

According to another embodiment of the first aspect of the present invention is provided a compound of Formula (I) wherein $Y^2$ is $CH_2$, J is $CH_2$ and $Z^1$ is $CH_2$.

According to another embodiment of the first aspect of the present invention is provided a compound of Formula (I) wherein $R^1$ is CN or $CF_3$ and $Y^2$ is $CH_2$, J is $CH_2$ and $Z^1$ is $CH_2$.

According to another embodiment of the first aspect of the present invention are provided compounds of Formula (I) according to the first embodiment of the first aspect wherein $Y^2$ is C(O), J is CH and $Z^1$ is CH.

According to another embodiment of the first aspect of the present invention are provided compounds of Formula (I) according to the first embodiment of the first aspect wherein $Y^2$ is CH, J is CH and $Z^1$ is C(O).

According to another embodiment of the first aspect of the present invention are provided compounds of Formula (I) according to the first embodiment of the first aspect wherein $Y^2$ is C(O), J is $CE^2$ and $Z^1$ is $CE^3$ wherein $E^2$ and $E^3$ together form $C_4$-alk(en)lyene optionally substituted with halogen.

According to another embodiment of the first aspect of the present invention are provided compounds of Formula (I) according to the first embodiment of the first aspect wherein $Y^2$ is $CE^1$, J is $CE^2$ and $Z^1$ is C(O) wherein $E^1$ and $E^2$ together form $C_4$-alk(en)lyene optionally substituted with halogen.

According to another embodiment of the first aspect of the present invention are provided compounds of Formula (I) according to the first embodiment of the first aspect wherein $Y^2$ is C(O), J is $CE^2$ and $Z^1$ is $CE^3$ wherein $E^2$ and $E^3$ together form $N(CH)_3$, $CHN(CH)_2$, $N(CH)_2N$, N=NCH=N or NCHNCH optionally substituted with halogen.

According to another embodiment of the first aspect of the present invention are provided compounds of Formula (I) according to the first embodiment of the first aspect wherein $Y^2$ is $CE^1$, J is $CE^2$ and $Z^1$ is C(O) wherein $E^1$ and $E^2$ together form $N(CH)_3$, $CHN(CH)_2$, $N(CH)_2N$, N=NCH=N or NCHNCH optionally substituted with halogen.

According to another embodiment of the first aspect of the present invention are provided compounds of Formula (I) according to the first embodiment of the first aspect wherein $Y^2$ is $CE^1$, J is a bond, $Z^1$ is $CE^3$ wherein $E^1$ and $E^3$ together form $C_4$-alk(en)lyene optionally substituted with halogen.

According to another embodiment of the first aspect of the present invention are provided compounds of Formula (I) according to the first embodiment of the first aspect wherein $Y^2$ is $CE^1$, J is a bond, $Z^1$ is $CE^3$ wherein $E^1$ and $E^3$ together form $N(CH)_3$ optionally substituted with halogen, methoxy, methyl or nitrile.

According to another embodiment of the first aspect of the present invention are provided compounds of Formula (I) according to the first embodiment of the first aspect wherein $R^2$ is $CH_2NR^3R^4$, $R^3$ is ethyl or propyl, $R^4$ is —$(CH_2)_2$-phenyl, $Y^2$ is $CE^1$, J is a bond, $Z^1$ is $CE^3$ wherein $E^1$ and $E^3$ together form $N(CH)_3$ optionally substituted with halogen, methoxy, methyl or nitrile.

According to another embodiment of the first aspect of the present invention are provided compounds of Formula (I) according to the first embodiment of the first aspect wherein $Y^2$ is $CE^1$, J is a bond, $Z^1$ is $CE^3$ wherein $E^1$ and $E^3$ together form $N(CH)_3$, $CHN(CH)_2$, $N(CH)_2N$, N=NCH=N or NCHNCH optionally substituted with halogen.

According to another embodiment of the first aspect of the present invention is provided a compound of Formula (I) wherein $R^1$ is methyl, $R^2$ is $C(O)NR^3R^4$, $R^3$ is propyl, $R^4$ is —$CH_2$-cyclopropyl, $Y^2$ is $CE^1$, J is a bond, $Z^1$ is $CE^3$, $E^1$ and $E^3$ together form —CH=C(F)CH=CH—, Z is N—V and V is 2,4,6-trimethyl-phenyl.

According to another embodiment of the first aspect of the present invention is provided a compound of Formula (I) wherein $R^1$ is methyl, $R^2$ is $C(O)NR^3R^4$, $R^3$ is propyl, $R^4$ is —$CH_2$-cyclopropyl, $Y^2$ is $CE^1$, J is a bond, $Z^1$ is $CE^3$, $E^1$ and $E^3$ together form —CH=CHCH=CH—, Z is N—V and V is 2,4,6-trimethyl-phenyl.

According to another embodiment of the first aspect of the present invention is provided a compound of Formula (I) wherein $R^1$ is ethyl, $R^2$ is $C(O)NR^3R^4$, $R^3$ is propyl, $R^4$ is —$CH_2$-cyclopropyl, $Y^2$ is $CE^1$, J is a bond, $Z^1$ is $CE^3$, $E^1$ and $E^3$ together form —CH=CHCH=CH—, Z is N—V and V is 2,4,6-trimethyl-phenyl.

According to another embodiment of the first aspect of the present invention is provided a compound of Formula (I) wherein $R^1$ is trifluoromethyl, $R^2$ is $C(O)NR^3R^4$, $R^3$ is propyl, $R^4$ is —$CH_2$-cyclopropyl, $Y^2$ is $CE^1$, J is a bond, $Z^1$ is $CE^3$, $E^1$ and $E^3$ together form —CH=CHCH=CH—, Z is N—V and V is 2,4,6-trimethyl-phenyl.

According to another embodiment of the first aspect of the present invention is provided a compound of Formula (I) wherein $R^1$ is methyl, $R^2$ is $C(O)NR^3R^4$, $R^3$ is propyl, $R^4$ is —$CH_2$-cyclopropyl, $Y^2$ is $CE^1$, J is a bond, $Z^1$ is $CE^3$, $E^1$ and $E^3$ together form —CH=CHCH=CH—, Z is N—V and V is 2,4-dichloro-phenyl.

According to another embodiment of the first aspect of the present invention is provided a compound of Formula (I) wherein $R^1$ is ethyl, $R^2$ is $C(O)NR^3R^4$, $R^3$ is propyl, $R^4$ is —$CH_2$-cyclopropyl, $Y^2$ is $CE^1$, J is a bond, $Z^1$ is $CE^3$, $E^1$ and $E^3$ together form —CH=C(F)CH=CH—, Z is N—V and V is 2,4,6-trimethyl-phenyl.

According to another embodiment of the first aspect of the present invention is provided a compound of Formula (I) wherein $R^1$ is methyl, $R^2$ is $CH_2NR^3R^4$, $R^3$ is propyl, $R^4$ is —$CH_2$-cyclopropyl, $Y^2$ is $CE^1$, J is a bond, $Z^1$ is $CE^3$, $E^1$ and $E^3$ together form —CH=C(F)CH=CH—, Z is N—V and V is 2,4,6-trimethyl-phenyl.

According to another embodiment of the first aspect of the present invention is provided a compound of Formula (I) wherein $R^1$ is methyl, $R^2$ is $CH_2NR^3R^4$, $R^3$ is propyl, $R^4$ is —$CH_2$-cyclopropyl, $Y^2$ is $CE^1$, J is a bond, $Z^1$ is $CE^3$, $E^1$ and $E^3$ together form —CH=CHCH=CH—, Z is N—V and V is 2,4,6-trimethyl-phenyl.

According to another embodiment of the first aspect of the present invention is provided a compound of Formula (I) wherein $R^1$ is ethyl, $R^2$ is $CH_2NR^3R^4$, $R^3$ is propyl, $R^4$ is —$CH_2$-cyclopropyl, $Y^2$ is $CE^1$, J is a bond, $Z^1$ is $CE^3$, $E^1$ and $E^3$ together form —CH=CHCH=CH—, Z is N—V and V is 2,4,6-trimethyl-phenyl.

According to another embodiment of the first aspect of the present invention is provided a compound of Formula (I) wherein $R^1$ is trifluoromethyl, $R^2$ is $CH_2NR^3R^4$, $R^3$ is propyl, $R^4$ is —$CH_2$-cyclopropyl, $Y^2$ is $CE^1$, J is a bond, $Z^1$ is CE³, E¹ and E³ together form —CH═CHCH═CH—, Z is N—V and V is 2,4,6-trimethyl-phenyl.

According to another embodiment of the first aspect of the present invention is provided a compound of Formula (I) wherein R¹ is ethyl, R² is CH₂NR³R⁴, R³ is propyl, R⁴ is —CH₂-cyclopropyl, Y² is CE¹, J is a bond, Z¹ is CE³, E¹ and E³ together form —CH═C(F)CH═CH—, Z is N—V and V is 2,4,6-trimethyl-phenyl.

According to another embodiment of the first aspect of the present invention is provided a compound of Formula (I) wherein "aryl" or "ar-" is phenyl or napthalenyl.

According to another embodiment of the first aspect of the present invention is provided a compound of Formula (I) wherein "heterocyclic" or "heterocyclo" is furyl, thienyl, benzothienyl, thiazolyl, imidazolyl, oxazolyl, oxadiazolyl, thiadiazolyl, benzthiazolyl, triazolyl, tetrazolyl, isoxazolyl, isothiazolyl, pyrrolyl, pyranyl, tetrahydropyranyl, pyrazolyl, pyridyl, pyrimidinyl, quinolinyl, isoquinolinyl, purinyl, carbazolyl, benzoxazolyl, benzimidazolyl, indolyl, isoindolyl, pyrazinyl, azetidinyl, piperidyl, piperazinyl, imidazolinyl, thiazolidinyl, 3-pyrrolidin-1-yl, morpholinyl, thiomorpholinyl or tetrahydropyranyl.

According to another embodiment of the first aspect of the present invention are compounds of Formula (I) and salts or solvates thereof selected from the group consisting of 2-methyl-7-(2,4,6-trimethyl-phenyl)-6,7-dihydro-5H-imidazo[1,2-α]imidazole-3-carboxylic acid cyclopropylmethyl-propyl-amide, 2-ethyl-7-(2,4,6-trimethylphenyl)-6,7-dihydro-5H-imidazo[1,2-α]imidazole-3-carboxylic acid cyclopropylmethyl-propyl-amide, 5-fluoro-2-methyl-8-(2,4,6-trimethylphenyl)-8H-1,3a,8-triaza-cyclopenta[a]indene-3-carboxylic acid cyclopropylmethyl-propyl-amide, 2-methyl-8-(2,4,6-trimethylphenyl)-8H-1,3a,8-triaza-cyclopenta[a]indene-3-carboxylic acid cyclopropylmethyl-propyl-amide, 2-ethyl-8-(2,4,6-trimethylphenyl)-8H-1,3a,8-triaza-cyclopenta[a]indene-3-carboxylic acid cyclopropylmethyl-propyl-amide, 2-trifluoromethyl-8-(2,4,6-trimethylphenyl)-8H-1,3a,8-triaza-cyclopenta[a]indene-3-carboxylic acid cyclopropylmethyl-propyl-amide, 8-(2,4-dichlorophenyl)-2-methyl-8H-1,3a,8-triaza-cyclopenta[a]indene-3-carboxylic acid cyclopropylmethyl-propyl-amide, 2-ethyl-5-fluoro-8-(2,4,6-trimethylphenyl)-8H-1,3a,8-triaza-cyclopenta[a]indene-3-carboxylic acid cyclopropylmethyl-propyl-amide, cyclopropylmethyl-[5-fluoro-2-methyl-8-(2,4,6-trimethylphenyl)-8H-1,3a,8-triaza-cyclopenta[a]inden-3-ylmethyl]-propyl-amine, cyclopropylmethyl-[2-methyl-8-(2,4,6-trimethylphenyl)-8H-1,3a,8-triaza-cyclopenta[a]inden-3-ylmethyl]-propyl-amine, cyclopropylmethyl-[2-ethyl-8-(2,4,6-trimethylphenyl)-8H-1,3a,8-triaza-cyclopenta[a]inden-3-ylmethyl]-propyl-amine, cyclopropylmethyl-propyl-(2-trifluoromethyl-8-(2,4,6-trimethylphenyl)-8H-1,3a,8-triaza-cyclopenta[a]inden-3-ylmethyl)-amine and cyclopropylmethyl-[2-ethyl-5-fluoro-8-(2,4,6-trimethylphenyl)-8H-1,3a,8-triaza-cyclopenta[a]inden-3-ylmethyl]-propyl-amine.

According to another embodiment of the first aspect of the present invention are compounds of Formula (I) and salts or solvates thereof selected from the group consisting of Cyclopropylmethyl-(2,2,2-trifluoro-ethyl)-[2-trifluoromethyl-8-(2,4,6-trimethyl-phenyl)-5,6,7,8-tetrahydro-imidazo[1,2-a]pyrimidin-3-ylmethyl]-amine,
Cyclopropylmethyl-(2,2,2-trifluoro-ethyl)-[2-trifluoromethyl-8-(2,4,6-trimethylphenyl-8H-1,3a,8-triaza-cyclopenta[a]inden-3-ylmethyl]-amine,
Ethyl-[2-methyl-8-(2,4,6-trimethyl-phenyl)-8H-1,3a,7,8-tetraaza-cyclopenta[α]inden-3-ylmethyl]-phenethyl-amine,
Cyclobutylmethyl-[2-methyl-8-(2,4,6-trimethyl-phenyl)-8H-1,3a,7,8-tetraaza-cyclopenta[α]inden-3 -ylmethyl]-propyl-amine,
[8-(2-Chloro-4,6-dimethyl-phenyl)-2-methyl-8H-1,3a,7,8-tetraaza-cyclopenta[a]inden-3-ylmethyl]-phenethyl-propyl-amine,
[8-(2-Chloro-4,6-dimethyl-phenyl)-2-methyl-8H-1,3a,7,8-tetraaza-cyclopenta[α]inden-3-ylmethyl]-cyclobutylmethyl-propyl-amine,
[8-(2-Chloro-4,6-dimethyl-phenyl)-2-methyl-8H-1,3a,7,8-tetraaza-cyclopenta[a]inden-3-ylmethyl]-ethyl-phenethyl-amine,
8-(2-Chloro-4,6-dimethyl-phenyl)-2-methyl-3-(3-phenyl-pyrrolidin-1-ylmethyl)-8H-1,3a,7,8-tetraaza-cyclopenta[α]indene,
6-Chloro-2-ethyl-7-(2,4-dichlorophenyl)-7H-imidazo[1,2-a]imidazole-3-carboxylic acid N,N-dipropylamide,
3-[(N,N-Dipropylamino)methyl]-6-chloro-2-ethyl-7-(2,4-diclorophenyl)-7H-imidazo[1,2-a]imidazole,
6-Chloro-2-ethyl-7-(2,4,6-trimethylphenyl)-7H-imidazo[1,2-a]imidazole-3-carboxylic acid N-cyclopropylmethyl-N-ethylamide,
3 -[(N-Cyclopropylmethyl-N-ethylamino)methyl]-6-chloro-2-ethyl-7-(2,4,6-trimethylphenyl)-7H-imidazo[1,2-a]imidazole,
6-Chloro-2-trifluoromethyl-7-(2,4,6-trimethyl-phenyl)-7H-imidazo[1,2-a]imidazol-3-ylmethyl]-cyclopropylmethyl-(2,2,2-trifluoro-ethyl)-amine,
6-Chloro-2-trifluoromethyl-7-(2,4,6-trimethyl-phenyl)-7H-imidazo[1,2-a]imidazol-3-ylmethyl]-cyclopropylmethyl-(2,2,3,3,3-pentafluoro-propyl)-amine,
[6-Chloro-2-trifluoromethyl-7-(2,4,6-trimethyl-phenyl)-7H-imidazo[1,2-a]imidazol-3-ylmethyl]-cyclopropylmethyl-ethyl-amine,
[6-Chloro-2-trifluoromethyl-7-(2,4,6-trimethyl-phenyl)-7H-imidazo[1,2-a]imidazol-3-ylmethyl]-cyclobutylmethyl-(2,2,2-trifluoro-ethyl)-amine,
[6-Chloro-2-trifluoromethyl-7-(2,4,6-trimethyl-phenyl)-7H-imidazo[1,2-a]imidazol-3-ylmethyl]-propyl-(3,3,3-trifluoro-propyl)-amine,
[6-Chloro-2-trifluoromethyl-7-(2,4,6-trimethyl-phenyl)-7H-imidazo[1,2-a]imidazol-3 -ylmethyl]-ethyl-phenethyl-amine,
[6-Chloro-2-trifluoromethyl-7-(2,4,6-trimethyl-phenyl)-7H-imidazo[1,2-a]imidazol-3-ylmethyl]-(2-cyclopropyl-ethyl)-(3,3,3-trifluoro-propyl)-amine, and
[6-Chloro-2-trifluoromethyl-7-(2,4,6-trimethyl-phenyl)-7H-imidazo[1,2-a]imidazol-3-ylmethyl]-(2-cyclopropyl-ethyl)-(2,2,2-trifluoro-ethyl)-amine.

According to various embodiments of a second aspect of the present invention are provided pharmaceutical compositions comprising compounds of Formula (I) as defined herein.

According to various embodiments of a second aspect of the present invention are provided methods of treating depression, anxiety, affective disorders, post-traumatic stress disorder, post-operative stress, headache, drug addiction, eating disorders and obesity, sudden death due to cardiac disorders, iritable bowel syndrome, hypertension, syndrome X, inflammatory disorders, stress-induced immune suppression, infertility, stress-induced insomnia and other sleep disorders, seizures, epilepsy, stroke and cerebral ischemia, traumatic brain injury, yet other disorders requiring neuroprotection, drug or alcohol withdrawal symptoms, other disorders including tachycardia, congestive heart failure, osteoporosis, premature birth, psychosocial dwarfism, ulcers, diarrhea, post-operative ileus and yet other conditions the treatment of which can be effected by the antagonism of the CRF-1 receptor by the administration of pharmaceutical compositions comprising compounds of the present invention as described herein.

According to a first embodiment of a third aspect of the present invention are provided compounds of Formula (WHH)

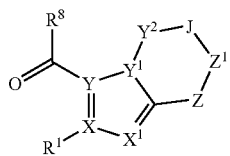

(WHH)

wherein
R¹ is H, $C_{1-6}$alkyl, $C_{1-6}$haloalkyl, $C_{1-6}$alkoxy, $C_{1-6}$thioalkyl, cyano, halo, $C_{3-7}$cycloalkyl, —$C_{1-6}$alkylene-$C_{3-7}$cycloalkyl, $C_{2-6}$alkenyl or $C_{3-6}$alkynyl;
R⁸ is O—$C_{1-4}$alkyl, —$N(CH_3)(OCH_3)$ or other suitable leaving group;
X is C;
Y is C;
X¹ is N;
Y¹ is N;
Y² is $CH_2$;
J is $CH_2$ or a bond;
Z¹ is $CH_2$ or C(O); and
Z is N—V, wherein V is phenyl, 2-pyridyl or 3-pyridyl substituted with two to three of the same or different substitutents selected from the group consisting of $C_{1-4}$alkyl, $C_{1-4}$alkoxy, $C_{1-6}$thioalkyl, $C_{1-4}$haloalkyl, halogen, $N(C_1$-$C_4$alkyl)$_2$ and CN.

According to another embodiment of a third aspect of the present invention are provided processes for preparing compounds of Formula (WHH)

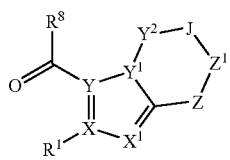

(WHH)

wherein
R¹ is H, $C_{1-6}$alkyl, $C_{1-6}$haloalkyl, $C_{1-6}$alkoxy, $C_{1-6}$thioalkyl, cyano, halo, $C_{3-7}$cycloalkyl, —$C_{1-6}$alkylene-$C_{3-7}$cycloalkyl, $C_{2-6}$alkenyl or $C_{3-6}$alkynyl;
R⁸ is O—$C_{1-4}$alkyl, —$N(CH_3)(OCH_3)$ or other suitable leaving group;
X is C;
Y is C;
X¹ is N;
Y¹ is N;
Y² is $CH_2$;
J is $CH_2$ or a bond;
Z¹ is $CH_2$ or C(O); and
Z is N—V, wherein V is phenyl, 2-pyridyl or 3-pyridyl substituted with two to three of the same or different substitutents selected from the group consisting of $C_{1-4}$alkyl, $C_{1-4}$alkoxy, $C_{1-6}$thioalkyl, $C_{1-4}$haloalkyl, halogen, $N(C_1$-$C_4$alkyl)$_2$ and CN;

comprising reacting a compound of Formula (UFF)

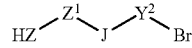

(UFF)

wherein
Z, Z¹, J and Y² are defined as for Formula (WHH);
with a compound of Formula (UFF')

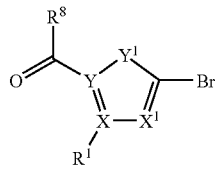

(UFF')

wherein
R¹, R⁸, X, Y, X¹ and Y¹ are defined as for Formula (WHH);
in the presence of a suitable base and polar aprotic solvent to yield a compound of Formula (VGG)

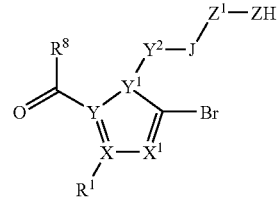

(VGG)

wherein
R¹, R⁸, X, Y, X¹, Y¹, Y², J, Z¹ and Z are defined as for Formula (WHH);

and reacting said compound of Formula (VGG) with a high-boiling point polar aprotic solvent and a suitable silver salt under suitably high temperature.

According to another embodiment of a third aspect of the present invention are provided compounds of Formula (Z')

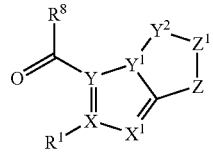

(Z')

wherein
R¹ is H, $C_{1-6}$alkyl, $C_{1-6}$haloalkyl, $C_{1-6}$alkoxy, $C_{1-6}$thioalkyl, cyano, halo, $C_{3-7}$cycloalkyl, —$C_{1-6}$alkylene-$C_{3-7}$cycloalkyl, $C_{2-6}$alkenyl or $C_{3-6}$alkynyl;
R⁸ is O—$C_{1-4}$alkyl, —$N(CH_3)(OCH_3)$ or other suitable leaving group;
X is C;
Y is C;
X¹ is N;
Y¹ is N;

$Y^2$ is CH or $CR^5$;

$R^5$ is selected from the group consisting of —CN, —$C_{1-4}$-alk(en)ylene-CN, halo, $C_{1-6}$alkyl, $C_{2-6}$alkenyl, $C_{3-6}$alkynyl, $C_{1-6}$haloalkyl, aryl, —$C_{1-4}$alk(en)ylene-aryl, —$C_{1-4}$alk(en)ylene-heterocyclo, heterocyclo, —$C_{1-4}$alk(en)ylene-amino, —$C_{1-4}$alkylene-amino-$C_{1-4}$alkyl, aryl-amino, -amino-($C_{1-6}$alk(en)yl)$_{1-2}$, -amino-aryl, -amino-heterocyclo, $C_{1-6}$alkoxy, —O-aryl and —O-heterocyclo;

$Z^1$ is C(O); and

Z is N—V, wherein V is phenyl, 2-pyridyl or 3-pyridyl substituted with two to three of the same or different substitutents selected from the group consisting of $C_{1-4}$alkyl, $C_{1-4}$alkoxy, $C_{1-6}$thioalkyl, $C_{1-4}$haloalkyl, halogen, $N(C_1-C_4alkyl)_2$ and CN.

According to another embodiment of a third aspect of the present invention are provided processes for preparing compounds of Formula (Z')

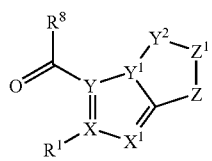
(Z')

wherein $R^1$ is H, $C_{1-6}$alkyl, $C_{1-6}$haloalkyl, $C_{1-6}$alkoxy, $C_{1-6}$thioalkyl, cyano, halo, $C_{3-7}$cycloalkyl, —$C_{1-6}$alkylene-$C_{3-7}$cycloalkyl, $C_{2-6}$alkenyl or $C_{3-6}$alkynyl;

$R^8$ is O—$C_{1-4}$alkyl, —$N(CH_3)(OCH_3)$ or other suitable leaving group;

X is C;

Y is C;

$X^1$ is N;

$Y^1$ is N;

$Y^2$ is CH or $CR^5$;

$R^5$ is selected from the group consisting of —CN, —$C_{1-4}$-alk(en)ylene-CN, halo, $C_{1-6}$allyl, $C_{2-6}$alkenyl, $C_{3-6}$alkynyl, $C_{1-6}$haloalkyl, aryl, —$C_{1-4}$alk(en)ylene-aryl, —$C_{1-4}$alk(en)ylene-heterocyclo, heterocyclo, —$C_{1-4}$alk(en)ylene-amino, —$C_{1-4}$alkylene-amino-$C_{1-4}$alkyl, aryl-amino, -amino-($C_{1-6}$alk(en)yl)$_{1-2}$, -amino-aryl, -amino-heterocyclo, $C_{1-6}$alkoxy, —O-aryl and —O-heterocyclo;

$Z^1$ is C(O); and

Z is N—V, wherein V is phenyl, 2-pyridyl or 3-pyridyl substituted with two to three of the same or different substitutents selected from the group consisting of $C_{1-4}$alkyl, $C_{1-4}$alkoxy, $C_{1-6}$thioalkyl, $C_{1-4}$haloalkyl, halogen, $N(C_1-C_4alkyl)_2$ and CN;

comprising reacting a compound of Formula (X')

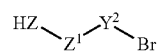
(X')

wherein

Z, $Z^1$ and $Y^2$ are defined as for Formula (Z');

with a compound of Formula (UFF')

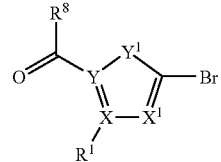
(X")

wherein $R^1$, $R^8$, X, Y, $X^1$ and $Y^1$ are defined as for Formula (Z');

in the presence of a suitable base and polar aprotic solvent to yield a compound of Formula (Y')

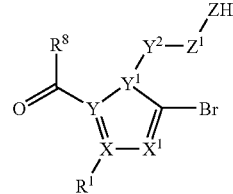
(Y')

wherein $R^1$, $R^8$, X, Y, $X^1$, $Y^1$, $Y^2$, $Z^1$ and Z are defined as for Formula (Z');

and reacting said compound of Formula (Y') with a high-boiling point polar aprotic solvent and a suitable silver salt under suitably high temperature.

According to another embodiment of a third aspect of the present invention are provided compounds of Formula (AA')

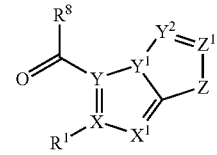
(AA')

wherein $R^1$ is H, $C_{1-6}$alkyl, $C_{1-6}$haloalkyl, $C_{1-6}$alkoxy, $C_{1-6}$thioalkyl, cyano, halo, $C_{3-7}$cycloalkyl, —$C_{1-6}$alkylene-$C_{3-7}$cycloalkyl, $C_{2-6}$alkenyl or $C_{3-6}$alkynyl;

$R^8$ is O—$C_{1-4}$alkyl, —$N(CH_3)(OCH_3)$ or other suitable leaving group;

X is C;

Y is C;

$X^1$ is N;

$Y^1$ is N;

$Y^2$ is CH or $CR^5$;

$R^5$ is selected from the group consisting of —CN, —$C_{1-4}$-alk(en)ylene-CN, halo, $C_{1-6}$alkyl, $C_{2-6}$alkenyl, $C_{3-6}$alkynyl, $C_{1-6}$haloalkyl, aryl, —$C_{1-4}$alk(en)ylene-aryl, —$C_{1-4}$alk(en)ylene-heterocyclo, heterocyclo, —$C_{1-4}$alk(en)ylene-amino, —$C_{1-4}$alkylene-amino-$C_{1-4}$alkyl, aryl-amino, -amino-($C_{1-6}$alk(en)yl)$_{1-2}$, -amino-aryl, -amino-heterocyclo, $C_{1-6}$alkoxy, —O-aryl and —O-heterocyclo;

$Z^1$ is $CR^7$;

wherein R⁷ is chloro or bromo; and
Z is N—V, wherein V is phenyl, 2-pyridyl or 3-pyridyl substituted with two to three of the same or different substitutents selected from the group consisting of $C_{1-4}$alkyl, $C_{1-4}$alkoxy, $C_{1-6}$thioalkyl, $C_{1-4}$haloalkyl, halogen, $N(C_1-C_4alkyl)_2$ and CN.

According to another embodiment of a third aspect of the present invention are provided processes for preparing compounds of Formula (AA')

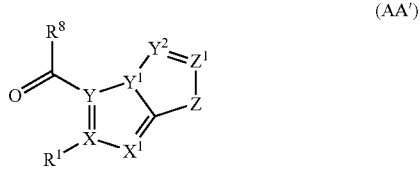

wherein
R¹ is H, $C_{1-6}$alkyl, $C_{1-6}$haloalkyl, $C_{1-6}$alkoxy, $C_{1-6}$thioalkyl, cyano, halo, $C_{3-7}$cycloalkyl, —$C_{1-6}$alkylene-$C_{3-7}$cycloalkyl, $C_{2-6}$alkenyl or $C_{3-6}$alkynyl;
R⁸ is O-$C_{1-4}$alkyl, —$N(CH_3)(OCH_3)$ or other suitable leaving group;
X is C;
Y is C;
X¹ is N;
Y¹ is N;
Y² is CH or CR⁵;
  R⁵ is selected from the group consisting of —CN, —$C_{1-4}$-alk(en)ylene-CN, halo, $C_{1-6}$alkyl, $C_{2-6}$alkenyl, $C_{3-6}$alkynyl, $C_{1-6}$haloalkyl, aryl, —$C_{1-4}$alk(en)ylene-aryl, —$C_{1-4}$alk(en)ylene-heterocyclo, heterocyclo, —$C_{1-4}$alk(en)ylene-amino, —$C_{1-4}$alkylene-amino-$C_{1-4}$alkyl, aryl-amino, -amino-($C_{1-6}$alk(en)yl)$_{1-2}$, -amino-aryl, -amino-heterocyclo, $C_{1-6}$alkoxy, —O-aryl and —O-heterocyclo;
Z¹ is CR⁷;
  wherein R⁷ is chloro or bromo; and
Z is N—V, wherein V is phenyl, 2-pyridyl or 3-pyridyl substituted with two to three of the same or different substitutents selected from the group consisting of $C_{1-4}$alkyl, $C_{1-4}$alkoxy, $C_{1-6}$thioalkyl, $C_{1-4}$haloalkyl, halogen, $N(C_1-C_4alkyl)_2$ and CN;

comprising reacting a compound of Formula (Z')

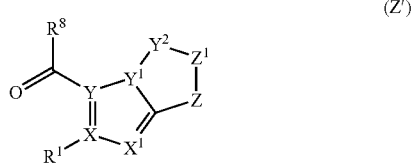

wherein
R¹, R⁸, X, Y, X¹, Y¹, Y², and Z are defined as for Formula (AA'); and
Z¹ is C(O);

with phosphoryl trichloride or phosphoryl tribromide, neat or with a suitable solvent and without a base or with a suitable base.

Other embodiments of the present invention may comprise a suitable combination of two or more of the embodiments and/or aspects disclosed herein.

Yet other embodiments and aspects of the invention will be apparent according to the description provided below.

DETAILED DESCRIPTION OF THE INVENTION

The description of the invention herein should be construed in congruity with the laws and principals of chemical bonding. An embodiment or aspect which depends from another embodiment or aspect, will describe only the variables having values and provisos that differ from the embodiment or aspect from which it depends.

As used herein, "aryl" or "ar-" includes phenyl or napthalenyl.

As used herein, "heterocyclic" or "heterocyclo" includes both heteroaryl and heteroalicyclic. "Heteroaryl" includes but is not limited to furyl, thienyl, benzothienyl, thiazolyl, imidazolyl, oxazolyl, oxadiazolyl, thiadiazolyl, benzthiazolyl, triazolyl, tetrazolyl, isoxazolyl, isothiazolyl, pyrrolyl, pyranyl, tetrahydropyranyl, pyrazolyl, pyridyl, pyrimidinyl, quinolinyl, isoquinolinyl, purinyl, carbazolyl, benzoxazolyl, benzimidazolyl, indolyl, isoindolyl or pyrazinyl. "Heteroalicyclic" includes but is not limited to azetidinyl, piperidyl, piperazinyl, imidazolinyl, thiazolidinyl, 3-pyrrolidin-1-yl, morpholinyl, thiomorpholinyl or tetrahydropyranyl. "Heteroalicyclic" further includes moieties otherwise heteroaromatic but for the addition of one or more hydrogen atoms, e.g., dihydropyridine.

As used herein, "halo" or "halogen" includes fluoro, chloro, bromo and iodo and further means one or more of the same or different halogens may be substituted on a respective moiety.

Unless specificied otherwise, alkyl, alkenyl and alkynyl may be branched or straight chained. As used herein, "alk (en)yl" or "alk(en)ylene" includes alkyl or alkenyl groups. Alkenyl and alkynyl groups may contain one or more double or triple bonds respectively. Where a range of carbon atoms is designated, e.g., C-$_{1-4}$alk(en)ylene, alkenyl groups it is understood that according to the principals of chemical bonding must have at least two carbons in length.

It is to be understood that the present invention may include any and all possible stereoisomers, geometric isomers, diastereoisomers, enantiomers, anomers and optical isomers, unless a particular description specifies otherwise.

The compounds of this invention may exist in the form of pharmaceutically acceptable salts. Such salts may include addition salts with inorganic acids such as, for example, hydrochloric acid and sulfuric acid, and with organic acids such as, for example, acetic acid, citric acid, methanesulfonic acid, toluenesulfonic acid, tartaric acid and maleic acid. Further, in case the compounds of this invention contain an acidic group, the acidic group may exist in the form of alkali metal salts such as, for example, a potassium salt and a sodium salt; alkaline earth metal salts such as, for example, a magnesium salt and a calcium salt; and salts with organic bases such as a triethylammonium salt and an arginine salt. The compounds of the present invention may be hydrated or non-hydrated.

The compounds of this invention can be administered in such oral dosage forms as tablets, capsules (each of which includes sustained release or timed release formulations), pills, powders, granules, elixirs, tinctures, suspensions, syrups and emulsions. The compounds of this invention may also be administered intravenously, intraperitoneally, subcutaneously, or intramuscularly, all using dosage forms well known to those skilled in the pharmaceutical arts. The compounds can be administered alone, but generally will be administered with a pharmaceutical carrier selected upon the basis of the chosen route of administration and standard pharmaceutical practice. Compounds of this invention can also be administered in intranasal form by topical use of suitable intranasal vehicles, or by transdermal routes, using transdermal skin patches. When compounds of this invention are administered transdermally the dosage will be continuous throughout the dosage regimen.

Compounds of the present invention may be used for the treatment of a variety of conditions including depression, anxiety, affective disorders, eating disorders and obesity (see Peripheral administration of CRF and urocortin: effects on food intake and the HPA axis in the marsupial Sminthopsis crassicaudata. Hope, P. J.; Tumbull, H.; Farr, S.; Morley, J. E.; Rice, K. C.; Chrousos, G. P.; Torpy, D. J.; Wittert, G. A. Department of Medicine, University of Adelaide, Royal Adelaide Hospital, South Australia, Australia. Peptides (N.Y.) (2000), 21(5), 669-677), sudden death due to cardiac disorders (see Use of corticotropin releasing factor (CRF) antagonists to prevent sudden death. Fossa, Anthony Andrea. (Pfizer Products Inc., USA). Eur. Pat. Appl. (2000), EP 1040831 A2), post-traumatic stress disorder, headache, post-operative stress (see WO 0158489 A1), drug addiction, iritable bowel syndrome (see Stress and the gastrointestinal tract III. Stress-related alterations of gut motor function: role of brain corticotropin-releasing factor receptors. Tache Y; Martinez V; Million M; Wang L CURE: Digestive Diseases Research Center, Department of Veterans Affairs Greater Los Angeles Healthcare System, Bldg. 115, Rm. 203, 11301 Wilshire Blvd., Los Angeles, Calif. 90073, USA. AMERICAN JOURNAL OF PHYSIOLOGY. GASTROINTESTINAL AND LIVER PHYSIOLOGY (2001 February), 280 (2), G173-7; Role of CRF receptor 1 in central CRF-induced stimulation of colonic propulsion in rats. Martinez, V.; Tache, Y. Digestive Disease Division and Brain Research Institute, Department of Medicine, CURE: Digestive Diseases Research Center, Veterans Administration Greater Los Angeles Healthcare System, University of California at Los Angeles, Los Angeles, Calif., USA. Brain Res. (2001), 893(1,2), 29-35; and Peripheral corticotropin-releasing factor and stress-stimulated colonic motor activity involve type 1 receptor in rats. Maillot, Celine; Million, Mulugeta; Wei, Jen Yu; Gauthier, Ariane; Tache, Yvette. Digestive Diseases Research Center, VA Greater Los Angeles Healthcare System, Department of Medicine, Division of Digestive Diseases, and Brain Research Institute, University of California School of Medicine, Los Angeles, Calif., USA. Gastroenterology (2000), 119(6), 1569-1579), hypertension (see Combinations of CRF antagonists and renin-angiotensin system inhibitors. Fossa, Anthony Andrea. (Pfizer Products Inc., USA). Eur. Pat. Appl. (2000), 21 pp. and Antalarmin blockade of corticotropin releasing hormone-induced hypertension in rats. Briscoe, R. J.; Cabrera, C. L.; Baird, T. J.; Rice, K. C.; Woods, J. H. Department of Pharmacology, University of Michigan, Ann Arbor, Mich., USA. Brain Res. (2000), 881(2), 204-207), syndrome X (also known as metabolic syndrome, plurimetabolic syndrome or insulin resistance syndrome) (see EP1 097 709 A2), inflammatory disorders and stress-induced immune suppression (see Stress, corticotropin-releasing hormone, glucocorticoids, and the immune/inflammatory response: acute and chronic effects. Elenkov, Ilia J.; Webster, Elizabeth L.; Torpy, David J.; Chrousos, George P. Pediatric Endocrinology Section, Developmental Endocrinology Branch, National Institute of Child Health and Human Development, and Inflammatory Joint Diseases Section, Arthritis and Rheumatism Branch, National Institute of Arthritis and Musculoskeletal and Skin Diseases, National Institutes of Health, Bethesda, Md., USA. Ann. N.Y. Acad. Sci. (1999), 876(Neuroendocrine Immune Basis of the Rheumatic Diseases), 1-13; Corticotropin-releasing hormone and inflammation. Webster, Elizabeth L.; Torpy, David J.; Elenkov, Ilia J.; Chrousos, George P. Pediatric Endocrinology Section, Developmental Endocrinology Branch, National Institute of Child Health and Development, National Institutes of Health, Bethesda, Md., USA. Ann. N.Y. Acad. Sci. (1998), 840(Neuroimmunomodulation), 21-32; and Peripheral corticotropin-releasing factor mediates the elevation of plasma IL-6 by immobilization stress in rats. Ando T; Rivier J; Yanaihara H; Arimura A United States-Japan Biomedical Research Laboratories, Tulane University Hebert Center, Belle Chasse, La. 70037-3001, USA AMERICAN JOURNAL OF PHYSIOLOGY (1998 November), 275(5 Pt 2), R1461-7), infertility (see Corticotropin-releasing factor (CRF) and stress-related reproductive failure: The brain as a state of the art or the ovary as a novel clue? Nappi, R. E.; Rivest, S. CHUL Research Center, Laval University, PQ, Can. J. Endocrinol. Invest. (1995), 18(11), 872-80)), stress-induced insomnia and other sleep disorders (see Use of CRF antagonists and related compositions for modifying circadian rhythm and treatment of depression and other conditions. Chen, Yuh-pyng Liang. (Pfizer Products Inc., USA). Eur. Pat. Appl. (2001), 29 pp EP 1082960 A2; Middle-Aged Men Show Higher Sensitivity of Sleep to the Arousing Effects of Corticotropin-Releasing Hormone Than Young Men: Clinical Implications. Vgontzas A N, Bixler E O, Wittman A M, Zachman K, Lin H M, Vela-Bueno A, Kales A, Chrousos G P. Sleep Research and Treatment Center, Department of Psychiatry and Department of Health Evaluation Sciences (H.-M. L.), Pennsylvania State University, Hershey, Pa. 17033. J. Clin. Endocrinol. Metab. (2001), 86 (4): 1489-1495; IL-1 is a mediator of increases in slow-wave sleep induced by CRH receptor blockade. Chang, Fang-Chia; Opp, Mark R. Neuroscience Graduate Program, University of Texas Medical Branch, Galveston, Tex., USA. Am. J. Physiol. (2000), 279(3, Pt. 2), R793-R802; Blockade of corticotropin-releasing hormone receptors reduces spontaneous waking in the rat. Chang, Fang-Chia; Opp, Mark R. Neuroscience Graduate Program, University of Texas Medical Branch, Galveston, Tex., USA. Am. J. Physiol. (1998), 275(3, Pt. 2), R793-R802; Non-peptidic corticotropin-releasing hormone receptor type 1 antagonist reverses restraint stress-induced shortening of sodium pentobarbital-induced sleeping time of rats: evidence that an increase in arousal induced by stress is mediated through CRH receptor type 1. Arai, Keiko; Ohata, Hisayuki; Shibasaki, Tamotsu. Department of Physiology, Nippon Medical School, Tokyo, Japan. Neurosci. Lett. (1998), 255(2), 103-106; Rat strain differences suggest a role for corticotropin-releasing hormone in modulating sleep. Opp, Mark R. Department of Psychiatry and Behavioral Sciences, University of Texas Medical Branch, Galveston, Tex., USA. Physiol. Behav. (1997), Volume Date 1998, 63(1), 67-74), seizures (see The effect of 'Astressin', a novel antagonist of corticotropin releasing hormone (CRH), on CRH-induced seizures in the infant rat: comparison with two other antagonists. Baram T Z; Koutsoukos Y; Schultz L; Rivier J Department of Pediatrics, University of California, Irvine 92717, USA MOLECULAR PSYCHIATRY (1996 July), 1(3), 223-6; and Astressin, a novel and potent CRF antagonist, is neuroprotective in the hippocampus when administered after a seizure. Maecker H; Desai A; Dash R; Rivier J; Vale W; Sapolsky R Department of Biological Sciences, Stanford University, Calif. 94305, USA BRAIN RESEARCH (1997 Jan. 2), 744(1), 166-70), epilepsy (see Infantile spasms. Hypothesis-driven therapy and pilot human infant experiments using corticotropin-releasing hormone receptor antagonists. Baram, Tallie Z.; Mitchell, Wendy G.; Brunson, Kristen; Haden, Elizabeth. Department Anatomy/Neurobiology, Univ. California Irvine, Irvine, Calif., USA. Dev. Neurosci. (Basel) (1999), 21(3-5), 281-289; and The pro-convulsant actions of corticotropin-releasing hormone in the hippocampus of infant rats. Hollrigel, G. S.; Chen, K.; Baram, T. Z.; Soltesz, I. Department of Anatomy and Neurobiology, University of California, Irvine, Calif., USA. Neuroscience (Oxford) (1998), 84(1), 71-79), stroke and cerebral ischemia (see Neuroprotection by corticotropin releasing factor during hypoxia in rat brain. Fox M W; Anderson R E; Meyer F B Department of Neurosurgery, Mayo Clinic, Rochester, Minn. 55905. STROKE (1993 July), 24(7), 1072-5; discussion 1075-6; Neuroprotective effects of corticotropin-releasing factor receptor antagonists. Loddick, S. A.; Chalmers, D. T.; Yatsushiro, K.; McCulloch, J.; Foster, A. C.; Rothwell, N. J.; De Souza, E. B. Neurocrine Biosciences, Inc., San Diego, Calif., USA. Editor(s): Krieglstein, Josef. Pharmacol. Cereb. Ischemia 1998, [Int. Symp.], 7th (1999), Meeting Date 1998, 371-378. Publisher: Medpharm Scientific Publishers, Stuttgart, Germany CODEN: 680ZA5 Conference; Corticotropin releasing factor antagonist reduces ischemic hippocampal neuronal injury. Lyons, Mark K.; Anderson, Robert E.; Meyer, Fredric B. Mayo Clin., Mayo Grad. Sch. Med., Rochester, Minn., USA. Brain Res. (1991), 545(1-2), 339-42; Focal cerebral ischemia induces CRH mRNA in rat cerebral cortex and amygdala. Wong M L; Loddick S A; Bongiomo P B; Gold P W; Rothwell N J; Licinio J Clinical Neuroendocrinology Branch, NIMH, NIH, Bethesda, Md. 20892-1284, USA NEUROREPORT (1995 Sep. 11), 6(13), 1785-8; ) traumatic brain injury (see Evidence for the involvement of corticotrophin-releasing hormone in the pathogenesis of traumatic brain injury. Roe S Y; McGowan E M; Rothwell N J School of Biological Sciences, University of Manchester, UK EUROPEAN JOURNAL OF NEUROSCIENCE (1998 February), 10(2), 553-9; The effects of human corticotrophin releasing factor on motor and cognitive deficits after impact acceleration injury. Beaumont, Andrew; Marmarou, Christina; Marmarou, Anthony. Division of Neurosurgery, Department of Physiology, Medical College of Virginia, Richmond, Va., USA. Neurol. Res. (2000), 22(7), 665-673) and yet other disorders requiring neuroprotection, drug or alcohol withdrawal symptoms, other disorders including tachycardia, congestive heart failure, osteoporosis, premature birth, psychosocial dwarfism, ulcer, diarrhea and post-operative ileus (see New uses for heterocyclic corticotropin-releasing factor (CRF) antagonists in treating cardiovascular diseases, osteoporosis, ulcers, and other disorders. Chen, Yuhpyng Liang; Fossa, Anthony Andrea. (Pfizer Inc., USA). Eur. Pat. Appl. (1997), 15 pp. EP 773023 A1) and yet other conditions the treatment of which can be effected by the antagonism of the CRF-1 receptor by the administration of pharmaceutical compositions comprising compounds of the present invention as described herein.

The dosage and dosage regimen and scheduling of a compounds of the present invention must in each case be carefully adjusted, utilizing sound professional judgment and considering the age, weight and condition of the recipient, the route of administration and the nature and extent of the disease condition. In accordance with good clinical practice, it is preferred to administer the instant compounds at a concentration level which will produce effective beneficial effects without causing any harmful or untoward side effects.

Compounds of the present invention may be synthesized according to the general schemes provided below. Variables corresponding to compounds of Formula (I) have been introduced in the schemes below at particular instances to further depict how said compounds may be synthesized. Variables provided in the schemes below are defined in accordance with the description of compounds of Formula (I) unless otherwise specified. Where a variable has been further defined in any one scheme below, said variable should assume the same values in subsequent schemes unless yet further defined. The definitions of compounds in the schemes below are not intended to narrow the scope of compounds described by Formula (I). Moreover, the schemes provided herein may be modified in a manner apparent to one skilled in the art to describe additional processes for making compounds of the present invention.

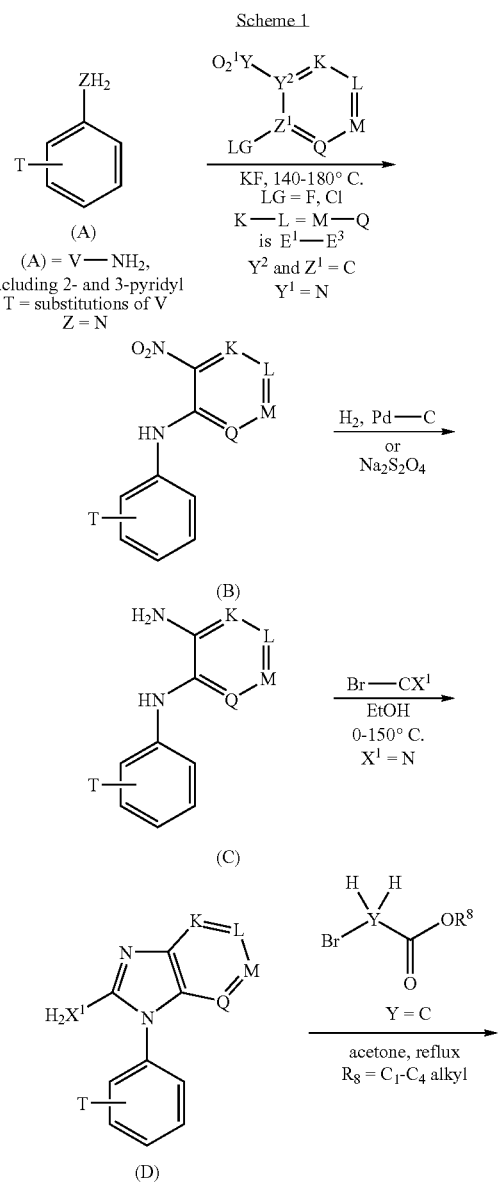

-continued
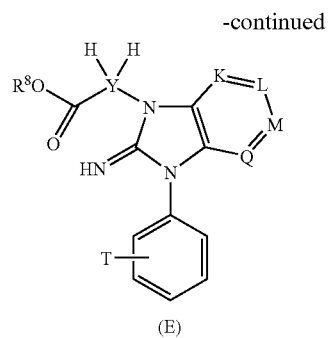 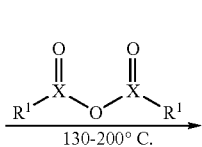 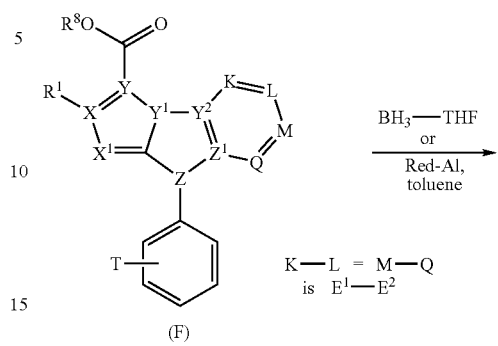
(E) → (F)
Scheme 2
K—L = M—Q is E¹—E²
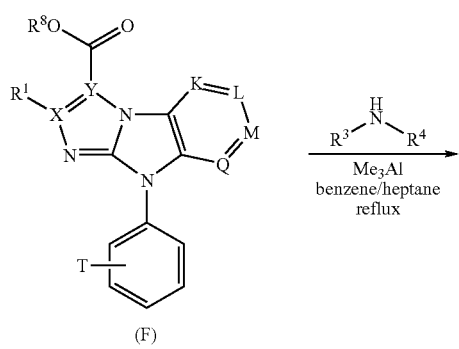 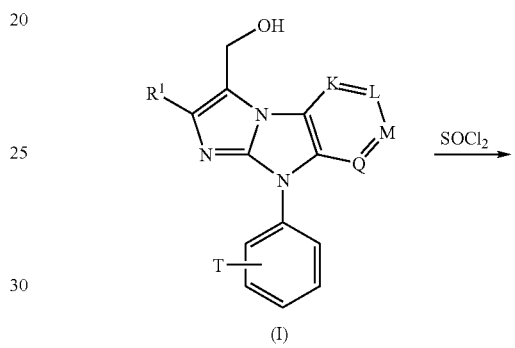
(F) (I)
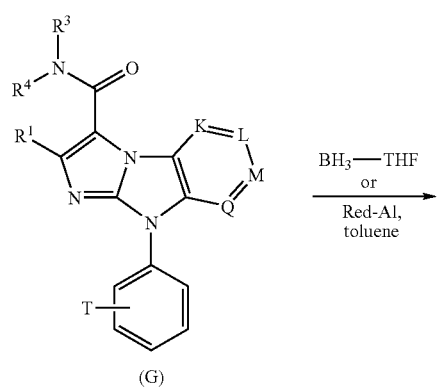 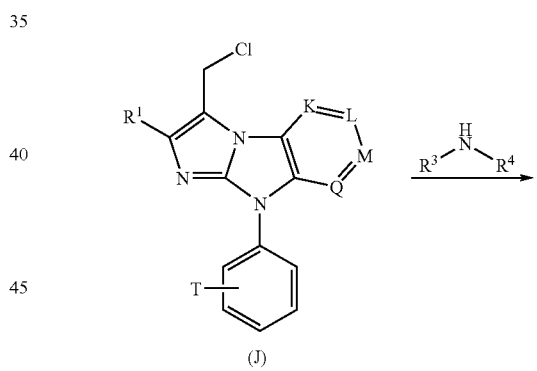
(G) (J)
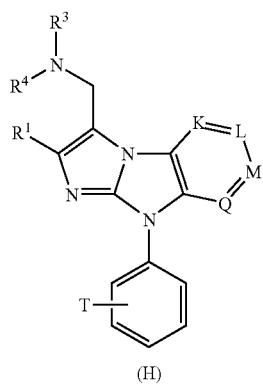 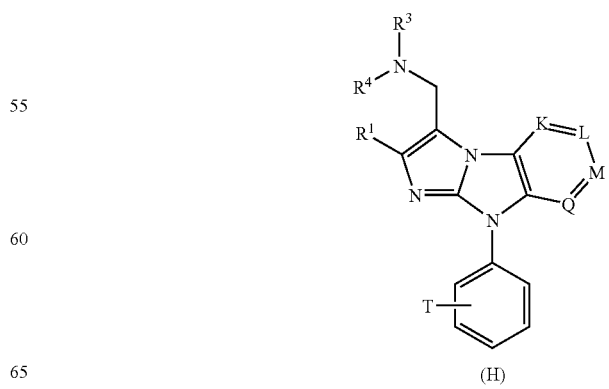
(H) (H)

Scheme 3
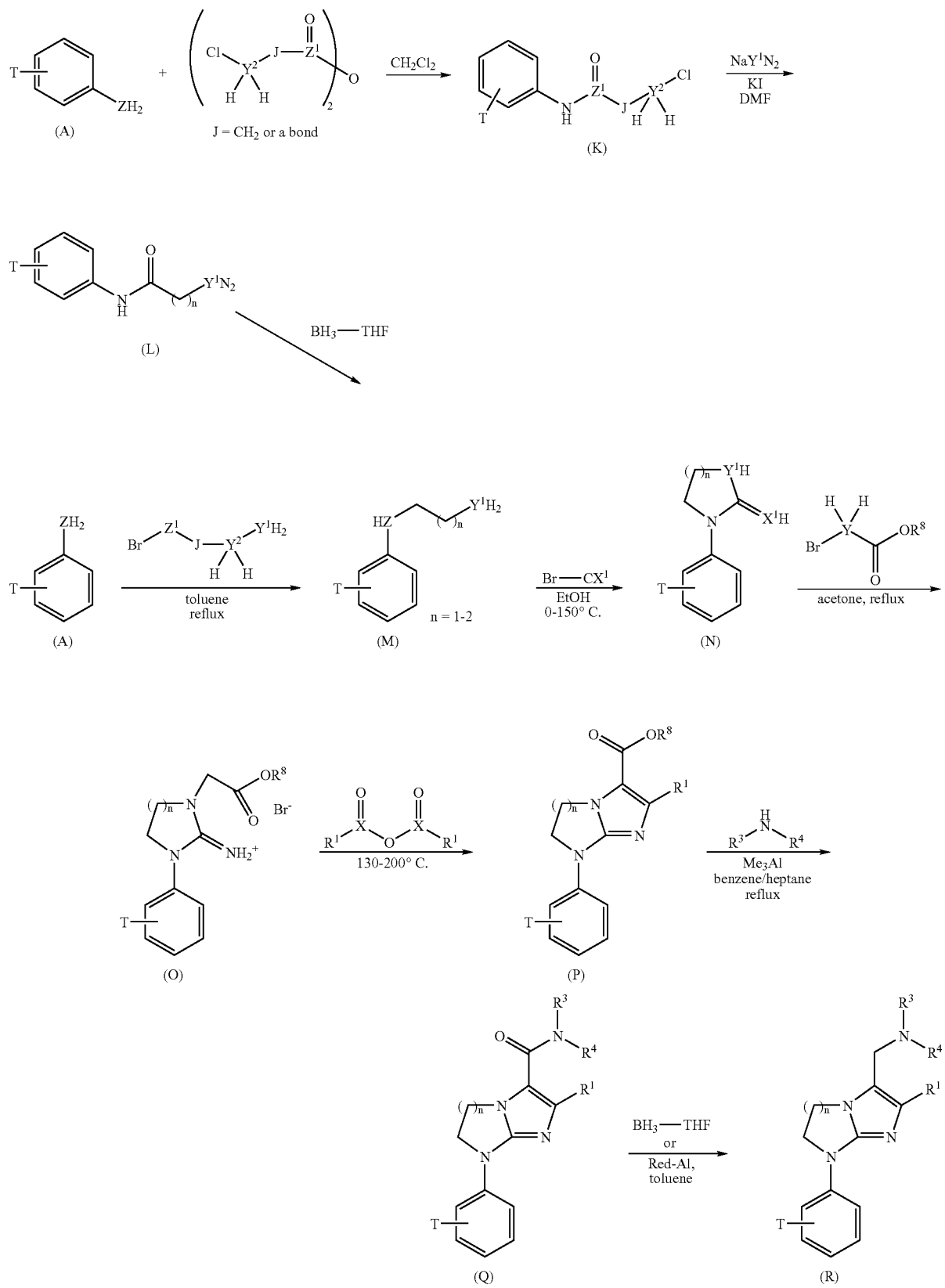

Scheme 4
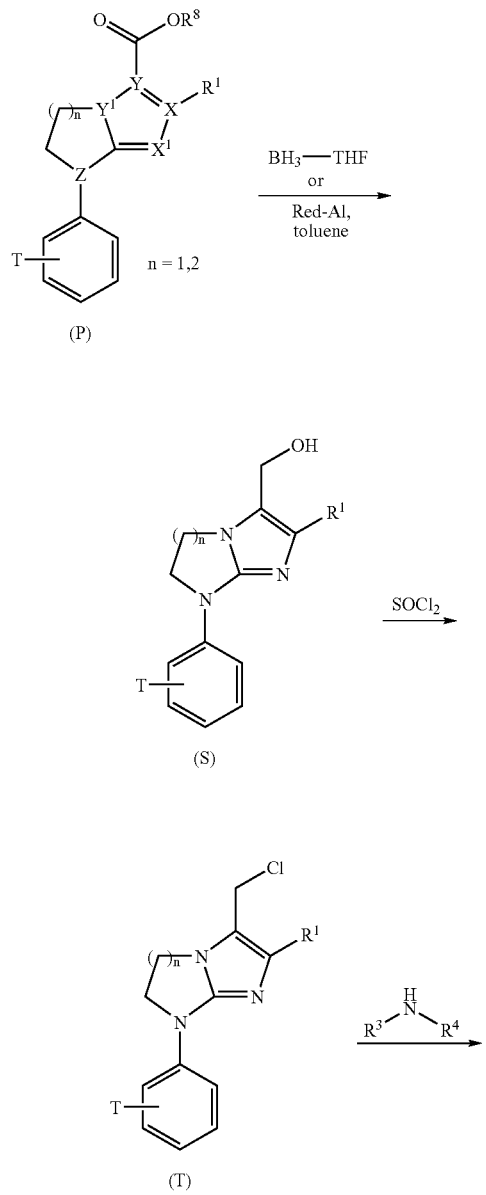
Scheme 5
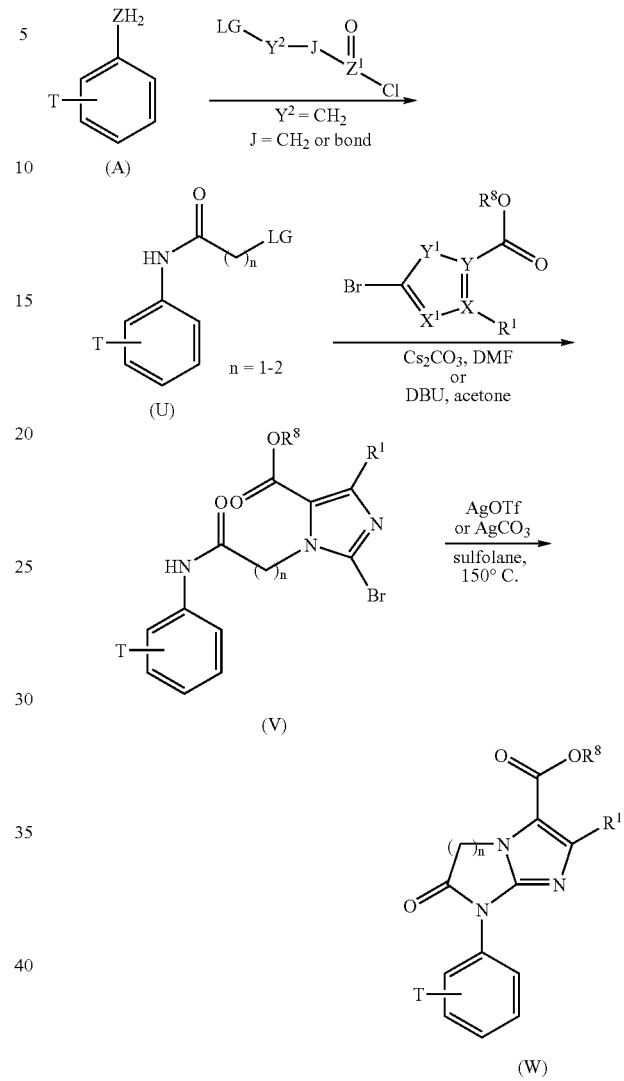
Scheme 6
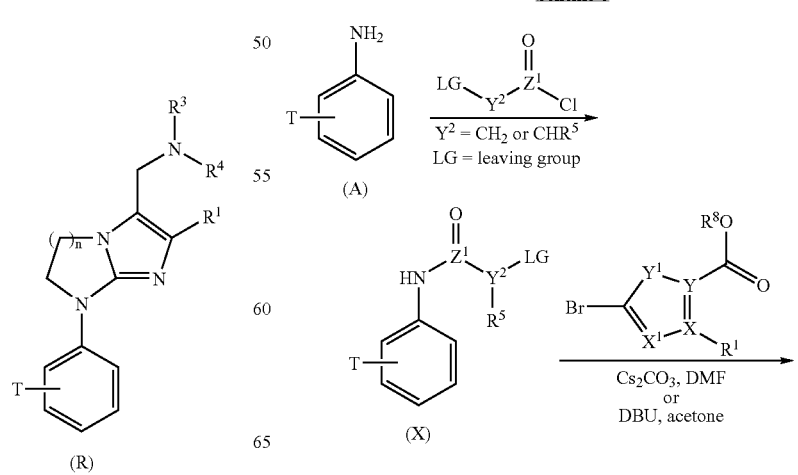

-continued
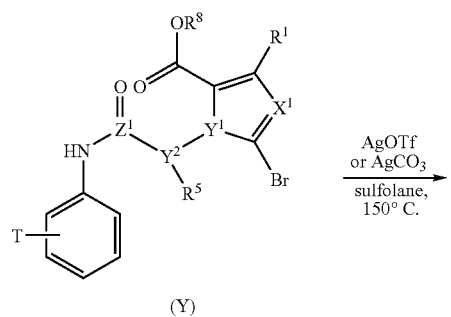
(Y)
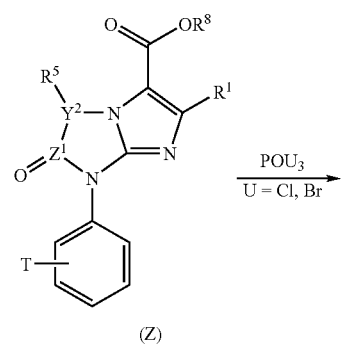
(Z)
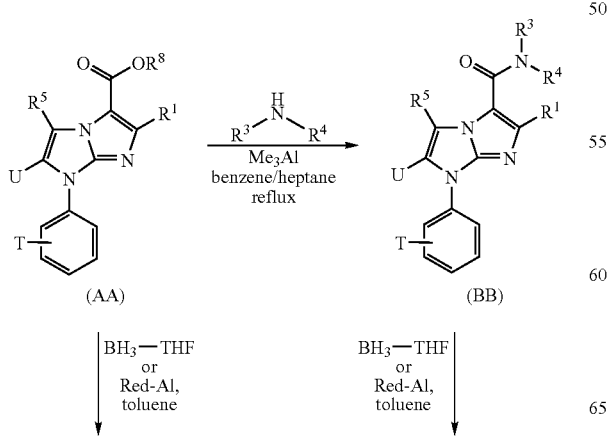
(AA) (BB)
-continued
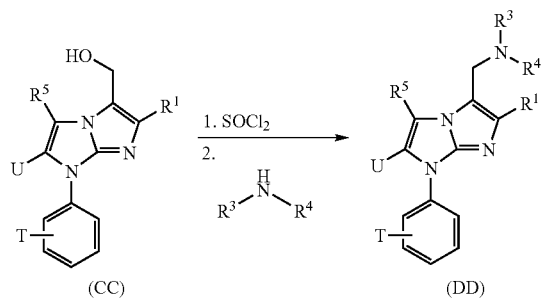
(CC) (DD)
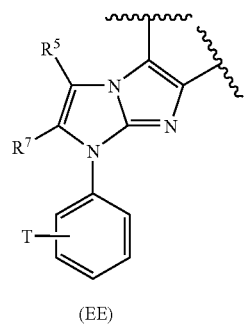
(AA), (BB), (CC), or (DD)
(EE)

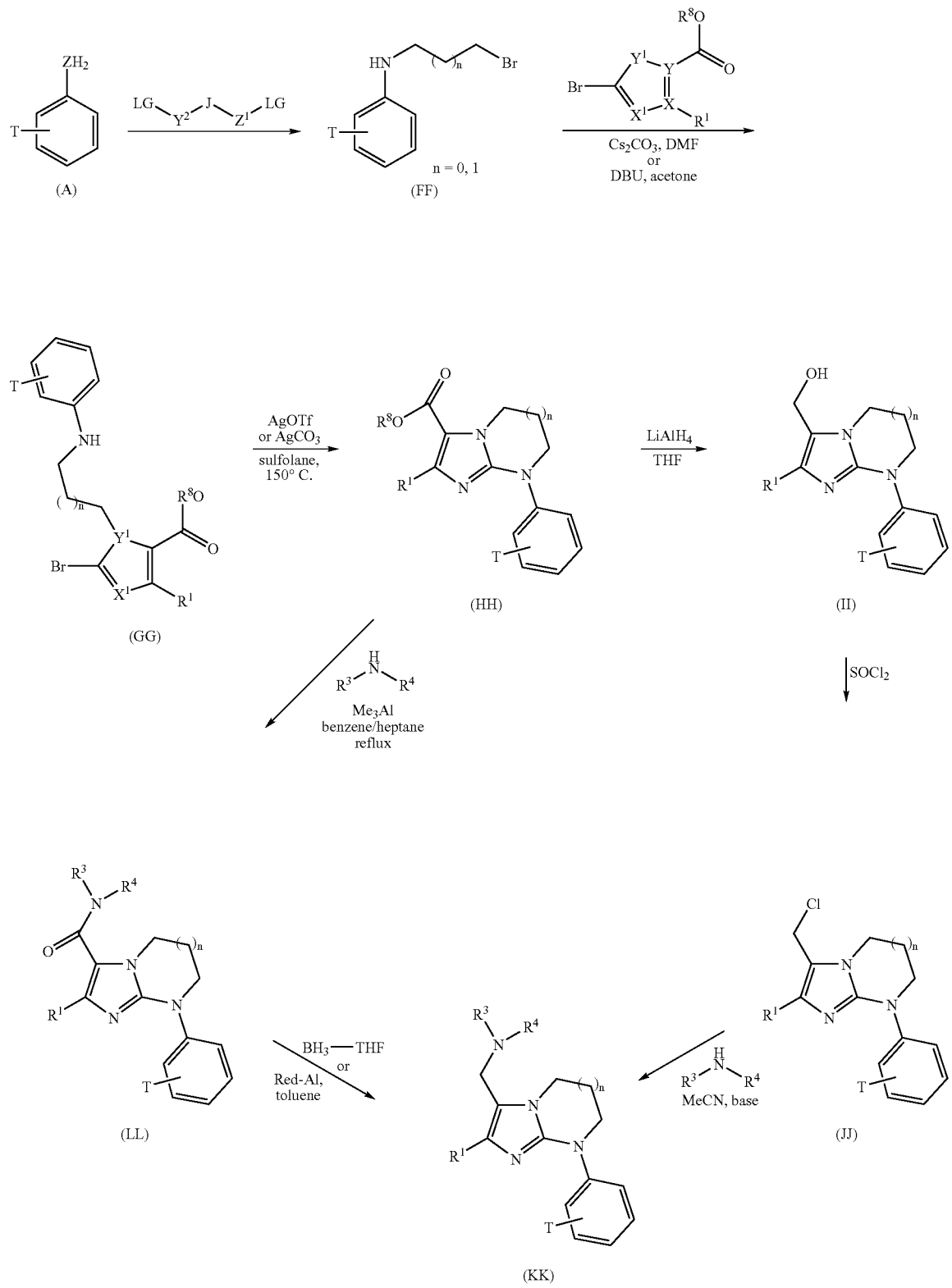

31
Scheme 8
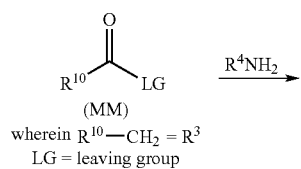
wherein R[10]—CH$_2$ = R[3]
LG = leaving group
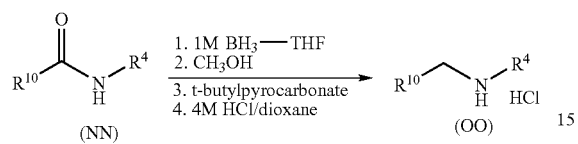
Scheme 9
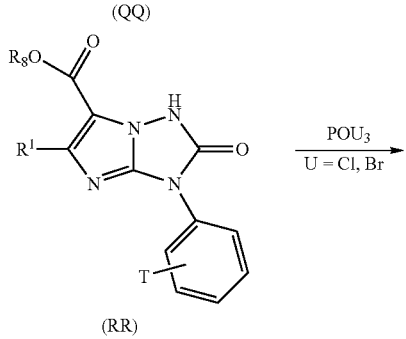
32
-continued
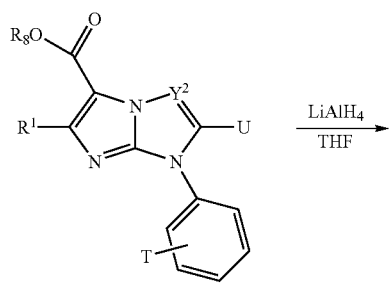
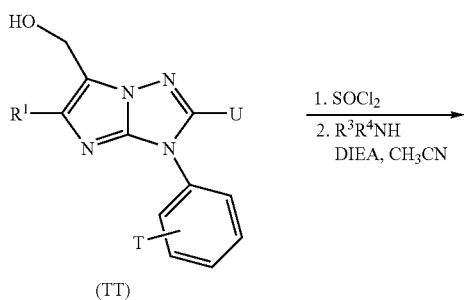
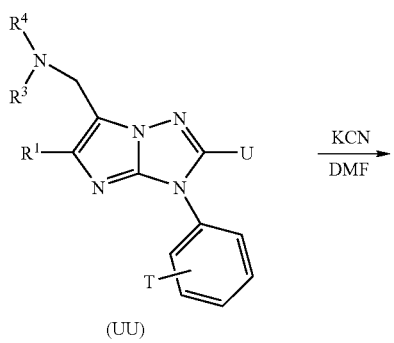
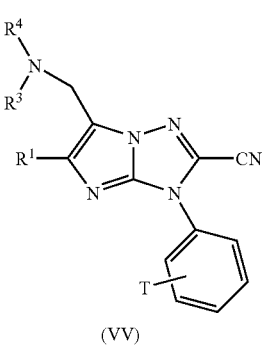
Scheme 10
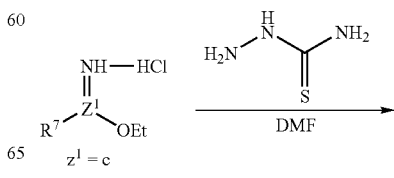
z[1] = c

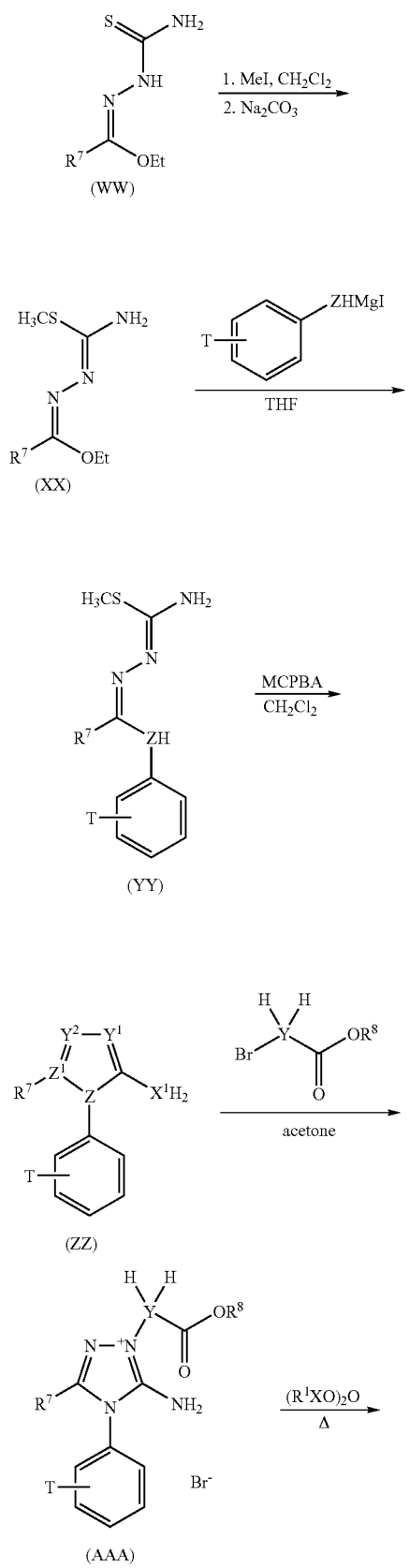
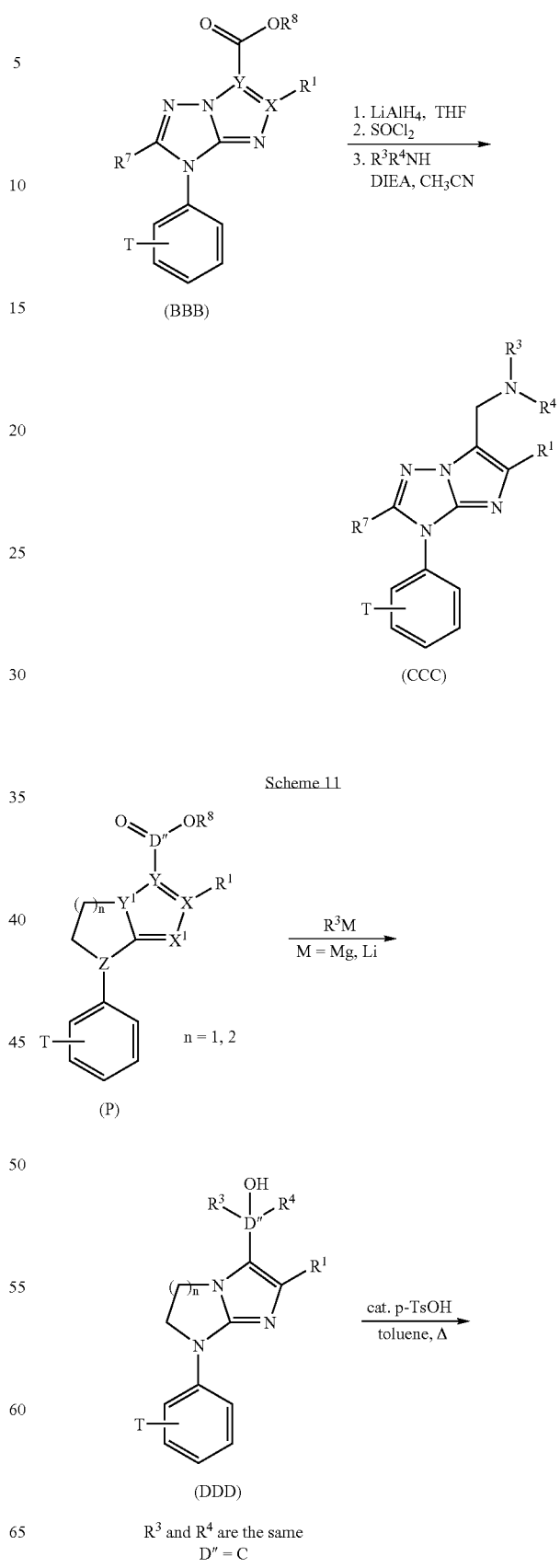

-continued
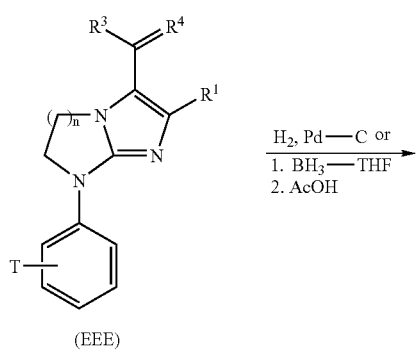
(EEE)
H₂, Pd—C or
1. BH₃—THF
2. AcOH
→
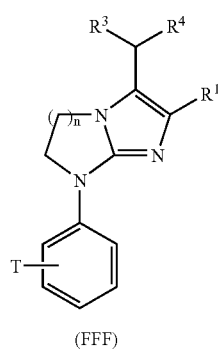
(FFF)
Scheme 12
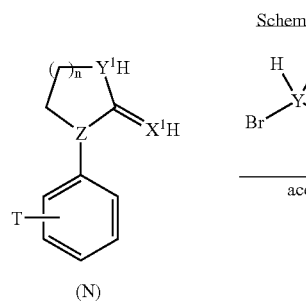
(N)
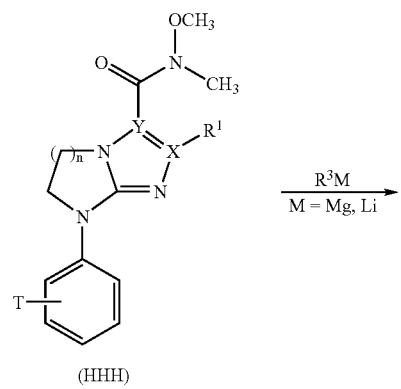
(HHH)
R³M
M = Mg, Li
→
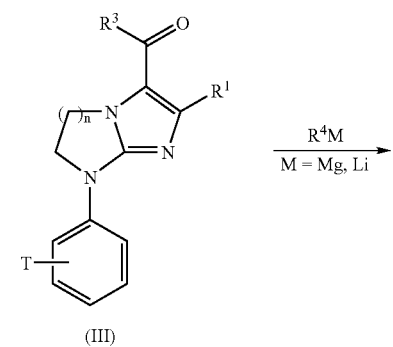
(III)
R⁴M
M = Mg, Li
→
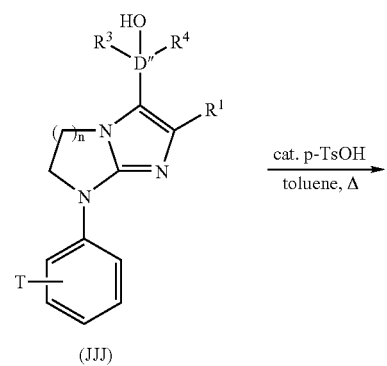
(JJJ)
cat. p-TsOH
toluene, Δ
→
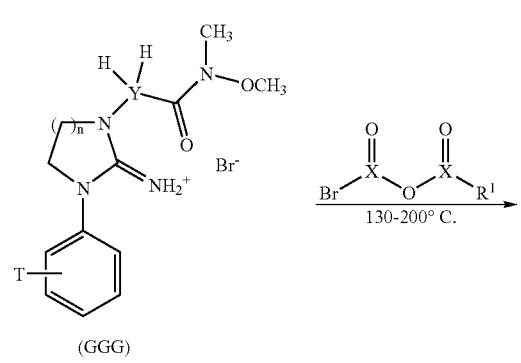
(GGG)
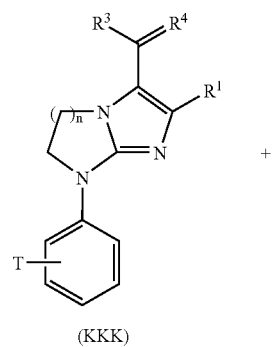
+
(KKK)

-continued

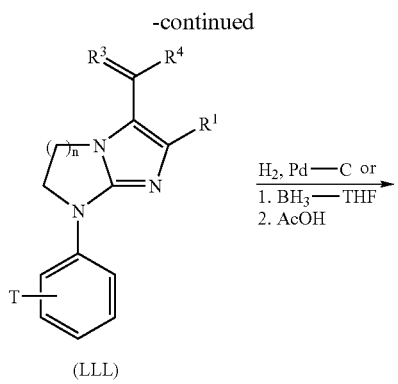

(LLL)

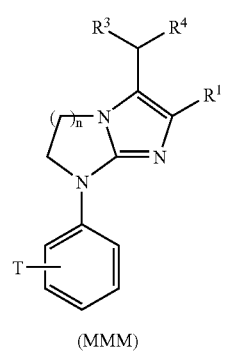

(MMM)

Scheme 13

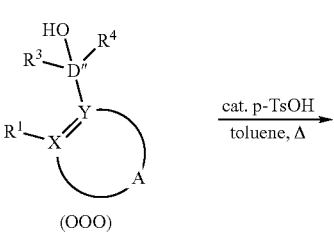

(NNN)

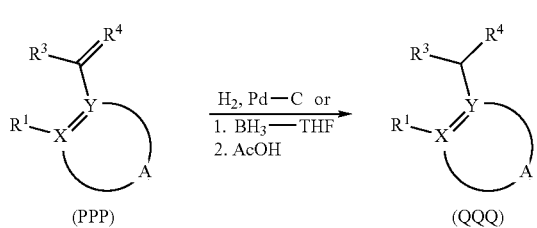

(OOO)

$R^3$ and $R^4$ are the same

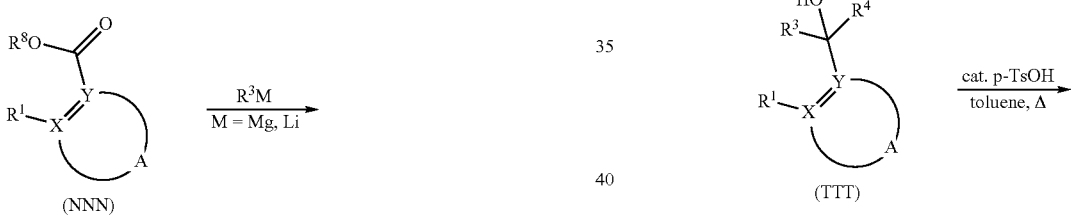

(PPP) (QQQ)

Scheme 14

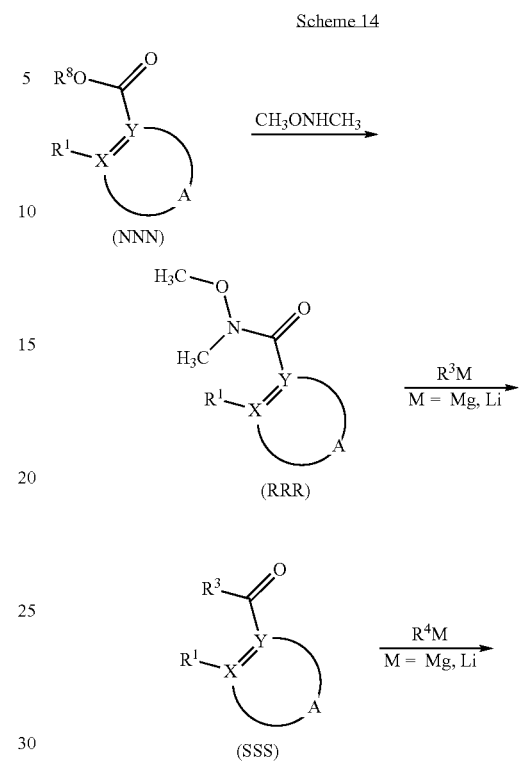

Other suitable means of synthesizing said compounds may also be available. More detailed descriptions of synthesizing compounds of the present invention are also provided as follows:

General. $^1$H and $^{13}$C NMR spectra in CDCl$_3$ were run on a Bruker 500 or 300 MHz instrument and chemical shifts were reported in ppm (δ) with reference to (CH$_3$)$_4$Si. All evaporations were carried out under reduced pressure.

Unless otherwise stated, LC/MS analyses were carried out on a Shimadzu instrument using a YMC C18 column (3×50 mm) employing a 2 min linear gradient of 0% to 100% solvent B in A in a 3 min run. For LC/MS and for Shimadzu Preparative HPLC system, Solvent A-was: 10% methanol/90% water/0.1% trifluoroacetic acid, and solvent B was 90% methanol/10% water/0.1% trifluoroacetic acid with a UV detector set at 220 nm.

The following Intermediates 1-5 may be used to synthesize Examples 1-26.

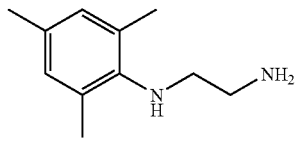

Intermediate 1

$N^1$-(2,4,6-Trimethyl-phenyl)-ethane-1,2-diamine, scheme 3: (M)

To a solution of 2,4,6-trimethylaniline (100. g, 0.740 mol) in anhydrous toluene (600 mL) was added 2-bromoethylamine hydrobromide (75.8 g, 0.370 mol). The flask containing the reaction mixture was fitted with a Dean-Stark trap/reflux condenser assembly. The reaction mixture was heated at reflux temperature for 5 h, during which time the mixture solidified. Upon cooling to room temperature, the solidified mass was treated with water (240 mL), toluene (160 mL), and 50% aqueous KOH (80 mL). The phases were separated, and the aqueous portion was saturated with NaCl and extracted with toluene (2×200 mL). The combined organic portions were washed with brine, dried over anhydrous $Na_2SO_4$, filtered, and concentrated under reduced pressure to remove the solvent. Vacuum distillation (2 mm Hg) afforded 42.4 g of a light yellow liquid, which was 92% pure based on $^1$H NMR. Eight percent of the material was unreacted 2,4,6-trimethylaniline. $^1$H NMR (CDCl$_3$, 300 MHz) δ 6.83 (s, 2H), 3.00-2.96 (m, 2H), 2.92-2.88 (m, 2H), 2.28 (s, 6H), 2.23 (s, 3H), 2.21 (s, 1H), 2.16 (s, 2H). LC/MS: $t_R$=0.87 min., (MH$^+$)=179.19.

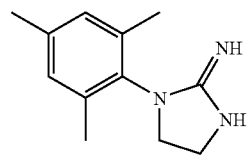

Intermediate 2

1-(2,4,6-Trimethyl-phenyl)4,5-dihydro-1H-imidazol-2-ylamine, scheme 3: (N)[1]

A solution of cyanogen bromide (1.8 g, 18.5 mmol) in anhydrous ethanol (3 mL) was added at 0° C. to a solution of $N^1$-(2,4,6-trimethyl-phenyl)-ethane-1,2-diamine (3.0 g, 16.9 mmol) in anhydrous ethanol (9 mL) under nitrogen. The reaction mixture was warmed up to room temperature for 10 min, then was heated at 155° C. for 40 min with a flow of nitrogen to remove ethanol. Upon cooling to r.t., the resulting solids were transferred to a separatory funnel via dichloromethane (70 mL), and washed sequentially with 1 N sodium hydroxide (2×35 mL), water and brine. The organic layer was dried over anhydrous sodium sulfate and solvents were removed in vacuo to afford the title compound as a pale white solid (3.08 g, 90% yield). The solids were used for the next step without further purification. $^1$H NMR (CDCl$_3$, 300 MHz) δ 6.70 (s, 2H), 3.46 (s, 4H), 2.06 (s, 3H), 1.99 (s, 6H); $^{13}$C NMR (CDCl$_3$, 75 MHz) δ 160.1, 138.2, 137.8, 132.2, 129.5, 48.8, 43.5, 20.8, 17.5. LC/MS: $t_R$=0.99 min., (MH$^+$)= 204.12.

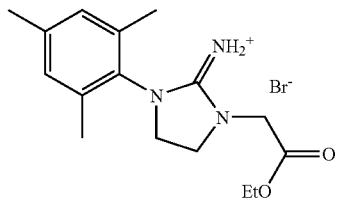

Intermediate 3

3-Ethoxycarbonylmethyl-1-(2,4,6-trimethyl-phenyl)-2-aminoimidazolium bromide, scheme 3: (O)

To a mixture of 1-(2,4,6-trimethyl-phenyl)-imidazolidin-2-ylideneamine (3.00 g, 0.0148 mol) and aluminum tri-tert-butoxide (1.0 g, 0.0041 mol) in dimethylformamide (15 mL) was added ethyl bromoacetate (1.65 mL, 2.48 g, 0.00148 mol). The reaction mixture was allowed to stir at room temperature for 1 h, after which LC-MS indicated a 4:1 ratio of desired product to starting material. The reaction mixture was filtered, and the filtrate was concentrated under reduced pressure to give a pale orange-yellow solid, which was then treated twice with toluene to azeotropically remove any water. The solid was triturated with toluene, collected by filtration, and placed under high vacuum for 6 h. $^1$H NMR (CDCl$_3$, 300 MHz) δ 7.01 (s, 2H), 4.87 (s, 2H), 4.29 (q, J=7 Hz, 2H), 3.96-3.89 (m, 4H), 2.32 (s, 3H), 2.25 (s, 6H), 1.34 (t, J=7 Hz, 3H). LC/MS: $t_R$=0.92 min., (MH$^+$)=290.43.

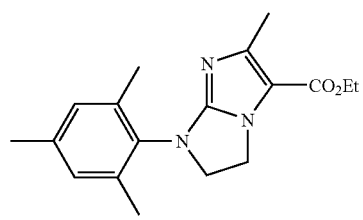

Intermediate 4

2-Methyl-7-(2,4,6-trimethyl-phenyl)-6,7-dihydro-5H-imidazo [1,2-α]imidazole-3-carboxylic acid ethyl ester, (scheme 3: (P)[2]

A mixture of 3-ethoxycarbonylmethyl-1-(2,4,6-trimethylphenyl)-2-aminoimidazolium bromide (1.0 g, 2.7 mmol), sodium acetate (0.55 g, 6.75 mmol) and acetic anhydride (5.0 mL) was heated at 160° C. for 12 hr. Upon cooling, the mixture was poured into a flask containing ice. While stirring, excess sodium bicarbonate was added to the above mixture in small portions, and the resulting mixture was stirred at room temperature for 6 hr. Then, the mixture was extracted with dichloromethane (2×40 mL). The organic extracts were washed with water and dried over anhydrous sodium sulfate. Solvents were removed in vacuo and the residue was subjected to chromatography using ethyl acetate/hexanes (1:4) as eluent to afford the title compound as a light yellow oil which solidified upon cooling (0.344 g, 41% yield). $^1$H NMR (CDCl$_3$, 300 MHz) δ 6.89 (s, 2H), 4.32 (q, J=7.1 Hz, 2H), 4.36-4.26 (m, 2H), 4.15-4.08 (m, 2H), 2.39 (s, 3H), 2.26 (s, 3H), 2.20 (s, 6H), 1.35 (t, J=7.1 Hz, 3H). Mass spec.: 314.15 (MH$^+$).

Intermediate 5

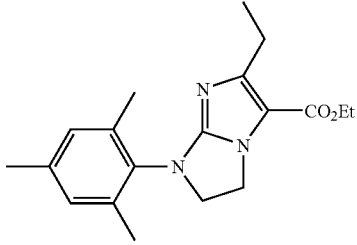

2-Ethyl-7-(2,4,6-trimethyl-phenyl)-6,7-dihydro-5H-imidazo[1,2-α]imidazole-3-carboxylic acid ethyl ester, scheme 3: (P)

Prepared as described for the example above. $^1$H NMR (CDCl$_3$, 300 MHz) δ 6.90 (s, 2H), 4.36 (t, J=8.4 Hz, 2H), 4.30 (q, J=7.2 Hz, 2H), 4.14 (t, J=8.4 Hz, 2H), 2.81 (q, J=7.4 Hz, 2H), 2.26 (s, 3H), 2.21 (s, 6H), 1.36 (t, J=7.1 Hz, 3H), 1.11 (t, J=7.5 Hz, 3H). LC/MS: $t_R$=1.35 min., (MH$^+$)= 328.19.

EXAMPLE 1

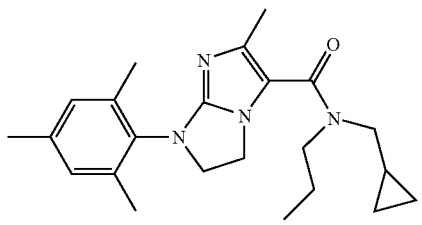

2-Methyl-7-(2,4,6-trimethyl-phenyl)-6,7-dihydro-5H-imidazo[1,2-α]imidazole-3-carboxylic acid cyclopropylmethyl-propyl-amide, scheme 3: (Q)

A solution of trimethyl aluminum (2.0 M in heptane, 2.2 mL, 4.4 mmol) was added to a solution of N-cyclopropylmethyl-N-propylamine (0.63 mL, 4.4 mmol) in benzene (3 mL) at 0° C. The mixture was warmed up to room temperature and stirred at this temperature for 1.5 h, and then added to a stirred solution of 2-methyl-7-(2,4,6-trimethyl-phenyl)-6,7-dihydro-5H-imidazo[1,2-α]imidazole-3-carboxylic acid ethyl ester (0.172 g, 0.55 mmol) in benzene (8.0 mL). The mixture was refluxed for 12 h. Upon cooling at 0° C., 1 N sodium hydroxide (25 mL) was added dropwise to the above mixture. The mixture was extracted with dicholoromethane (40 mL), and the organic layer was dried over anhydrous sodium sulfate. Solvents were removed in vacuo and the residue was subjected to chromatography using ethyl acetate/hexanes (1:1) as eluent to afford the title compound as a light yellow oil which solidified upon cooling (0.209 g, 100% yield). $^1$H NMR (CDCl$_3$, 300 MHz) δ; $^{13}$C NMR (CDCl$_3$, 75 MHz) δ 163.1, 156.0, 141.0, 136.5, 136.1, 132.7, 128.7, 115.8, 52.6, 50.3, 47.1, 42.1, 20.1, 19.9, 17.3, 14.6, 10.3, 9.2, 2.8. Mass spec.: 381.26 (MH$^+$).

EXAMPLE 2

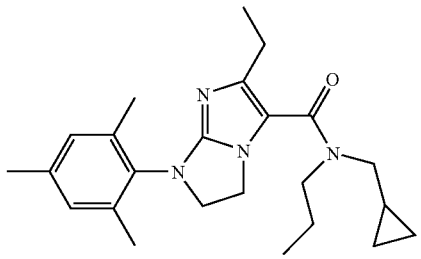

2-Ethyl-7-(2,4,6-trimethyl-phenyl)-6,7-dihydro-5H-imidazo[1,2-α]imidazole-3-carboxylic acid cyclopropylmethyl-propyl-amide, scheme 3: (Q)

Prepared as described for the example above. $^1$H NMR (CDCl$_3$, 300 MHz) δ 6.83 (s, 2H), 4.12-4.01 (m, 4H), 3.56 (t, J=7.1 Hz, 2H), 3.35 (d, J=6.8 Hz, 2H), 2.42 (q, J=7.5 Hz, 2H), 2.21 (s, 3H), 2.17 (s, 6H), 1.59 (quintet, J=7.2 Hz, 2H), 1.11 (t, J=7.5 Hz, 3H), 0.99-0.95 (m, 1H), 0.86 (t, J=7.3 Hz, 3H), 0.51-0.48 (m, 2H), 0.17-0.13 (m, 2H); $^{13}$C NMR (CDCl$_3$, 75 MHz) δ 164.1, 156.9, 147.6, 137.3, 136.9, 133.9, 129.6, 115.6, 53.6, 51.2, 48.1, 42.9, 22.6, 21.0, 20.9, 18.2, 13.7, 11.3, 10.0, 3.75. LC/MS: $t_R$=1.36 min., (MH$^+$)= 395.27.

EXAMPLE 3

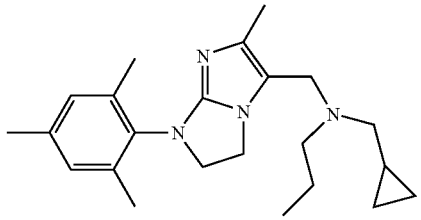

Cyclopropylmethyl-[2-methyl-7-(2,4,6-trimethyl-phenyl)-6,7-dihydro-5H-imidazo[1,2-α]imidazol-3-ylmethyl]-propyl-amine, scheme 3: (R)

A solution of Red-Al (3.3 M in toluene, 0.70 mL, 2.33 mmol) was added dropwise to a solution of 2-ethyl-7-(2,4,6-trimethyl-phenyl)-6,7-dihydro-5H-imidazo[1,2-α]imidazole-3-carboxylic acid cyclopropylmethyl-propyl-amide (0.177 g, 0.46 mmol) in toluene (3 mL) at 0° C. After stirring at room temperature for 24 h, the reaction mixture was cooled to 0° C. and I N sodium hydroxide (10 mL) was added dropwise. The above mixture was extracted with dichloromethane (40 mL), and the organic extracts were washed with water and dried over anhydrous sodium sulfate. Solvents were removed in vacuo to afford the title compound as a light yellow oil which solidified upon cooling (109 mg, 65% yield). The purity of the product was determined to be 91% by LC/MS. $^1$H NMR (CDCl$_3$, 300 MHz) δ 6.85 (s, 2H), 4.09-3.96 (m, 4H), 3.45 (s, 2H), 2.44 (t, J=7.1 Hz, 2H), 2.29 (d, J=6.5 Hz, 2H), 2.23 (s, 3H), 2.19 (s, 6H), 2.04 (s, 3H), 1.46 (quintet, J=7.3 Hz, 2H), 1.28-1.25 (m, 1H), 0.87 (t, J=7.2 Hz, 3H), 0.49-0.46 (m, 2H), 0.09-0.06 (m, 2H); $^{13}$C NMR (CDCl$_3$, 75 MHz) δ 155.4, 137.1, 136.9, 136.0, 135.0, 129.7, 117.7, 58.5, 55.5, 53.8, 48.0, 42.4, 20.9, 20.3, 18.2, 13.3, 12.0, 8.9, 4.0. Mass spec.: 367.24 (MH$^+$).

EXAMPLE 4

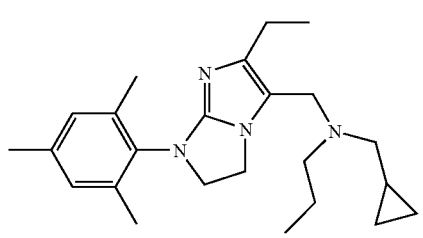

Cyclopropylmethyl-[2-ethyl-7-(2,4,6-trimethyl-phenyl)-6,7-dihydro-5H-imidazo[1,2-α]imidazol-3-ylmethyl]-propyl-amine, scheme 3: (R)

Prepared as described for the example above. $^1$H NMR (CDCl$_3$, 300 MHz) δ 6.86 (s, 2H), 4.13-3.97 (m, 4H), 3.47 (s, 2H), 2.45 (t, J=7.2 Hz, 2H), 2.39 (q, J=7.6 Hz, 2H), 2.31 (d, J=6.5 Hz, 2H), 2.24 (s, 3H), 2.19 (s, 6H), 1.48-1.42 (m, 2H), 1.32-1.26 (m, 1H), 1.06 (t, J=7.4 Hz, 3H), 0.87 (t, J=7.2 Hz, 3H), 0.50-0.46 (m, 2H), 0.09-0.07 (m, 2H). Mass spec.: 381.28 (MH$^+$).

EXAMPLE 5

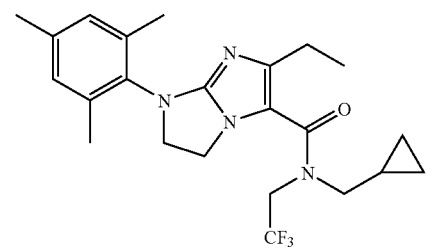

2-Ethyl-7-(2,4,6-trimethyl-phenyl)-6,7-dihydro-5H-imidazo[1,2-a]imidazole-3-carboxylic acid cyclopropylmethyl-(2,2,2-trifluoro-ethyl)-amide, scheme 3: (Q)

Prepared as described for the example above. LC/MS: $t_R$=1.51 min., (MH$^+$)=435.36.

EXAMPLE 6

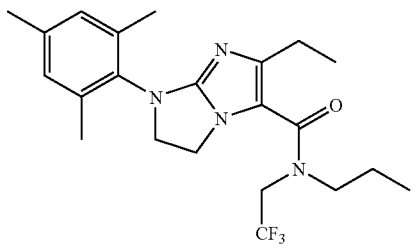

2-Ethyl-7-(2,4,6-trimethyl-phenyl)-6,7-dihydro-5H-imidazo[1,2-a]imidazole-3-carboxylic acid propyl-(2,2,2-trifluoro-ethyl)-amide, scheme 3: (Q)

Prepared as described for the example above. LC/MS: $t_R$=1.25 min., (MH$^+$)=423.37.

EXAMPLE 7

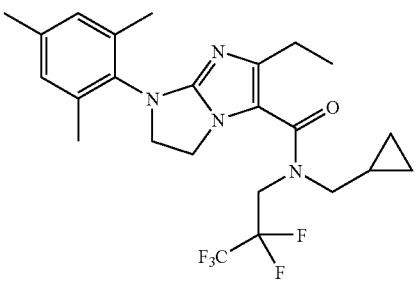

2-Ethyl-7-(2,4,6-trimethyl-phenyl)-6,7-dihydro-5H-imidazo[1,2-a]imidazole-3-carboxylic acid cyclopropylmethyl-(3,3,3,2,2-pentafluoro-propyl)-amide, scheme 3: (Q)

Prepared as described for the example above. LC/MS: $t_R$=1.43 min., (MH$^+$)=485.35.

EXAMPLE 8

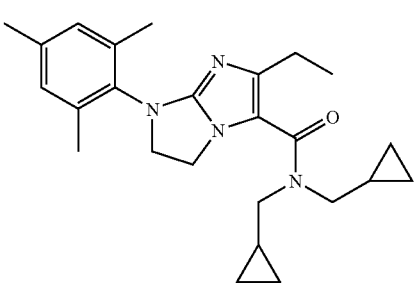

2-Ethyl-7-(2,4,6-trimethyl-phenyl)-6,7-dihydro-5H-imidazo[1,2-a]imidazole-3-carboxylic acid cyclopropylmethyl-(cyclopropylmethyl)-amide, scheme 3: (Q)

Prepared as described for the example above. LC/MS: $t_R$=1.28 min., (MH$^+$)=407.42.

EXAMPLE 9

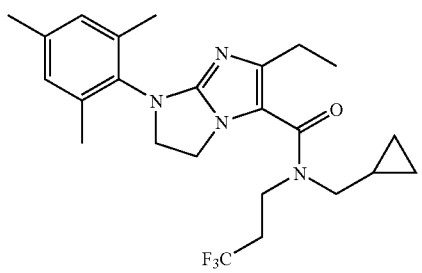

2-Ethyl-7-(2,4,6-trimethyl-phenyl)-6,7-dihydro-5H-imidazo[1,2-a]imidazole-3-carboxylic acid cyclopropylmethyl-(3,3,3-trifluoro-propyl)-amide, scheme 3: (Q)

Prepared as described for the example above. LC/MS: $t_R$=1.28 min., (MH$^+$)=449.37.

EXAMPLE 10

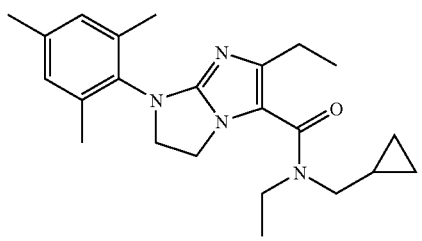

2-Ethyl-7-(2,4,6-trimethyl-phenyl)-6,7-dihydro-5H-imidazo[1,2-a]imidazole-3-carboxylic acid cyclopropylmethyl-(ethyl)-amide, scheme 3: (Q)

Prepared as described for the example above. LC/MS: $t_R$=1.41 min., (MH$^+$)=381.36.

EXAMPLE 11

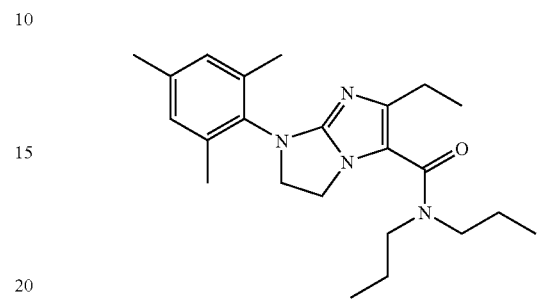

2-Ethyl-7-(2,4,6-trimethyl-phenyl)-6,7-dihydro-5H-imidazo[1,2-a]imidazole-3-carboxylic acid dipropyl-amide, scheme 3: (Q)

Prepared as described for the example above. LC/MS: $t_R$=1.26 min., (MH$^+$)=383.41.

EXAMPLE 12

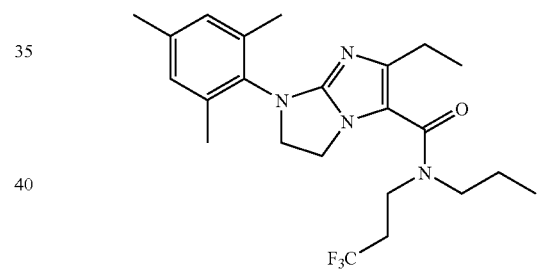

2-Ethyl-7-(2,4,6-trimethyl-phenyl)-6,7-dihydro-5H-imidazo[1,2-a]imidazole-3-carboxylic acid propyl-(3,3,3-trifluoropropyl)-amide, scheme 3: (Q)

Prepared as described for the example above. LC/MS: $t_R$=1.28 min., (MH$^+$)=437.33.

EXAMPLE 13

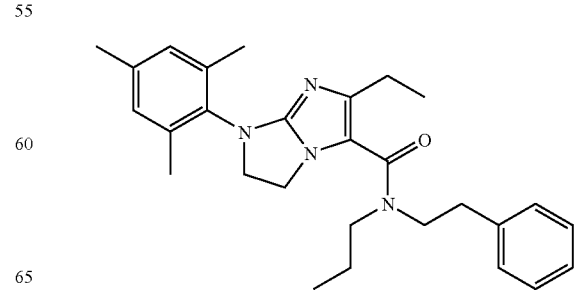

2-Ethyl-7-(2,4,6-trimethyl-phenyl)-6,7-dihydro-5H-imidazo[1,2-a]imidazole-3-carboxylic acid phenethyl-propyl-amide, scheme 3: (Q)

Prepared as described for the example above. LC/MS: $t_R$=1.45 min., (MH$^+$)=445.37.

EXAMPLE 14

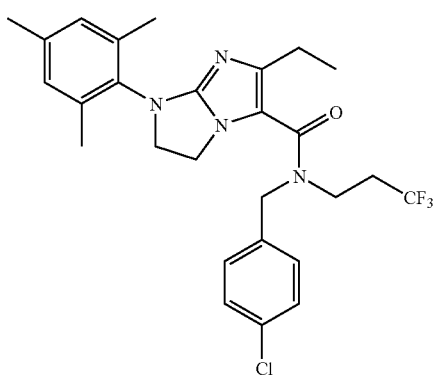

2-Ethyl-7-(2,4,6-trimethyl-phenyl)-6,7-dihydro-5H-imidazo[1,2-a]imidazole-3-carboxylic acid (4-chloro-benzyl)-(3,3,3-trifluoro-propyl)-amide, scheme 3: (Q)

Prepared as described for the example above. LC/MS: $t_R$=1.48 min., (MH$^+$)=519.35.

EXAMPLE 15

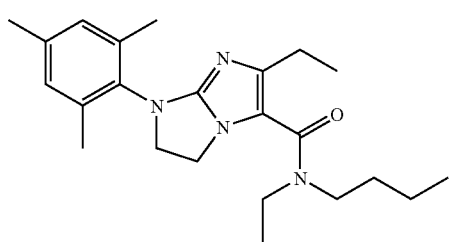

2-Ethyl-7-(2,4,6-trimethyl-phenyl)-6,7-dihydro-5H-imidazo[1,2-a]imidazole-3-carboxylic acid butyl-ethyl-amide, scheme 3: (Q)

Prepared as described for the example above, except that N-ethylbutylamine was used rather than its HCl salt. LC/MS: $t_R$=1.41 min., (MH$^+$)=383.37.

EXAMPLE 16

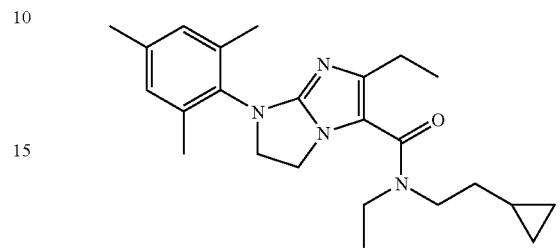

2-Ethyl-7-(2,4,6-trimethyl-phenyl)-6,7-dihydro-5H-imidazo[1,2-a]imidazole-3-carboxylic acid (2-cyclopropyl-ethyl)-ethyl-amide, scheme 3: (Q)

Prepared as described for the example above. LC/MS: $t_R$=1.38 min., (MH$^+$)=395.45.

EXAMPLE 17

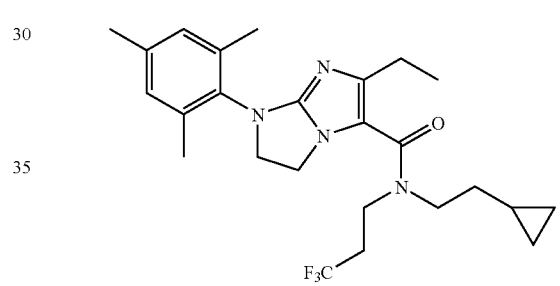

2-Ethyl-7-(2,4,6-trimethyl-phenyl)-6,7-dihydro-5H-imidazo[1,2-a]imidazole-3-carboxylic acid (2-cyclopropyl-ethyl)-(3,3,3-trifluoro-propyl)-amide, scheme 3: (Q)

Prepared as described for the example above. LC/MS: $t_R$=1.33 min., (MH$^+$)=395.45.

EXAMPLE 18

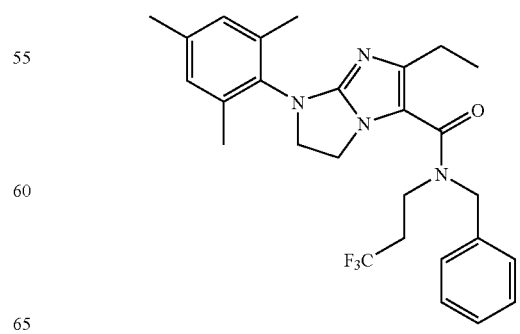

2-Ethyl-7-(2,4,6-trimethyl-phenyl)-6,7-dihydro-5H-imidazo[1,2-a]imidazole-3-carboxylic acid benzyl-(3,3,3-trifluoro-propyl)-amide, scheme 3: (Q)

Prepared as described for the example above. LC/MS: $t_R$=1.51 min., (MH$^+$)=485.39.

EXAMPLE 19

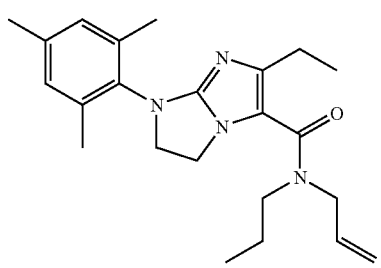

2-Ethyl-7-(2,4,6-trimethyl-phenyl)-6,7-dihydro-5H-imidazo[1,2-a]imidazole-3-carboxylic acid allyl-propyl-amide, scheme 3: (Q)

Prepared as described for the example above. LC/MS: $t_R$=1.31 min., (MH$^+$)=381.36.

EXAMPLE 20

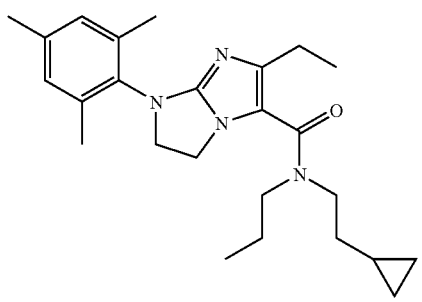

2-Ethyl-7-(2,4,6-trimethyl-phenyl)-6,7-dihydro-5H-imidazo[1,2-a]imidazole-3-carboxylic acid (2-cyclopropyl-ethyl)-propyl-amide, scheme 3: (Q)

Prepared as described for the example above. LC/MS: $t_R$=1.33 min., (MH$^+$)=409.43.

EXAMPLE 21

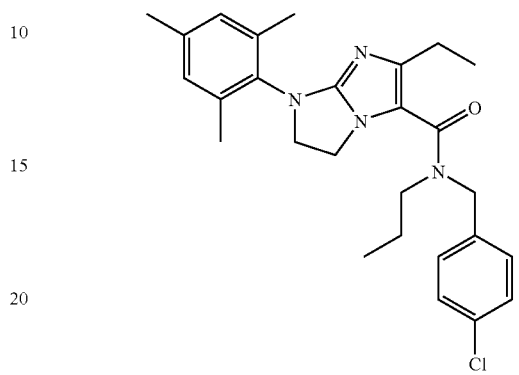

2-Ethyl-7-(2,4,6-trimethyl-phenyl)-6,7-dihydro-5H-imidazo[1,2-a]imidazole-3-carboxylic acid (4-chloro-benzyl)-propyl-amide, scheme 3: (Q)

Prepared as described for the example above. LC/MS: $t_R$=1.40 min., (MH$^+$)=465.35.

EXAMPLE 22

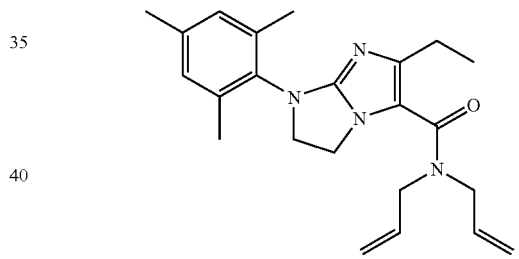

2-Ethyl-7-(2,4,6-trimethyl-phenyl)-6,7-dihydro-5H-imidazo[1,2-a]imidazole-3-carboxylic acid diallylamide, scheme 3: (Q)

Prepared as described for the example above. LC/MS: $t_R$=1.39 min., (MH$^+$)=379.40.

EXAMPLE 23

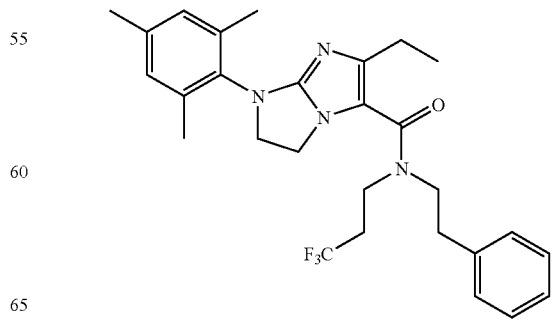

2-Ethyl-7-(2,4,6-trimethyl-phenyl)-6,7-dihydro-5H-imidazo[1,2-a]imidazole-3-carboxylic acid phenethyl-(3,3,3-trifluoro-propyl)-amide, scheme 3: (Q)

Prepared as described for the example above. LC/MS: $t_R$=1.39 min., (MH$^+$)=499.38.

EXAMPLE 24

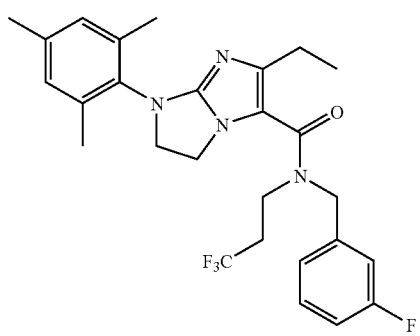

2-Ethyl-7-(2,4,6-trimethyl-phenyl)-6,7-dihydro-5H-imidazo[1,2-a]imidazole-3-carboxylic acid (3-fluoro-benzyl)-(3,3,3-trifluoro-propyl)-amide, scheme 3: (Q)

Prepared as described for the example above. LC/MS: $t_R$=1.50 min., (MH$^+$)=503.17.

EXAMPLE 25

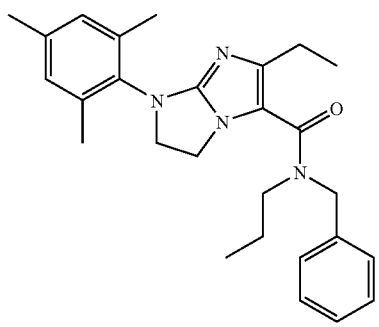

2-Ethyl-7-(2,4,6-trimethyl-phenyl)-6,7-dihydro-5H-imidazo[1,2-a]imidazole-3-carboxylic acid benzyl-propyl-amide, scheme 3: (Q)

Prepared as described for the example above. LC/MS: $t_R$=1.41 min., (MH$^+$)=431.34.

EXAMPLE 26

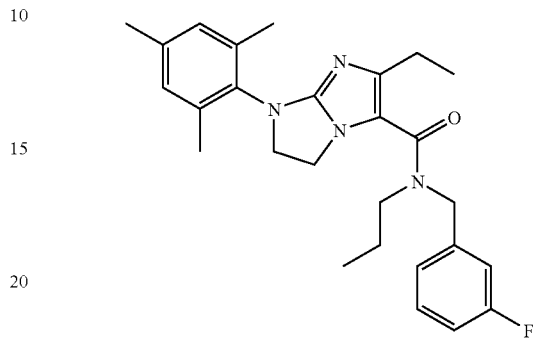

2-Ethyl-7-(2,4,6-trimethyl-phenyl)-6,7-dihydro-5H-imidazo[1,2-a]imidazole-3-carboxylic acid (3-fluoro-benzyl)-propyl-amide, scheme 3: (Q)

Prepared as described for the example above. LC/MS: $t_R$=1.38 min., (MH$^+$)=449.35.

The following Intermediates 6-10 may be used to synthesize Examples 27-29.

Intermediate 6

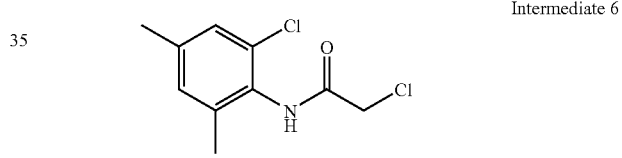

2-Chloro-N-(2-chloro-4,6-dimethyl-phenyl)-acetamide, scheme 3: (K)

To a solution of 2-chloro-4,6-dimethylaniline (0.300 g, 0.00193 mol) in dichloroethane (6 mL) was added chloroacetic anhydride (0.460 g, 0.0027 mol). The reaction was allowed to stir at room temperature for 1 h and was then quenched with saturated aqueous NaHCO$_3$ and allowed to stir for another 15 min. The reaction mixture was extracted with ethyl acetate (2×15 mL), and the combined organic portions were washed sequentially with saturated aqueous NaHCO$_3$ and brine. After drying over anhydrous Na$_2$SO$_4$, the organic portion was concentrated under reduced pressure to give 0.40 g (0.0017 mol, 90%) of white solid. $^1$H NMR (CDCl$_3$, 300 MHz) δ 7.94 (br s, 1H), 7.12 (s, 1H), 6.98 (s, 1H), 4.25 (s, 2H), 2.3 (s, 3H), 2.24 (s, 3H). LC/MS: $t_R$=1.22 min., (MH$^+$)=232.02.

Intermediate 7

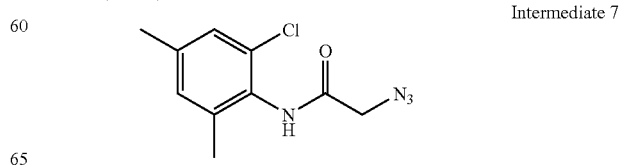

2-Azido-N-(2-chloro-4,6-dimethyl-phenyl)-acetamide, scheme 3: (L)

A mixture of 2-Chloro-N-(2-chloro-4,6-dimethyl-phenyl)-acetamide (0.100 g, 0.00043 mol), potassium iodide (0.0072 g, 0.00043 mol), sodium azide (0.056 g, 0.00086 mol), and anhydrous dimethylformamide (7 mL) was heated in a 50° C. oil bath for 4 h. Upon cooling to room temperature, the reaction mixture was cooled to 0° C., water (10 mL) was added, and the solid product was collected by suction filtration, washed several times with water, and placed in a vacuum oven set at low heat for 4 h. The dried product amounted to 0.0934 g (0.391 mmol, 91%). $^1$H NMR (CDCl$_3$, 300 MHz) δ 7.70 (br s 1H), 7.12 (s, 1H), 6.98 (s, 1H), 4.2 (s, 2H), 2.3 (s, 3H), 2.23 (s, 3H). LC/MS: $t_R$=1.23 min., (MH$^+$)=239.06.

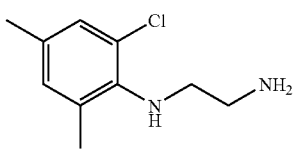

Intermediate 8

N$^1$-(2-chloro-4,6-dimethyl-phenyl)-ethane-1,2-diamine, scheme 3: (M)

2-Azido-N-(2-chloro-4,6-dimethyl-phenyl)-acetamide (0.210 g, 0.00126 mol) was dissolved in cold 1.0 M BH$_3$-tetrahydrofuran (7.6 mL), and the reaction mixture was allowed to stand for approximately 15 min. and was then heated at reflux temperature for 14 h. Upon cooling to room temperature, the reaction was quenched with excess methanol, and the solvents were removed in vacuo. The residue was dissolved in 10 mL 1:1 methanol: 10% aqueous HCl and heated at reflux temperature for 3 h. Upon cooling to room temperature, the reaction solution was basified with 2 N aqueous NaOH and extracted with ethyl acetate (3×20 mL). The combined organic portions were washed with water and brine, dried over anhydrous Na$_2$SO$_4$, and concentrated under reduced pressure to give 0.220 g (0.00111 mol, 88%) of pale yellow liquid. $^1$H-NMR δ (CDCl$_3$, 300 MHz) 2.22 (s, 3H), 2.29 (s, 3H), 2.86 (t, 2H), 3.06 (t, 2H), 6.84 (d, 1H), 6.99 (d, 1H), LC/MS: $t_R$=1.90 min., (MH$^+$)=199.08.

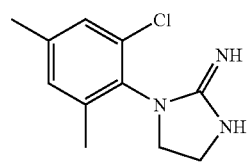

Intermediate 9

1-(2-chloro-4,6-dimethyl-phenyl)-imidazolidin-2-ylideneamine, scheme 3: (N)

Prepared as described for 1-(2,4,6-trimethyl-phenyl)-imidazolidin-2-ylideneamine. $^1$H-NMR δ (CDCl$_3$, 300 MHz) 2.22 (s, 3H), 2.26 (s, 3H), 3.63 (m, 1H), 3.73 (m, 2H), 3.86 (m, 1H), 6.07 (br, 2H), 6.96 (s, 1H), 7.08 (s, 1H). LC/MS: $t_R$=0.87 min., (MH$^+$)=224.15.

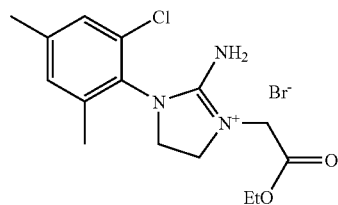

Intermediate 10

3-Ethoxycarbonylmethyl-1-(2-chloro-4,6-dimethyl-phenyl)-2-aminoimidazolium bromide, scheme 3: (O)

Prepared as described for 3-ethoxycarbonylmethyl-1-(2,4,6-trimethyl-phenyl)-2-aminoimidazolium bromide. LC/MS: $t_R$=0.98 min., (MH$^+$)=310.17.

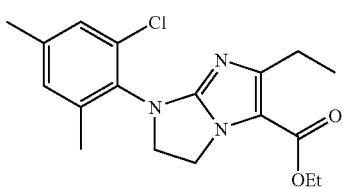

Intermediate 11

7-(2-chloro-4,6-dimethyl-phenyl)-2-ethyl-6,7-dihydro-5H-imidazo[1,2-a]imidazole-3-carboxylic acid ethyl ester, scheme 3: (P)

Prepared as described for 2-ethyl-7-(2,4,6-trimethylphenyl)-6,7-dihydro-5H-imidazo[1,2-a]imidazole-3-carboxylic acid ethyl ester. LC/MS: $t_R$=1.33 min., (MH$^+$)=348.17.

EXAMPLE 27

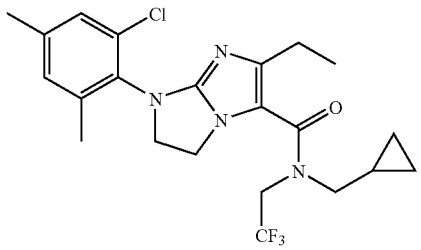

7-(2-chloro-4,6-dimethyl-phenyl)-2-ethyl-6,7-dihydro-5H-imidazo[1,2-a]imidazole-3-carboxylic acid cyclopropylmethyl-(2,2,2-trifluoro-ethyl)-amide, scheme 3: (Q)

Prepared as described for 2-ethyl-7-(2,4,6-trimethyl-phenyl)-6,7-dihydro-5H-imidazo[1,2-a]imidazole-3-carboxylic acid cyclopropylmethyl-(2,2,2-trifluoro-ethyl)-amide. LC/MS: $t_R$=1.36 min., (MH$^+$)=455.19.

EXAMPLE 28

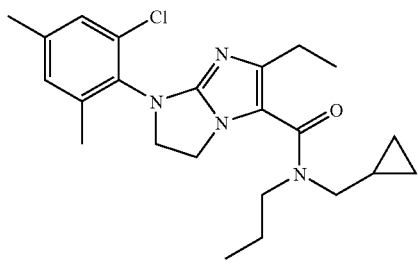

7-(2-chloro-4,6-dimethyl-phenyl)-2-ethyl-6,7-dihydro-5H-imidazo[1,2-a]imidazole-3-carboxylic acid cyclopropylmethyl-propyl-amide, scheme 3: (Q)

Prepared as described for the example above. LC/MS: $t_R$=1.41 min., (MH$^+$)=415.24.

EXAMPLE 29

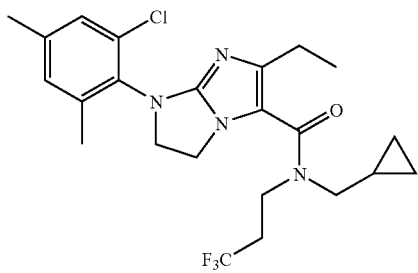

7-(2-Chloro-4,6-dimethyl-phenyl)-2-ethyl-6,7-dihydro-5H-imidazo[1,2a]imidazole-3-carboxylic acid cyclopropylmethyl-(3,3,3-trifluoro-propyl)-amide, scheme 3: (Q)

Prepared as described for the example above. LC/MS: $t_R$=1.38 min., (MH$^+$)=469.20.

The following Intermediates 12-17 may be used to synthesize Examples 30-33.

Intermediate 12

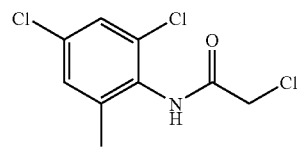

2-Chloro-N-(2,4-dichloro-6-methyl-phenyl)-acetamide, scheme 3: (K)

Prepared as described for 2-chloro-N-(2-chloro-4,6-dimethyl-phenyl)-acetamide. Mass spec.: 253.94 (MH$^+$).

Intermediate 13

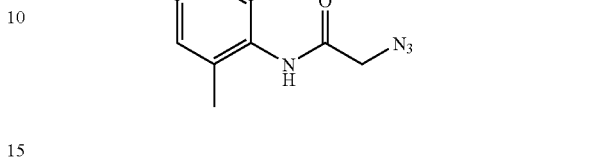

2-Azido-N-(2,4-dichloro-6-methyl-phenyl)-acetamide, scheme 3: (L)

Prepared as described for 2-azido-N-(2-chloro-4,6-dimethyl-phenyl)-acetamide.

Intermediate 14

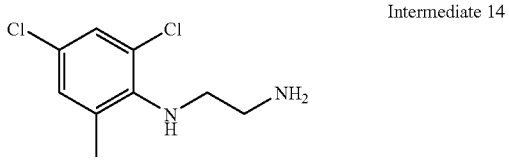

N$^1$-(2,4-Dichloro-6-methyl-phenyl)-ethane-1,2-diamine, scheme 3: (M)

Prepared as described for N$^1$-(2-chloro-4,6-dimethyl-phenyl)-ethane-1,2-diamine. $^1$H-NMR δ (CDCl$_3$, 300 MHz) 2.28 (s, 3H), 2.84 (t, 2H), 3.07 (t, 2H), 6.98 (d, 1H), 7.15 (d, 1H); Mass spec.: 219.04 (MH$^+$).

Intermediate 15

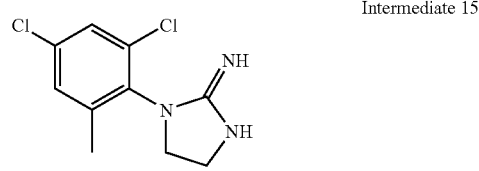

1-(2,4-Dichloro-6-methyl-phenyl)-imidazolidin-2-ylideneamine, scheme 3: (N)

Prepared as described for 1-(2-chloro-4,6-dimethyl-phenyl)-imidazolidin-2-ylideneamine. Mass spec.: 244.03 (MH$^+$).

Intermediate 16

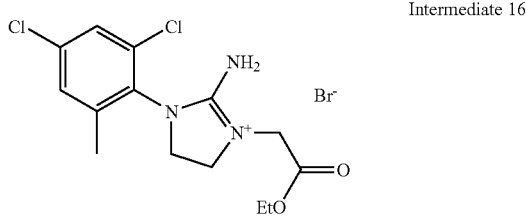

3-Ethoxycarbonylmethyl-1-(2,4-chloro-6-methyl-phenyl)-2-aminoimidazolium bromide, scheme 3: (O)

Prepared as described for 3-ethoxycarbonylmethyl-1-(2-chloro-4,6-dimethyl-phenyl)-2-aminoimidazolium bromide. LC/MS: $t_R$=1.12 min., (MH$^+$) 410.05.

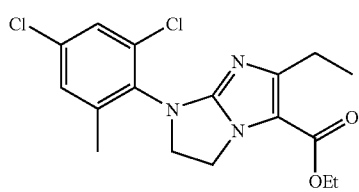

Intermediate 17

7-(2,4-Dichloro-6-methyl-phenyl)-2-ethyl-6,7-dihydro-5H-imidazo[1,2-a]imidazole-3-carboxylic acid ethyl ester, scheme 3: (P)

Prepared as described for 7-(2-chloro-4,6-dimethyl-phenyl)-2-ethyl-6,7-dihydro-5H-imidazo[1,2-a]imidazole-3-carboxylic acid ethyl ester. LC/MS: $t_R$=1.39 min., (MH$^+$)=368.16.

EXAMPLE 30

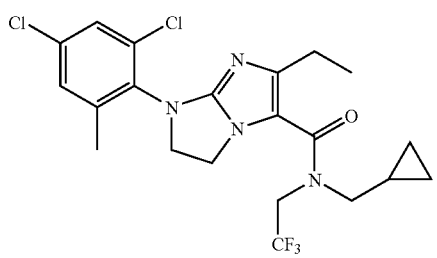

7-(2,4-Dichloro-6-methyl-phenyl)-2-ethyl-6,7-dihydro-5H-imidazo[1,2-a]imidazole-3-carboxylic acid cyclopropylmethyl-(2,2,2-trifluoro-ethyl)-amide, scheme 3: (Q)

Prepared as described for 7-(2-chloro-4,6-dimethyl-phenyl)-2-ethyl-6,7-dihydro-5H-imidazo[1,2-a]imidazole-3-carboxylic acid cyclopropylmethyl-(2,2,2-trifluoro-ethyl)-amide. LC/MS: $t_R$=1.46 min., (MH$^+$)=475.19.

EXAMPLE 31

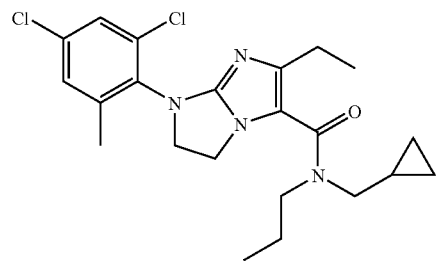

7-(2,4-Dichloro-6-methyl-phenyl)-2-ethyl-6,7-dihydro-5H-imidazo[1,2-a]imidazole-3-carboxylic acid cyclopropylmethyl-propyl-amide, scheme 3: (Q)

Prepared as described for the example above. LC/MS: $t_R$=1.42 min., (MH$^+$)=435.18.

EXAMPLE 32

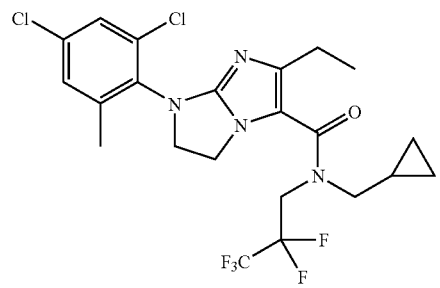

7-(2,4-Dichloro-6-methyl-phenyl)-2-ethyl-6,7-dihydro-5H-imidazo[1,2-a]imidazole-3-carboxylic acid cyclopropylmethyl-(2,2,3,3,3-pentafluoro-propyl)-amide, scheme 3: (Q)

Prepared as described for the example above. LC/MS: $t_R$=1.50 min., (MH$^+$)=525.13.

EXAMPLE 33

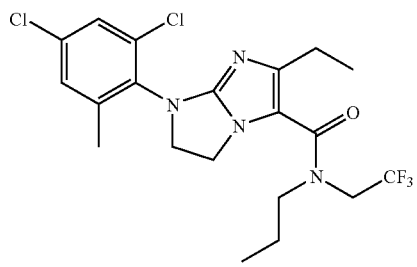

7-(2,4-Dichloro-6-methyl-phenyl)-2-ethyl-6,7-dihydro-5H-imidazo[1,2-a]imidazole-3-carboxylic acid propyl-(2,2,2-trifluoro-ethyl)-amide, scheme 3: (Q)

Prepared as described for the example above. LC/MS: $t_R$=1.41 min., (MH$^+$)=463.19.

The following Intermediates 18-23 may be used to synthesize Examples 34-40.

Intermediate 18

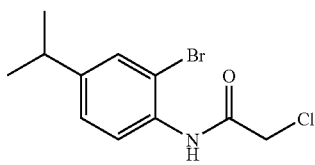

N-(2-Bromo4-isopropyl-phenyl)-2-chloro-acetamide, scheme 3: (K)

Prepared as described for 2-chloro-N-(2,4-dichloro-6-methyl-phenyl)-acetamide. Mass spec.: 291.97 (MH$^+$).

Intermediate 19

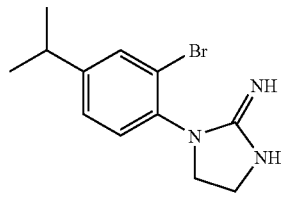

2-Azido-N-(2-bromo-4-isopropyl-phenyl)-acetamide, scheme 3: (L)

Prepared as described for 2-azido-N-(2,4-dichloro-6-methyl-phenyl)-acetamide.

Intermediate 20

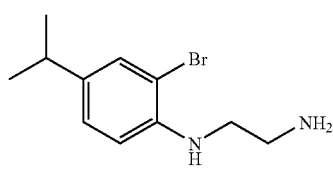

N$^1$-(2-Bromo-4-isopropyl-phenyl)-ethane-1,2-diamine, scheme 3: (M)

Prepared as described for N$^1$-(2,4-dichloro-6-methyl-phenyl)-ethane-1,2-diamine. Mass spec.: 270.08 (MH$^+$).

Intermediate 21

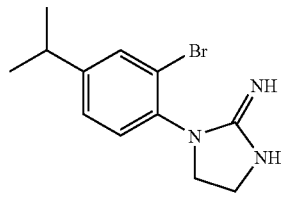

1-(2-Bromo-4-isopropyl-phenyl)-imidazolidin-2-ylideneamine, scheme 3: (N)

Prepared as described for 1-(2,4-dichloro-6-methyl-phenyl)-imidazolidin-2-ylideneamine. Mass spec.: 284.09 (MH$^+$).

Intermediate 22

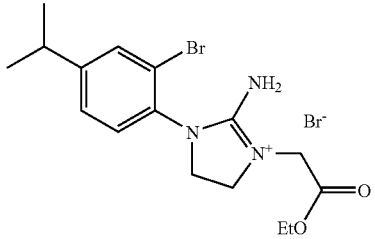

2-Amino-3-(2-bromo-4-isopropyl-phenyl)-1-ethoxycarbonylmethyl-4,5-dihydro-3H-imidazol-1-ium; bromide, scheme 3: (O)

Prepared as described for 3-ethoxycarbonylmethyl-1-(2,4-chloro-6-methyl-phenyl)-2-aminoimidazolium bromide. LC/MS: $t_R$=1.29 min., (MH$^+$) 368.20.

Intermediate 23

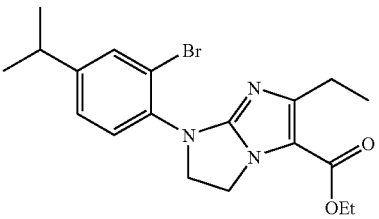

7-(2-Bromo-4-isopropyl-phenyl)-2-ethyl-6,7-dihydro-5H-imidazo[1,2-a]imidazole-3-carboxylic acid ethyl ester, scheme 3: (P)

Prepared as described for 7-(2,4-dichloro-6-methyl-phenyl)-2-ethyl-6,7-dihydro-5H-imidazo[1,2-a]imidazole-3-carboxylic acid ethyl ester. LC/MS: $t_R$=1.46 min., (MH$^+$)= 408.23.

EXAMPLE 34

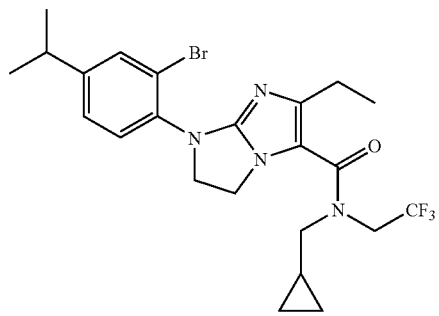

7-(2-Bromo-4-isopropyl-phenyl)-2-ethyl-6,7-dihydro-5H-imidazo[1,2-a]imidazole-3-carboxylic acid cyclopropylmethyl-(2,2,2-trifluoro-ethyl)-amide, scheme 3: (Q)

Prepared as described for 7-(2,4-dichloro-6-methyl-phenyl)-2-ethyl-6,7-dihydro-5H-imidazo[1,2-a]imidazole-3-carboxylic acid cyclopropylmethyl-(2,2,2-trifluoro-ethyl)-amide. LC/MS: $t_R$=1.58 min., (MH$^+$)=513.15.

EXAMPLE 35

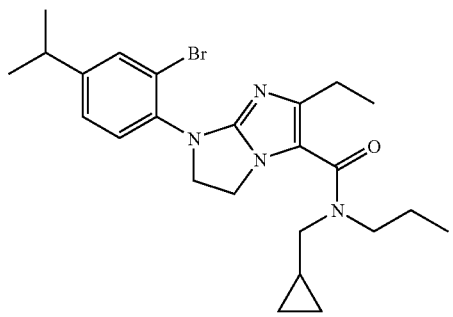

7-(2-Bromo-4-isopropyl-phenyl)-2-ethyl-6,7-dihydro-5H-imidazo[1,2-a]imidazole-3-carboxylic acid cyclopropylmethyl-propyl-amide, scheme 3: (Q)

Prepared as described for the example above. LC/MS: $t_R$=1.47 min., (MH$^+$)=473.21.

EXAMPLE 36

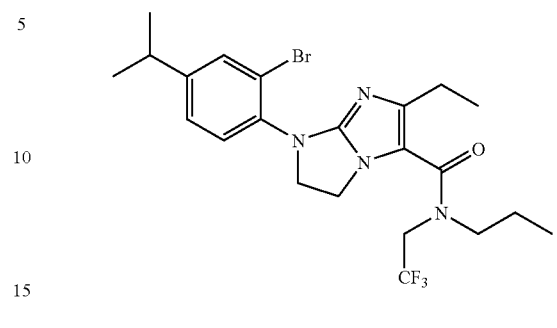

7-(2-Bromo-4-isopropyl-phenyl)-2-ethyl-6,7-dihydro-5H-imidazo[1,2-a]imidazole-3-carboxylic acid propyl-(2,2,2-trifluoro-ethyl)-amide, scheme 3: (Q)

Prepared as described for the example above. LC/MS: $t_R$=1.47 min., (MH$^+$)=501.02.

EXAMPLE 37

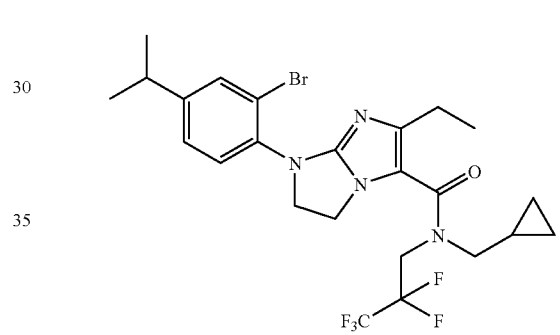

7-(2-Bromo-4-isopropyl-phenyl)-2-ethyl-6,7-dihydro-5H-imidazo[1,2-a]imidazole-3-carboxylic acid cyclopropylmethyl-(2,2,3,3,3-pentafluoro-propyl)-amide, scheme 3: (Q)

Prepared as described for the example above. LC/MS: $t_R$=1.61 min., (MH$^+$)=564.29.

EXAMPLE 38

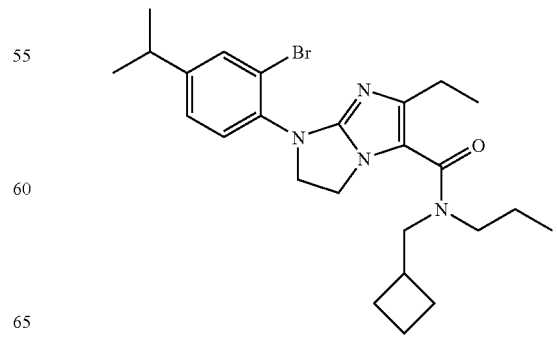

7-(2-Bromo-4-isopropyl-phenyl)-2-ethyl-6,7-dihydro-5H-imidazo[1,2-a]imidazole-3-carboxylic acid cyclobutylmethyl-propyl-amide, scheme 3: (Q)

Prepared as described for the example above. LC/MS: $t_R$=1.56 min., (MH$^+$)=487.21.

EXAMPLE 39

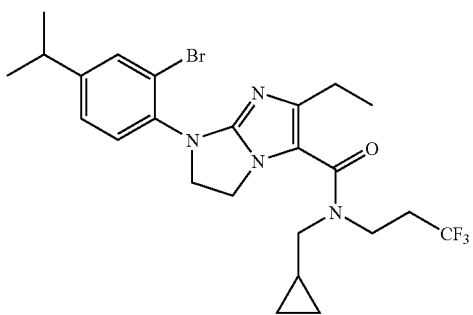

7-(2-Bromo-4-isopropyl-phenyl)-2-ethyl-6,7-dihydro-5H-imidazo[1,2-a]imidazole-3-carboxylic acid cyclopropylmethyl-(3,3,3-trifluoro-propyl)-amide, scheme 3: (Q)

Prepared as described for the example above. LC/MS: $t_R$=1.51 min., (MH$^+$)=527.15.

EXAMPLE 40

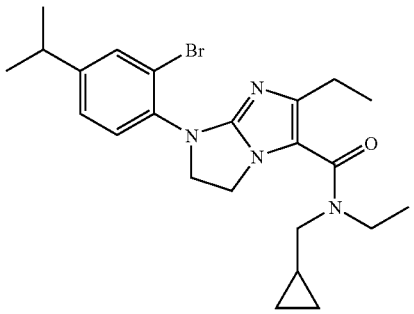

7-(2-Bromo4-isopropyl-phenyl)-2-ethyl-6,7-dihydro-5H-imidazo[1,2-a]imidazole-3-carboxylic acid cyclopropylmethyl-ethyl-amide, scheme 3: (Q)

Prepared as described for the example above. LC/MS: $t_R$=1.43 min., (MH$^+$)=459.18.

The following Intermediates 24-29 may be used to synthesize Examples 41-49.

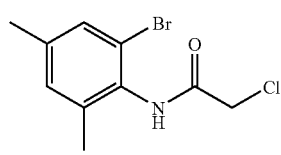

Intermediate 24

N-(2-bromo4,6-dimethyl-phenyl)-2-chloro-acetamide, scheme 3: (K)

Prepared as described for 2-chloro-N-(2,4-dichloro-6-methyl-phenyl)-acetamide.
Mass spec.: 277.95 (MH$^+$).

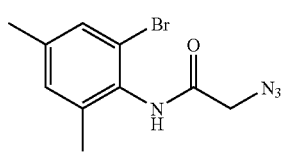

Intermediate 25

2-Azido-N-(2-bromo4,6-dimethyl-phenyl)-acetamide, scheme 3: (L)

Prepared as described for 2-azido-N-(2,4-dichloro-6-methyl-phenyl)-acetamide.

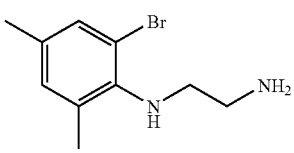

Intermediate 26

N$^1$-(2-bromo-4,6-dimethyl-phenyl)-ethane-1,2-diamine, scheme 3: (M)

Prepared as described for N$^1$-(2,4-dichloro-6-methyl-phenyl)-ethane-1,2-diamine.
$^1$H NMR δ (CDCl$_3$, 300 MHz) 2.22 (s, 3H), 2.31 (s, 3H), 2.87 (t, 2H), 3.04 (t, 2H), 6.88 (d, 1H), 7.17 (d, 1H). Mass spec.: 245.11 (MH$^+$).

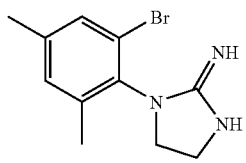

Intermediate 27

1-(2-Bromo4,6-dimethyl-phenyl)-imidazolidin-2-ylideneamine, scheme 3: (N)

Prepared as described for 1-(2,4-dichloro-6-methyl-phenyl)-imidazolidin-2-ylideneamine. LC/MS: $t_R$=0.91 min., (MH$^+$)=270.08.

Intermediate 28

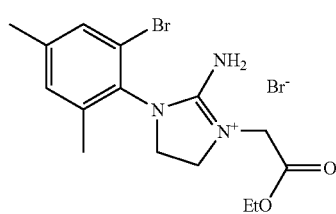

2-Amino-3-(2-bromo4,6-dimethyl-phenyl)-1-ethoxy-carbonylmethyl-4,5-dihydro-3H-imidazol-1-ium bromide, scheme 3: (O)

Prepared as described for 3-ethoxycarbonylmethyl-1-(2,4-chloro-6-methyl-phenyl)-2-aminoimidazolium bromide. LC/MS: $t_R$=1.03 min., (MH$^+$)=356.26.

Intermediate 29

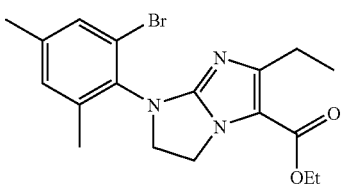

7-(2-Bromo4,6-dimethyl-phenyl)-2-ethyl-6,7-dihydro-5H-imidazo[1,2-a]imidazole-3-carboxylic acid ethyl ester, scheme 3: (P)

Prepared as described for 7-(2,4-dichloro-6-methyl-phenyl)-2-ethyl-6,7-dihydro-5H-imidazo[1,2-a]imidazole-3-carboxylic acid ethyl ester. LC/MS: $t_R$=1.33 min., (MH$^+$)=394.31.

EXAMPLE 41

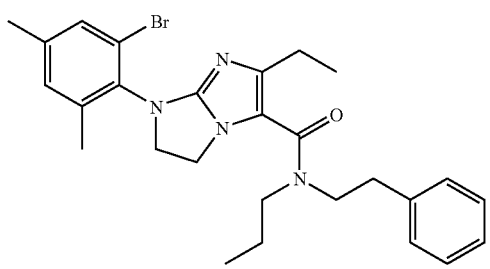

7-(2-Bromo4,6-dimethyl-phenyl)-2-ethyl-6,7-dihydro-5H-imidazo[1,2-a]imidazole-3-carboxylic acid phenethyl-propyl-amide, scheme 3: (Q)

Prepared as described for 7-(2,4-dichloro-6-methyl-phenyl)-2-ethyl-6,7-dihydro-5H-imidazo[1,2-a]imidazole-3-carboxylic acid cyclopropylmethyl-(2,2,2-trifluoro-ethyl)-amide. LC/MS: $t_R$=1.42 min., (MH$^+$)=511.35.

EXAMPLE 42

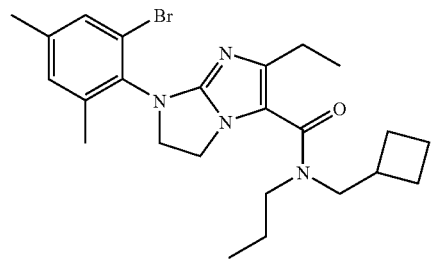

7-(2-Bromo-4,6-dimethyl-phenyl)-2-ethyl-6,7-dihydro-5H imidazo[1,2-a]imidazole-3-carboxylic acid cyclobutylmethyl-propyl-amide, scheme 3: (Q)

Prepared as described for the example above. LC/MS: $t_R$=1.68 min., (MH$^+$)=475.21.

EXAMPLE 43

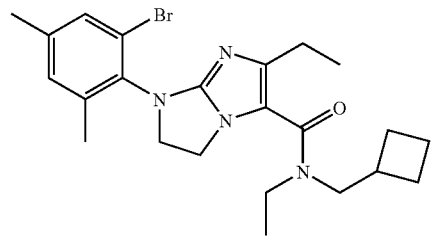

7-(2-Bromo4,6-dimethyl-phenyl)-2-ethyl-6,7-dihydro-5H-imidazo[1,2-a]imidazole-3-carboxylic acid cyclobutylmethyl-ethyl-amide, scheme 3: (Q)

Prepared as described for the example above. LC/MS: $t_R$=1.58 min., (MH$^+$)=461.35.

EXAMPLE 44

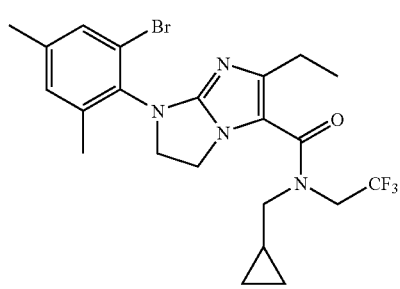

7-(2-Bromo4,6-dimethyl-phenyl)-2-ethyl-6,7-dihydro-5H-imidazo[1,2-a]imidazole-3-carboxylic acid cyclopropylmethyl-(2,2,2-trifluoro-ethyl)-amide, scheme 3: (Q)

Prepared as described for the example above. LC/MS: $t_R$=1.28 min., (MH$^+$)=501.16.

EXAMPLE 45

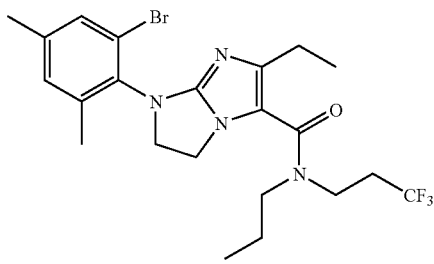

7-(2-Bromo4,6-dimethyl-phenyl)-2-ethyl-6,7-dihydro-5H-imidazo[1,2-a]imidazole-3-carboxylic acid propyl-(3,3,3-trifluoro-propyl)-amide, scheme 3: (Q)

Prepared as described for the example above. LC/MS: $t_R$=1.60 min., (MH$^+$)=503.15.

EXAMPLE 46

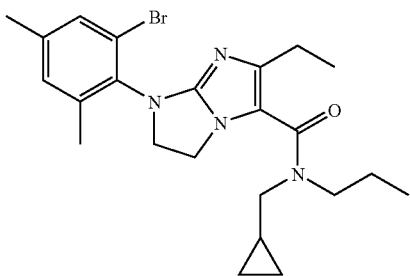

7-(2-Bromo4,6-dimethyl-phenyl)-2-ethyl-6,7-dihydro-5H-imidazo[1,2-a]imidazole-3-carboxylic acid cyclopropylmethyl-propyl-amide, scheme 3: (Q)

Prepared as described for the example above. LC/MS: $t_R$=1.56 min., (MH$^+$)=461.37.

The following examples 47-48 were prepared from Intermediate 5.

EXAMPLE 47

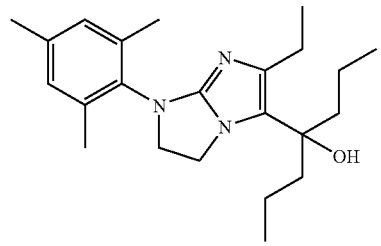

4-[2-Ethyl-7-(2,4,6-trimethyl-phenyl)-6,7-dihydro-5H-imidazo[1,2-a]imidazol-3-yl]-heptan-4-ol, scheme 11: (DDD)

To a 0° C. solution of 2-ethyl-7-(2,4,6-trimethyl-phenyl)-6,7-dihydro-5H-imidazo[1,2-a]imidazole-3-carboxylic acid ethyl ester (1 mL of a 0.14M solution in toluene) in tetrahydrofuran (1 mL) was added n-propylmagnesium chloride (0.84 mL of 1.0M in tetrahydrofuran). The resulting solution was removed from the ice bath and allowed to stir for 15 min. It was then heated at reflux for 14 h. Upon cooling to room temperature, the reaction solution was quenched with saturated aqueous ammonium chloride, and the phases were separated. The aqueous phase was extracted twice with ether, and the combined organic portions were washed with brine, dried over anhydrous Na$_2$SO$_4$, and concentrated under reduced pressure to give a yellow semi-solid (0.0448 g, 86%). LC/MS: $t_R$=1.58 min., (MH$^+$)=370.31.

EXAMPLE 48

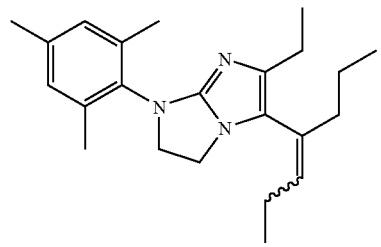

6-Ethyl-5-(1-propyl-but-1-enyl)-1-(2,4,6-trimethyl-phenyl)-2,3-dihydro-1H-imidazo[1,2-a]imidazole scheme 11: (EEE)

A mixture of 4-[2-ethyl-7-(2,4,6-trimethyl-phenyl)-6,7-dihydro-5H-imidazo[1,2-a]imidazol-3-yl]-heptan-4-ol (0.0444 g, 0.000120 mol) and p-toluenesulfonic acid-H$_2$O (15 mole %) in toluene (3 mL) was heated at reflux for 1 h. Upon cooling to room temperature, the solvent was evaporated under reduced pressure, and the residue was partitioned between ether and saturated aqueous sodium bicarbonate. The organic phase was washed with brine, dried over anhydrous Na$_2$SO$_4$, and concentrated to give the desired product in quantitative yield. LC-MS indicated the presence of two regioisomers in an approximate ratio of 2:1.

LC/MS: $t_R$=1.52 min. and 1.63 min., (MH$^+$)=352.28.

EXAMPLE 49

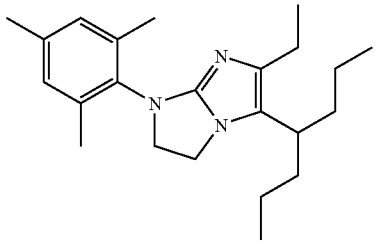

6-Ethyl-5-(1-propyl-butyl)-1-(2,4,6-trimethyl-phenyl)-2,3-dihydro-1H-imidazo[1,2-a]imidazole, scheme 11: (FFF)

6-Ethyl-5-(1-propyl-but-1-enyl)-1-(2,4,6-trimethyl-phenyl)-2,3-dihydro-1H-imidazo[1,2-a]imidazole (0.013 g, 0.000037 mol) in anhydrous tetrahydrofuran was treated with cold BH$_3$-THF (0.15 mL 1.0M in tetrahydrofuran), and the mixture was heated at reflux for 1.5 h. The mixture was cooled to 0° C., treated with glacial acetic acid (0.25 mL), heated at reflux for 1.5 h, re-cooled to 0° C., treated with 1.5 mL methanol, and heated again at reflux for 1 h. Upon cooling to room temperature, the reaction mixture was concentrated under reduced pressure, and the residue was partitioned between 2.5 N NaOH and ether. The organic phase was washed with water and brine, and was then dried over anhydrous Na$_2$SO$_4$ and evaporated to give a pale yellow oil. The crude product was chromatographed on silica, eluting with 15% ethyl acetate /hexanes to give a glassy solid. LC/MS: $t_R$=1.81 min., (MH$^+$)=354.30.

The following examples 50-51 were prepared from Intermediates 11 and 30.

Intermediate 30

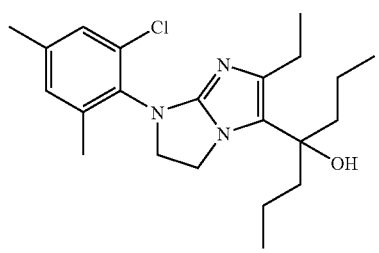

4-[7-(2-chloro-4,6-dimethyl-phenyl)-2-ethyl-6,7-dihydro-5H-imidazo[1,2-a]imidazol-3-yl]-heptan-4-ol, scheme 11: (DDD)

Prepared as described for 4-[2-ethyl-7-(2,4,6-trimethyl-phenyl)-6,7-dihydro-5H-imidazo[1,2-a]imidazol-3-yl]-heptan-4-ol. The crude product was chromatographed on silica, eluting with 25% ethyl acetate/hexanes to afford only one of the possible elimination products. $^1$H NMR δ (CDCl$_3$, 300 MHz) 7.12 (s, 1H), 7.03 (s, 1H), 5.59-5.34 (t, 1H), 4.33-4.08 (br m, 4H), 2.57-2.38 (q, 2H), 2.33 (s, 3H), 2.26(s, 3H), 2.22-2.15 (t, 2H), 1.74-1.48 (br m, 2H), 1.40-1.33 (q, 2H), 1.25-1.2 (t, 3H), 1.08-1.03 (t, 3H), 0.92-0.88 (t, 3H). LC/MS: $t_R$=1.74 min., (MH$^+$)=390.25.

EXAMPLE 50

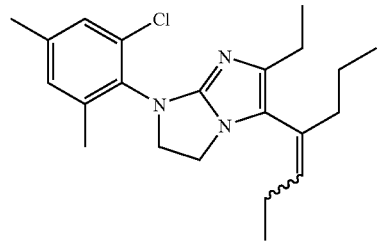

1-(2-chloro-4,6-dimethyl-phenyl)-6-ethyl-5-(1-propyl-but-1-enyl)-2,3-dihydro-1H-imidazo[1,2-a]imidazole, scheme 11: (EEE)

Prepared as described for 6-ethyl-5-(1-propyl-but-1-enyl)-1-(2,4,6-trimethyl-phenyl)-2,3-dihydro-1H-imidazo[1,2-a]imidazole. LC/MS: $t_R$=1.74 min., (MH$^+$)=372.25.

EXAMPLE 51

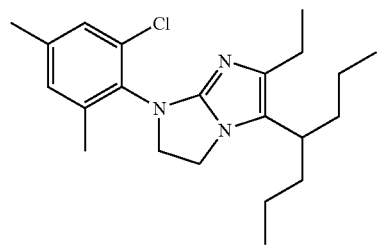

1-(2-chloro-4,6-dimethyl-phenyl)-6-ethyl-5-(1-propyl-butyl)-2,3-dihydro-1H-imidazo[1,2-a]imidazole, scheme 11: (FFF)

Prepared as described for 6-ethyl-5-(1-propyl-butyl)-1-(2,4,6-trimethyl-phenyl)-2,3-dihydro-1H-imidazo[1,2-a]imidazole. LC/MS: $t_R$=1.74 min., (MH$^+$)=374.21.

The following Intermediates 17 and 31 were used to prepare Examples 52 and 53.

Intermediate 31

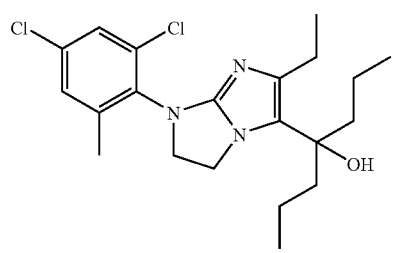

4-[7-(2,4-Dichloro-6-methyl-phenyl)-2-ethyl-6,7-dihydro-5H-imidazo[1,2-a]imidazole-3-yl]-heptan4-ol, Scheme 11: (DDD)

Prepared as described for 4-[2-ethyl-7-(2,4,6-trimethyl-phenyl)-6,7-dihydro-5H-imidazo[1,2-a]imidazole-3-yl]-heptan-4-ol. LC/MS: $t_R$=1.74 min., (MH$^+$)=410.17.

EXAMPLE 52

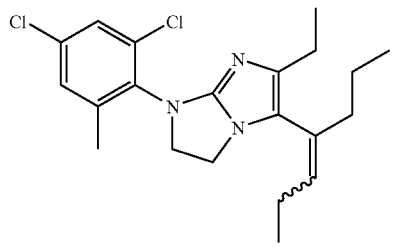

1-(2,4-Dichloro-6-methyl-phenyl)-6-ethyl-5-(1-propyl-but-1-enyl)-2,3-dihydro-1H-imidazo[1,2-a]imidazole, Scheme 11: (EEE)

Prepared as described for 6-ethyl-5-(1-propyl-but-1-enyl)-1-(2,4,6-trimethyl-phenyl)-2,3-dihydro-1H-imidazo[1,2-a]imidazole. LC/MS: $t_R$=1.54 min. and 1.65 min., (MH$^+$)=392.18.

EXAMPLE 53

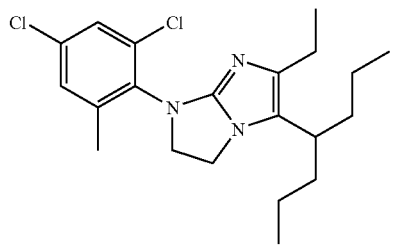

1-(2,4-Dichloro-6-methyl-phenyl)-6-ethyl-5-(1-propyl-butyl)-2,3-dihydro-1H-imidazo[1,2-a]imidazole, Scheme 11: (FFF)

Prepared as described for 6-ethyl-5-(1-propyl-butyl)-1-(2,4,6-trimethyl-phenyl)-2,3-dihydro-1H-imidazo[1,2-a]imidazole. LC/MS: $t_R$=1.68 min., (MH$^+$)=394.10.

The following Intermediates 32-43 may be used to synthesize Examples 54-55.

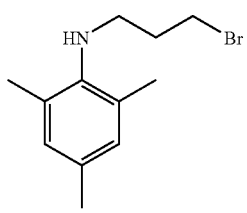

Intermediate 32

(3-Bromo-propyl)-(2,4,6-trimethyl-phenyl)-amine, Scheme 7: (FF)

To a stirred ice-cold solution of 2,4,6-trimethylaniline (13.5 g, 100 mmol) in dioxane (50 mL) under argon was added 1.2 equivalents of 1.6 M n-BuLi in hexane drop-wise. The brown mixture was allowed to warm up to room temperature during 1 h. At the end 50 mL (approx. 5 equiv.) of 1,3-dibromopropane was added in one lot and stirred for 42 h. Precipitated LiBr was filtered and the volatiles were removed in vacuo. The residue was partitioned between ethyl acetate (300 mL) and water (3×100 mL). The organic layer was dried (Na$_2$SO$_4$) and evaporated to give the crude product whose purity by LC-MS analysis was 61%. Silica gel chromatography of the crude product with acetone/hexane (1:9) as eluent gave pure bromopropyl aniline (3.3 g) and an impure fraction which upon crystallization from ethyl acetate hexane gave an additional 2.4 g. (22% yield). LC/MS: $t_R$=1.2 min; [M+H]=256, 258 (bromine pattern), $^1$H NMR (CD$_3$OD) δ 7.07 (2 H, s), 3.59 (2 H, t, J$_{vic}$=6.4 Hz), 3.51 (2 H, t, J$_{vic}$=8.1 Hz), 2.46 (6 H, s), 2.45-2.38 (2 H, m), 2.30 (3 H, s).

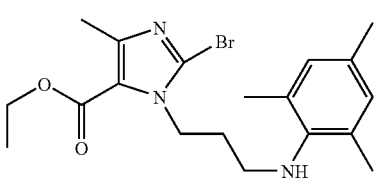

Intermediate 33

2-Bromo-5-methyl-3-[3-(2,4,6-trimethyl-phenylamino)-propyl]-3H-imidazole-4-carboxylic acid ethyl ester, Scheme 7: GG)

A solution of (1.26 g, 5.4 mmol) bromoimidazole in acetone (43 mL) was combined with (3-bromopropyl)-2,4,6-trimethylaniline (1.1 g, 4.25 mmol) and diazabicycloundecene (1.2 equiv). After 96 h, acetone was evaporated and the residue was partitioned between ethyl acetate (250 mL) and water (3×50 mL). The organic layer was dried (Na$_2$SO$_4$) and evaporated. The residue was purified by silica gel column chromatography using a step gradient of 0% to 70% ethyl acetate in hexane to give 1.1 g (50% yield) of the required alkylated product. $t_R$=1.3 min., MS: [M+H]=408, 410 (bromine pattern), $^1$H NMR (CDCl$_3$) δ 6.82 (2 H, s), 4.45 (2 H, t, J$_{vic}$=7.5 Hz), 4.32 (2 H, q, J$_{vic}$=7.1 Hz), 3.05 (2

H, t, $J_{vic}$=7.0 Hz), 2.46 (3 H, s), 2.29 (6 H, s), 2.29 (3 H, s), 2.05 (2 H, m), 1.37 (3 H, t $J_{vic}$=7.1 Hz). $^{13}$CNMR (CDCl$_3$) δ 160.3, 148.7, 129.7, 124.7, 121.1, 60.6, 46.0, 45.7, 20.6, 18.5, 16.1, 14.3. A more polar product (0.04 g) which corresponded to cyclization product from the N-3 alkylation of imidazole was also obtained from the later fractions.

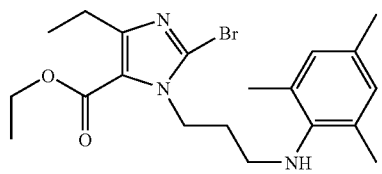

Intermediate 34

2-Bromo-5-ethyl-3-[3-(2,4,6-trimethyl-phenylamino)-propyl]-3H-imidazole-4-carboxylic acid ethyl ester, Scheme 7: (GG)

This compound was prepared from the corresponding 2-bromoimidazole on a 12.9 mmol scale as described in the previous example. Silica gel chromatography of the crude product using a step gradient of 20-70% ethyl acetate in hexane provided N3-derived cyclization product (0.47 g, 11% yield), $t_R$=1.3 min., MS: [M+H]=342, and N1-derived alkylation product (2.9 g, 54% yield); LC/MS: $t_R$=1.5 min., [M+H]=422, 424 (bromine pattern), $^1$H NMR (CD$_3$OD) δ 6.74 (2 H, s), 4.40 (2 H, t, $J_{vic}$=7.6 Hz), 4.31 (2 H, q, $J_{vic}$=7.2 Hz), 2.94 (2 H, t, $J_{vic}$=7.1 Hz), 2.83 (2 H, q, $J_{vic}$=7.6 Hz), 2.19 (6 H, s), 2.16 (3 H, s), 1.93 (2H, m,) 1.34 (3 H, t, $J_{vic}$=7.2 Hz), 1.19 (3 H, t, $J_{vic}$=7.6 Hz). $^{13}$CNMR (CD$_3$OD) δ 161.2, 154.8, 144.0, 132.7, 130.9, 130.5, 126.2, 121.8, 62.0, 47.10, 46.59, 32.2, 23.70, 20.8, 18.7, 14.6, 14.5, 14.3.

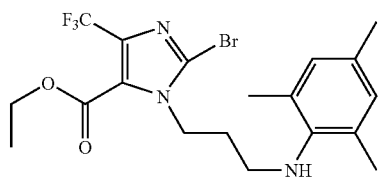

Intermediate 35

2-Bromo-5-trifluoromethyl-3-[3-(2,4,6-trimethyl-phenylamino)-propyl]-3H-imidazole-4-carboxylic acid ethyl ester, Scheme 7: (GG)

To a 0.1M dimethylformamide solution containing 5.3 mmol each of the bromoimidazole and bromopropyl aniline was added 1.2 equivalents of Cs$_2$CO$_3$. The reaction mixture was stirred at ambient temperature for 96 h. LC-MS indicated approximately 50% conversion to a single alkylated product. Diluted with ethyl acetate (500 mL) and washed with water (3×100 mL). Approx. 5 mL ethanol had to be used to break up an emulsion. The ethyl acetate layer was dried (Na$_2$SO$_4$), evaporated in vacuo. The crude product was purified by silica gel chromatography with ethyl acetate:hexane (1:9) as eluent. Fractions containing the required compound were combined and evaporated to give 0.51 g (21% yield). LC/MS: $t_R$=1.5 min., [M+H]=462, 464 (bromine pattern), $^1$H NMR (CD$_3$OD) δ 6.74 (2 H, s), 4.44 (2 H, t, $J_{vic}$=7.5 Hz), 4.35 (2 H, t, $J_{vic}$=7.1 Hz), 2.96 (2 H, t, $J_{vic}$=7.1 Hz), 2.20 (6 H, s), 2.15 (3H, s), 1.97 (2 H, m), 1.33 (3 H, t, $J_{vic}$=7.1 Hz).

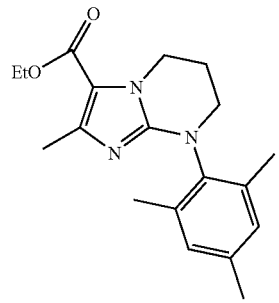

Intermediate 36

2-Methyl-8-(2,4,6-trimethyl-phenyl)-5,6,7,8-tetrahydro-imidazo[1,2-a]pyrimidine-3-carboxylic acid ethyl ester, Scheme 7: (HH)

The appropriate N1-alkylated 2-bromoimidazole (1 g, 2.1 mmol) in sulfolane (50 mL) was heated under argon in the dark with 1.2 equivalents of Ag$_2$CO$_3$ for 24 h. The reaction mixture was cooled to ambient temperature. Filtered, diluted with water containing 0.1% trifluoroacetic acid to 250 mL. The dark filtrate was applied to an octadecyl silica gel (C18) column (4×15 cm) pre-equilibrated with water containing 0.1% trifluoroacetic acid. Elution with the same solvent was continued until all the sulfolane was removed. The solvent was then changed to methanol:0.1% trifluoroacetic acid in water (2:3) collecting 25 mL size fractions which were combined after LC-MS analysis to give 0.9 g of the required product as trifluoroacetate salt of 93% purity. LC/MS: $t_R$=1.1 min., [M+H]=328, $^1$H NMR (CD$_3$OD) δ 6.94 (2 H, s), 4.29-4.24 (4 H, m), 3.47 (2 H, t, $J_{vic}$ 5.5 Hz), 2.27 (3 H, s), 2.25 (3 H, s), 2.29 (3 H, s), 2.24 (2 H, m), 2.12 (6 H, s), 1.34 (3 H, t, $J_{vic}$=7.0 Hz). $^{13}$CNMR (CD$_3$OD) δ 162.7, 150.3, 147.9, 139.1, 138.8, 137.8, 130.7, 115.2, 60.8, 47.6, 44.4, 23.2, 21.2, 18.3, 15.2, 14.9.

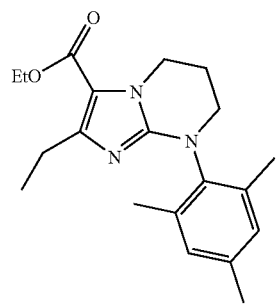

Intermediate 37

2-Ethyl-8-(2,4,6-trimethyl-phenyl)-5,6,7,8-tetrahydro-imidazo[1,2-a]pyrimidine-3-carboxylic acid ethyl ester, Scheme 7: (HH)

To the N1-alkylated 2-bromo-4-ethyl imidazole derivative (2.83 g, 6.7 mmol) in sulfolane (67 mL) was added 1.1 equivalents of silver triflate. The resulting solution was stirred in the dark at 150° C. under argon. Within 10 min the solution turned dark and it was stirred for 24 h when LC-MS indicated complete conversion to cyclized product. The reaction mixture was cooled to ambient temperature. Filtered, diluted with water containing 0.1% trifluoroacetic acid to 335 mL and filtered again. The dark filtrate was applied to an octadecyl silica gel (C18) column (4×15 cm) pre-equilibrated with water containing 0.1% trifluoroacetic acid. Elution with the same solvent was continued until all the sulfolane was removed. The solvent was then changed to methanol:0.1% trifluoroacetic acid in water (2:3) collecting 25 mL size fractions which were combined after LC-MS analysis to give two major fractions. Cyclization product that was 84% pure (1.5 g) and pure cyclization product (570 mg). LC/MS: $t_R$=1.3 min., [M+H]=342, Intermediate 38

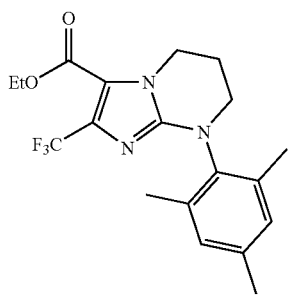

2-Trifluoromethyl-8-(2,4,6-tri methyl-phenyl)-5,6,7,8-tetrahydro-imidazo[1,2a]pyrimidine-3-carboxylic acid ethyl ester, Scheme 7: (HH)

The appropriate N1-alkylated-2-bromoimidazole (0.473 g, 1.02 mmol) was subjected to silver triflate mediated cyclization in sulfolane (10 mL) as described above except that the reaction was carried out for 48 h. At the end, the mixture was diluted with ethanol (10 mL) filtered through a bed (2×4.5 cm) of C18 silica gel and washed with another 50 mL more ethanol. The filtrate was concentrated in vacuo to ca. 20 mL. It was then purified by preparative HPLC using a 20 min. linear gradient (25 min run) of 30-100% B in A in ten injections. Fractions containing the cyclization product were combined and evaporated. The residue (0.39 g) in 20 mL anhydrous ethanol was stirred with (0.168 g, 2 mmol) NaHCO₃ for 1.5 h. Filtered and evaporated to dryness to give 0.23 g (60% yield) of cyclized product. LC/MS: $t_R$=1.8 min., [M+H]=382.

Intermediate 39

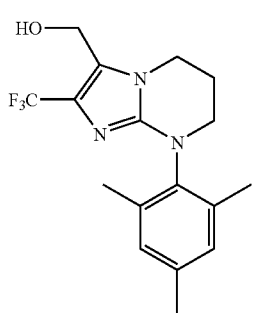

[2-Trifluoromethyl-8-(2,4,6-trimethyl-phenyl)-5,6,7,8-tetrahydro-imidazo[1,2-a]pyrimidin-3-yl]-methanol, Scheme 7: (II)

The appropriate ethyl ester (0.032 g ) in 1 mL of anhydrous tetrahydrofuran was treated with an excess (0.3 mL) of 1 M LiAlH₄ in tetrahydrofuran at ambient temperature. After 1 h, 1 M NaOH (5 mL) was carefully added. Most of the tetrahydrofuran was then evaporated. The residue was partitioned between ethyl acetate (2×30 mL) and additional 10 mL 1 M NaOH. Organic layer was dried (Na₂SO₄) and evaporated. The residue after silica gel chromatography with methanol:methylene chloride (1:99) yielded (0.025 g) of alcohol. LC/MS: $t_R$=1.0 min., [M+H]=340, ¹H NMR (CD₃OD) δ 6.93 (2 H, s), 4.62 (2 H, s), 4.10 (2 H, t, $J_{vic}$=6.1 Hz), 3.51 (2 H, t, $J_{vic}$=5.4 Hz), 2.29 (2 H, m), 2.27 (3H, s), 2.13 (6 H, s). Gradient NOESY experiment revealed NOE between exo methylene group and the methylene at 6 position confirming the regiochemistry.

Intermediate 40

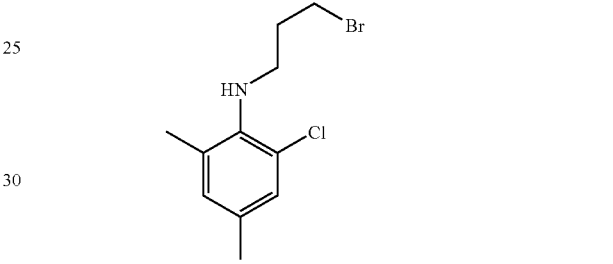

(3-Bromo-propyl)-(2-chloro-4,6-dimethyl-phenyl)-amine, Scheme 7: FF)

To a solution of the 2-chloro-4,6-dimethyl aniline (16.9 g, 108 mmol) in 1,4-dioxane (80 mL) was added n-butyl lithium solution (2.5 M in hexanes, 48 mL), dropwise, at 0° C. under argon. The reaction mixture was warmed up to rt and stirred for 20 min. 1,3-Dibromopropane (109 g, 543 mmol) was added and the reaction mixture was stirred overnight. The mixture was filtered through celite and concentrated. Purification was carried out by reverse phase chromatography using water, methanol and trifluoroacetic acid to obtain product (20.01 g, 72.5 mmol, 67%) as brown oil. LC/MS: $t_R$=1.5 min. [M+H] 277. ¹H NMR (CD₃OD) δ: 7.12 (s, 1H), 6.99 (s, 1H), 3.52 (t, J=6.65 Hz, 2H), 3.36 (t, J=6.75 Hz, 2H), 2.36 (s, 3H), 2.29 (s, 3H), 2.14 (m, 2H).

Intermediate 41

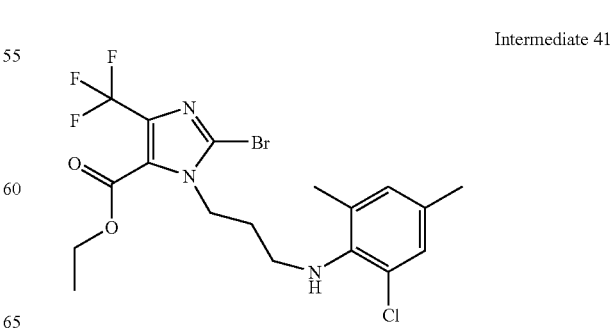

2-Bromo-3-[3-(2-chloro-4,6-dimethyl-phenylamino)-propyl]-5-trifluoromethyl-3H-imidazole4-carboxylic acid ethyl ester, Scheme 7: (GG)

To a solution of the imidazole (5.08 g, 17.7 mmol) in dry dimethylformamide (120 mL) was added the 3-bromopropyl aniline (5.37 g, 19.5 mmol) and cesium carbonate (8.64 g, 26.5 mmol) at RT under argon. The reaction mixture was heated at 55° C. overnight, cooled and diluted with ethyl acetate (400 mL). The organic phase was washed with water (2×), brine and dried (MgSO₄). Purification by silica gel column chromatography using hexanes/ethyl acetate (90:10 to 70:30) afforded product (5.98 g, 12.4 mmol, 70%) as brown oil. LC/MS: t_R=2.2 min. [M+H] 483. ¹H NMR (CD₃OD) δ: 6.98 (s, 1H), 6.86 (s, 1H), 4.49 (t, J=7.55 Hz, 2H), 4.36 (q, J=7.1 Hz, 2H), 3.10 (t, J=6.95 Hz, 2H), 2.25 (s, 3H), 2.19 (s, 3H), 2.00 (m, 2H), 1.34 (t, J=7.1 Hz, 3H).

Intermediate 42

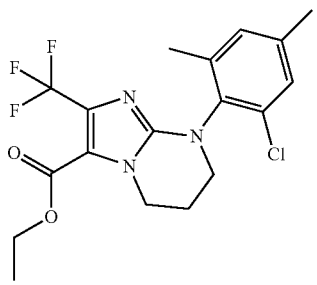

1-(2-chloro-4,6-dimethyl-phenyl)-6-trifluoromethyl-2,3,4,4a-tetrahydro-1H-[1]pyrindine-5-carboxylic acid ethyl ester, Scheme 7: HH)

To a solution of the alkylated imidazole (5.98 g, 12.4 mmol) in sulfolane (50 mL) was added silver triflate (4.77 g, 18.6 mmol) at rt under argon. The flask was fitted with a reflux condenser and heated at 150° C. overnight. The whole setup was covered with aluminum foil to keep the reaction mixture in dark. The reaction mixture was filtered through celite and purified by reverse phase chromatography, using water, methanol and trifluoroacetic acid. Product (3.43 g, 8.54 mmol, 69%) was obtained as brown solid. LC/MS: t_R=2.1 min. [M+H] 402.

¹H NMR (CD₃OD) δ: 7.01 (s, 1H), 6.92 (s, 1H), 4.38 (m, 2H), 4.32 (q, J=7.15 Hz, 2H), 4.65 (m, 2H), 2.30 (m, 2H), 2.26 (s, 3H), 2.19 (s, 3H), 2.00 (m, 2H), 1.33 (t, J=7.1 Hz, 3H).

Intermediate 43

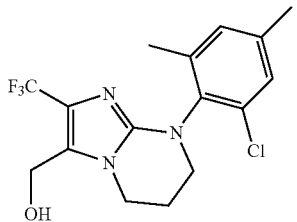

[8-(2-Chloro-4,6-dimethyl-phenyl)-2-trifluoromethyl-5,6,7,8-tetrahydro-imidazole[1,2-a]pyrimidin-3-yl]-methanol, Scheme 7: (II)

To a solution of the ester (3.43 g, 8.54 mmol) in anhydrous tetrahydrofuran (100 mL) at 0° C. under argon was added dropwise a solution of Lithium aluminum hydride (1 M in hexanes, 86 mL). The reaction mixture was stirred for an hour and an aqueous solution of Rochelle salt was added dropwise to quench excess of LAH. The reaction mixture was extracted with ethyl acetate (3×100 mL). The combined organic layer was washed with water (2×), brine and dried (MgSO₄). Purification by silica gel column chromatography, using hexanes, ethyl acetate (90:10 to 60:40) afforded product (2.12 g, 5.89 mmol, 69%) as off white solid. LC/MS: t_R=1.5 min. [M+H] 360. ¹H NMR (CDCl₃) δ: 7.10 (s, 1H), 6.97 (s, 1H), 4.04 (m, 2H), 3.65 (m, 2H), 3.42 (m, 2H), 2.32 (m, 2H), 2.28 (s, 3H), 2.19 (s, 3H).

EXAMPLE 54

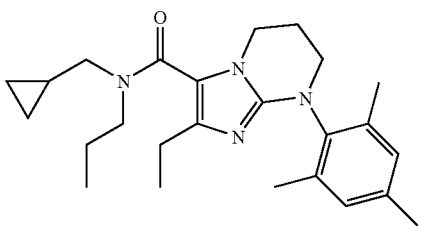

2-Ethyl-8-(2,4,6-trimethyl-phenyl)-5,6,7,8-tetrahydro-imidazo[1,2-a]pyrimidine-3-carboxylic acid cyclopropylmethyl-propyl-amide, Scheme 7: (LL)

A solution of 0.15 g of N-cyclopropylmethyl, N-propyl amine (1.3 mmol) in toluene (5 mL) was treated with 0.47 mL of 2 M trimethylaluminum in hexanes (0.94 mmol). After 1 h anhydrous toluene solution (2 mL) of the appropriate ethyl ester (59 mg, 0.17 mmol) was added. Refluxed for 4 h. Allowed to cool to ambient temperature, diluted with 25 mL dichloromethane and washed with 1M NaOH (8 mL), and water (8 mL). Organic layer was evaporated and the residue in 2 mL dimethylformamide was purified by prep HPLC using a 20 min linear gradient of 30-100% B in A in a 25 min run. Fractions containing the required compound were combined to give 11 mg of the amide. LC/MS: t_R=1.4 min., [M+H]=409. ¹H NMR (CD₃OD) δ 7.10 (2 H, s), 4.20-3.20 (8H, 4×m), 2.47 (2 H, m), 2.38 (2H, m), 2.33 (3 H, s), 2.23 (6 H, s), 1.80-1.57 (2 H, m), 1.22-0.20 (11 H, 4×m). Fractions containing unchanged ethyl ester were combined to recover the starting ethyl ester (43 mg) as trifluoroacetate salt.

EXAMPLE 55

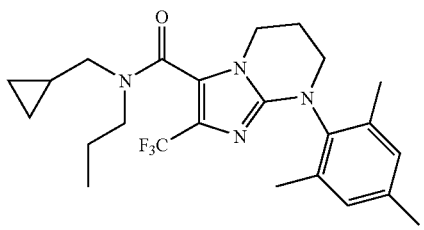

2-Trifluoromethyl-8-(2,4,6-trimethyl-phenyl)-5,6,7,8-tetrahydro-imidazo[1,2 a]pyrimidine-3-carboxylic acid cyclopropylmethyl-propyl-amide, Scheme 7: (LL)

The corresponding ethyl ester was subjected to Weinreb amidation using standard protocols. The amide obtained was purified by Preparative HPLC with a 15 min linear gradient of B in A in a 20 min run. Combined fractions were evaporated in vacuo to give the required product. LC/MS: $t_R$=1.8 min., [M+H]=449, $^1$H NMR (CD$_3$OD) δ 7.03 (2 H, s), 4.04-3.97 (2H, 2×m), 3.64 (2 H, t, $J_{vic}$=5.6 Hz), 3.62-3.02 (4 H, 4×m), 2.47-2.32 (2 H, m), 2.31 (3 H, s), 2.21 (3 H, s), 2.20 (3H, s), 1.81-1.07 (3 H, 3×m), 1.06-0.82 (3 H, 2×m), 0.70-0.20 (4 H, 3×m).

Internediate 44

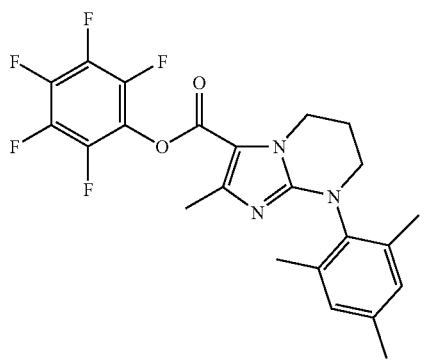

2-Methyl-8-(2,4,6-trimethyl-phenyl)-5,6,7,8-tetrahydro-imidazo[1,2-a]pyrimidine-3-carboxylic acid pentafluorophenyl ester, Scheme 7: (HH)

The corresponding ethyl ester (0.17 mg, 0.52 mmol) and LiOH—H$_2$O (110 mg) in dimethoxyethane:water (1:1, 113 mL) was heated to 55° C. for 24 h. Dimethoxyethane and water were evaporated. The residue in 3 mL dimethyl formamide was treated with pentafluorophenyl trifluoroacetate (2.5 mL) and stirred for 2 h. Volatiles were evaporated and the residue was purified by silica gel column chromatography with methylene chloride and 2-propanol: methylene chloride (3:47). Fractions containing the required activated pentafluorophenyl ester were combined to give 0.15 g, 32% yield). LC/MS: $t_R$=1.5 min., [M+H]=466.

General Procedure for amide formation preparation of Example 56-58 from Intermediate 44: The pentafluorophenyl ester (15 mg, 0.036 mmol) in 1 mL dimethylformamide was stirred with 0.18 mmol of appropriate amine and 0.18-0.36 mmol Cs$_2$CO$_3$ at 70° C. for 18 h. The mixture was diluted with water (0.8 mL) and trifluoroacetic acid (0.2 mL). The resulting solution was purified by preparative HPLC using a 20 min linear gradient with 30-100% B in A as eluent in a 25 min run. Fractions containing the required product were combined and evaporated to give the appropriate amide in 20-50% yield.

EXAMPLE 56

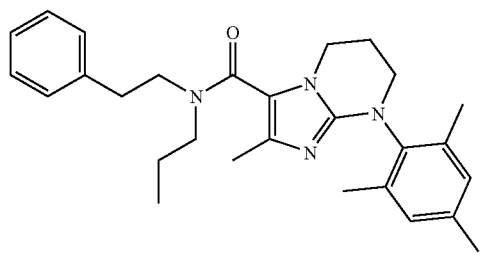

2-Methyl-8-(2,4,6-trimethyl-phenyl)-5,6,7,8-tetrahydro-imidazo[1,2-a]pyrimidine-3-carboxylic acid phenethyl-propyl-amide, Scheme 7: (LL)

Prepared as described for the example above. LC/MS: $t_R$=1.3 min., [M+H]=445, $^1$H NMR (CD$_3$OD) δ 7.31-7.16 (5 H, m), 7.09 (2 H, s), 4.31-2.72 (12 H, 7×m), 2.32 (3 H, s), 2.20 (6 H, s), 2.05-1.43 (5 H, m), 1.28-0.77 (3 H, 2×m).

EXAMPLE 57

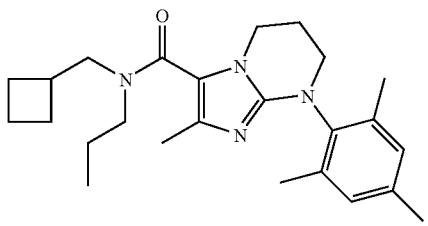

2-Methyl-8-(2,4,6-trimethyl-phenyl)-5,6,7,8-tetrahydro-imidazo[1,2-a]pyrimidine-3-carboxylic acid cyclobutylmethyl-propyl-amide, Scheme 7: (LL)

LC/MS: $t_R$=1.3 min., [M+H]=409, $^1$H NMR (CD$_3$OD) δ 7.10 (2 H, s), 4.43-3.79 (2 H, m), 3.70 (2 H, t, $J_{vic}$=5.5 Hz), 3.62-3.10 (4 H, m), 2.91-2.53 (1 H, m), 2.38-2.36 (2 H, m), 2.33 (3 H, s), 2.22 (6 H, s), 2.10-1.22 (11 H, 4×m), 1.16-0.79(3H, m).

EXAMPLE 58

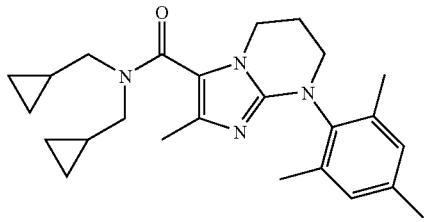

2-Methyl-8-(2,4,6-trimethyl-phenyl)-5,6,7,8-tetrahydro-imidazo[1,2-a]pyrimidine-3-carboxylic acid bis-cyclopropylmethyl-amide, Scheme 7: (LL)

LC/MS: $t_R$=1.4 min., [M+H]=409, $^1$H NMR (CD$_3$OD) δ 7.10 (2 H, s), 4.15-3.95 (2 H, m), 3.70 (2 H, t, $J_{vic}$=5.5 Hz), 3.68-3.36 (4 H, m), 2.39-2.36 (2 H, m), 2.33 (3 H, s), 2.23 (6 H, s), 2.09 (3 H, s), 1.25-1.05 (4 H, m), 0.41-0.05 (4 H, m).

Intermediate 39 Was Used to Prepare Examples 59-95 and 331.

EXAMPLE 59

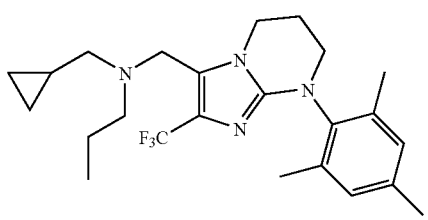

Cyclopropylmethyl-propyl-[2-trifluoromethyl-8-(2,4,6-trimethyl-phenyl)-5,6,7,8-tetrahydro-imidazo[1,2-a]pyrimidin-3-ylmethyl]-amine, Scheme 7: (KK)

Intermediate 39 was dissolved in benzene (50 mL) and treated with thionyl chloride (5 mL). The solution was heated at reflux for 2 h. The volatiles were evaporated. The residue was evaporated twice with heptane (50 mL). The resulting gum was dissolved in acetonitrile (30 mL) and treated with excess N-cyclopropylmethyl, N-propyl-amine (1 mL). After 1 h LC-MS indicated clean conversion to the required dialkylaminomethyl derivative. Acetonitrile was evaporated and the residue was purified by C18 column chromatography with a step gradient elution using 20-60% methanol in water containing 0.1% trifluoroacetic acid. Fractions containing the required product were combined and evaporated in vacuo to give the required amine (0.17 g, 51% overall yield from the cyclization product). LC/MS: $t_R$=1.3 min., [M+H]=435, $^1$H NMR (CD$_3$OD) δ 6.98 (2 H, s), 4.56 (2H, s), 4.16 (2 H, t, $J_{vic}$=5.8 Hz), 3.60 (2 H, t, $J_{vic}$=5.5 Hz), 3.23-3.18 (4 H, 2×m), 2.36 (2 H, m), 2.29 (3 H, s), 2.15 (6 H, s), 1.81-1.76 (2 H, m), 1.28-1.21 (1 H, m), 1.02 (3 H, t, $J_{vic}$=7.3 Hz), 0.86-0.82 (2 H, m), 0.51-0.47 (2 H, m).

EXAMPLE 60

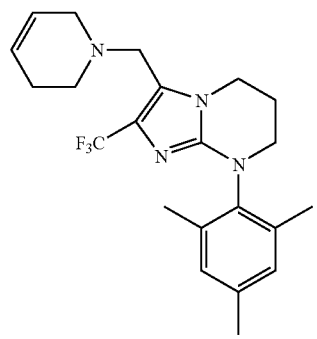

3-(3,6-Dihydro-2H-pyridin-1-ylmethyl)-2-trifluoromethyl-8-(2,4,6-trimethyl-phenyl)-5,6,7,8-tetrahydro-imidazo[1,2-a]pyrimidine, Scheme 7: (KK)

Prepared as described for the example above. LC/MS: $t_R$=1.3 min., MS: [M+H]=405.

EXAMPLE 61

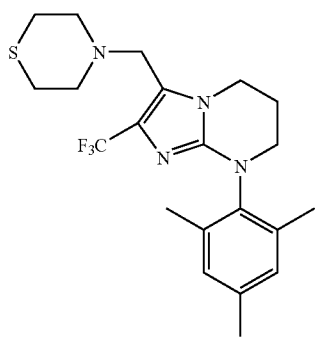

3-Thiomorpholin4-ylmethyl-2-trifluoromethyl-8-(2,4,6-trimethyl-phenyl)-5,6,7,8-tetrahydro-imidazo[1,2-a]pyrimidine, Scheme 7: (KK)

Prepared as described for the example above. LC/MS: $t_R$=1.5 min., MS: [M+H]=425.

EXAMPLE 62

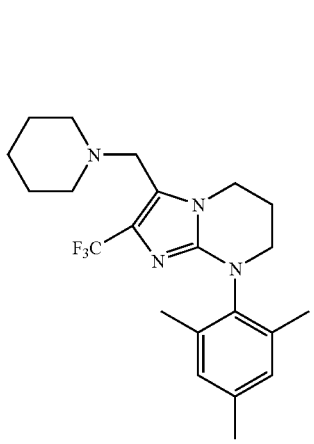

3-Piperidin-1-ylmethyl-2-trifluoromethyl1-8-(2,4,6-trimethyl-phenyl)-5,6,7,8-tetrahydro-imidazo[1,2-a]pyrimidine, Scheme 7: (KK)

Prepared as described for the example above. LC/MS: $t_R$=1.5 min., MS: [M+H]=407.

EXAMPLE 63

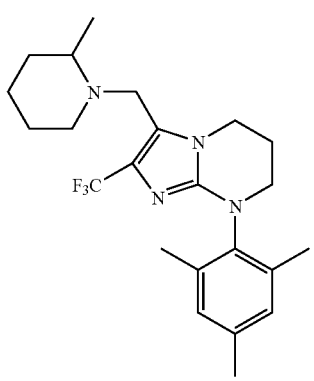

3-(2-Methyl-piperidin-1-ylmethyl)-2-trifluoromethyl-8-(2,4,6-trimethyl-phenyl)-5,6,7,8-tetrahydro-imidazo[1,2-a]pyrimidine, Scheme 7: (KK)

Prepared as described for the example above. LC/MS: $t_R$=1.4 min., MS: [M+H]=421.

EXAMPLE 64

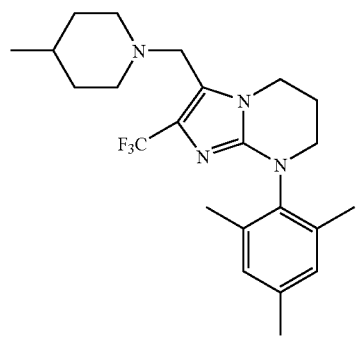

3-(4-Methyl-piperidin-1-ylmethyl)-2-trifluoromethyl-8-(2,4,6-trimethyl-phenyl)-5,6,7,8-tetrahydro-imidazo[1,2-a]pyrimidine, Scheme 7: (KK)

Prepared as described for the example above. LC/MS: $t_R$=1.5 min., MS: [M+H]=421.

EXAMPLE 65

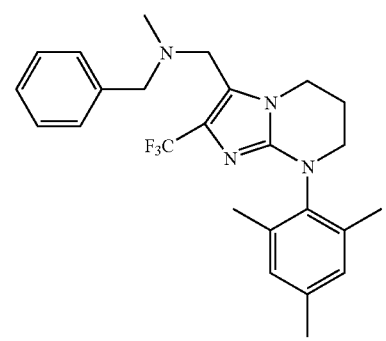

Benzyl-methyl-[2-trifluoromethyl-8-(2,4,6-trimethyl-phenyl)-5,6,7,8-tetrahydro-imidazo[1,2-a]pyrimidin-3-ylmethyl]-amine, Scheme 7: (KK)

Prepared as described for the example above. LC/MS: $t_R$=1.5 min., MS: [M+H]=443.

EXAMPLE 66

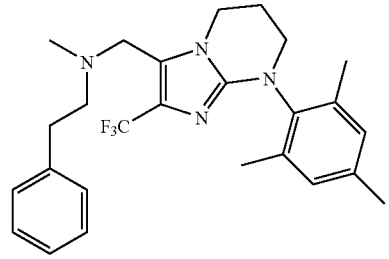

Methyl-phenethyl-[2-trifluoromethyl-8-(2,4,6-trimethyl-phenyl)-5,6,7,8-tetrahydro-imidazo[1,2-a]pyrimidin-3-ylmethyl]-amine, Scheme 7: (KK)

Prepared as described for the example above. LC/MS: $t_R$=1.5 min., MS: [M+H]=457.

EXAMPLE 67

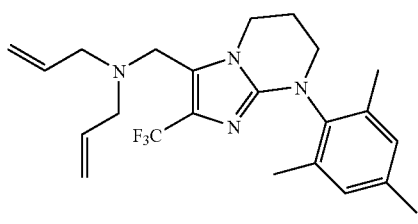

Diallyl-[2-trifluoromethyl-8-(2,4,6-trimethyl-phenyl)-5,6,7,8-tetrahydro-imidazo[1,2-a]pyrimidin-3-ylmethyl]-amine, Scheme 7: (KK)

Prepared as described for the example above. LC/MS: $t_R$=1.4 min., MS: [M+H]=419.

EXAMPLE 68

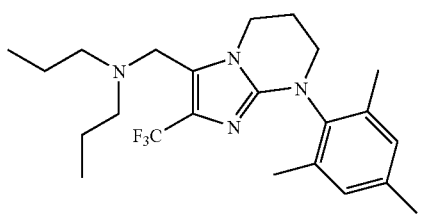

Dipropyl-[2-trifluoromethyl-8-(2,4,6-trimethyl-phenyl)-5,6,7,8-tetrahydro-imidazo[1,2-a]pyrimidin-3-ylmethyl]-amine, Scheme 7: (KK)

Prepared as described for the example above. LC/MS: $t_R$=1.4 min., MS: [M+H]=423.

EXAMPLE 69

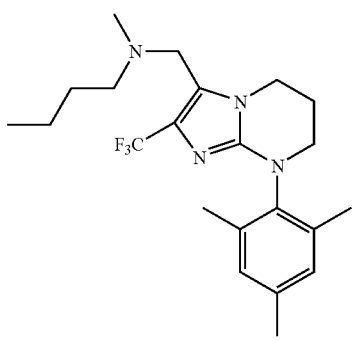

Butyl-methyl-[2-trifluoromethyl-8-(2,4,6-trimethyl-phenyl)-5,6,7,8-tetrahydro-imidazo[1,2-a]pyrimidin-3-ylmethyl]-amine, Scheme 7: (KK)

Prepared as described for the example above. LC/MS: $t_R$=1.4 min., MS: [M+H]=409.

EXAMPLE 70

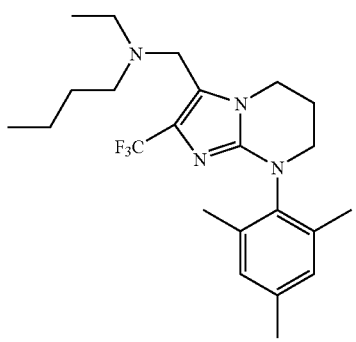

Butyl-ethyl-[2-trifluoromethyl-8-(2,4,6-trimethyl-phenyl)-5,6,7,8-tetrahydro-imidazo[1,2-a]pyrimidin-3-ylmethyl]-amine, Scheme 7: (KK)

Prepared as described for the example above. LC/MS: $t_R$=1.4 min., MS: [M+H]=423.

EXAMPLE 71

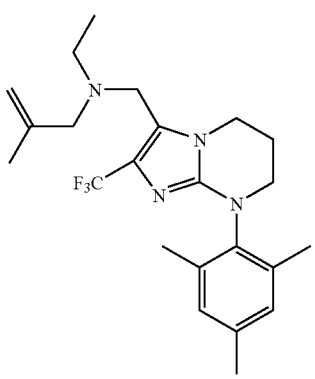

Ethyl-(2-methyl-allyl)-[2-trifluoromethyl-8-(2,4,6-trimethyl-phenyl)-5,6,7,8 tetrahydro-imidazo[1,2-a]pyrimidin-3-ylmethyl]-amine, Scheme 7: (KK)

Prepared as described for the example above. LC/MS: $t_R$=1.6 min., MS: [M+H]=421.

EXAMPLE 72

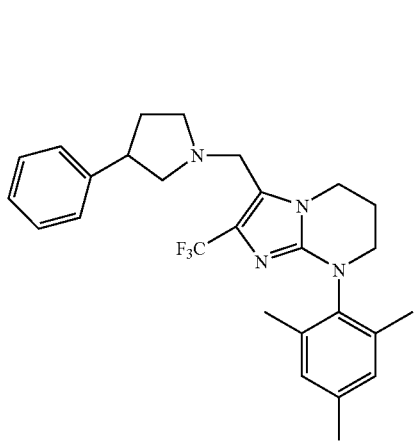

3-(3-Phenyl-pyrrolidin-1-ylmethyl)-2-trifluoromethyl-8-(2,4,6-trimethyl-phenyl)-5,6,7,8-tetrahydro-imidazo[1,2-a]pyrimidine, Scheme 7: (KK)

Prepared as described for the example above. LC/MS: $t_R$=1.8 min., MS: [M+H]=469.

EXAMPLE 73

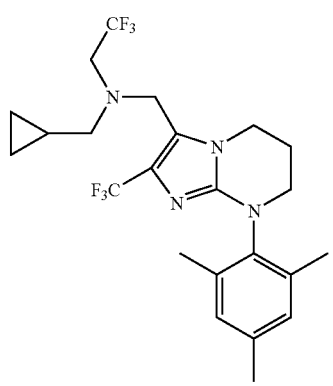

Cyclopropylmethyl-(2,2,2-trifluoro-ethyl)-[2-trifluoromethyl-8-(2,4,6-trimethyl-phenyl)-5,6,7,8-tetrahydro-imidazo[1,2-a]pyrimidin-3-ylmethyl]-amine, Scheme 7: (KK)

Prepared as described for the example above. LC/MS: $t_R$=1.8 min., MS: [M+H]=475.

EXAMPLE 74

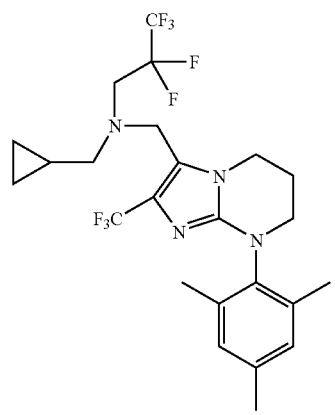

Cyclopropylmethyl-(2,2,3,3-pentafluoro-propyl)-[2trifluoromethyl-8-(2,4,6-trimethyl-phenyl)-5,6,7,8-tetrahydro-imidazo[1,2-a]pyrimidin-3-ylmethyl]-amine, Scheme 7: (KK)

Prepared as described for the example above. LC/MS: $t_R$=1.9 min., MS: [M+H]=525.

EXAMPLE 75

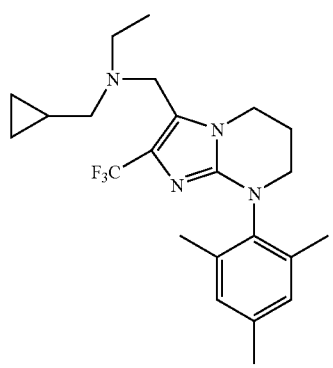

Cyclopropylmethyl-ethyl-[2-trifluoromethyl-8-(2,4,6-trimethyl-phenyl)-5,6,7,8-tetrahydro-imidazo[1,2-a]pyrimidin-3-ylmethyl]-amine, Scheme 7: (KK)

Prepared as described for the example above. LC/MS: $t_R$=1.3 min., MS: [M+H]=421.

EXAMPLE 76

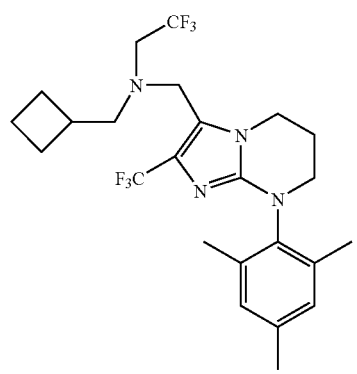

Cyclobutylmethyl-(2,2,2-trifluoro-ethyl)-[2-trifluoromethyl-8-(2,4,6-trimethyl-phenyl)-5,6,7,8-tetrahydro-imidazo[1,2-a]pyrimidin-3-ylmethyl]-amine, Scheme 7: (KK)

Prepared as described for the example above. LC/MS: $t_R$=1.9 min., MS: [M+H]=489.

EXAMPLE 77

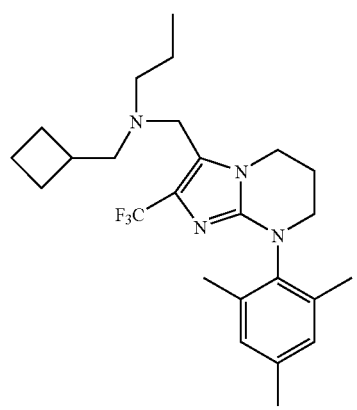

Cyclobutylmethyl-propyl-[2-trifluoromethyl-8-(2,4,6-trimethyl-phenyl)-5,6,7,8-tetrahydro-imidazo[1,2-a]pyrimidin-3-ylmethyl]-amine, Scheme 7: (KK)

Prepared as described for the example above. LC/MS: $t_R$=1.7 min., MS: [M+H]=449.

EXAMPLE 78

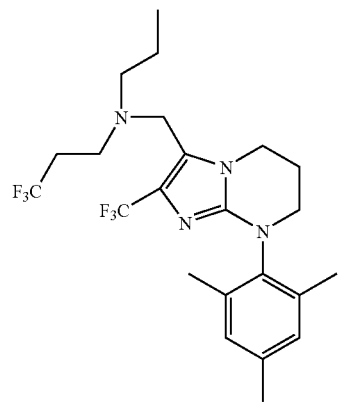

Propyl-[2-trifluoromethyl-8-(2,4,6-trimethyl-phenyl)-5,6,7,8-tetrahydro-imidazo[1,2-a]pyrimidin-3-ylmethyl]-(3,3,3-trifluoro-propyl)-amine, Scheme 7: (KK)

Prepared as described for the example above. LC/MS: $t_R$=1.8 min., MS: [M+H]=477.

EXAMPLE 79

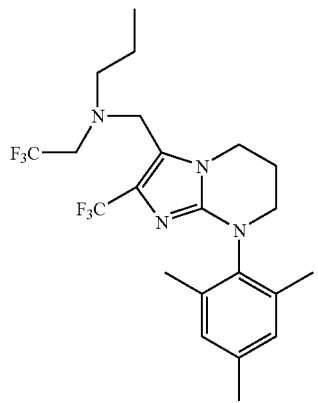

Propyl-(2,2,2-trifluoro-ethyl)-[2-trifluoromethyl-8-(2,4,6-trimethyl-phenyl)-5,6,7,8-tetrahydro-imidazo[1,2-a]pyrimidin-3-ylmethyl]-amine, Scheme 7: (KK)

Prepared as described for the example above. LC/MS: $t_R$=1.9 min., MS: [M+H]=463.

EXAMPLE 80

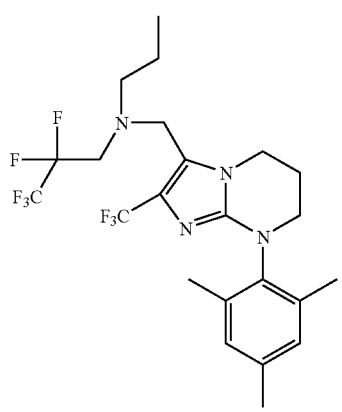

(2,2,3,3,3-Pentafluoro-propyl)-propyl-[2-trifluoromethyl-8-(2,4,6-trimethyl-phenyl)-5,6,7,8-tetrahydro-imidazo[1,2-a]pyrimidin-3-ylmethyl]-amine, Scheme 7: (KK)

Prepared as described for the example above. LC/MS: $t_R$=2.0 min., MS: [M+H]=513.

EXAMPLE 81

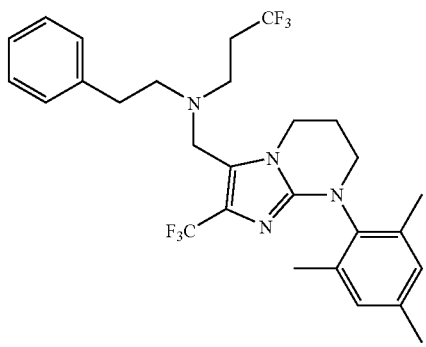

Phenethyl-[2-trifluoromethyl-8-(2,4,6-trimethyl-phenyl)-5,6,7,8-tetrahydro-imidazo[1,2-a]pyrimidin-3-ylmethyl]-(3,3,3-trifluoro-propyl)-amine, Scheme 7: (KK)

Prepared as described for the example above. LC/MS: $t_R$=2.0 min., MS: [M+H]=539.

EXAMPLE 82

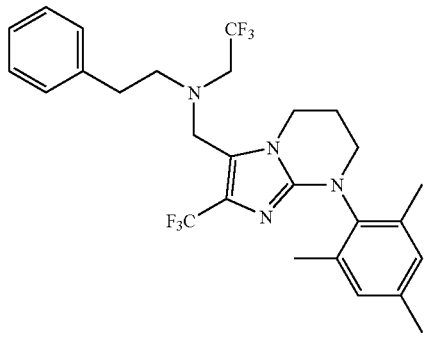

Phenethyl-(2,2,2-trifluoro-ethyl)-[2-trifluoromethyl-8-(2,4,6-trimethyl-phenyl)-5,6,7,8-tetrahydro-imidazo[1,2-a]pyrimidin-3-ylmethyl]-amine, Scheme 7: (KK)

Prepared as described for the example above. LC/MS: $t_R$=1.9 min., MS: [M+H]=525.

EXAMPLE 83

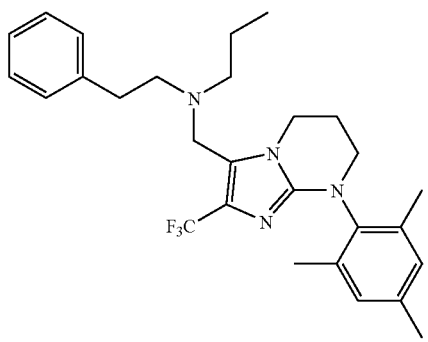

Phenethyl-propyl-[2-trifluoromethyl-8-(2,4,6-trimethyl-Phenyl)-5,6,7,8-tetrahydro-imidazo[1,2-a]pyrimidin-3-ylmethyl]-amine, Scheme 7: (KK)

Prepared as described for the example above. LC/MS: $t_R$=1.8 min., MS: [M+H]=485.

EXAMPLE 84

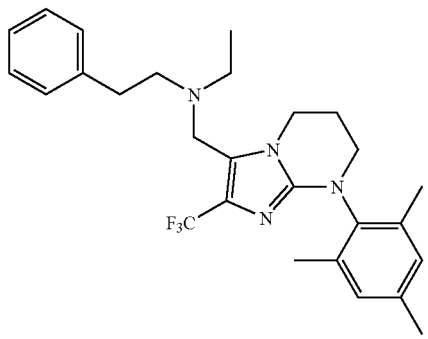

Ethyl-phenethyl-[2-trifluoromethyl-8-(2,4,6-trimethyl-phenyl)-5,6,7,8-tetrahydro-imidazo[1,2-a]pyrimidin-3-ylmethyl]-amine, Scheme 7: (KK)

Prepared as described for the example above. LC/MS: $t_R$=1.7 min., MS: [M+H]=471.

EXAMPLE 85

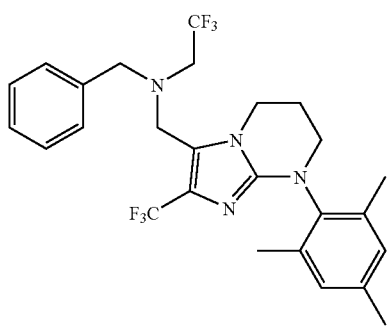

Benzyl-(2,2,2-trifluoro-ethyl)-[2-trifluoromethyl-8-(2,4,6-trimethyl-phenyl)-5,6,7,8-tetrahydro-imidazo[1,2-a]pyrimidin-3-ylmethyl]-amine, Scheme 7: (KK)

Prepared as described for the example above. LC/MS: $t_R$=1.8 min., MS: [M+H]=511.

EXAMPLE 86

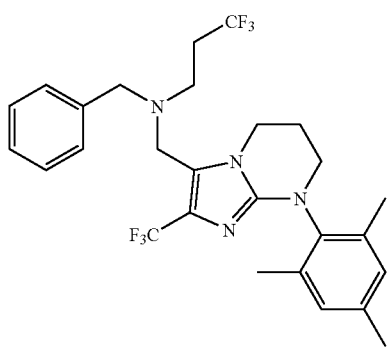

Benzyl-[2-trifluoromethyl-8-(2,4,6-trimethyl-phenyl)-5,6,7,8-tetrahydro-imidazo[1,2-a]pyrimidin-3-ylmethyl]-(3,3,3-trifluoro-propyl)-amine, Scheme 7: (KK)

Prepared as described for the example above. LC/MS: $t_R$=1.8 min., MS: [M+H]=525.

EXAMPLE 87

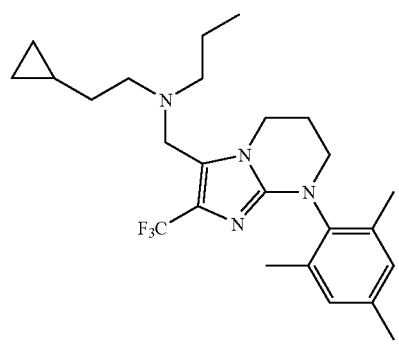

(2-Cyclopropyl-ethyl)-propyl-[2-trifluoromethyl-8-(2,4,6-trimethyl-phenyl)-5,6,7,8-tetrahydro-imidazo[1,2-a]pyrimidin-3-ylmethyl]-amine, Scheme 7: (KK)

Prepared as described for the example above. LC/MS: $t_R$=1.7 min., MS: [M+H]=449.

EXAMPLE 88

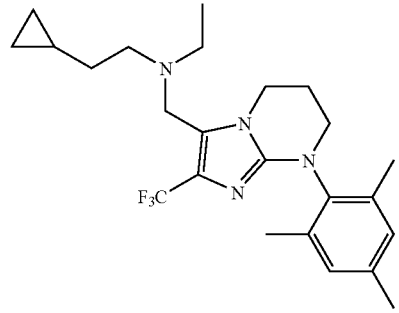

(2-Cyclopropyl-ethyl)-ethyl-[2-trifluoromethyl-8-(2,4,6-trimethyl-phenyl)-5,6,7,8-tetrahydro-imidazo[1,2-a]pyrimidin-3-ylmethyl]-amine, Scheme 7: (KK)

Prepared as described for the example above. LC/MS: $t_R$=1.5 min., MS: [M+H]=435.

EXAMPLE 89

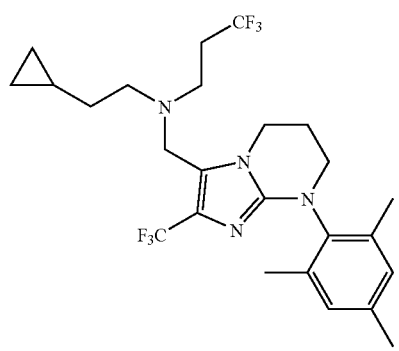

(2-Cyclopropyl-ethyl)-[2-trifluoromethyl-8-(2,4,6-trimethyl-phenyl)-5,6,7,8-tetrahydro-imidazo[1,2-a]pyrimidin-3-ylmethyl]-(3,3,3-trifluoro-propyl)-amine, Scheme 7: (KK)

Prepared as described for the example above. LC/MS: $t_R$=2.0 min., MS: [M+H]=503.

EXAMPLE 90

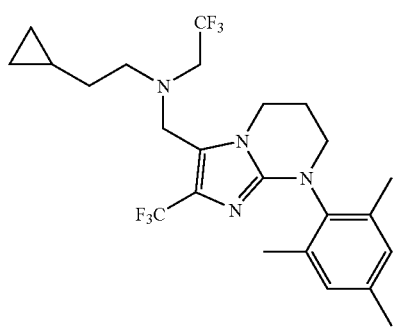

(2-Cyclopropyl-ethyl)-(2,2,2-trifluoro-ethyl)-[2-trifluoromethyl-8-(2,4,6-trimethyl-phenyl)-5,6,7,8-tetrahydro-imidazo[1,2-a]pyrimidin-3-ylmethyl]-amine, Scheme 7: (KK)

Prepared as described for the example above. LC/MS: $t_R$=1.8 min., MS: [M+H]=489.

EXAMPLE 91

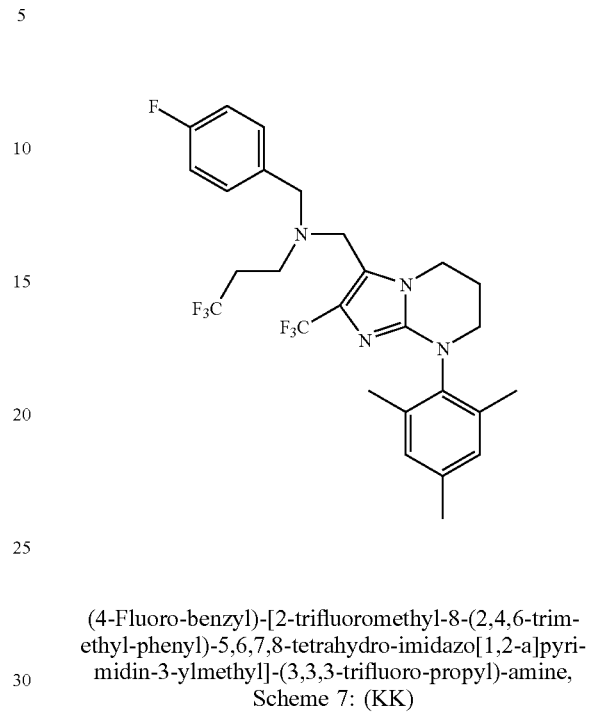

(4-Fluoro-benzyl)-[2-trifluoromethyl-8-(2,4,6-trimethyl-phenyl)-5,6,7,8-tetrahydro-imidazo[1,2-a]pyrimidin-3-ylmethyl]-(3,3,3-trifluoro-propyl)-amine, Scheme 7: (KK)

Prepared as described for the example above. LC/MS: $t_R$=1.8 min., MS: [M+H]=543.

EXAMPLE 92

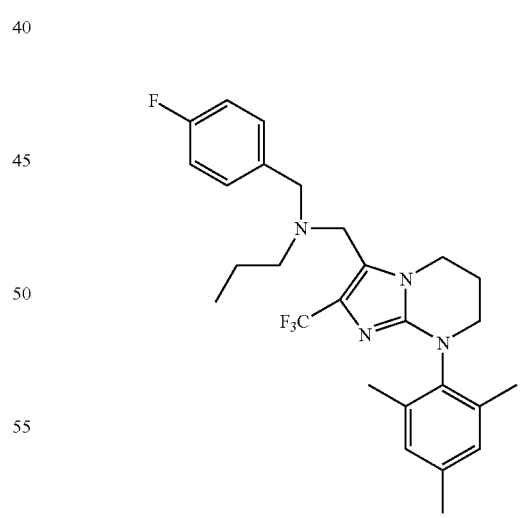

(4-Fluoro-benzyl)-propyl-[2-trifluoromethyl-8-(2,4,6-trimethyl-phenyl)-5,6,7,8-tetrahydro-imidazo[1,2-a]pyrimidin-3-ylmethyl]-amine, Scheme 7: (KK)

Prepared as described for the example above. LC/MS: $t_R$=1.7 min., MS: [M+H]=489.

EXAMPLE 93

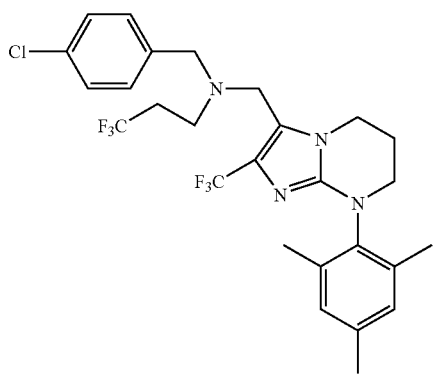

(4-Chloro-benzyl)-[2-trifluoromethyl-8-(2,4,6-trimethyl-phenyl)-5,6,7,8-tetrahydro-imidazo[1,2-a]pyrimidin-3-ylmethyl]-(3,3,3-trifluoro-propyl)-amine, Scheme 7: (KK)

Prepared as described for the example above. LC/MS: $t_R$=1.9 min., MS: [M+H]=559.

EXAMPLE 94

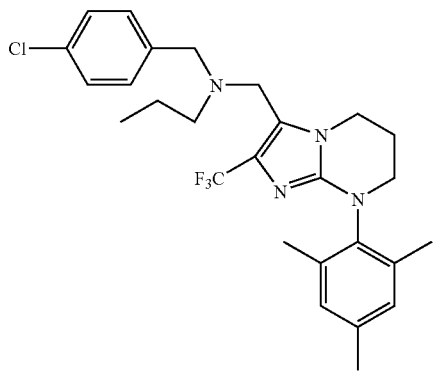

(4-Chloro-benzyl)-propyl-[2-trifluoromethyl-8-(2,4,6-trimethyl-phenyl)-5,6,7,8-tetrahydro-imidazo[1,2-a]pyrimidin-3-ylmethyl]-amine, Scheme 7: (KK)

Prepared as described for the example above. LC/MS: $t_R$=1.8 min., MS: [M+H]=505.

EXAMPLE 95

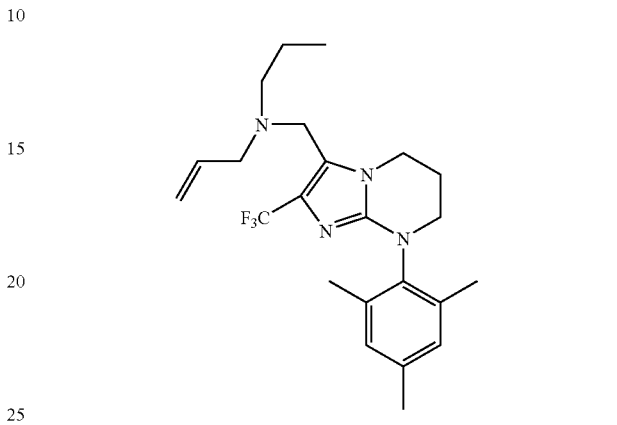

Allyl-propyl-[2-trifluoromethyl-8-(2,4,6-trimethyl-phenyl)-5,6,7,8-tetrahydro-imidazo[1,2-a]pyrimidin-3-ylmethyl]-amine, Scheme 7: (KK)

Prepared as described for the example above. LC/MS: $t_R$=1.5 min., MS: [M+H]=421.

Intermediate 43 Was Used to Prepare Examples 96-138.

EXAMPLE 96

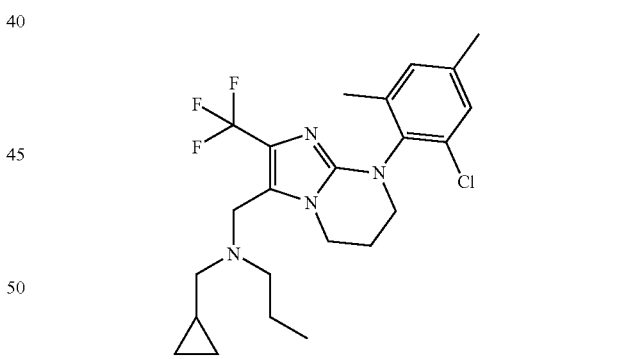

[8-(2-chloro-4,6-dimethyl-phenyl)-2-trifluoromethyl-5,6,7,8-tetrahydro-imidazo[1,2-a]pyrimidin-3-ylmethyl]-cyclopropylmethyl-propyl-amine, Scheme 7: (KK)

To a solution of the appropriate alcohol (0.092 mg, 0.25 mmol) in benzene (20 mL) was added thionyl chloride (0.15 g, 1.28 mmol) at 0° C., under argon. The reaction mixture was stirred for an hour the solvent was removed on a rotary evaporator. Traces of thionyl chloride were removed by co-evaporating with dichloromethane 3 times. The residue was dissolved in dichloromethane (50 mL) and to that solution was added the N-propyl-cyclopropylmethylamine (0.058 g, 0.512 mmol) and diisopropylethyl amine (0.099 g, 0.768 mmol) at rt. The reaction mixture was stirred overnight. Solvent was concentrated, the residue dissolved in methanol (2 mL) and purification carried out by reverse phase preparative HPLC using water, methanol, trifluoroacetic acid to obtain the product (0.084 g, 0.15 mmol, 70%) as colorless oil. LC/MS: $t_R$=1.4 min. [M+H] 455. $^1$H NMR (CD$_3$OD) δ 7.20 (s, 1H), 7.11 (s, 1H), 4.58 (m, 2H), 4.19 (m, 2H), 3.68 (m, 1H), 3.59 (m, 1H), 3.23 (m, 4H), 2.39 (m, 2H), 2.33 (s, 3H), 2.23 (s, 3H), 1.79 (m, 2H), 1.22 (m, 1H), 1.01 (t, J=7.3 Hz, 3H0, 0.83 (m, 2H), 0.50 (m, 2H).

EXAMPLE 97

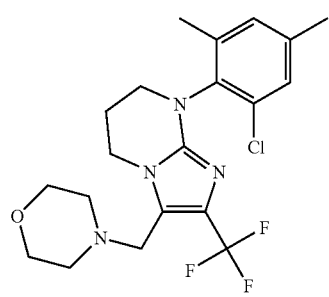

8-(2-chloro-4,6-dimethyl-phenyl)-3-morpholin4-ylmethyl-2-trifluoromethyl-5,6,7,8-tetrahydro-imidazo[1,2-a]pyrimidine, Scheme 7: (KK)

Prepared as described for the example above. LC/MS: $t_R$=1.3 min. [M+H] 429.

EXAMPLE 98

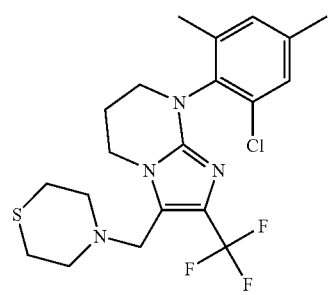

8-(2-chloro-4,6-dimethyl-phenyl)-3-thiomorpholin4-ylmethyl-2-trifluoromethyl-5,6,7,8-tetrahydro-imidazo[1,2-a]pyrimidine, Scheme 7: (KK)

Prepared as described for the example above. LC/MS: $t_R$=1.3 min. [M+H] 445.

EXAMPLE 99

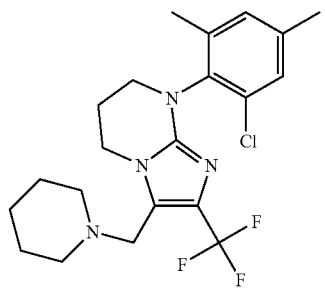

8-(2-chloro-4,6-dimethyl-phenyl)-3-piperidin-1-ylmethyl-2-trifluoromethyl-5,6,7,8-tetrahydro-imidazo[1,2-a]pyrimidine, Scheme 7: (KK)

Prepared as described for the example above. LC/MS: $t_R$=1.4 min. [M+H] 427.

EXAMPLE 100

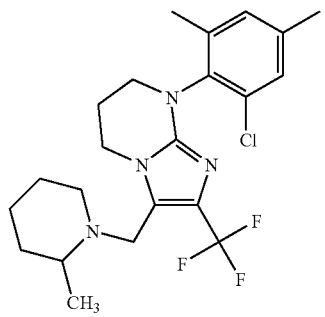

8-(2-Chloro-4,6-dimethyl-phenyl)-3-(2-methyl-piperidin-1-ylmethyl)-2-trifluoromethyl-5,6,7,8-tetrahydro-imidazo[1,2-a]pyrimidine, Scheme 7: (KK)

Prepared as described for the example above. LC/MS: $t_R$=1.4 min. [M+H] 441.

EXAMPLE 101

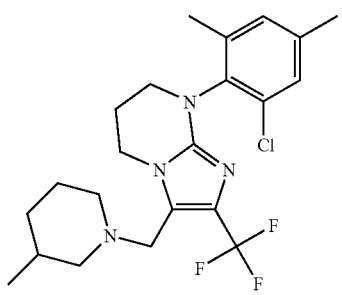

101

8-(2-chloro-4,6-dimethyl-phenyl)-3-(3-methyl-piperidin-1-ylmethyl)-2-trifluoromethyl-5,6,7,8-tetrahydro-imidazo[1,2-a]pyrimidine, Scheme 7: (KK)

Prepared as described for the example above. LC/MS: $t_R$=1.4 min. [M+H] 441.

EXAMPLE 102

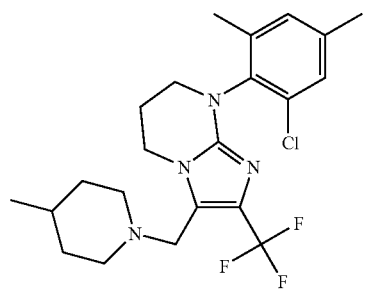

8-(2-chloro-4,6-dimethyl-phenyl)-3-(4-methyl-piperidin-1-ylmethyl)-2-trifluoromethyl-5,6,7,8-tetrahydro-imidazo[1,2-a]pyrimidine, Scheme 7: (KK)

Prepared as described for the example above. LC/MS: $t_R$=1.4 min. [M+H] 441.

EXAMPLE 103

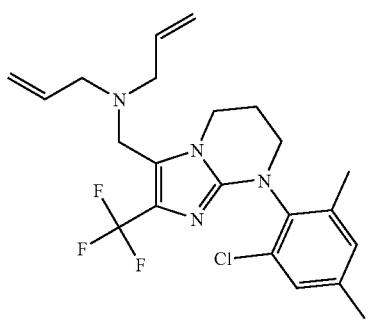

Diallyl-[8-(2-chloro-4,6-dimethyl-phenyl)-2-trifluoromethyl-5,6,7,8-tetrahydro-imidazo[1,2-a]pyrimidin-3-ylmethyl]-amine, Scheme 7: (KK)

Prepared as described for the example above. LC/MS: $t_R$=1.4 min. [M+H] 439.

EXAMPLE 104

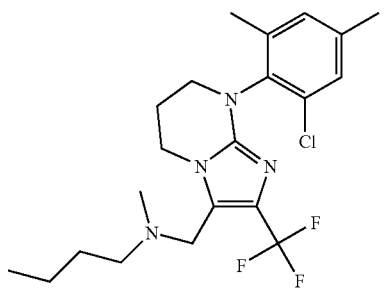

Butyl-[8-(2-chloro-4,6-dimethyl-phenyl)-2-trifluoromethyl-5,6,7,8-tetrahydro-imidazo[1,2-a]pyrimidin-3-ylmethyl]-methyl-amine, Scheme 7: (KK)

Prepared as described for the example above. LC/MS: $t_R$=1.4 min. [M+H] 429.

EXAMPLE 105

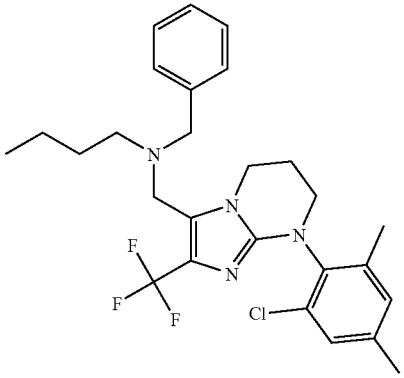

Benzyl-butyl-[8-(2-chloro-4,6-dimethyl-phenyl)-2-trifluoromethyl-5,6,7,8-tetrahydro-imidazo[1,2-a]pyrimidin-3-ylmethyl]-amine, Scheme 7: (KK)

Prepared as described for the example above. LC/MS: $t_R$=1.6 min. [M+H] 506.

EXAMPLE 106

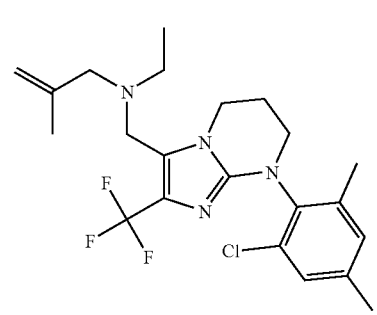

[8-(2-Chloro-4,6-dimethyl-phenyl)-2-trifluoromethyl-5,6,7,8-tetrahydro-imidazo[1,2-a]pyrimidin-3-ylmethyl]-ethyl-(2-methyl-allyl)-amine, Scheme 7: (KK)

Prepared as described for the example above. LC/MS: $t_R$=1.4 min. [M+H] 441.

EXAMPLE 107

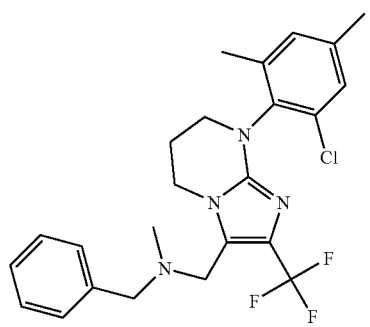

Benzyl-[8-(2-chloro-4,6-dimethyl-phenyl)-2-trifluoromethyl-5,6,7,8-tetrahydro-imidazo[1,2-a]pyrimidin-3-ylmethyl]-methyl-amine, Scheme 7: (KK)

Prepared as described for the example above. LC/MS: $t_R$=1.5 min. [M+H] 463.

EXAMPLE 108

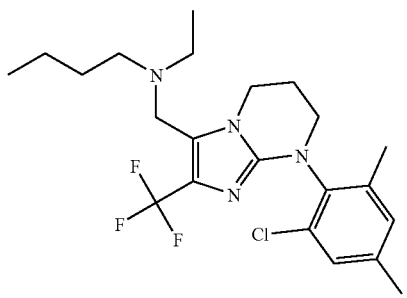

Butyl-[8-(2-chloro-4,6-dimethyl-phenyl)-2-trifluoromethyl-5,6,7,8-tetrahydro-imidazo[1,2-a]pyrimidin-3-ylmethyl]-ethyl-amine, Scheme 7: (KK)

Prepared as described for the example above. LC/MS: $t_R$=1.4 min. [M+H] 443.

EXAMPLE 109

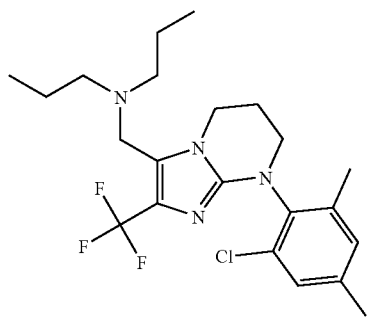

[1-(2-Chloro 4,6-dimethyl-phenyl)-2-trifluoromethyl-5,6,7,8-tetrahydro-imidazo[1,2-a]pyrimidin-3-ylmethyl]-dipropyl-amine, Scheme 7 (KK)

Prepared as described for the example above. LC/MS: $t_R$=1.4 min. [M+H] 443.

EXAMPLE 110

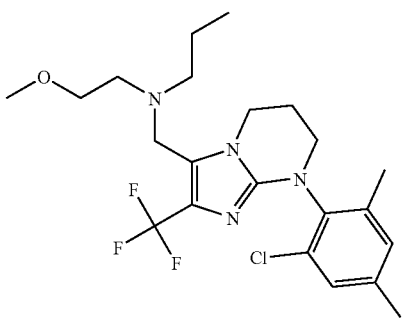

[8-(2-Chloro-4,6-dimethyl-phenyl)-2-trifluoromethyl-5,6,7,8-tetrahydro-imidazo[1,2-a]pyrimidin-3-ylmethyl]-(2-methoxy-ethyl)-propyl-amine, Scheme 7: (KK)

Prepared as described for the example above. LC/MS: $t_R$=1.4 min. [M+H] 459.

EXAMPLE 111

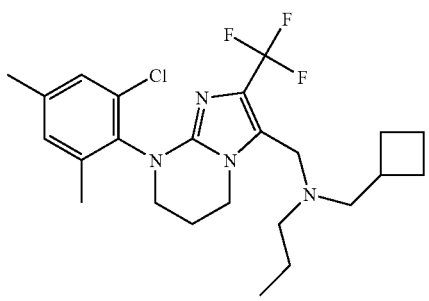

[8-(2-Chloro-4,6-dimethyl-phenyl)-2-trifluoromethyl-5,6,7,8-tetrahydro-imidazo[1,2-a]pyrimidin-3-ylmethyl]-cyclobutylmethyl-propyl-amine, Scheme 7: (KK)

Prepared as described for the example above. LC/MS: $t_R$=1.5 min. [M+H] 470.

EXAMPLE 112

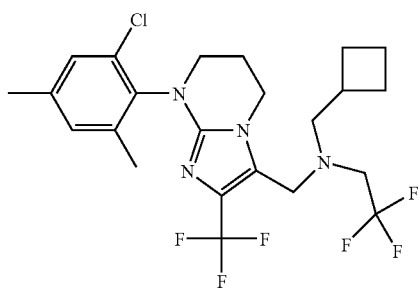

[8-(2-Chloro-4,6-dimethyl-phenyl)-2-trifluoromethyl-5,6,7,8-tetrahydro-imidazo[1,2-a]pyrimidin-3-ylmethyl]-cyclobutylmethyl-(2,2,2-trifluoro-ethyl)-amine, Scheme 7: (KK)

Prepared as described for the example above. LC/MS: $t_R$=1.9 min. [M+H] 509.

EXAMPLE 113

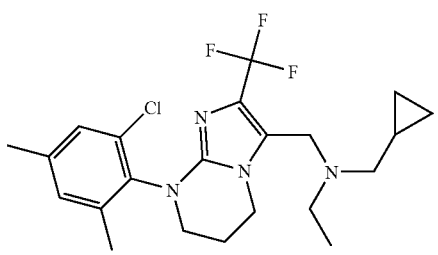

[8-(2-Chloro-4,6-dimethyl-phenyl)-2-trifluoromethyl-5,6,7,8-tetrahydro-imidazo[1,2-a]pyrimidin-3-ylmethyl]-cyclopropylmethyl-ethyl-amine, Scheme 7: (KK)

Prepared as described for the example above. LC/MS: $t_R$=1.4 min. [M+H] 441.

EXAMPLE 114

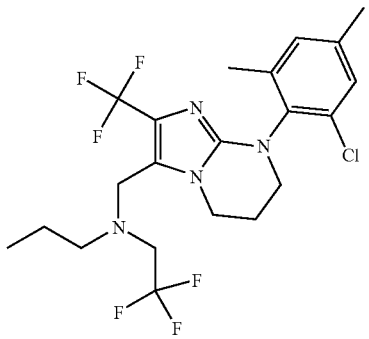

[8-(2-Chloro-4,6-dimethyl-phenyl)-2-trifluoromethyl-5,6,7,8-tetrahydro-imidazo[1,2-a]pyrimidin-3-ylmethyl]-propyl-(2,2,2-trifluoro-ethyl)-amine, Scheme 7: (KK)

Prepared as described for the example above. LC/MS: $t_R$=1.8 min. [M+H] 483.

EXAMPLE 115

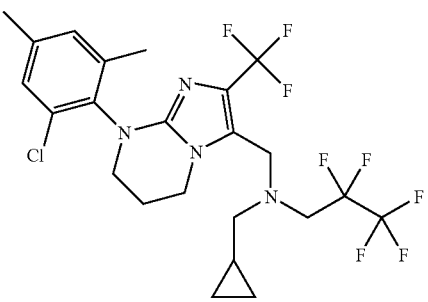

[8-(2-Chloro-4,6-dimethyl-phenyl)-2-trifluoromethyl-5,6,7,8-tetrahydro-imidazo[1,2-a]pyrimidin-3-ylmethyl]-cyclopropylmethyl-(2,2,3,3,3-pentafluoropropyl)-amine, Scheme 7: (KK)

Prepared as described for the example above. LC/MS: $t_R$=1.9 min. [M+H] 545.

EXAMPLE 116

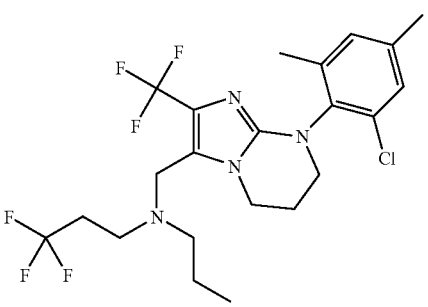

[8-(2-Chloro-4,6-dimethyl-phenyl)-2-trifluorom-
ethyl-5,6,7,8-tetrahydro-imidazo[1,2-a]pyrimidin-3-
ylmethyl]-propyl-(3,3,3-trifluoro-propyl)-amine,
Scheme 7: (KK)

Prepared as described for the example above. LC/MS: $t_R$=1.7 min. [M+H] 497.

EXAMPLE 117

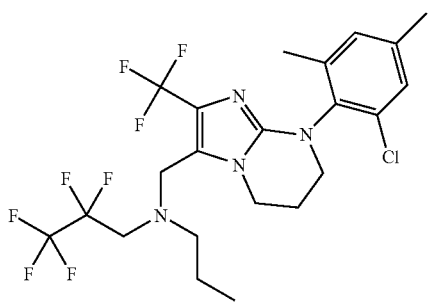

[8-(2-Chloro-4,6-dimethyl-phenyl)-2-trifluorom-
ethyl-5,6,7,8-tetrahydro-imidazo[1,2-a]pyrimidin-3-
ylmethyl]-(2,2,3,3,3-pentafluoro-propyl)-propyl-
amine, Scheme 7: (KK)

Prepared as described for the example above. LC/MS: $t_R$=1.9 min. [M+H] 533.

EXAMPLE 118

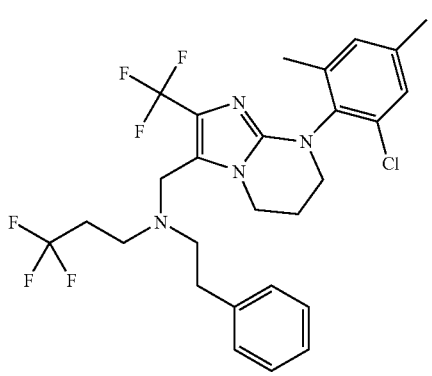

[8-(2-Chloro-4,6-dimethyl-phenyl)-2-trifluorom-
ethyl-5,6,7,8-tetrahydro-imidazo[1,2-a]pyrimidin-3-
ylmethyl]-phenethyl-(3,3,3-trifluoro-propyl)-amine,
Scheme 7: (KK)

Prepared as described for the example above. LC/MS: $t_R$=1.9 min. [M+H] 560.

EXAMPLE 119

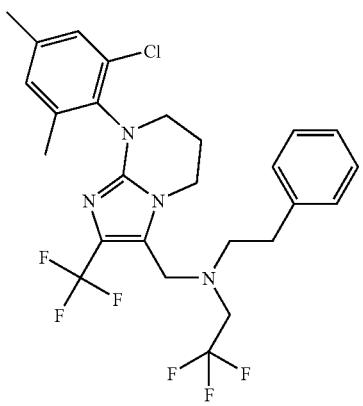

[8-(2-Chloro-4,6-dimethyl-phenyl)-2-trifluorom-
ethyl-5,6,7,8-tetrahydro-imidazo[1,2-a]pyrimidin-3-
ylmethyl]-phenethyl-(2,2,2-trifluoro-ethyl)-amine,
Scheme 7: (KK)

Prepared as described for the example above. LC/MS: $t_R$=1.9 min. [M+H] 545.

EXAMPLE 120

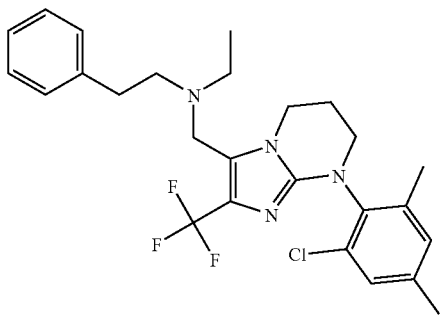

[8-(2-Chloro-4,6-dimethyl-phenyl)-2-trifluorom-
ethyl-5,6,7,8-tetrahydro-imidazo[1,2-a]pyrimidin-3-
ylmethyl]-ethyl-phenethyl-amine, Scheme 7: (KK)

Prepared as described for the example above. LC/MS: $t_R$=1.6 min. [M+H] 491.

EXAMPLE 121

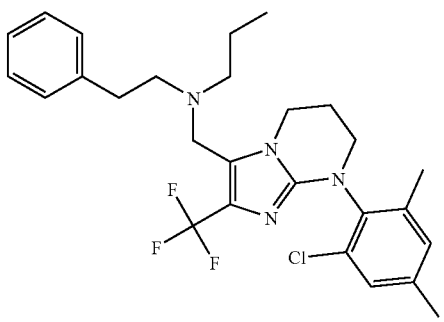

[8-(2-Chloro-4,6-dimethyl-phenyl)-2-trifluorom-
ethyl-5,6,7,8-tetrahydro-imidazo[1,2-a]pyrimidin-3-
ylmethyl]-phenethyl-propyl-amine, Scheme 7: (KK)

Prepared as described for the example above. LC/MS: $t_R$=1.6 min. [M+H] 505.

EXAMPLE 122

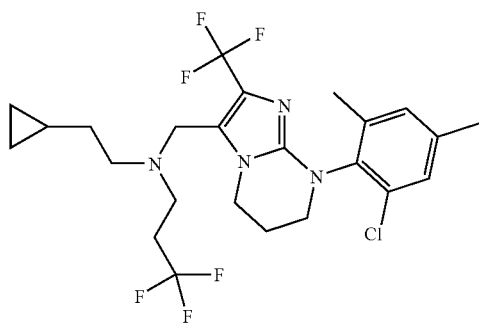

[8-(2-Chloro-4,6-dimethyl-phenyl)-2-trifluorom-
ethyl-5,6,7,8-tetrahydro-imidazo[1,2-a]pyrimidin-3-
ylmethyl]-(2-cyclopropyl-ethyl)-(3,3,3-trifluoro-
propyl)-amine, Scheme 7: (KK)

Prepared as described for the example above. LC/MS: $t_R$=1.8 min. [M+H] 523.

EXAMPLE 123

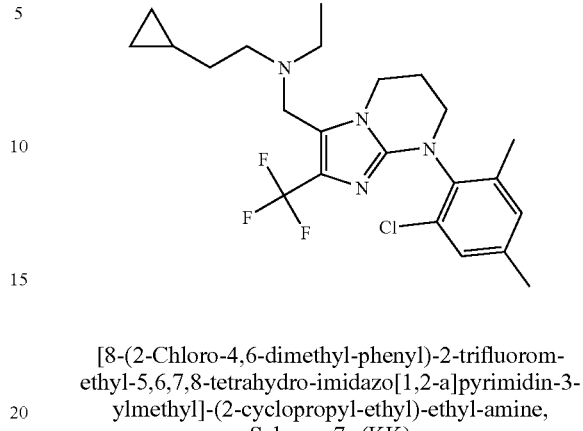

[8-(2-Chloro-4,6-dimethyl-phenyl)-2-trifluorom-
ethyl-5,6,7,8-tetrahydro-imidazo[1,2-a]pyrimidin-3-
ylmethyl]-(2-cyclopropyl-ethyl)-ethyl-amine,
Scheme 7: (KK)

Prepared as described for the example above. LC/MS: $t_R$=1.5 min. [M+H] 455.

EXAMPLE 124

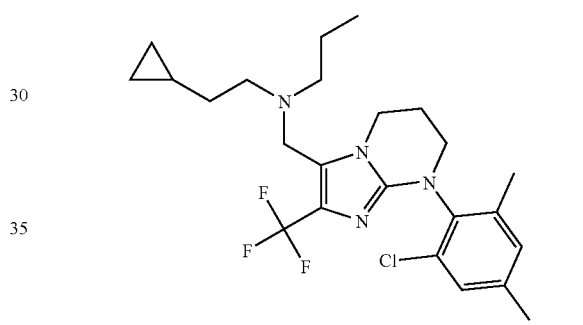

[8-(2-Chloro-4,6-dimethyl-phenyl)-2-trifluorom-
ethyl-5,6,7,8-tetrahydro-imidazo[1,2-a]pyrimidin-3-
ylmethyl]-(2-cyclopropyl-ethyl)-propyl-amine,
Scheme 7: (KK)

Prepared as described for the example above. LC/MS: $t_R$=1.5 min. [M+H] 469.

EXAMPLE 125

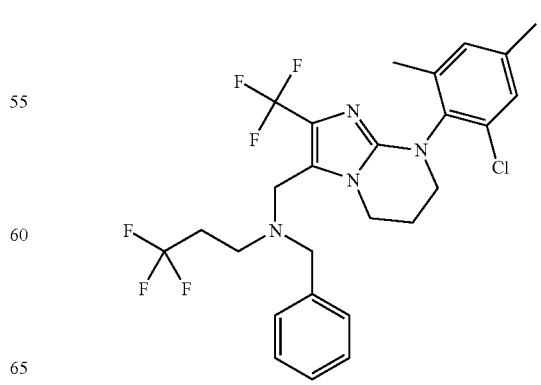

Benzyl-[8-(2-chloro-4,6-dimethyl-phenyl)-2-trifluoromethyl-5,6,7,8-tetrahydro-imidazo[1,2-a]pyrimidin-3-ylmethyl]-(3,3,3-trifluoro-propyl)-amine, Scheme 7: (KK)

Prepared as described for the example above. LC/MS: $t_R$=1.8 min. [M+H] 545.

EXAMPLE 126

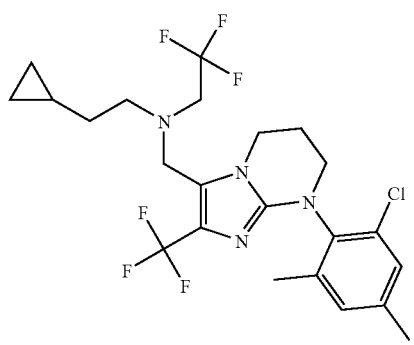

[8-(2-Chloro-4,6-dimethyl-phenyl)-2-trifluoromethyl-5,6,7,8-tetrahydro-imidazo[1,2-a]pyrimidin-3-ylmethyl]-(2-cyclopropyl-ethyl)-(2,2,2-trifluoro-ethyl)-amine, Scheme 7: (KK)

Prepared as described for the example above. LC/MS: $t_R$=1.8 min. [M+H] 509.

EXAMPLE 127

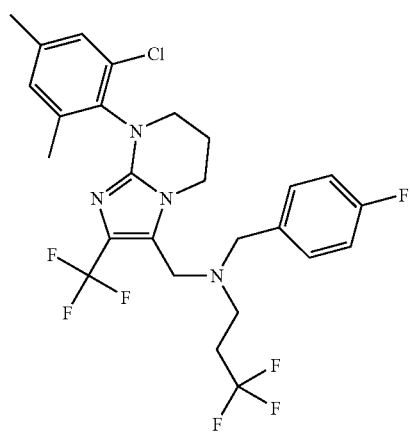

[8-(2-Chloro-4,6-dimethyl-phenyl)-2-trifluoromethyl-5,6,7,8-tetrahydro-imidazo[1,2-a]pyrimidin-3-ylmethyl]-(4-fluoro-benzyl)-(3,3,3-trifluoro-propyl)-amine, Scheme 7: (KK)

Prepared as described for the example above. LC/MS: $t_R$=1.8 min. [M+H] 563.

EXAMPLE 128

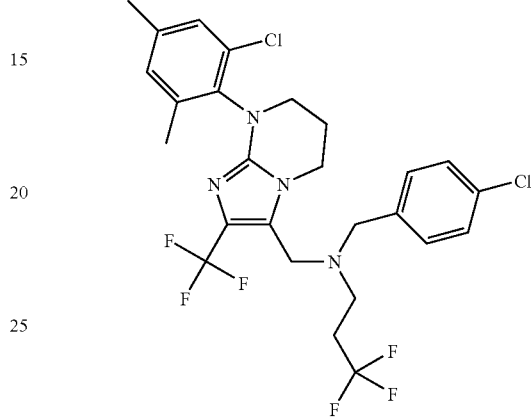

(4-Chloro-benzyl)-[8-(2-chloro-4,6-dimethyl-phenyl)-2-trifluoromethyl-5,6,7,8-tetrahydro-imidazo[1,2-a]pyrimidin-3-ylmethyl]-(3,3,3-trifluoro-propyl)-amine, Scheme 7: (KK)

Prepared as described for the example above. LC/MS: $t_R$=1.8 min. [M+H] 580.

EXAMPLE 129

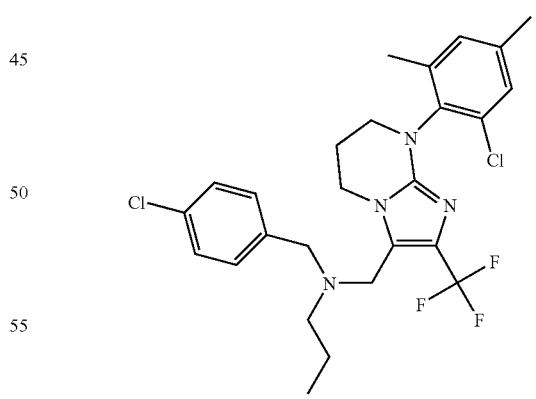

(4-Chloro-benzyl)-[8-(2-chloro-4,6-dimethyl-phenyl)-2-trifluoromethyl-5,6,7,8-tetrahydro-imidazo[1,2-a]pyrimidin-3-ylmethyl]-propyl-amine, Scheme 7: (KK)

Prepared as described for the example above. LC/MS: $t_R$=1.7 min. [M+H] 526.

EXAMPLE 130

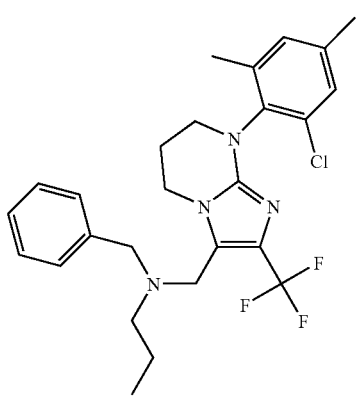

Benzyl-[8-(2-chloro-4,6-dimethyl-phenyl)-2-trifluoromethyl-5,6,7,8-tetrahydro-imidazo[1,2-a]pyrimidin-3-ylmethyl]-propyl-amine, Scheme 7: (KK)

Prepared as described for the example above. LC/MS: $t_R$=1.5 min. [M+H] 491.

EXAMPLE 131

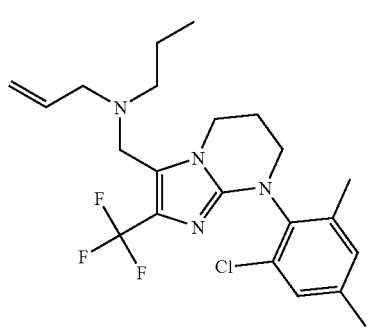

Allyl-[8-(2-chloro-4,6-dimethyl-phenyl)-2-trifluoromethyl-5,6,7,8-tetrahydro-imidazo[1,2-a]pyrimidin-3-ylmethyl]-propyl-amine, Scheme 7: (KK)

Prepared as described for the example above. LC/MS: $t_R$=1.4 min. [M+H] 441.

EXAMPLE 132

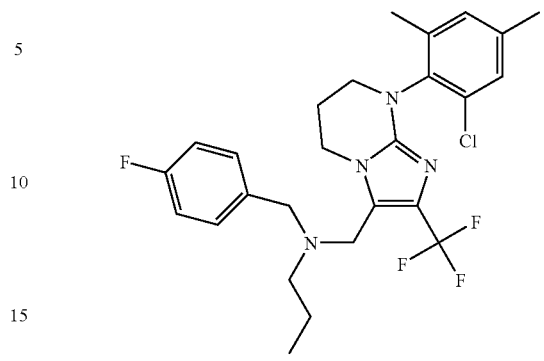

[8-(2-Chloro-4,6-dimethyl-phenyl)-2-trifluoromethyl-5,6,7,8-tetrahydro-imidazo[1,2-a]pyrimidin-3-ylmethyl]-(4-fluoro-benzyl)-propyl-amine, Scheme 7: (KK)

Prepared as described for the example above. LC/MS: $t_R$=1.6 min. [M+H] 509.

EXAMPLE 133

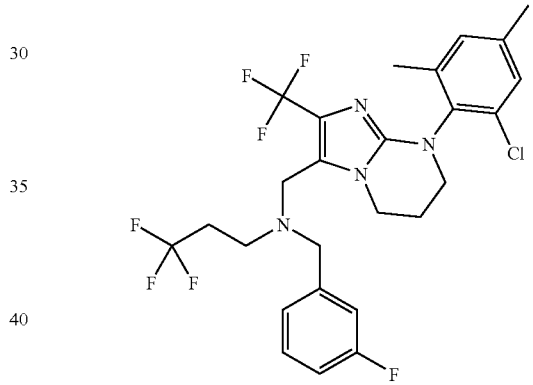

[8-(2-Chloro -4,6-dimethyl-phenyl)-2-trifluoromethyl-5,6,7,8-tetrahydro-imidazo[1,2-a]pyrimidin-3-ylmethyl]-(3-fluoro-benzyl)-(3,3,3-trifluoro-propyl)-amine, Scheme 7: (KK)

Prepared as described for the example above. LC/MS: $t_R$=1.8 min. [M+H] 563.

EXAMPLE 134

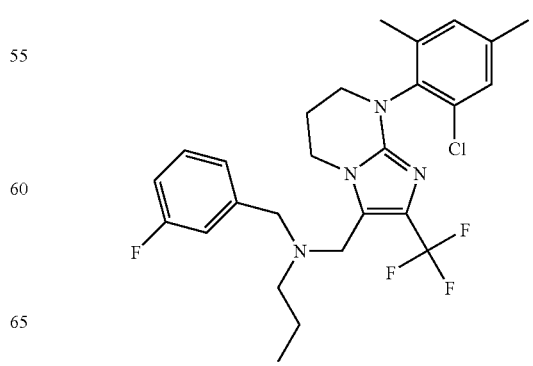

[8-(2-Chloro-4,6-dimethyl-phenyl)-2-trifluoromethyl-5,6,7,8-tetrahydro-imidazo[1,2-a]pyrimidin-3-ylmethyl]-(3-fluoro-benzyl)-propyl-amine, Scheme 7: (KK)

Prepared as described for the example above. LC/MS: $t_R$=1.6 min. [M+H] 509.

EXAMPLE 135

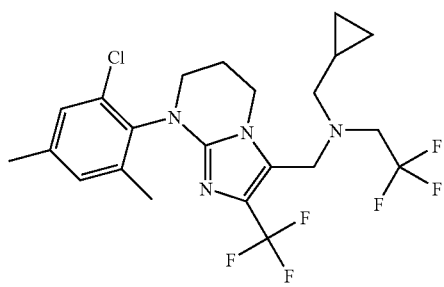

[8-(2-Chloro-4,6-dimethyl-phenyl)-2-trifluoromethyl-5,6,7,8-tetrahydro-imidazo[1,2-a]pyrimidin-3-ylmethyl]-cyclopropylmethyl-(2,2,2-trifluoro ethyl)-amine, Scheme 7: (KK)

Prepared as described for the example above. LC/MS: $t_R$=1.8 min. [M+H] 495.

EXAMPLE 136

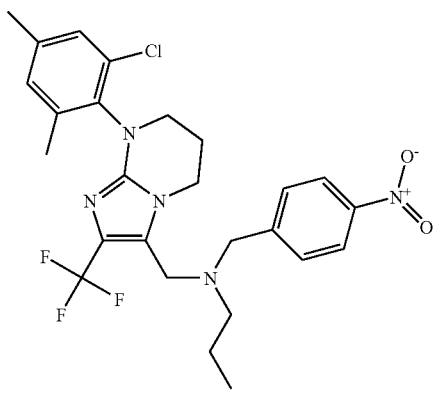

[8-(2-Chloro-4,6-dimethyl-phenyl)-2-trifluoromethyl-5,6,7,8-tetrahydro-imidazo[1,2-a]pyrimidin-3-ylmethyl]-(4-nitro-benzyl)-propyl-amine, Scheme 7: (KK)

Prepared as described for the example above. LC/MS: $t_R$=1.7 min. [M+H] 536.

EXAMPLE 137

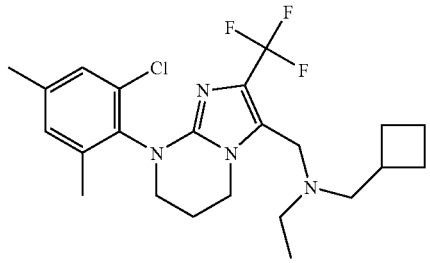

[8-(2-Chloro-4,6-dimethyl-phenyl)-2-trifluoromethyl-5,6,7,8-tetrahydro-imidazo[1,2-a]pyrimidin-3-ylmethyl]-cyclobutylmethyl-ethyl-amine, Scheme 7: (KK)

Prepared as described for the example above. LC/MS: $t_R$=1.4 min. [M+H] 455.

EXAMPLE 138

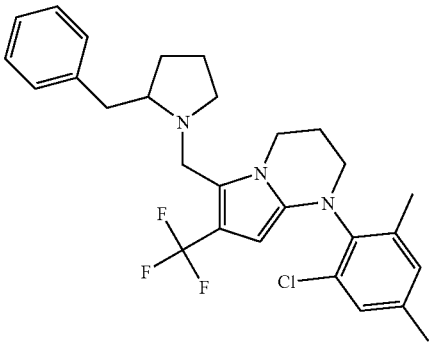

3-(2-Benzyl-pyrrolidin-1-ylmethyl)-8-(2-chloro-4,6-dimethyl-phenyl)-2-trifluoromethyl-5,6,7,8-tetrahydro-imidazo[1,2-a]pyrimidine, Scheme 7: (KK)

LC/MS: $t_R$=1.5 min. [M+H] 503.
The following Intermediates 45-94 may be used to synthesize Examples 139-282.

Intermediate 45

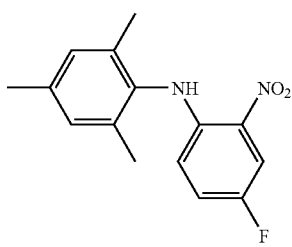

(4-Fluoro-2-nitro-phenyl)-(2,4,6-trimethyl-phenyl)-amine[1], Scheme 1:(B)

A mixture of 2,4,6-trimethlaniline (42.1 mL, 300 mmol), 2,5-difluoro-nitrobenzene (16.3 mL, 150 mmol) and anhydrous potassium fluoride (10.5 g, 180 mmol) was heated and stirred at 180° C. for 60 h. After cooling, the mixture was partitioned between dichloromethane (170 mL) and water (150 mL). The aqueous layer was extracted with dichloromethane (60 mL). The combined organic layers were washed with water and brine. Solvents were removed in vacuo and the residue purified by silica gel chromatography eluting with 40% dichloromethane/hexanes to afford the title compound as a red solid (36.92 g, 100% yield). ¹H NMR (CDCl₃, 300 MHz) δ 9.00 (s, 1H), 7.93 (dd, J=9.1, 3.0 Hz, 1H), 7.12-7.05 (m, 1H), 6.99 (s, 2H), 6.37 (dd, J=9.4, 4.7 Hz, 1H), 2.33 (s, 3H), 2.14 (s, 6H); ¹³C NMR (CDCl₃, 75 MHz) δ 154.6, 151.4, 141.8, 137.6, 136.3, 132.6, 129.6, 124.9 (d, J=23.8 Hz), 116.5 (d, J=7.0Hz), 111.75 (d, J=26.2 Hz).

Intermediate 46

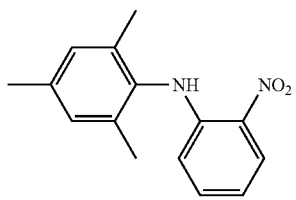

(2-Nitro-phenyl)-(2,4,6-trimethyl-phenyl)-amine:³, Scheme 1: (B)

Prepared as described for the example above. Chromatography using dichloromethane/hexanes (30%) as eluent and recrystallization from anhydrous ethanol afforded the title compound as orange needle crystals (15.4 g, 40% yield).

¹H NMR (CDCl₃, 300 MHz) δ 9.13 (br s, 1H), 8.23 (d, J=8.4 Hz, 1H), 7.28 (t, J=7.2 Hz, 1H), 7.00 (s, 2H), 6.70 (t, J=7.2 Hz, 1H), 6.39 (d, J=8.4 Hz, 1H), 2.35 (s, 3H), 2.16 (s, 6H).

Intermediate 47

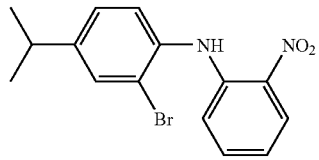

(2-Bromo4-isopropyl-phenyl)-(2-nitro-phenyl)-amine, Scheme 1: (B)

Prepared as described for the example above. Chromatography using dichloromethane/hexanes (20%) as eluent and vacuum distillation to remove unreacted 2-bromo-4-isopropylaniline afforded the title compound as a red solid (12 g, 24% yield). ¹H NMR (CDCl₃, 300 MHz) δ 9.41 (br s, 1H), 8.21 (dd, J=8.6, 1.6 Hz, 1H), 7.54 (d, J=2.0 Hz, 1H), 7.38-7.33 (m, 2H), 7.20 (dd, J=8.1, 2.0 Hz, 1H), 7.08 (dd, J=8.6, 1.0 Hz, 1H), 6.81 (t, J=7.0 Hz, 1H), 2.92 (septet, J=7.0 Hz, 1H), 1.27 (d, J=6.9 Hz, 6H).

Intermediate 48

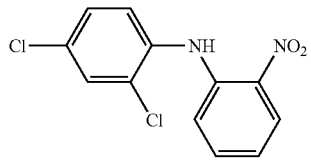

(2,4-Dichloro-phenyl)-(2-nitro-phenyl)-amine, Scheme 1: (B)

Prepared as described for the example above. Chromatography using dichloromethane/hexanes (10% and 20%) as eluent and recrystallization from 95% ethanol afforded the title compound as red needle crystals (8.5 g, 20% yield). ¹H NMR (CDCl₃, 400 MHz) δ 9.39 (s, 1H), 8.22 (dd, J=8.5, 1.5 Hz, 1H), 7.51 (d, J=2.3 Hz, 1H), 7.45-7.38 (m, 2H), 7.27 (dd, J=8.6, 2.3 Hz, 1H), 7.13 (dd, J=8.6, 1.0 Hz, 1H), 6.88 (td, J=7.8, 1.2 Hz, 1H); ¹³C NMR (CDCl₃, 100 MHz) δ 141.0, 135.7, 135.1, 134.6, 130.5, 130.3, 129.3, 127.9, 126.8, 124.8, 118.9, 116.2.

Intermediate 49

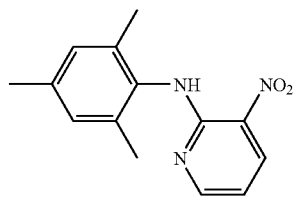

(3-Nitro-pyridin-2-yl)-(2,4,6-trimethyl-phenyl)-amine, Scheme 1: (B)

A mixture of 2-chloro-3-nitro-pyridine (24.05 g, 152 mmol), 2,4,6-trimethylaniline (60 ml, 427 mmol), and Cs₂CO₃ (59.4 g, 182.4 mmol) was heated at 100° C. For 24 h. Flash chromatography using 1) methylene chloride/Hexanes (1:4) and 2) methylene chloride, followed by recrystallization from 95% ethanol. The title compound was obtained as an orange-yellow crystals (17.0 g, 44% yield). ¹H NMR (CDCl₃, 5 MHz) δ 9.38 (s, 1H), 8.51 (d, J=5.8 Hz, 1H), 8.38 (s, 1H), 7.00 (s, 2H), 6.73 (s, 1H), 2.34 (s, 3H), 2.18(s, 6H); ¹³C NMR (CDCl₃, 100 MHz) δ 156.2, 152.1, 137.2, 135.7, 135.4, 132.3, 129.1, 128.3, 112.8, 21.1, 18.5.

Intermediate 50

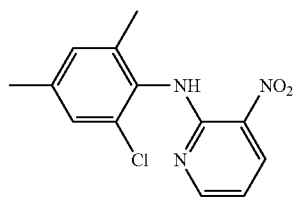

(2-chloro-4,6-dimethylphenyl)-(3-nitro-pyridin-2-yl)-amine, scheme 1: (B)

A mixture of 2-chloro-3-nitro-pyridine (55.8 g, 352 mmol), 2-chloro-4,6-trimethylaniline (110 g, 704 mmol), and KF (28.6 g, 493 mmol) was heated at 190° C. For 40 h. After cooling to room temperature, the mixture was extracted with methylene chloride and IN NaOH. The combined organic layers were washed with water and brine, then dried over MgSO₄. Solvents were removed in vacuo, and the residue was subjected to vacuum distillation to remove unreacted 2-chloro-4,6-trimethylaniline. The resulting brownish solid was subjected to flash chromatography using 1) methylene chloride/hexanes (1:1) and 2) methylene chloride, followed by recrystallization from 95% ethanol. The title compound was obtained as yellow crystals (9.8 g, 10% yield). $^1$H NMR (CDCl₃, 500 MHz) δ 9.39 (br s, 1H), 8.51 (dd, J=8.3, 1.8 Hz, 1H), 8.37 (dd, J=4.5, 1.7 Hz, 1H), 7.18 (s, 1H), 7.04 (s, 1H), 6.78 (dd, J=8.3, 4.5 Hz, 1H), 2.33 (s, 3H), 2.21 (s, 3H).

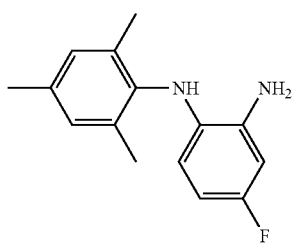

Intermediate 51

4-Fluoro-N$^1$-(2,4,6-trimethyl-phenyl)-benzene-1,2-diamine, scheme 1: (C)

Palladium on carbon (10%) (0.54 g) was added to a solution of (4-fluoro-2-nitro-phenyl)-(2,4,6-trimethyl-phenyl)-amine (5.32 g, 19.4 mmol) in ethyl acetate (40 mL) under nitrogen at room temperature in a 500 mL round-bottomed flask. The flask was evacuated under high vacuum (<2 mm Hg) and purged with hydrogen six times at room temperature, then it was attached to a balloon filled with hydrogen. After the reaction mixture was stirred at room temperature for 4.0 h under 1 atmosphere of hydrogen, the balloon was removed and a stream of nitrogen was bubbled through the reaction mixture for 10 min. The reaction mixture was filtered through a pad of celite and solvents were removed in vacuo to afford the title compound as a red solid (4.74 g, 100% yield). The purity of this compound was determined to be 98% by LC/MS. $^1$H NMR (CDCl₃, 300 MHz) δ 6.93 (s, 2H), 6.52 (dd, J=9.8, 2.7 Hz, 1H), 6.32 (td, J=8.6, 2.7 HZ, 1H), 6.22 (dd, J=8.7, 5.7 Hz, 1H), 2.32 (s, 3H), 2.12 (s, 6H); $^{13}$C NMR (CDCl₃, 75 MHz) δ 159.8, 156.7, 138.2 (d, J=10.5 Hz), 137.6, 133.5, 132.3, 129.5, 117.3 (d, J=9.5 Hz), 105.1 (d, J=22 Hz), 102.9 (d, J=25.5 Hz),20.8, 18.0; Mass spec.: 245.14 (MH⁺)

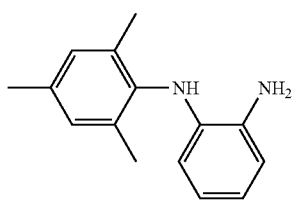

Intermediate 52

N-(2,4,6-Trimethyl-phenyl)-benzene-1,2-diamine, scheme 1: (C)

Prepared as described for the example above. $^1$H NMR (CDCl₃, 300 MHz) δ 6.92 (s, 2H), 6.88 (d, J=7.5 Hz, 1H), 6.78-6.70 (m, 2H), 6.25 (d, J=7.2 Hz, 1H), 4.95 (br s, 2H), 2.31 (s, 3H), 2.13 (s, 6H); Mass spec.: 227.15 (MH⁺)

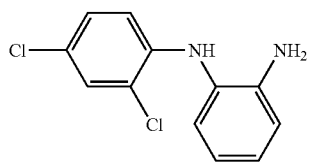

Intermediate 53

N-(2,4-Dichloro-phenyl)-benzene-1,2-diamine, scheme 1: (C)

Prepared as described for the example above. $^1$H NMR (CDCl₃, 300 MHz) δ 7.31-7.00 (m, 4H), 6.89-6.79 (m, 2H), 6.52 (d, J=8.8 Hz, 1H), 5.74 (s, 1H), 4.27 (br s, 2H); Mass spec.: 253.12 (MH⁺)

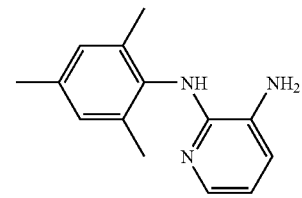

Intermediate 54

N$^2$-(2,4,6-Trimethyl-phenyl)-pyridine-2,3-diamine, scheme 1: (C)

Prepared as described for the example above. Mass spec.: 228.16 (MH⁺)

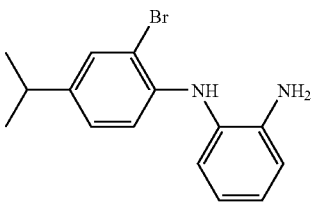

Intermediate 55

N-(2-Bromo4-isopropyl-phenyl)-benzene-1,2-diamine$^2$, scheme 1: (C)

To a solution of (2-bromo-4-isopropyl-phenyl)-(2-nitro-phenyl)-amine (8.2 g, 24.5 mmol) in tetrahydrofuran (35 mL) and water (35 mL) at room temperature, was added NH₄OH (33.6 mL) and Na₂S₂O₄ (21.3 g, 122.5 mmol). After stirring at room temperature for 5 h, water (70 mL) was added and the mixture was extracted with ethyl acetate (175 mL). After separation, the aqueous layer was saturated with NaCl, and extracted with ethyl acetate (3×60 mL). The combined organic layers were washed with sat. NaHCO₃, water, brine, and dried over Na₂SO₄. Solvents were removed in vacuo to afford the title compound a red viscous liquid (5.3 g, 71% yield). The purity of this compound was determined to be 95% by LC/MS and it was used for the next step without further purification. Mass spec.: 307.08 (MH⁺).

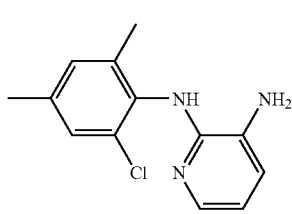

Intermediate 56

N2-(2-Chloro-4,6-dimethyl-phenyl)-pyridine-2,3-diamine, scheme 1: (C)

Prepared as described for the example above. $^1$H NMR (CDCl$_3$, 300 MHz) δ 7.71 (dd, J=5.0, 1.5 Hz, 1H), 7.11 (s, 1H), 6.97 (dd, J=7.5, 1.6 Hz, 1H), 6.96 (s, 1H), 6.67 (dd, J=7.5, 5.0 Hz, 1H), 5.89 (br s, 1H), 3.53 (br s, 2H), 2.29 (s, 3H), 2.13 (s, 3H); Mass spec.: 228.16 (MH⁺)

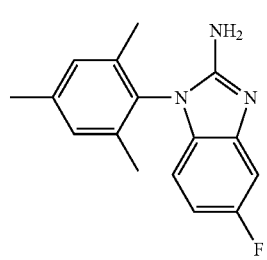

Intermediate 57

5-Fluoro-1-(2,4,6-trimethyl-phenyl)-1H-benzoimidazol-2-ylamine:³, scheme 1: (D)

A solution of cyanogen bromide (2.67 g, 25.2 mmol) in anhydrous ethanol (10 mL) was added at 0° C. to a solution of 4-fluoro-N$^1$-(2,4,6-trimethyl-phenyl)-benzene-1,2-diamine (4.74 g, 19.4 mmol) in anhydrous ethanol (20 mL) under nitrogen. The reaction mixture was warmed up to room temperature for 10 min, then was heated at 155° C. For 40 min with a flow of nitrogen to remove ethanol. Upon cooling to room temperature, the resulting solids were transferred to a separatory funnel via dichloromethane (70 mL), and washed sequentially with 1 N sodium hydroxide (2×35 mL), water and brine. The organic layer was dried over anhydrous sodium sulfate and solvents were removed in vacuo to afford the title compound as a red solid (5.11 g, 98% yield). The purity of this compound was determined to be 95% by LC/MS. $^1$H NMR (CDCl$_3$, 300 MHz) δ 7.12 (dd, J=9.7, 2.4 Hz, 1H), 7.06 (s, 2H), 6.69 (td, J=9.1, 2.4 Hz, 1H), 6.56 (dd, J=8.5, 4.7 Hz, 1H), 2.38 (s, 3H), 1.98 (s, 6H); $^{13}$C NMR (CDCl$_3$, 75 MHz) δ 161.0, 157.9, 154.2, 143.3, 139.9, 137.4, 129.8, 128.8, 107.8 (d, J=10.2 Hz), 106.9 (d, J=25.3 Hz), 103.1 (d, J=25.2 Hz)21.1, 17.5; Mass spec.: 270.17 (MH⁺).

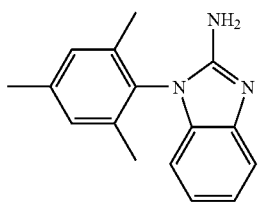

Intermediate 58

1-(2,4,6-Trimethyl-phenyl)-1H-benzoimidazol-2-ylamine, scheme 1: (D)

Prepared as described for the example above. $^1$H NMR (CDCl$_3$, 300 MHz) δ 7.46 (d, J=8.1 Hz, 1H), 7.16 (td, J=7.6, 1.2 Hz, 1H), 7.06 (s, 2H), 7.01 (td, J=7.2, 0.6 Hz, 1H), 6.71 (dd, J=7.8, 0.6 Hz, 1H), 2.38 (s, 3H), 1.98 (s, 6H); Mass spec.: 252.09 (MH⁺)

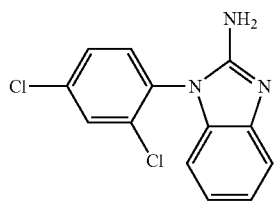

Intermediate 59

1-(2,4-Dichloro-phenyl)-1H-benzoimidazol-2-ylamine, scheme 1: (D)

Prepared as described for the example above. $^1$H NMR (CDCl$_3$, 300 MHz) δ 7.67 (d, J=1.5 Hz, 1H), 7.49-7.41 (m, 2H), 7.23-7.16 (m, 2H), 7.04 (t, J=7.7 Hz, 1H), 6.77 (d, J=7.9 Hz, 1H); Mass spec.: 278.08 (MH⁺)

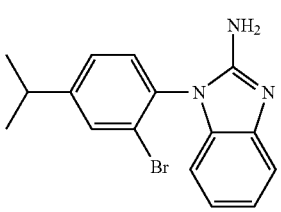

Intermediate 60

1-(2-Bromo4-isopropyl-phenyl)-1H-benzoimidazol-2-ylamine, scheme 1: (D)

Prepared as described for the example above. Mass spec.: 330.08 (MH⁺)

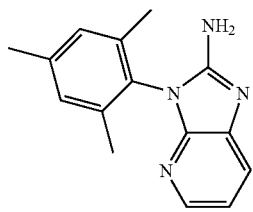

Intermediate 61

3-(2,4,6-Trimethyl-phenyl)-3H-imidazo[4,5-b]pyridin-2-ylamine, scheme 1: (D)

To a mixture of N²-(2,4,6-Trimethyl-phenyl)-pyridine-2,3-diamine (3.05 g, 13.4 mmol), NaHCO₃ (2.03 g, 24.1 mmol) in ethanol (40 mL) at 0° C., was added a solution of BrCN (2.55 g, 24.1 mmol) in ethanol (6 mL). The resulting mixture was stirred at 0° C. For 1 h, room temperature for 8 h, and then 80° C. For 8 h. Ethanol was removed in vacuo and the residue was taken up into a separatory funnel with methylene chloride (100 mL). The mixture was washed sequentially with 1N NaOH, water and brine, then the organic layer was dried over Na₂SO₄. After removing solvents, a brown solid was obtained. By LC-MS, the solid was a mixture of the desired product and the unreacted starting material in a ratio of 4:1 in favor of the desired product. Mass spec.: 253.17 (MH⁺).

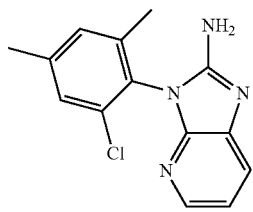

Intermediate 62

3-(2-Chloro-4,6-dimethyl-phenyl)-3H-imidazo[4,5-b]pyridin-2-ylamine, scheme 1: (D)

Prepared as described for the example above. Mass spec.273.20 (MH⁺)

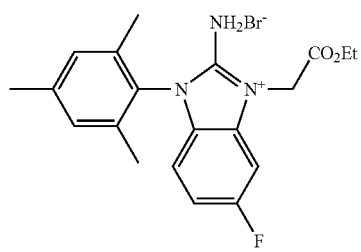

Intermediate 63

3-Ethoxycarbonylmethyl-1-(2,4,6-trimethylphenyl)-2-amino-5-fluoro-benimidazolium bromide:⁴, scheme 1: (E)

Ethyl bromoacetate (2.3 mL, 20.9 mmol) was added at room temperature to a solution of 5-fluoro-1-(2,4,6-trimethyl-phenyl)-1H-benzoimidazol-2-ylamine (5.11 g, 19.0 mmol) in acetone (100 mL). The resulting mixture was heated at reflux for 14 h. Upon cooling to room temperature, acetone was removed in vacuo. Solids were transferred onto a filtering funnel and washed with ether (2×15 mL) to afford the title compound as a pink solid (7.42 g, 90%). The solids were used for the next step without further purification. ¹H NMR (CDCl₃, 300 MHz) δ 8.44 (s, 2H), 7.11 (s, 2H), 7.11-6.96 (m, 2H), 6.78 (dd, J=8.6, 4.1 Hz, 1H), 5.69 (s, 2H), 4.28 (qd, J=7.1, 1.0 Hz, 2H), 2.38 (s, 3H), 2.02 (s, 6H), 1.32 (td, J=7.1, 1.2 Hz, 3H); ¹³C NMR (CDCl₃, 75 MHz) δ 165.8, 162.0, 158.7, 151.1, 142.3, 136.9, 130.7, 126.2, 124.7, 112.4 (d, J=25.0 Hz), 111.2 (d, J=9.4 Hz), 98.7 (d, J=29.2 Hz), 63.0, 46.8, 21.3, 17.4, 14.1.

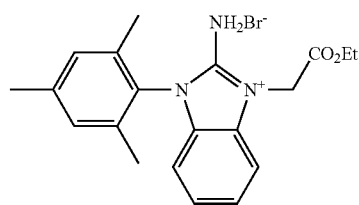

Intermediate 64

3-Ethoxycarbonylmethyl-1-(2,4,6-trimethylphenyl)-2-aminobenimidazolium bromide, scheme 1: (E)

Prepared as described for the example above. ¹H NMR (CDCl₃, 300 MHz) δ 8.21 (s, 2H), 7.37 (dd, J=7.5, 1.2 Hz, 1H), 7.32-7.28 (m, 2H), 7.12 (s, 2H), 6.86 (d, J=7.8 Hz, 1H), 5.71 (s, 2H), 4.29 (q, J=7.2 Hz, 2H), 2.40 (s, 3H), 2.03 (s, 6H), 1.33 (t, J=7.5 Hz, 3H).

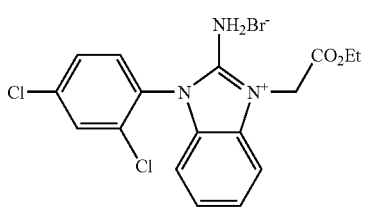

Intermediate 65

3-Ethoxycarbonylmethyl-1-(2,4-dichlorolphenyl)-2-aminobenimidazolium bromide, scheme 1: (E)

Prepared as described for the example above. ¹H NMR (CDCl₃, 300 MHz) δ 9.16 (s, 2H), 7.68 (d, J=1.9 Hz, 1H), 7.60-7.55 (m, 2H), 7.34-7.19 (m, 3H), 6.83 (d, J=7.8 Hz, 1H), 5.55 (s, 2H), 4.26 (q, J=7.6 Hz, 2H), 1.30 (t, J=7.8 Hz, 3H).

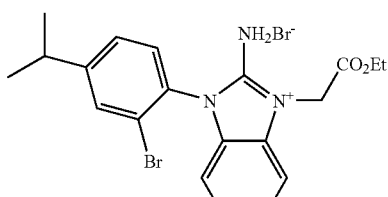

Intermediate 66

2-Amino-3-(2-bromo-4-isopropyl-phenyl)-1-ethoxy-carbonylmethyl-3H-benzoimidazol-1-ium bromide, scheme 1: (E)

Prepared as described for the example above. $^1$H NMR (CDCl$_3$, 300 MHz) δ 8.48 (s, 2H), 7.72 (s, 1H), 7.47 (s, 2H), 7.39-7.24 (m,3H), 6.91 (d, J=7.8 Hz, 1H), 5.66 (s, 2H), 4.30 (q, J=7.1 Hz, 2H), 3.03 (sept., J=6.9 Hz, 1H), 1.32 (d, J=6.9 Hz, 6H), 1.30 (t, J=7.1 Hz, 3H).

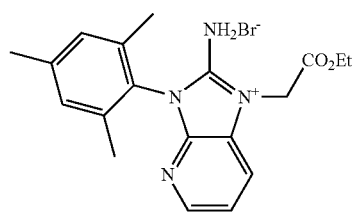

Intermediate 67

2-Amino-1-ethoxycarbonylmethyl-3-(2,4,6-trimethyl-phenyl-3H-imidazo[4,5-b]pyridin-1-ium bromide, scheme 1: (E)

Prepared as described for the example above. Mass spec.: 339.21 (M−HBr+H)$^+$.

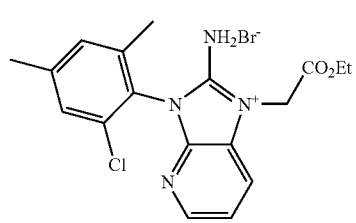

Intermediate 68

2-Amino-3-(2-chloro-4,6-dimethyl-phenyl)-1-ethoxycarbonylmethyl-3H-imidazo[4,5-b]pyridin-1-ium bromide, scheme 1: (E)

Prepared as described for the example above. Mass spec.: 359.20 (M−HBr+H)$^+$.

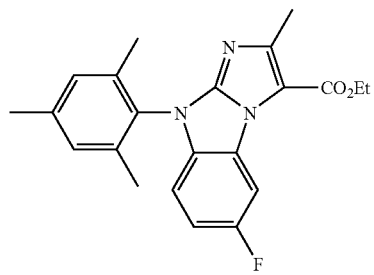

Intermediate 69

5-Fluoro-2-methyl-8-(2,4,6-trimethyl-phenyl)-8H-1,3a,8-triaza-cyclopenta[a]indene-3-carboxylic acid ethyl ester:$^4$, scheme 1: (F)

A mixture of 3-ethoxycarbonylmethyl-1-(2,4,6-trimethylphenyl)-2-amino-5-fluoro-benimidazolium bromide (2.0 g, 4.59 mmol), sodium acetate (0.94 g, 11.4 mmol) and acetic anhydride (14.0 mL) was heated at 160° C. for 20 h. Upon cooling, the mixture was poured into a flask containing ice. While stirring, excess sodium bicarbonate was added to the above mixture in small portions, and the resulting mixture was stirred at room temperature for 6 h. Then, the mixture was extracted with dichloromethane (2×70 mL). The organic extracts were washed with water and dried over anhydrous sodium sulfate. Solvents were removed in vacuo and the residue was subjected to chromatography using ethyl acetate/hexanes (1:9) as eluent to afford the title compound as a white solid (1.33 g, 76% yield). $^1$H NMR (CDCl$_3$, 300 MHz) δ 8.39 (d, J=9.3 Hz, 1H), 7.03 (s, 2H), 6.98 (dd, J=9.0, 2.2 Hz, 1H), 6.81 (dd, J=8.8, 4.5 Hz, 1H), 4.47 (q, J=7.1 Hz, 2H), 2.63 (s, 3H), 2.35 (s, 3H), 1.95 (s, 6H), 1.48 (t, J=7.1 Hz, 3H); $^{13}$C NMR (CDCl$_3$, 75 MHz) δ 161.1, 159.6, 156.4, 153.1, 149.3, 139.7, 136.9, 129.9 (d, J=228 Hz), 129.7, 125.8 (d, J=13.6 Hz), 112.9, 111.1 (d, J=25.0 Hz), 110.4 (d, J=9.5 Hz), 103.2 (d, J=30 Hz), 60.3, 21.1, 17.7, 16.6, 14.7; Mass spec.: 380.21 (MH$^+$).

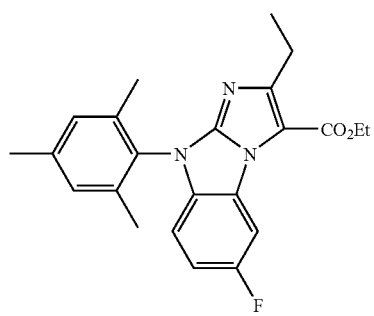

Intermediate 70

2-Ethyl-5-fluoro-8-(2,4,6-trimethyl-phenyl)-8H-1,3a,8-triaza-cyclopenta[a]indene-3-carboxylic acid ethyl ester, scheme 1: (F)

Prepared as described for the example above. ¹H NMR (CDCl₃, 300 MHz) δ 8.38 (dd, J=9.4, 2.4 Hz, 1H), 7.03 (s, 2H), 7.01-6.95 (m, 1H), 6.80 (dd, J=8.8, 4.5 Hz, 1H), 4.47 (q, J=7.1 Hz, 2H), 3.01 (q, J=7.6 Hz, 2H), 2.35 (s, 3H), 1.95 (s, 6H), 1.47 (t, J=7.1 Hz, 3H), 1.27 (t, J=7.6 Hz, 3H); ¹³C NMR (CDCl₃, 75 MHz) δ 161.0, 159.6, 159.0, 156.4, 149.7, 139.7, 136.9, 130.0 (d, J=227 Hz), 129.8, 125.7 (d, J=14.0 Hz), 112.8, 111.1 (d, J=24.9 Hz), 110.4 (d, J=9.6 Hz), 103.3 (d, J=29.6 Hz), 60.3, 23.7, 21.1, 17.7, 14.6, 14.4; Mass spec.: 394.19 (MH⁺)

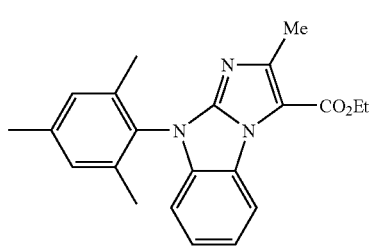

Intermediate 71

2-Methyl-8-(2,4,6-trimethyl-phenyl)-8H-1,3a,8-triaza-cyclopenta[α]indene-3-carboxylic acid ethyl ester, scheme 1: (F)

Prepared as described for the example above. ¹H NMR (CDCl₃, 300 MHz) δ 8.43-8.40 (m, 1H), 7.12-7.06 (m, 2H), 6.85 (s, 2H), 6.73-6.70 (m, 1H), 4.29 (q, J=7.2 Hz, 2H), 2.46 (s, 3H), 2.17 (s, 3H), 1.77 (s, 6H), 1.29 (t, J=7.2 Hz, 3H); ¹³C NMR (CDCl₃, 75 MHz) δ 161.1, 152.6, 148.4, 139.5, 136.9, 135.0, 129.6, 128.5, 125.8, 123.7, 121.3115.3, 113.0, 110.1, 60.1, 21.1, 17.6, 16.6, 14.6; Mass spec.: 362.10 (MH⁺)

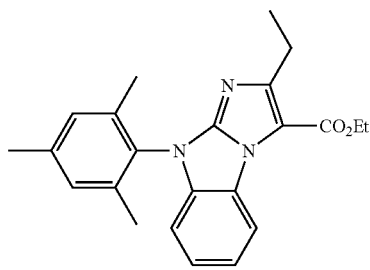

Intermediate 72

2-Ethyl-8-(2,4,6-trimethyl-phenyl)-8H-1,3a8-triaza-cyclopenta[a]indene-3-carboxylic acid ethyl ester, scheme 1: (F)

Prepared as described for the example above. ¹H NMR (CDCl₃, 300 MHz) δ 8.61-8.58 (m, 1H), 7.30-7.23 (m, 2H), 7.03 (s, 2H), 6.91-6.88 (m, 1H), 4.48 (q, J=7.1 Hz, 3H), 3.03 (q, J=7.5 Hz, 2H), 2.36 (s, 3H), 1.96 (s, 6H), 1.48 (t, J=7.2 Hz, 3H), 1.28 (t, J=7.4 Hz); Mass spec.: 376.23 (MH⁺)

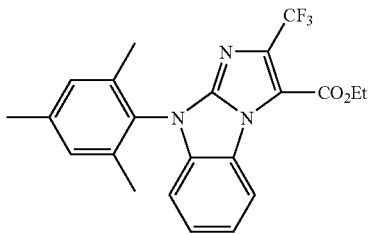

Intermediate 73

2-Trifluoromethyl-8-(2,4,6-trimethyl-phenyl)-8H-1,3a,8-triaza-cyclopenta[a]indene-3-carboxylic acid ethyl ester, scheme 1: (F)

Prepared as described for the example above but in a sealed bomb (170° C., 60 h). ¹H NMR (CDCl₃, 300 MHz) δ 8.76-8.73 (m, 1H), 7.43-7.34 (m, 2H), 7.08 (s, 2H), 7.01-6.98 (m, 1H), 4.54 (q, J=7.12 Hz, 2H), 2.39 (s, 3H), 1.99 (s, 6H), 1.50 (t, J=7.2 Hz, 3H); ¹³C NMR (CDCl₃, 75 MHz) δ 159.1, 147.0, 139.9, 139.1 (q, J=39.0 Hz), 136.9, 135.7, 129.7, 128.0, 125.4, 125.0, 121.9, 120.9 (q, J=268 Hz), 116.4, 110.6, 61.4, 21.0, 17.6, 14.0; Mass spec.: 416.09 (MH⁺)

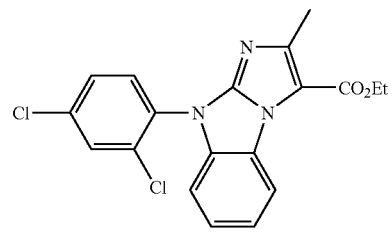

Intermediate 74

8-(2,4-Dichloro-phenyl)-2-methyl-8H-1,3a,8-triaza-cyclopenta[a]indene-3-carboxylic acid ethyl ester, scheme 1: (F)

Prepared as described for the example above. ¹H NMR (CDCl₃, 300 MHz) δ 8.59-8.56 (m, 1H), 7.64 (d, J=2.0 Hz, 1H), 7.53 (d, J=8.5 Hz, 1H), 7.44 (dd, J=8.4, 2.1 Hz, 1H), 7.31-7.24 (m, 2H), 7.02-6.99 (m, 1H), 4.44 (q, J=7.0 Hz, 2H), 2.62 (s, 3H), 1.45 (t, J=7.1 Hz, 3H); 13C NMR (CDCl₃, 75 MHz) δ 161.0, 152.3, 148.4, 136.2, 135.0, 133.9, 131.1, 131.0, 130.5, 128.8, 126.1, 123.9, 122.1, 115.5, 113.5, 110.6, 60.3, 16.6, 14.6; Mass spec.: 388.10 (MH⁺).

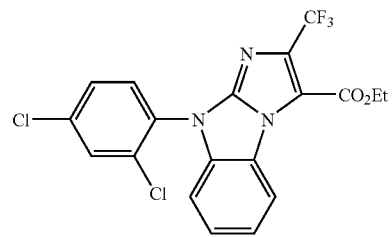

Intermediate 75

8-(2,4-Dichloro-phenyl)-2-trifluoromethyl-8H-1,3a,8-triaza-cyclopenta[α]indene-3-carboxylic acid ethyl ester, scheme 1: (F)

Prepared as described for the example above but in a sealed bomb (170° C., 60 h). ¹H NMR (CDCl₃, 500 MHz) δ 8.69 (d, J=8.2 Hz, 1H), 7.68 (d, J=2.2 Hz, 1H), 7.54 (d, J=8.4 Hz, 1H), 7.49 (dd, J=8.5, 2.2 Hz, 1H), 7.43-7.37 (m, 2H), 7.09 (d, J=8.2 Hz, 1H), 4.51 (q, J=7.2 Hz, 2H), 1.47 (t, J=7.2 Hz, 3H); Mass spec.: 442.05 (MH⁺).

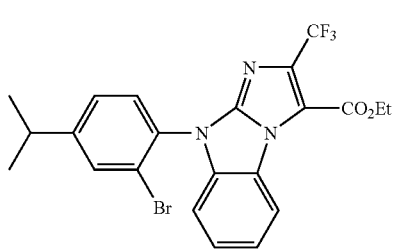

Intermediate 76

8-(2-Bromo4-isopropyl-phenyl)-2-trifluoromethyl-8H-1,3a,8-triaza-cyclopenta[α]indene-3-carboxylic acid ethyl ester, scheme 1: (F)

Prepared as described for the example above but in a sealed bomb (170° C., 60 h). Mass spec.: 494.10 (MH⁺).

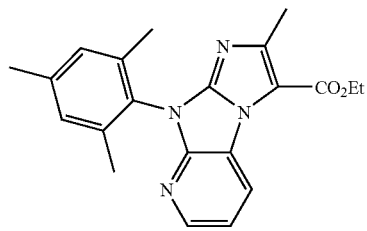

Intermediate 77

2-Methyl-8-(2,4,6-trimethyl-phenyl)-8H-1,3a,7,8-tetraaza-cyclopenta[α]indene-3-carboxylic acid ethyl ester, scheme 1: (F)

Prepared as described for the example. ¹H NMR (CDCl₃, 500 MHz) δ 8.77 (dd, J=8.1, 1.2 Hz, 1H), 8.29 (dd, J=4.9, 1.2 Hz, 1H), 7.23 (dd, J=8.1, 5.0 Hz, 1H), 7.04 (s, 2H), 4.48 (q, J=7.1 Hz, 2H), 2.65 (s, 3H), 2.34 (s, 3H), 1.98 (s, 6H), 1.49 (t, J=7.1 Hz, 3H). Mass spec.: 363.22 (MH⁺).

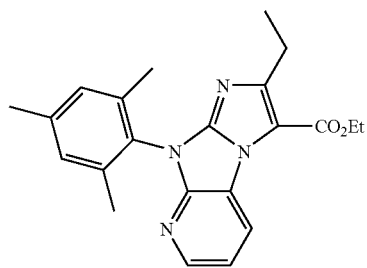

Intermediate 78

2-Ethyl-8-(2,4,6-trimethyl-phenyl)-8H-1,3a,7,8-tetraaza-cyclopenta[α]indene-3-carboxylic acid ethyl ester, scheme 1: (F)

Prepared as described for the example above. ¹H NMR (CDCl₃, 300 MHz) δ 8.78 (dd, J=8.1, 1.4 Hz, 1H), 8.28 (dd, J=5.0, 1.4 Hz, 1H), 7.23 (dd, J=8.1, 5.0 Hz, 1H), 7.04 (s, 2H), 4.49 (q, J=7.1 Hz, 2H), 3.01 (q, J=7.5 HZ, 2H), 2.34 (s, 3H), 1.98 (s, 6H), 1.47 (t, J=7.1 HZ, 3H), 1.28 (t, J=7.5 Hz, 3H). Mass spec.: 377.20 (MH⁺).

Intermediate 79

2-Trifluoromethyl-8-(2,4,6-trimethyl-phenyl)-8H-1,3a,7,8-tetraaza-cyclopenta[α]indene-3-carboxylic acid ethyl ester, scheme 1: (F)

Prepared as described for the example above but in a sealed bomb (170° C., 60 h). ¹H NMR (CDCl₃, 500 MHz) δ 8.93 (dd, J=8.1, 1.4 Hz, 1H), 8.41 (dd, J=4.9, 1.4 Hz, 1H), 7.32 (dd, J=8.1, 4.9 HZ, 1H), 7.06 (s, 2H), 4.51 (q, J=7.1 Hz, 2H), 2.36 (s, 3H), 1.98 (s, 6H), 1.47 (t, J=7.1 Hz, 3H). Mass spec.: 417.20 (MH⁺).

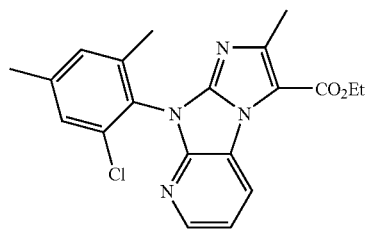

Intermediate 80

8-(2-chloro-4,6-dimethylphenyl)-2-methyl-8H-1,3a,7,8-tetraaza-cyclopenta[α]indene-3-carboxylic acid ethyl ester, scheme 1: (F)

Prepared as described for the example above. ¹H NMR (CDCl₃, 300 MHz) δ 8.78 (dd, J=8.1, 1.4 Hz, 1H), 8.29 (dd, J=5.0, 1.5 Hz, 1H), 7.26 (s, 1H), 7.25 (dd, J=8.1, 5.0 Hz, 1H), 7.14 (s, 1H), 4.48 (q, J=7.2 Hz, 2H), 2.65 (s, 3H), 2.38 (s, 3H), 2.12 (s, 3H), 1.48 (t, J=7.2 Hz, 3H). Mass spec.: 383.16 (MH+).

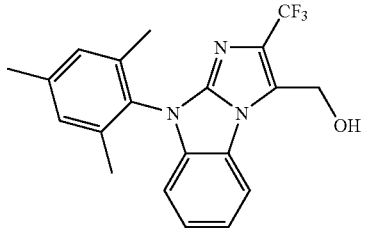

Intermediate 81

[2-Trifluoromethyl-8-(2,4,6-trimethylphenyl)-8H-1, 3a,8-triaza-cyclopenta[a]inden-3-yl]-methanol, scheme 2: (1)

To a solution of trifluoromethyl-trimethylphenyl-8H-1,3a, 8-triaza-cyclopenta[a]indene-3-carboxylic acid ethyl ester (2.51 g, 6.05 mmol) in tetrahydrofuran (40 mL) was added LiAlH$_4$ (1.0 M solution in ether, 18.2 mL, 18.2 mmol) at 0° C. The resulting clear solution was stirred at 0° C. for 1 h and then quenched at 0° C. by the sequential additions of water (0.69 mL), 15% aq.NaOH (0.69 mL) and water (2.1 mL). The mixture was warmed up to room temperature and filtered through a pad of celite®. After removing solvents in vacuo, the title compound was obtained as an off-white solid (2.26 g, 100% yield), which was pure by LC-MS and $^1$H NMR. $^1$H NMR (CDCl$_3$, 500 MHz) δ 7.97 (dd, J=7.2, 1.8 Hz, 1H), 7.32-7.29 (m, 2H), 7.03 (s, 2H), 6.92 (dd, J=7.2, 2.0 Hz, 1H), 5.14 (s, 2H), 2.35 (s, 3H), 1.98 (s, 6H); Mass spec: 374.23 (MH+).

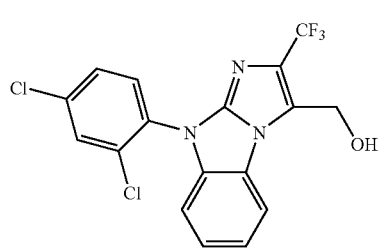

Intermediate 82

[8-(2,4-Dichlorophenyl)-2-trifluoromethyl-8H-1,3a, 8-triaza-cyclopenta[a]inden-3-yl]-methanol, scheme 2: (I)

To a solution of 8-(2,4-Dichloro-phenyl)-2-trifluoromethyl-8H-1,3a,8-triaza-cyclopenta[α]indene-3-carboxylic acid ethyl ester (490 mg, 1.11 mmol) in methylene chloride (20 mL), was added at 0° C. a toluene solution of DIBAL-H (5.55 mL, 5.55 mmol). After stirring at 0° C. for 75 min, the reaction mixture was cooled down to −78° C. and methanol (2.2 mL) was added dropwise, followed by additions of ground Na$_2$SO$_4$-10H$_2$O (15.2 g) and celite (2.6 mL). The resulting mixture was warmed up to room temperature in 4 h. After filtration, the solvents were removed in vacuo to afford the title compound as an off white solid (443 mg, 100% yield). $^1$H NMR (CDCl$_3$, 500 MHz) δ 8.00-7.93 (m, 1H), 7.65 (d, J=2.2 Hz, 1H0, 7.57 (d, J=7.4 Hz, 1H), 7.46 (dd, J=8.6, 2.3 Hz, 1H), 7.37-7.33 (m, 2H), 7.08-7.05 (m, 1H); Mass spec.: 400.02 (MH+).

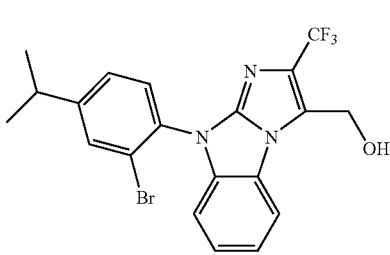

Intermediate 83

[8-(2-Bromo4-isopropyl-phenyl)-2-trifluoromethyl-8H-1,3a,8-triaza-cyclopenta[α]inden-3-yl]-methanol, scheme 2: (I)

Prepared as the example shown above (DIBAL-H reduction) in 100% yield and used for the next step without further purification. $^1$H NMR (CDCl$_3$, 300 MHz) δ 7.96 (d, J=8.9 Hz, 1H), 7.65 (d, J=1.8 Hz, 1H), 7.46 (d, J=8.1 Hz, 1H), 7.36-7.31 (m, 2H), 7.17 (d, J=7.3 Hz, 1H), 7.08 (d, J=9.0 Hz, 1H), 5.12 (s, 2H), 2.97 (sept., J=6.9 Hz, 1H), 2.36 (s, 1H), 1.30 (d, J=6.9 Hz, 6H); Mass spec.: 454.07 (MH+).

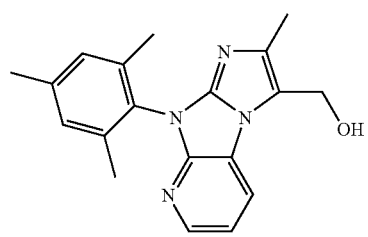

Intermediate 84

[2-Methyl-8-(2,4,6-trimethyl-phenyl)-8H-1,3a,7,8-tetraaza-cyclopenta[α]inden-3-yl]-methanol, scheme 2: (I)

Prepared as the example shown above (DIBAL-H reduction). Mass spec.: 321.20 (MH+)

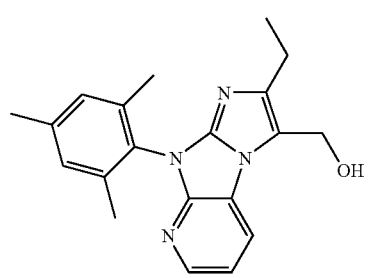

Intermediate 85

[2-Ethyl-8-(2,4,6-trimethyl-phenyl)-8H-1,3a,7,8-tetraaza-cyclopenta[α]inden-3-yl]-methanol, scheme 2: (I)

Prepared as the example shown above (DIBAL-H reduction). $^1$H NMR (CDCl$_3$, 300 MHz) δ 8.22 (dd, J=5.1, 1.4 Hz, 1H), 8.04 (dd, J=7.9 Hz, 1H), 7.16 (dd, J=7.9, 5.1 Hz, 1H), 7.03 (s, 2H), 4.95 (d, J=4.6 Hz, 2H), 2.68 (q, J=7.5 Hz, 2H), 2.36 (s, 3H), 2.02 (s, 6H), 1.25 (t, J=7.5 Hz, 3H); Mass spec.: 335.25 (MH$^+$).

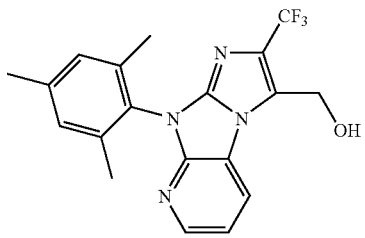

Intermediate 86

[2-Trifluoromethyl-8-(2,4,6-trimethyl-phenyl)-8H-1,3a,7,8-tetraaza-cyclopenta[α]inden-3-yl]-methanol, scheme 2: (I)

Prepared as the example shown above (DIBAL-H reduction). $^1$H NMR (CDCl$_3$, 500 MHz) δ 8.34 (dd, J=5.0, 1.4 Hz, 1H), 8.23 (dd, J=8.0, 1.4 Hz, 1H), 7.24 (dd, J=8.0, 5.0 Hz, 1H), 7.04 (s, 2H), 5.11 (s, 2H), 2.33 (s, 3H), 2.01 (s, 6H); Mass spec.: 375.20 (MH$^+$).

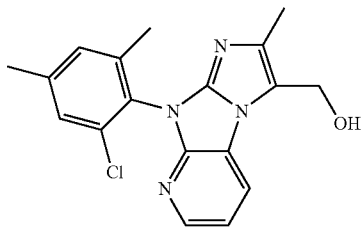

Intermediate 87

[8-(2-Chloro-4,6-dimethyl-phenyl)-2-methyl-8H-1,3a,7,8-tetraaza-cyclopenta[α]inden-3-yl]-methanol, scheme 2: (I)

Prepared as the example shown above (DIBAL-H reduction). $^1$H NMR (CDCl$_3$, 300 MHz) δ 8.23 (dd, J=5.1, 1.3 Hz, 1H), 8.04n (dd, J=7.9, 1.4 Hz, 1H), 7.24 (s, 1H), 7.17 (dd, J=7.9, 5.1 Hz, 1H), 7.11 (s, 1H), 4.93 (s, 2H), 2.36)s, 3H), 2.31 (s, 3H), 2.14 (s, 3H); Mass spec.: 341.15 (MH$^+$).

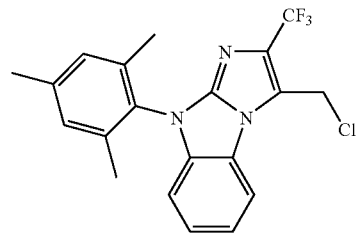

Intermediate 88

3-Chloromethyl-2-trifluoromethyl-8-(2,4,6-trimethyl-phenyl)-8H-1,3a,8-triaza-cyclopenta[a    ] indene:$^5$, scheme 2: (J)

A sealed tube containing (trifluoromethyl-trimethylphenyl-8H-1,3a,8-triaza-cyclopenta[a    ]inden-3-yl)-methanol (1.1 g, 2.95 mmol) and SOCl$_2$ (3.5 mL) was heated at 80° C. for 1 h. After removing SOCl$_2$ in vacuo, the title compound was obtained as a light brown viscous liquid (1.15 g, 100% yield), which was pure by $^1$H NMR. $^1$H NMR (CDCl$_3$, 500 MHz) d 7.94-7.92 (m, 1H), 7.39-7.37 (m, 2H), 7.05 (s, 2H), 7.00-6.98 (m, 1H), 5.18 (s, 2H), 2.37 (s, 3H), 1.99 (s, 6H); Mass spec. 388.30 [M−Cl+OMe+H]$^+$.

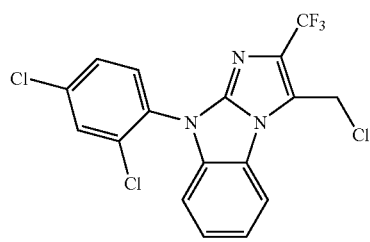

Intermediate 89

3-Chloromethyl-8-(2,4-dichloro-phenyl)-2-trifluoromethyl-8H-1,3a,8-triaza-cyclopenta[α]indene, scheme 2: (J)

Prepared as the example shown above (SOCl$_2$ neat, 80° C., 30 min). Mass spec. 414.08 [M−Cl+OMe+H]$^+$.

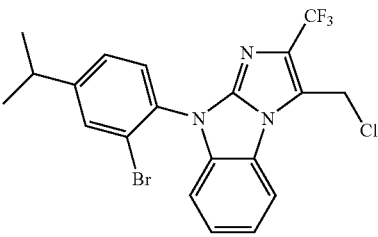

Intermediate 90

8-(2-Bromo-4-isopropyl-phenyl)-3-chloromethyl-2-trifluoromethyl-8H-1,3a,8-triaza-cyclopenta[α]indene, scheme 2: (J)

Prepared as the example shown above (SOCl$_2$ neat, 80° C., 30 min). Mass spec. 466.10 [M−Cl+OMe+H]$^+$.

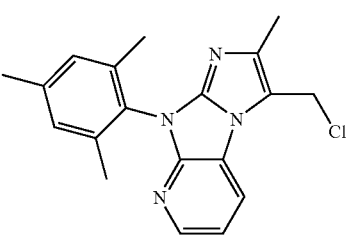

Intermediate 91

3-Chloromethyl-2-methyl-8-(2,4,6-trimethyl-phenyl)-8H-1,3a,7,8-tetraaza-cyclopenta[α]indene:[6], scheme 2: (J)

Thionyl chloride (0.164 mL, 2.25 mmol) was added at 0° C. to a solution of [2-methyl-8-(2,4,6-trimethyl-phenyl)-8H-1,3a,7,8-tetraaza-cyclopenta[α]inden-3-yl]-methanol (0.36 g, 1.12 mmol) in CH$_2$Cl$_2$ (10 mL). After 2 h, solvents was removed and the title compound was obtained as a brownish oil (100% yield). Mass spec.: 335.24 (M–Cl+OMe+H)$^+$.

Intermediate 92

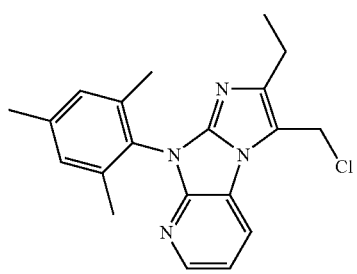

3-Chloromethyl-2-ethyl-8-(2,4,6-trimethyl-phenyl)-8H-1,3a,7,8-tetraaza-cyclopenta[α]indene, scheme 2: (J)

Prepared as the example shown above (SOCl$_2$, CH$_2$Cl$_2$, 0° C., 2 h). Mass spec.: 349.22 (M–Cl+OMe+H)$^+$.

Intermediate 93

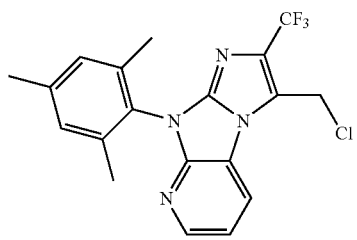

3-Chloromethyl-2-trifluoromethyl-8-(2,4,6-trimethyl-phenyl)-8H-1,3a,7,8-tetraaza-cyclopenta[α]indene, scheme 2: (J)

Prepared as the example shown above (SOCl$_2$, CH$_2$Cl$_2$, 0° C., 2 h). Mass spec.: 389.20 (M–Cl+OMe+H)$^+$.

Intermediate 94

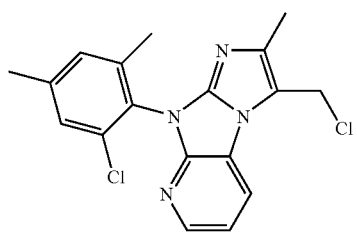

8-(2-chloro-4,6-dimethyl-phenyl)-3-chloromethyl-2-methyl-8H-1,3a,7,8-tetraaza-cyclopenta[α]indene, scheme 2: (J)

Prepared as the example shown above (SOCl$_2$, CH$_2$Cl$_2$, 0° C., 2 h). Mass spec.: 355.16 (M–Cl+OMe+H)$^+$.

For Examples 139-141 and 143-149, LC/MS were run using the following conditions: Column, YMC ODS S7 3.0×50 mm; run time, 3 mins. For Example 142, the LC/MS was run using the following conditions: Column, YMC C18 S5 4.6×50 mm; run time, 4 mins.

EXAMPLE 139

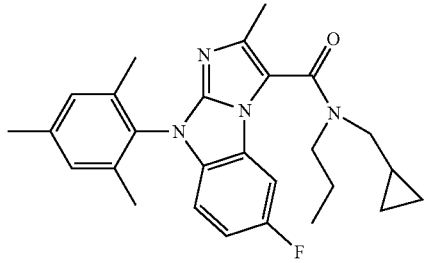

5-Fluoro-2-methyl-8-(2,4,6-trimethyl-phenyl)-8H-1,3a,8-triaza-cyclopenta[a]indene-3-carboxylic acid cyclopropylmethyl-propyl-amide:[7], scheme 1: (G)

A solution of trimethylaluminum (2.0 M in heptane, 1.4 mL, 2.8 mmol) was added to a solution of N-cyclopropylmethyl-N-propylamine (0.40 mL, 2.8 mmol) in benzene (3 mL) at 0° C. The mixture was warmed up to room temperature and stirred at this temperature for 1.5 hours, and then added to a stirred solution of 5-fluoro-2-methyl-8-(2,4,6-trimethyl-phenyl)-8H-1,3a,8-triaza-cyclopenta[a]indene-3-carboxylic acid ethyl ester (0.13 g, 0.35 mmol) in benzene (2.0 mL). The mixture was refluxed for 12 hours. Upon cooling at 0° C., 1 N sodium hydroxide (15 mL) was added dropwise to the above mixture. The mixture was extracted with dicholoromethane (30 mL), and the organic layer was dried over anhydrous sodium sulfate. Solvents were removed in vacuo and the residue was subjected to chromatography using ethyl acetate/hexanes (3:7) as eluent to afford the title compound as an off-white solid (0.156 g, 100% yield). $^1$H NMR (CDCl$_3$, 300 MHz) δ 7.60 (dd, J=8.7, 2.5 Hz, 1H), 6.99 (s, 2H), 6.92 (td, J=9.0, 2.5 Hz, 1H), 6.75 (dd, J=8.8, 4.4 Hz, 1H), 3.66 (t, J=7.1 Hz, 2H), 3.46 (d, J=6.9 Hz, 2H), 2.35 (s, 3H), 2.32 (s, 3H), 1.92 (s, 6H), 1.71-1.63 (m, 2H), 1.11-1.05 (m, 1H), 0.88 (t, J=7.2 Hz, 3H), 0.57-0.53 (m, 2H), 0.19-0.16 (m, 2H); $^{13}$C NMR (CDCl$_3$, 75 MHz) δ 163.6, 159.4, 156.3, 148.9, 143.3, 139.4, 137.0, 131.6, 129.7, 128.7, 124.8 (d, J=13 Hz), 114.2, 110.6 (d, J=25 Hz), 101.2 (d, J=29 Hz), 51.3, 48.6, 21.1, 21.0, 17.8, 15.7, 11.3, 10.1, 3.8. LC/MS: t$_R$=1.95 min, 447.22 (MH$^+$).

EXAMPLE 140

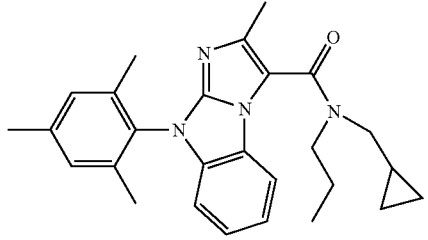

2-Methyl-8-(2,4,6-trimethyl-phenyl)-8H-1,3a,8-triaza-cyclopenta[a]indene-3-carboxylic acid cyclopropylmethyl-propyl-amide, scheme 1: (G)

Prepared as described for the example above. ¹H NMR (CDCl₃, 300 MHz) δ 7.86-7.82 (m, 1H), 7.23-7.19 (m, 2H), 7.02 (s, 2H), 6.89-6.86 (m, 1H), 3.69 (t, J=7.0 Hz, 2H), 3.49 (d, J=6.9 Hz, 2H), 2.39 (s, 3H), 2.35 (s, 3H), 1.98 (s, 6H), 1.74-1.65 (m, 2H), 1.16-1.06 (m, 1H), 0.90 (t, J=7.2 Hz, 3H), 0.59-0.53 (m, 2H), 0.23-0.20 (m, 2H); ¹³C NMR (CDCl₃, 75 MHz) δ 163.7, 147.9, 139.2, 137.0, 135.2, 129.5, 128.8, 124.8, 123.3, 121.0, 114.2, 113.1, 110.2, 60.3, 51.1, 21.0, 17.7, 15.4, 11.2, 10.1, 3.8; LC/MS: $t_R$=1.95 min, 429.13 (MH⁺).

EXAMPLE 141

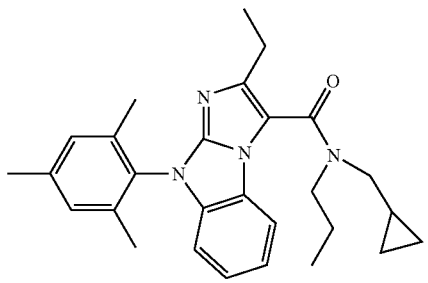

2-Ethyl-8-(2,4,6-trimethyl-phenyl)-8H-1,3a,8-triaza-cyclopenta[a]indene-3-carboxylic acid cyclopropylmethyl-propyl-amide, scheme 1: (G)

Prepared as described for the example above. ¹H NMR (CDCl₃, 300 MHz) δ 7.81-7.76 (m, 1H), 7.23-7.16 (m, 2H), 7.02 (s, 2H), 6.87-6.84 (m, 1H), 3.68 (t, J=6.6 Hz, 2H), 3.49 (d, J=6.7 Hz, 2H), 2.70 (q, J=7.4 Hz, 2H), 2.35 (s, 3H), 1.98 (s, 6H), 1.73-1.63 (m, 2H), 1.28 (t, J=7.4 Hz, 3H), 1.15-1.05 (m, 1H), 0.89 (t, J=7.3 Hz, 3H), 0.57-0.54 (m, 2H), 0.25-0.20 (m, 2H); LC/MS: $t_R$=1.95 min, 443.23 (MH⁺).

EXAMPLE 142

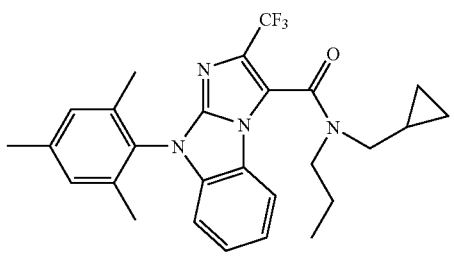

2-trifluoromethyl-8-(2,4,6-trimethylphenyl)-8H-1,3a,8-triaza-cyclopenta[a]indene-3-carboxylic acid cyclopropylmethyl-propyl-amide, scheme 1: (G)

Prepared as described for the example above. ¹H NMR (CDCl₃, 300 MHz) δ 7.72-7.66 (m, 1H), 7.32-7.20 (m, 2H), 7.02 (s, 2H), 6.91 (d, J=7.8 Hz, 1H), 3.80-3.26 (m, 4H), 2.33 (s, 3H), 1.97 (s, 6H), 1.82-1.53 (m, 2H), 1.33-1.20 (m, 1H), 1.04 (t, J=7.2 Hz, 3H), 0.95-0.83 (m, 2H), 0.74-0.59 (m, 2H); LC/MS: $t_R$=2.86 min, 483.30 (MH⁺).

EXAMPLE 143

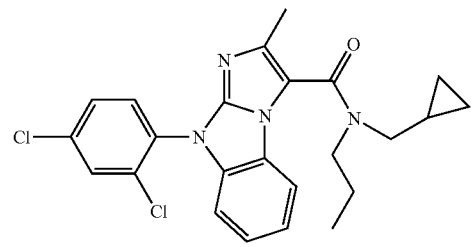

8-(2,4-Dichloro-phenyl)-2-methyl-8H-1,3a,8-triaza-cyclopenta[a]indene-3-carboxylic acid cyclopropylmethyl-propyl-amide, scheme 1: (G)

Prepared as described for the example above. ¹H NMR (CDCl₃, 300 MHz) δ 7.82-7.79 (m, 1H), 7.65 (d, J=2.2 Hz, 1H), 7.53 (d, J=8.5 Hz, 1H), 7.44 (dd, J=8.5, 2.2 Hz, 1H), 7.25-7.22 (m, 2H), 7.02-6.99 (m, 1H), 3.68 (t, J=7.0 Hz, 2H), 3.48 (d, J=6.8 Hz, 2H), 2.38 (s, 3H), 1.75-1.63 (m, 2H), 1.13-1.07 (m, 1H), 0.90 (t, J=7.8 Hz, 3H), 0.59-0.53 (m, 2H) 0.22-0.19 (m, 2H); LC/MS: $t_R$=1.88 min, 455.11 (MH⁺).

EXAMPLE 144

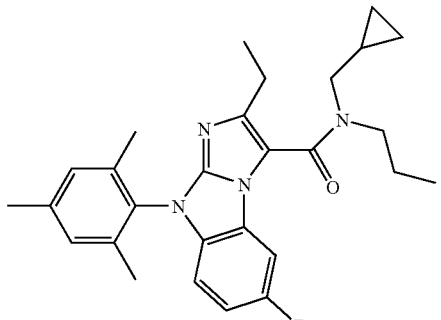

2-Ethyl-5-fluoro-8-(2,4,6-trimethyl-phenyl)-8H-1,3a,8-triaza-cyclopenta[a]indene-3-carboxylic acid cyclopropylmethyl-propyl-amide, scheme 1: (G)

Prepared as described for the example above. ¹H NMR (CDCl₃, 300 MHz) δ 7.58 (dd, J=8.6, 2.5 Hz, 1H), 7.02 (s, 2H), 6.95 (t, J=9.6 Hz, 1H), 6.79-6.76 (m,1H), 3.68 (t, J=6.9 Hz, 2H), 3.49 (d, J=6.8 Hz, 2H), 2.70 (q, J=7.3 Hz, 2H), 2.35 (s, 3H), 1.98 (s, 6H), 1.73-1.63 (m,2H), 1.28 (t, J=7.4 Hz, 3H), 1.15-1.10 (m, 1H), 0.92 (t, J=7.3 Hz, 3H), 0.59-0.54 (m 2H), 0.22-0.19 (m, 2H); ¹³C NMR (CDCl₃, 75 MHz) δ 163.7, 159.4, 156.2, 148.9, 139.4, 137.0, 131.6, 129.7, 128.8, 124.7 (d, J=9.0 Hz), 113.0, 110.5 (d, J=11.4 Hz), 110.3, 101.0, 51.4, 48.7, 22.8, 21.1, 17.8, 13.8, 11.3, 10.1, 3.8; LC/MS: $t_R$=2.05 min, 461.26 (MH⁺).

EXAMPLE 145

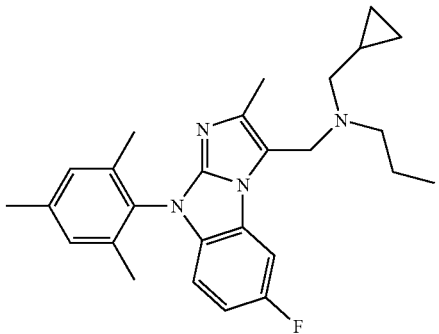

Cyclopropylmethyl-[5-fluoro-2-methyl-8-(2,4,6-trimethyl-phenyl)-8H-1,3a,8-triaza-cyclopenta[a]inden-3-ylmethyl]-propyl-amine:[8], scheme 1: (H)

A solution of Red-Al (3.3 M in toluene, 0.25 mL, 0.8 mmol) was added dropwise to a solution of 2-methyl-8-(2,4,6-trimethyl-phenyl)-8H-1,3a,8-triaza-cyclopenta[a]indene-3-carboxylic acid cyclopropylmethyl-propyl-amide (73 mg, 0.16 mmol) in toluene (2 mL) at 0° C. After stirring at room temperature for 24 hours, the reaction mixture was cooled to 0° C. and 1 N sodium hydroxide (10 mL) was added dropwise. The above mixture was extracted with dichloromethane (30 mL), and the organic extracts were washed with water and dried over anhydrous sodium sulfate. Solvents were removed in vacuuo and the residue was subjected to chromatography using ethyl acetate/hexanes as eluent to afford the title compound as a white solid (59.4 mg, 86% yield). $^1$H NMR (CDCl$_3$, 300 MHz) δ 7.87 (dd, J=9.1, 2.2 Hz, 1H), 7.00 (s, 2H), 6.88 (td, J=−9.0, 2.5 Hz, 1H), 6.70 (dd, J=8.8, 4.5 Hz, 1H), 3.89 (s, 2H), 2.52 (t, J=7.3 Hz, 2H), 2.46 (d, J=6.6 Hz, 2H), 2.34 (s, 3H), 2.29 (s, 3H), 1.97 (s, 6H), 1.49-1.42 (m, 2H), 1.05-1.00 (m, 1H), 0.74 (t, J=7.3 Hz, 3H), 0.56-0.51 (m, 2H), 0.16-0.14 (m, 2H); $^{13}$C NMR (CDCl$_3$, 75 MHz) δ 159.3, 156.2, 148.3, 139.0, 138.8, 137.2, 130.5 (d, J=179.5 Hz), 129.6, 125.4 (d, J=13.0 Hz)115.8, 109.6, 109.3 (d, J=25.8 Hz), 101.3 (d, J=29.2 Hz), 59.0, 55.3, 48.8, 21.1, 19.7, 17.7, 13.8, 12.0, 8.7, 4.3; LC/MS: $t_R$=1.57 min, 433.22 (MH$^+$).

EXAMPLE 146

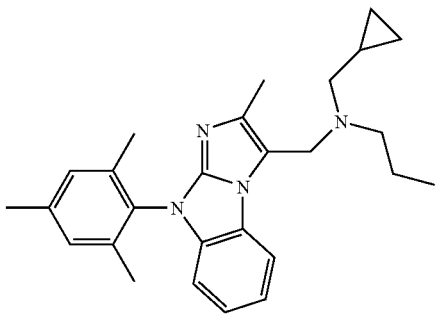

Cyclopropylmethyl-[2-methyl-8-(2,4,6-trimethyl-phenyl)-8H-1,3a,8-triaza-cyclopenta[α]inden-3-ylmethyl]-propyl-amine, scheme 1: (H)

Prepared as described for the example above. $^1$H NMR (CDCl$_3$, 300 MHz) δ 8.05-7.99 (m, 1H), 7.18-7.12 (m, 2H), 6.94 (s, 2H), 6.80-6.74 (m, 1H), 3.96 (s, 2H), 2.52 (t, J=6.8 Hz, 2H), 2.44 (d, J=6.9 Hz, 2H), 2.36 (s, 3H), 2.30 (s, 3H), 1.98 (s, 6H), 1.50-1.44 (m, 2H), 1.05-0.98 (m, 1H), 0.77 (t, J=7.2 Hz, 3H), 0.55-0.50 (m, 2H), 0.16-0.12 (m 2H); LC/MS: $t_R$=1.39 min, 415.23 (MH$^+$).

EXAMPLE 147

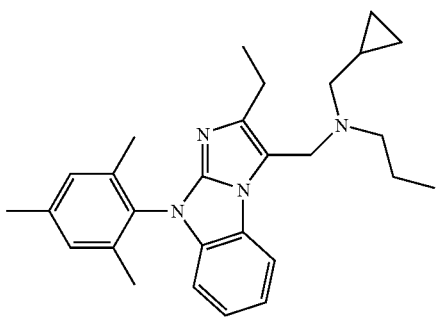

Cyclopropylmethyl-[2-ethyl-8-(2,4,6-trimethyl-phenyl)-8H-1,3a,8-triaza-cyclopenta[α]inden-3-ylmethyl]-propyl-amine, scheme 1: (H)

Prepared as described for the example above. $^1$H NMR (CDCl$_3$, 300 MHz) δ 8.05-8.01 (m, 1H), 7.19-7.12 (m, 2H), 7.11 (s, 2H), 6.82-6.79 (m, 1H), 3.93 (s, 2H), 2.65 (q, J=7.5 Hz, 2H), 2.55 (t, J=7.4 Hz, 2H), 2.48 (d, J=6.6 Hz, 2H), 2.35 (s, 3H), 1.98 (s, 6H), 1.49-1.42 (m, 2H), 1.23 (t, J=7.5 Hz, 3H), 1.08-0.98 (m, 1H), 0.74 (t, J=7.3 Hz, 3H), 0.53-0.49 (m, 2H), 0.13-0.10 (m, 2H); LC/MS: $t_R$=1.71 min, 429.25 (MH$^+$).

EXAMPLE 148

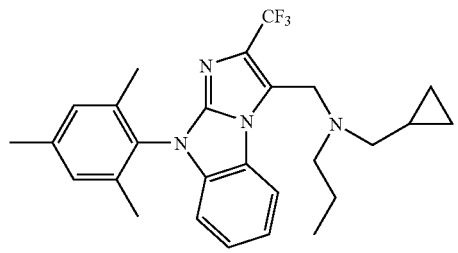

Cyclopropylmethyl-propyl-(trifluoromethyl-trimethylphenyl-8H-1,3a,8-triaza-cyclopenta[α]inden-3-ylmethyl)-amine, scheme 1: (H)

Prepared as described for the example above. $^1$H NMR (CDCl$_3$, 300 MHz) δ 7.37-7.33 (m, 1H), 7.27-7.24 (m, 1H), 7.16 (d, J=7.4 Hz, 1H), 7.04 (s, 2H), 6.97-6.94 (m, 1H), 4.95 (s, 2H), 3.27-3.16 (m, 4H), 2.22 (s, 3H), 1.96 (s, 6H), 1.87-1.79 (m, 2H), 1.23-1.20 (m, 1H), 0.97 (t, J=7.2 Hz, 3H), 0.84-0.80 (m, 2H), 0.46-0.43 (m, 2H); LC/MS: $t_R$=1.57 min, 469.31 (MH$^+$).

EXAMPLE 149

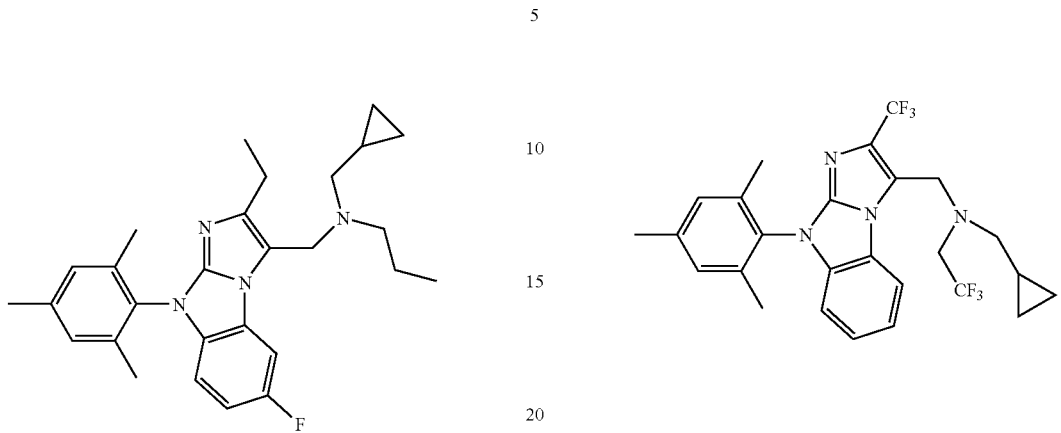

Cyclopropylmethyl-[2-ethyl-5-fluoro-8-(2,4,6-trimethyl-phenyl)-8H-1,3a,8-triaza-cyclopenta[α]inden-3-ylmethyl]-propyl-amine, scheme 1: (H)

Prepared as described for the example above. $^1$H NMR (CDCl$_3$, 300 MHz) δ 7.89 (dd, J=9.1, 2.5 Hz, 1H), 7.00 (s, 2H), 6.87 (td, J=9.1, 2.6 Hz, 1H), 6.69 (dd, J=8.8, 4.5 Hz, 1H), 3.90 (s, 2H), 2.63 (q, J=7.5 Hz, 2H), 2.53 (t, J=7.3 Hz, 2H), 2.47 (d, J=6.6 Hz, 2H), 2.34 (s, 3H), 1.97 (s, 6H), 1.48-1.41 (m, 2H), 1.23 (t, J=7.5 Hz, 3H), 1.05-0.95 (m, 1H), 0.74 (t, J=7.3 Hz, 3H), 0.56-0.52 (m, 2H), 0.15-0.12 (m, 2H); $^{13}$C NMR (CDCl$_3$, 75 MHz) δ 159.3, 156.1, 148.4, 145.1, 139.0, 137.2, 130.6 (d, J=174 Hz), 129.6, 125.5 (d, J=13.3 Hz), 115.0, 109.6, 109.2 (d, J=24.8 Hz), 101.4 (d, J=29.2 Hz), 59.1, 55.4, 48.8, 21.4, 21.1, 19.8, 17.8, 15.2, 12.0, 8.8, 4.3; LC/MS: $t_R$=1.78 min, 447.27 (MH$^+$).

General Procedure for the Sunthesis of Examples 150-282:

(For Examples 150-252 LC/MS were run using the following conditions: Column, YMC S5 4.6×50 mm; run time, 4 mins.)

An amine hydrochloride salt or a free amine (0.65 mmol, 5 equiv.) was added to an oven-dried 11 mL vial. After the addition of anhydrous acetonitrile (1 mL) and anhydrous i-Pr$_2$NEt (0.16 mL, 0.91 mmol, 7 equiv in the case of an amine-HCl salt, or 43 µL, 0.26 mmol, 2 equiv in the case of a free amine), the mixture was stirred at room temperature for 1 h, followed by the addition of a solution of a chloromethyl compound (0.13 mmol) in MeCN (1 mL). The resulting mixture was stirred at room temperature for 24 h, or heated at 80° C. for 16 h if a trifluoromethyl-containing amine hydrochloride salt was employed. After removing solvents and excess of i-Pr$_2$NEt in vacuo, the residue was dissolved in dimethylformamide or acetonitrile (2 mL) and CF$_3$CO$_2$H (30 µL) was added. The mixture (in most cases, a clear solution) was filtered into a Prep-HPLC vial, and title compounds were obtained by Prep-HPLC.

EXAMPLE 150

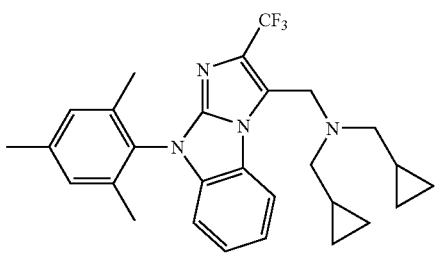

Cyclopropylmethyl-(2,2,2-trifluoro-ethyl)-[2-trifluoromethyl-8-(2,4,6-trimethylphenyl-8H-1,3a,8-triaza-cyclopenta[α]inden-3-ylmethyl]-amine, scheme 2: (H)

Prepared as described for the example above. LC/MS: $t_R$=2.99 min, 509.23 (MH$^+$).

EXAMPLE 151

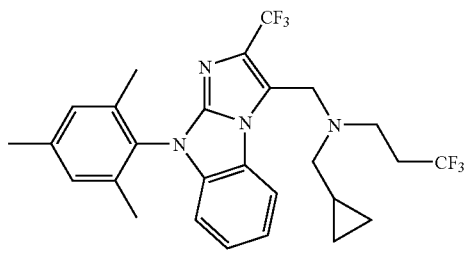

Bis-cyclopropylmethyl-[2-trifluoromethyl-8-(2,4,6-trimethyl-phenyl)-8H-1,3a,8-triaza-cyclopenta[α]inden-3-ylmethyl]-amine, scheme 2: (H)

Prepared as described for the example above. LC/MS: $t_R$=2.15 min, 481.28 (MH$^+$).

EXAMPLE 152

Cyclopropylmethyl-[2-trifluoromethyl-8-(2,4,6-trimethyl-phenyl)-8H-1,3a,8-triaza-cyclopenta[α]inden-3-ylmethyl]-(3,3,3-trifluoro-propyl)-amine, scheme 2: (H)

Prepared as described for the example above. LC/MS: $t_R$=2.86 min, 523.24 (MH⁺).

EXAMPLE 148

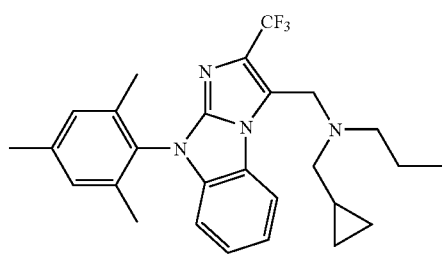

Cyclopropylmethyl-propyl-[2-trifluoromethyl-8-(2,4,6-trimethyl-phenyl)-8H-1,3a,8-triaza-cyclopenta[α]inden-3-ylmethyl]-amine, scheme 2: (H)

Prepared as described for the example above. LC/MS: $t_R$=1.57 min, 469.26 (MH⁺).

EXAMPLE 153

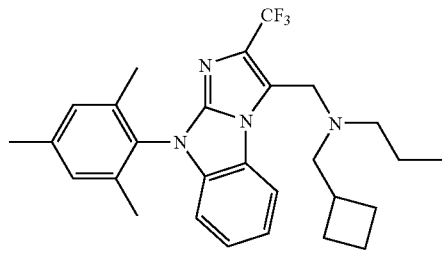

Cyclobutylmethyl-propyl-[2-trifluoromethyl-8-(2,4,6-trimethyl-phenyl)-8H-1,3a,8-triaza-cyclopenta[α]inden-3-ylmethyl]-amine, scheme 2: (H)

Prepared as described for the example above. LC/MS: $t_R$=2.28 min, 483.29 (MH⁺).

EXAMPLE 154

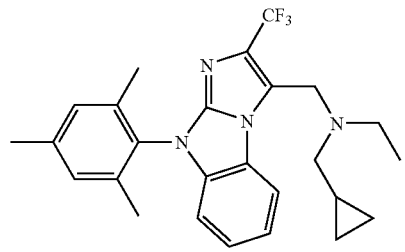

Cyclopropylmethyl-ethyl-[2-trifluoromethyl-8-(2,4,6-trimethyl-phenyl)-8H-1,3a,8-triaza-cyclopenta[α]inden-3-ylmethyl]-amine, scheme 2: (H)

Prepared as described for the example above. LC/MS: $t_R$=2.06 min, 455.24 (MH⁺).

EXAMPLE 155

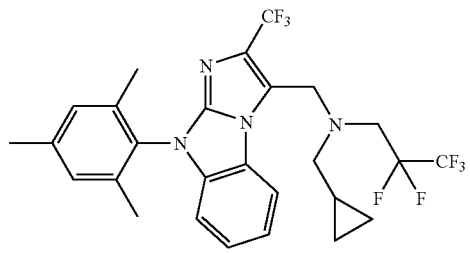

Cyclopropylmethyl-(2,2,3,3,3-pentafluoro-propyl)-[2-trifluoromethyl-8-(2,4,6-trimethyl-phenyl)-8H-1,3a,8-triaza-cyclopenta[α]inden-3-ylmethyl]-amine, scheme 2: (H)

Prepared as described for the example above. LC/MS: $t_R$=3.06 min, 559.22 (MH⁺).

EXAMPLE 156

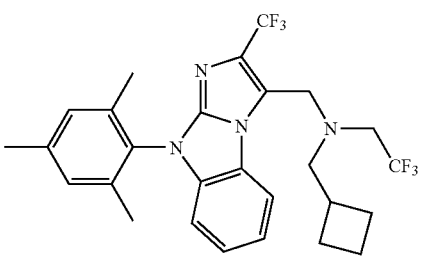

Cyclobutylmethyl-(2,2,2-trifluoro-ethyl)-[2-trifluoromethyl-8-(2,4,6-trimethyl-phenyl)-8H-1,3a,8-triaza-cyclopenta[α]inden-3-ylmethyl]-amine, scheme 2: (H)

Prepared as described for the example above. LC/MS: $t_R$=3.08 min, 523.23 (MH⁺).

EXAMPLE 157

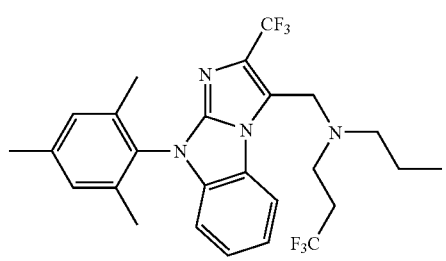

Propyl-[2-trifluoromethyl-8-(2,4,6-trimethyl-phenyl)-8H-1,3a,8-triaza-cyclopenta[α]inden-3-ylmethyl]-(3,3,3-trifluoro-propyl)-amine, scheme 2: (H)

Prepared as described for the example above. LC/MS: $t_R$=2.87 min, 511.23 (MH⁺).

EXAMPLE 158

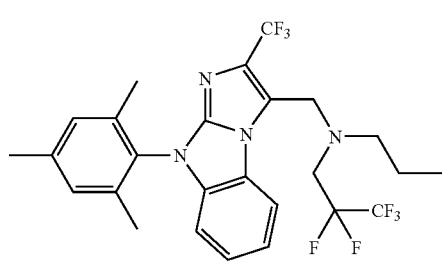

(2,2,3,3,3-Pentafluoro-propyl)-propyl-[2-trifluoromethyl-8-(2,4,6-trimethyl-phenyl)-8H-1,3a,8-triaza-cyclopenta[α]inden-3-ylmethyl]-amine, scheme 2: (H)

Prepared as described for the example above. LC/MS: $t_R$=3.06 min, 547.22 (MH⁺).

EXAMPLE 159

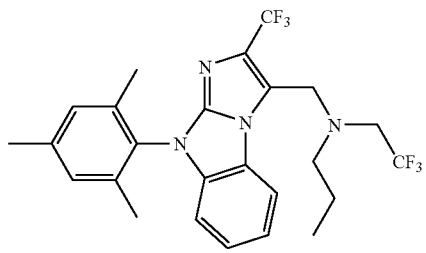

lp;1p

Propyl-(2,2,2-trifluoro-ethyl)-[2-trifluoromethyl-8-(2,4,6-trimethyl-phenyl)-8H-1,3a,8-triaza-cyclopenta[α]inden-3-ylmethyl]-amine, scheme 2: (H)

Prepared as described for the example above. LC/MS: $t_R$=2.98 min, 497.23 (MH⁺).

EXAMPLE 160

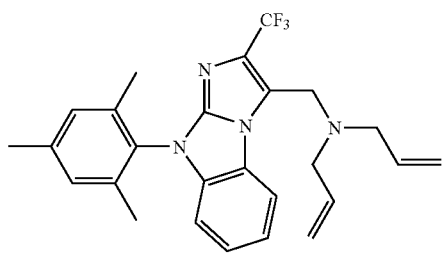

Diallyl-[2-trifluoromethyl-8-(2,4,6-trimethyl-phenyl)-8H-1,3a,8-triaza-cyclopenta[α]inden-3-ylmethyl]-amine, scheme 2: (H)

Prepared as described for the example above. LC/MS: $t_R$=2.26 min, 453.27.

EXAMPLE 161

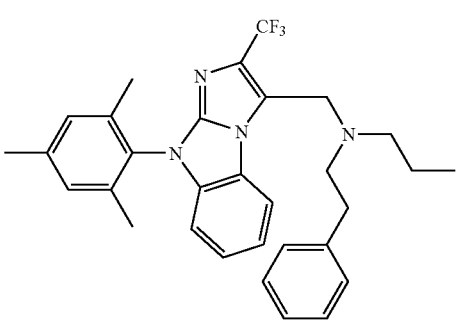

Phenethyl-propyl-[2-trifluoromethyl-8-(2,4,6-trimethyl-phenyl)-8H-1,3a,8-triaza-cyclopenta[α]inden-3-ylmethyl]-amine, scheme 2: (H)

Prepared as described for the example above. LC/MS: $t_R$=2.42 min, 519.44 (MH$^+$).

EXAMPLE 162

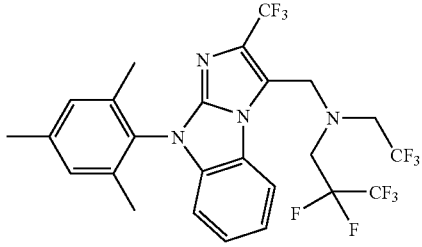

(2,2,3,3,3-Pentafluoro-propyl)-(2,2,2-trifluoro-ethyl)-[2-trifluoromethyl-8-(2,4,6-trimethyl-phenyl)-8H-1,3a,8-triaza-cyclopenta[α]inden-3-ylmethyl]-amine, scheme 2: (H)

Prepared as described for the example above. LC/MS: $t_R$=2.87 min, 551.18 (MH$^+$).

EXAMPLE 163

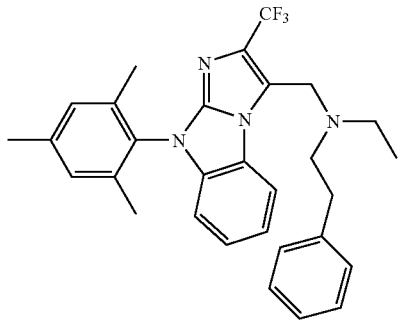

Ethyl-phenethyl-[2-trifluoromethyl-8-(2,4,6-trimethyl-phenyl)-8H-1,3a,8-triaza-cyclopenta[α]inden-3-ylmethyl]-amine, scheme 2: (H)

Prepared as described for the example above. LC/MS: $t_R$=2.31 min, 505.43 (MH$^+$).

EXAMPLE 164

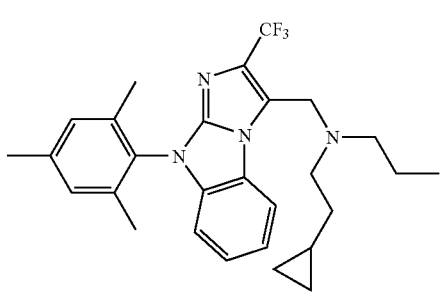

(2-Cyclopropyl-ethyl)-propyl-[2-trifluoromethyl-8-(2,4,6-trimethyl-phenyl)-8H-1,3a,8-triaza-cyclopenta[α]inden-3-ylmethyl]-amine, scheme 2: (H)

Prepared as described for the example above. LC/MS: $t_R$=2.25 min, 483.30 (MH$^+$).

EXAMPLE 165

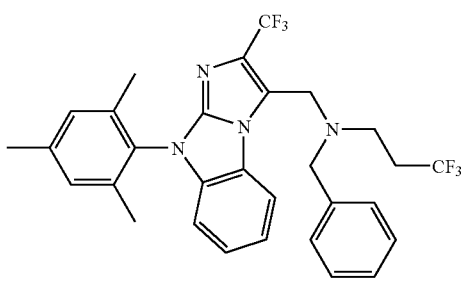

Benzyl-[2-trifluoromethyl-8-(2,4,6-trimethyl-phenyl)-8H-1,3a,8-triaza-cyclopenta[α]inden-3-ylmethyl]-(3,3,3-trifluoro-propyl)-amine, scheme 2: (H)

Prepared as described for the example above. LC/MS: $t_R$=3.06 min, 559.24 (MH$^+$).

EXAMPLE 166

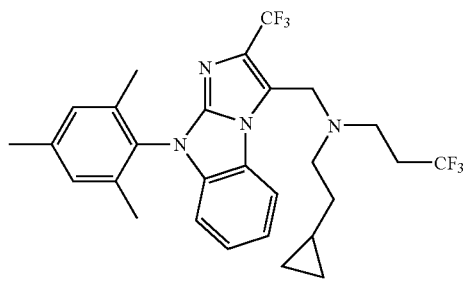

(2-Cyclopropyl-ethyl)-[2-trifluoromethyl-8-(2,4,6-trimethyl-phenyl)-8H-1,3a,8-triaza-cyclopenta[α]inden-3-ylmethyl]-(3,3,3-trifluoro-propyl)-amine, scheme 2: (H)

Prepared as described for the example above. LC/MS: $t_R$=2.99 min, 537.25 (MH$^+$).

EXAMPLE 167

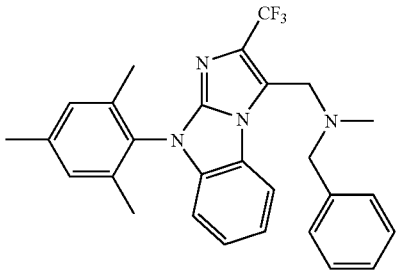

Benzyl-methyl-[2-trifluoromethyl-8-(2,4,6-trimethyl-phenyl)-8H-1,3a,8-triaza-cyclopenta[α]inden-3-ylmethyl]-amine, scheme 2: (H)

Prepared as described for the example above. LC/MS: $t_R$=2.24 min, 477.25 (MH$^+$).

EXAMPLE 168

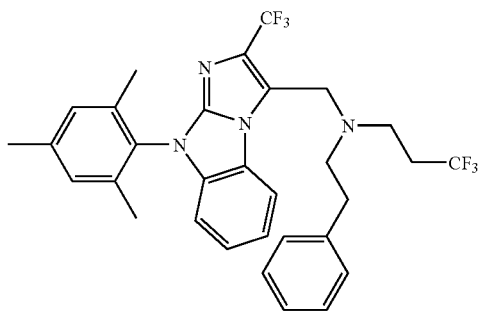

Phenethyl-[2-trifluoromethyl-8-(2,4,6-trimethyl-phenyl)-8H-1,3a,8-triaza-cyclopenta[α]inden-3-ylmethyl]-(3,3,3-trifluoro-propyl)-amine, scheme 2: (H)

Prepared as described for the example above. LC/MS: $t_R$=3.10 min, 585.12 (MH$^+$).

EXAMPLE 169

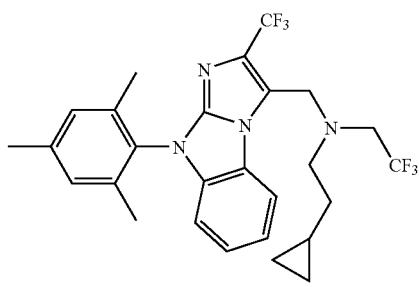

(2-Cyclopropyl-ethyl)-(2,2,2-trifluoro-ethyl)-[2-trifluoromethyl-8-(2,4,6-trimethyl-phenyl)-8H-1,3a,8-triaza-cyclopenta[α]inden-3-ylmethyl]-amine, scheme 2: (H)

Prepared as described for the example above. LC/MS: $t_R$=3.04 min, 523.24 (MH$^+$).

EXAMPLE 170

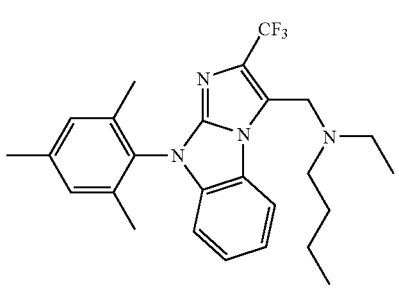

Butyl-ethyl-[2-trifluoromethyl-8-(2,4,6-trimethyl-phenyl)-8H-1,3a,8-triaza-cyclopenta[α]inden-3-ylmethyl]-amine, scheme 2: (H)

Prepared as described for the example above. LC/MS: $t_R$=2.14 min, 457.26 (MH$^+$).

EXAMPLE 171

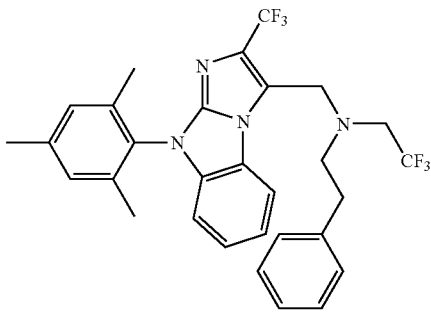

Phenethyl-(2,2,2-trifluoro-ethyl)-[2-trifluoromethyl-8-(2,4,6-trimethyl-phenyl)-8H-1.3a,8-triaza-cyclopenta[α]inden-3-ylmethyl]-amine, scheme 2: (H)

Prepared as described for the example above. LC/MS: $t_R$=3.06 min, 559.24 (MH$^+$).

EXAMPLE 172

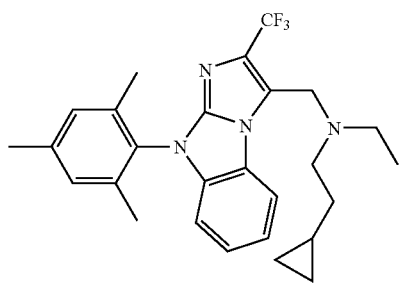

(2-Cyclopropyl-ethyl)-ethyl-[2-trifluoromethyl-8-(2,4,6-trimethyl-phenyl)-8H-1,3a,8-triaza-cyclopenta[α]inden-3-ylmethyl]-amine, scheme 2: (H)

Prepared as described for the example above. LC/MS: $t_R$=2.17 min, 469.29 (MH$^+$).

EXAMPLE 173

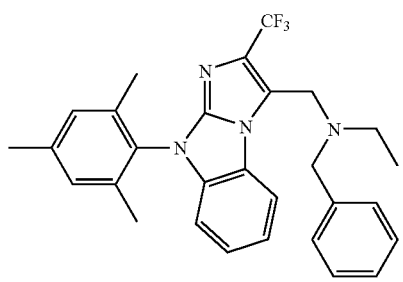

Benzyl-ethyl-[2-trifluoromethyl-8-(2,4,6-trimethyl-phenyl)-8H-1,3a,8-triaza-cyclopenta[α]inden-3-ylm-ethyl]-amine, scheme 2: (H)

Prepared as described for the example above. LC/MS: $t_R$=2.70 min, 491.26 (MH$^+$).

EXAMPLE 174

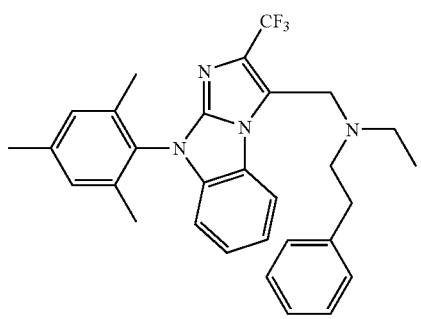

Ethyl-phenethyl-[2-trifluoromethyl-8-(2,4,6-trim-ethyl-phenyl)-8H-1,3a,8-triaza-cyclopenta[α]inden-3-ylmethyl]-amine, scheme 2: (H)

Prepared as described for the example above. LC/MS: $t_R$=3.02 min, 505.43 (MH$^+$).

EXAMPLE 175

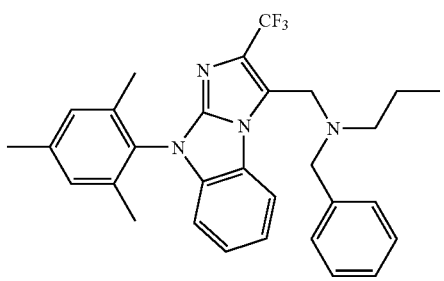

Benzyl-propyl-[2-trifluoromethyl-8-(2,4,6-trimethyl-phenyl)-8H-1,3a,8-triaza-cyclopenta[α]inden-3-ylm-ethyl]-amine, scheme 2: (H)

Prepared as described for the example above. LC/MS: $t_R$=2.46 min, 505.26 (MH$^+$).

EXAMPLE 176

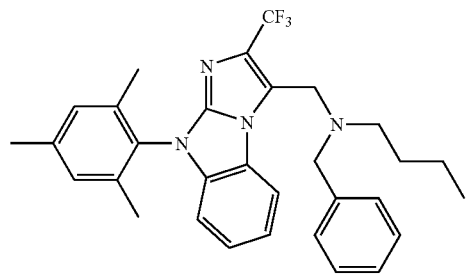

Benzyl-butyl-[2-trifluoromethyl-8-(2,4,6-trimethyl-phenyl)-8H-1,3a,8-triaza-cyclopenta[α]inden-3-ylm-ethyl]-amine, scheme 2: (H1)

Prepared as described for the example above. LC/MS: $t_R$=2.57 min, 519.27 (MH$^+$).

EXAMPLE 177

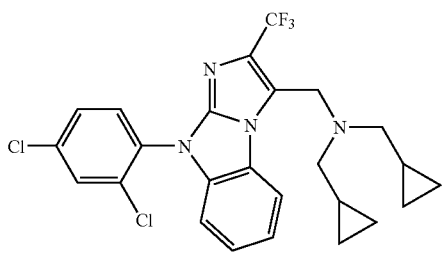

Bis-cyclopropylmethyl-[8-(2,4-dichloro-phenyl)-2-trifluoromethyl-8H-1,3a,8-triaza-cyclopenta[α]in-den-3-ylmethyl]-amine, scheme 2: (H)

Prepared as described for the example shown above. LC/MS: $t_R$=2.08 min, 507.15 (MH$^+$).

EXAMPLE 178

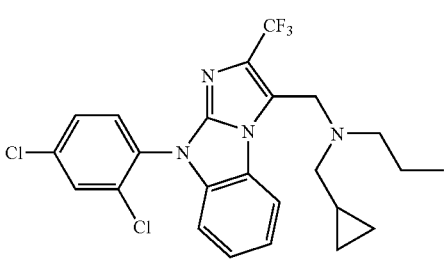

Cyclopropylmethyl-[8-(2,4-dichloro-phenyl)-2-trif-
luoromethyl-8H-1,3a,8-triaza-cyclopenta[α]inden-3-
ylmethyl]-propyl-amine, scheme 2: (H)

Prepared as described for the example above. LC/MS: $t_R$=2.07 min, 495.17 (MH$^+$).

EXAMPLE 179

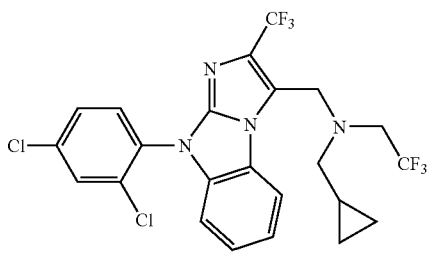

Cyclopropylmethyl-[8-(2,4-dichloro-phenyl)-2-trif-
luoromethyl-8H-1,3a,8-triaza-cyclopenta[α]inden-3-
ylmethyl]-(2,2,2-trifluoro-ethyl)-amine, scheme 2:
(H)

Prepared as described for the example above. LC/MS: $t_R$=2.92 min, 535.09 (MH$^+$).

EXAMPLE 180

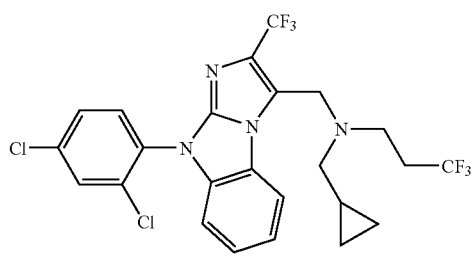

Cyclopropylmethyl-[8-(2,4-dichloro-phenyl)-2-trif-
luoromethyl-8H-1,3a,8-triaza-cyclopenta[α]inden-3-
ylmethyl]-(3,3,3-trifluoro-propyl)-amine, scheme 2:
(H)

Prepared as described for the example above. LC/MS: $t_R$=2.76 min, 549.11 (MH$^+$).

EXAMPLE 181

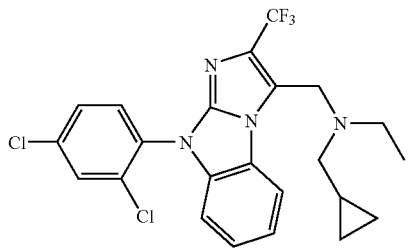

Cyclopropylmethyl-[8-(2,4-dichloro-phenyl)-2-trif-
luoromethyl-8H-1,3a,8-triaza-cyclopenta[α]inden-3-
ylmethyl]-ethyl-amine, scheme 2: (H) Pre pared as described for the example above. LC/MS: $t_R$=1.98 min, 481.13 (MH$^+$).

EXAMPLE 182

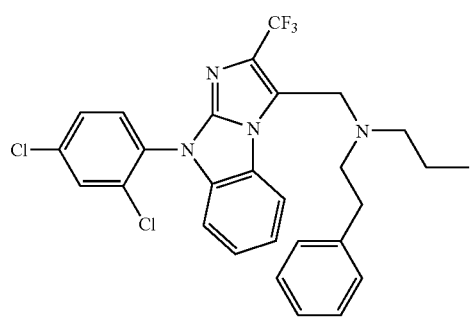

[8-(2,4-Dichloro-phenyl)-2-trifluoromethyl-8H-1,3a,
8-triaza-cyclopenta[α]inden-3-ylmethyl]-phenethyl-
propyl-amine, scheme 2: (H)

Prepared as described for the example above. LC/MS: $t_R$=2.39 min, 545.17 (MH$^+$).

EXAMPLE 183

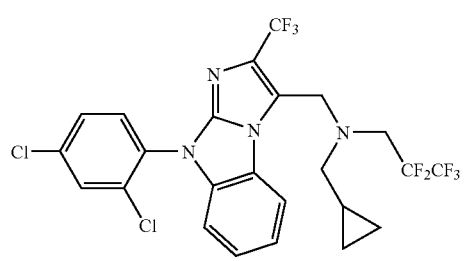

155

Cyclopropylmethyl-[8-(2,4-dichloro-phenyl)-2-trifluoromethyl-8H-1,3a,8-triaza-cyclopenta[α]inden-3-ylmethyl]-(2,2,3,3,3-pentafluoro-propyl)-amine, scheme 2: (H)

Prepared as described for the example above. LC/MS: $t_R$=2.99 min, 585.09 (MH$^+$).

EXAMPLE 184

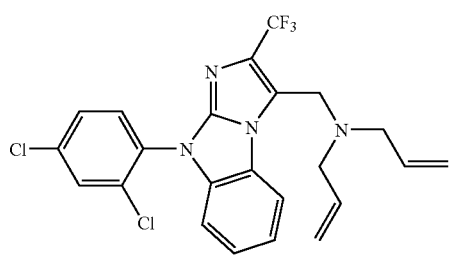

Diallyl-[8-(2,4-dichloro-phenyl)-2-trifluoromethyl-8H-1,3a,8-triaza-cyclopenta[α]inden-3-ylmethyl]-amine, scheme 2: (H)

Prepared as described for the example above. LC/MS: $t_R$=2.17 min, 479.14 (MH$^+$).

EXAMPLE 185

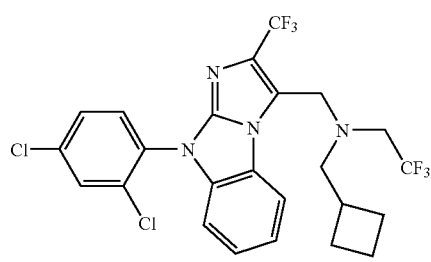

156

Cyclobutylmethyl-[8-(2,4-dichloro-phenyl)-2-trifluoromethyl-8H-1,3a,8-triaza-cyclopenta[α]inden-3-ylmethyl]-(2,2,2-trifluoro-ethyl)-amine, scheme 2: (H)

Prepared as described for the example above. LC/MS: $t_R$=3.00 min, 549.12 (MH$^+$).

EXAMPLE 186

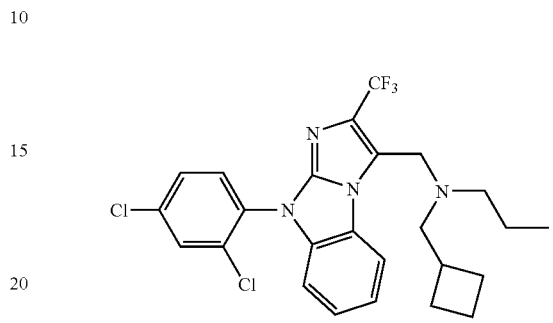

Cyclobutylmethyl-[8-(2,4-dichloro-phenyl)-2-trifluoromethyl-8H-1,3a,8-triaza-cyclopenta[α]inden-3-ylmethyl]-propyl-amine, scheme 2: (H)

Prepared as described for the example above. LC/MS: $t_R$=2.18 min, 509.16 (MH$^+$).

EXAMPLE 187

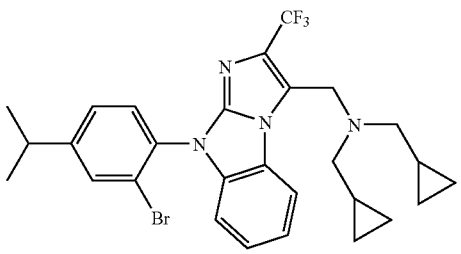

[8-(2-Bromo-4-isopropyl-phenyl)-2-trifluoromethyl-8H-1,3a,8-triaza-cyclopenta[α]inden-3-ylmethyl]-bis-cyclopropylmethyl-amine, scheme 2: (H)

Prepared as described for the example shown above. LC/MS: $t_R$=2.29 min, 559.28 (MH$^+$).

EXAMPLE 188

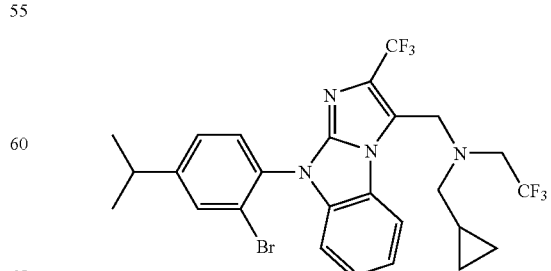

[8-(2-Bromo-4-isopropyl-phenyl)-2-trifluoromethyl-8H-1,3a,8-triaza-cyclopenta[α]inden-3-ylmethyl]-cyclopropylmethyl-(2,2,2-trifluoro-ethyl)-amine, scheme 2: (H)

Prepared as described for the example above. LC/MS: $t_R$=3.04 min, 589.22 (MH$^+$).

EXAMPLE 189

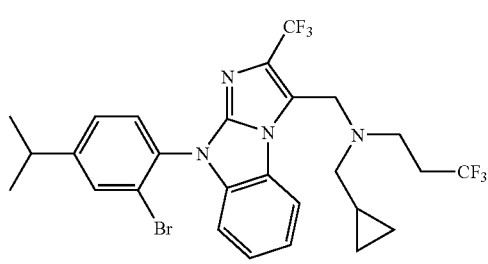

[8-(2-Bromo4-isopropyl-phenyl)-2-trifluoromethyl-8H-1,3a,8-triaza-cyclopenta[α]inden-3-ylmethyl]-cyclopropylmethyl-(3,3,3-trifluoro-propyl)-amine, scheme 2: (H)

Prepared as described for the example above. LC/MS: $t_R$=2.87 min, 603.24 (MH$^+$).

EXAMPLE 190

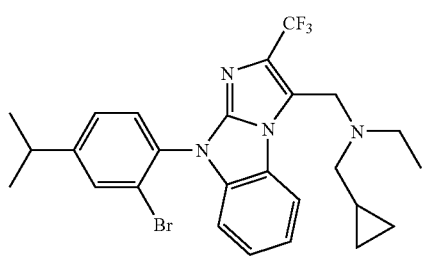

[8-(2-Bromo-4-isopropyl-phenyl)-2-trifluoromethyl-8H-1,3a,8-triaza-cyclopenta[α]inden-3-ylmethyl]-cyclopropylmethyl-ethyl-amine, scheme 2: (H)

Prepared as described for the example above. LC/MS: $t_R$=2.32 min, 535.26 (MH$^+$).

EXAMPLE 191

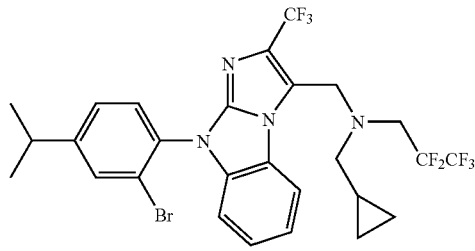

[8-(2-Bromo-4-isopropyl-phenyl)-2-trifluoromethyl-8H-1,3a,8-triaza-cyclopenta[α]inden-3-ylmethyl]-cyclopropylmethyl-(2,2,3,3,3-pentafluoro-propyl)-amine, scheme 2: (H)

Prepared as described for the example above. LC/MS: $t_R$=3.07 min, 639.22 (MH$^+$).

EXAMPLE 192

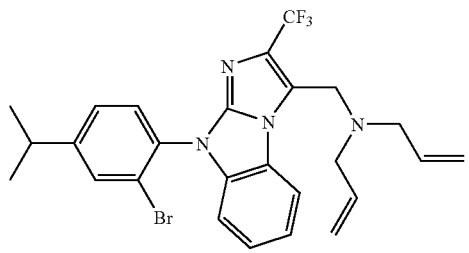

Diallyl-[8-(2-bromo-4-isopropyl-phenyl)-2-trifluoromethyl-8H-1,3a,8-triaza-cyclopenta[α]inden-3-ylmethyl]-amine, scheme 2: (H)

Prepared as described for the example above. LC/MS: $t_R$=2.39 min, 533.24 (MH$^+$).

EXAMPLE 193

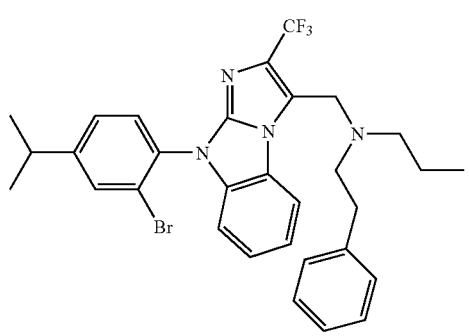

[8-(2-Bromo-4-isopropyl-phenyl)-2-trifluoromethyl-
8H-1,3a,8-triaza-cyclopenta[α]inden-3-ylmethyl]-
phenethyl-propyl-amine, scheme 2: (H)

Prepared as described for the example above. LC/MS: $t_R$=2.53 min, 599.30 (MH$^+$).

EXAMPLE 194

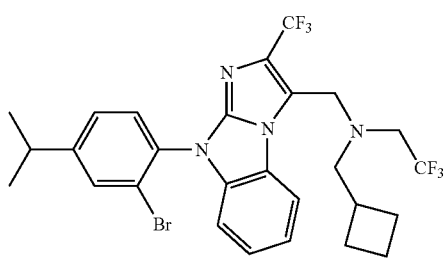

[8-(2-Bromo-4-isopropyl-phenyl)-2-trifluoromethyl-
8H-1,3a,8-triaza-cyclopenta[α]inden-3-ylmethyl]-
cyclobutylmethyl-(2,2,2-trifluoro-ethyl)-amine,
scheme 2: (H)

Prepared as described for the example above. LC/MS: $t_R$=3.09 min, 603.25 (MH$^+$).

EXAMPLE 195

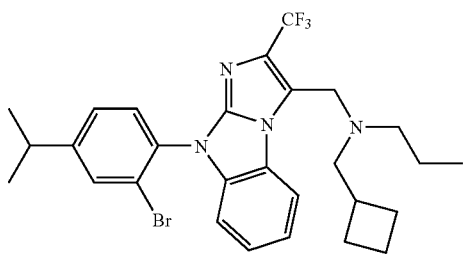

[8-(2-Bromo-4-isopropyl-phenyl)-2-trifluoromethyl-
8H-1,3a,8-triaza-cyclopenta[α]inden-3-ylmethyl]-
cyclobutylmethyl-propyl-amine, scheme 2: (H)

Prepared as described for the example above. LC/MS: $t_R$=2.38 min, 563.29 (MH$^+$).

EXAMPLE 196

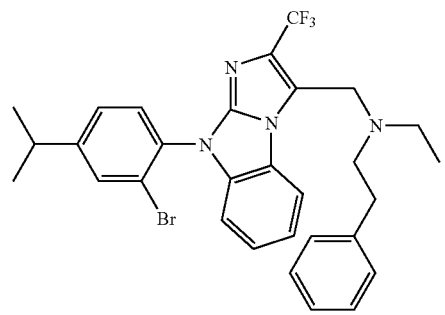

[8-(2-Bromo-4-isopropyl-phenyl)-2-trifluoromethyl-
8H-1,3a,8-triaza-cyclopenta[α]inden-3-ylmethyl]-
ethyl-phenethyl-amine, scheme 2: (H)

Prepared as described for the example above. LC/MS: $t_R$=2.42 min, 585.27 (MH$^+$).

EXAMPLE 197

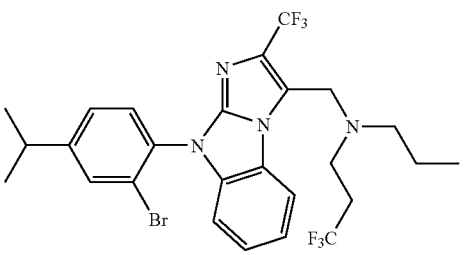

[8-(2-Bromo-4-isopropyl-phenyl)-2-trifluoromethyl-
8H-1,3a,8-triaza-cyclopenta[α]inden-3-ylmethyl]-
propyl-(3,3,3-trifluoro-propyl)-amine, scheme 2:
(H)

Prepared as described for the example above. LC/MS: $t_R$=2.88 min, 591.24 (MH$^+$).

EXAMPLE 198

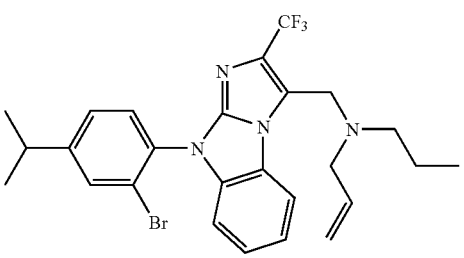

Allyl-[8-(2-bromo-4-isopropyl-phenyl)-2-trifluorom-
ethyl-8H-1,3a,8-triaza-cyclopenta[α]inden-3-ylm-
ethyl]-propyl-amine, scheme 2: (H)

Prepared as described for the example above. LC/MS: $t_R$=2.29 min, 535.26 (MH$^+$).

EXAMPLE 199

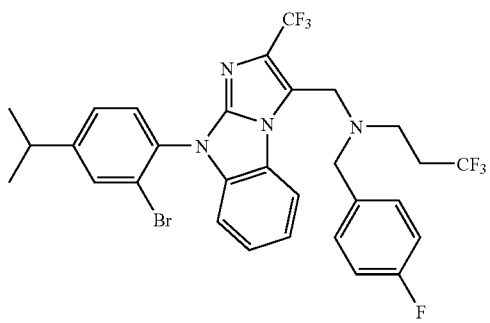

[8-(2-Bromo-4-isopropyl-phenyl)-2-trifluoromethyl-
8H-1,3a,8-triaza-cyclopenta[α]inden-3-ylmethyl]-(4-
fluoro-benzyl)-(3,3,3-trifluoro-propyl)-amine,
scheme 2: (H)

Prepared as described for the example above. LC/MS: $t_R$=3.05 min, 657.22 (MH$^+$).

EXAMPLE 200

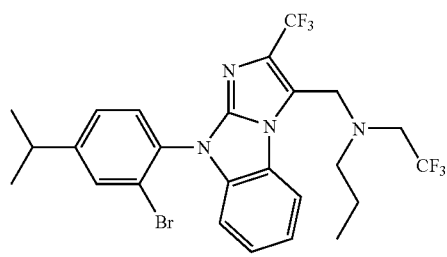

[8-(2-Bromo-4-isopropyl-phenyl)-2-trifluoromethyl-
8H-1,3a,8-triaza-cyclopenta[α]inden-3-ylmethyl]-
propyl-(2,2,2-trifluoro-ethyl)-amine, scheme 2: (H)

Prepared as described for the example above. LC/MS: $t_R$=3.00 min, 577.23 (MH$^+$).

EXAMPLE 201

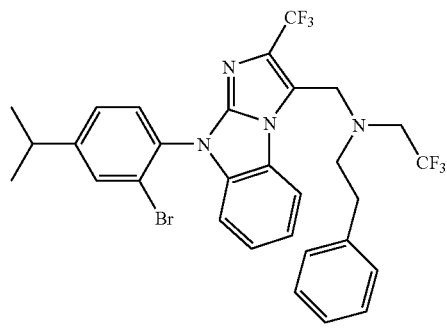

[8-(2-Bromo-4-isopropyl-phenyl)-2-trifluoromethyl-
8H-1,3a,8-triaza-cyclopenta[α]inden-3-ylmethyl]-
phenethyl-(2,2,2-trifluoro-ethyl)-amine, scheme 2:
(H)

Prepared as described for the example above. LC/MS: $t_R$=3.08 min, 639.24 (MH$^+$).

EXAMPLE 202

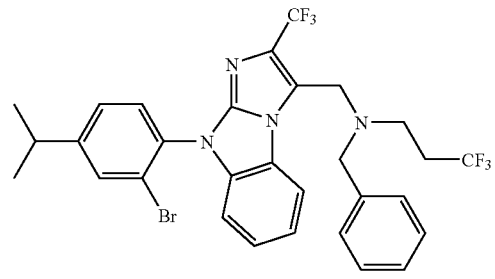

Benzyl-[8-(2-bromo-4-isopropyl-phenyl)-2-trifluo-
romethyl-8H-1,3a,8-triaza-cyclopenta[α]inden-3-
ylmethyl]-(3,3,3-trifluoro-propyl)-amine, scheme 2:
(H)

Prepared as described for the example above. LC/MS: $t_R$=3.06 min, 639.23 (MH$^+$).

EXAMPLE 203

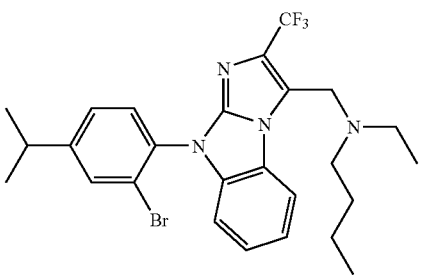

[8-(2-Bromo-4-isopropyl-phenyl)-2-trifluoromethyl-
8H-1,3a,8-triaza-cyclopenta[α]inden-3-ylmethyl]-
butyl-ethyl-amine, scheme 2: (H)

Prepared as described for the example above. LC/MS: $t_R$=2.27 min, 537.27 (MH$^+$).

EXAMPLE 204

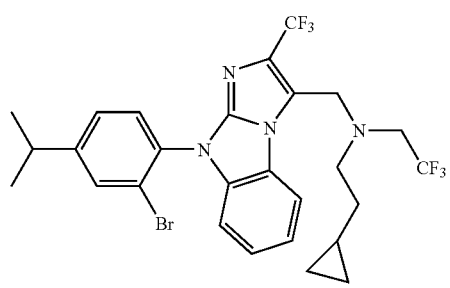

[8-(2-Bromo-4-isopropyl-phenyl)-2-trifluoromethyl-8H-1,3a,8-triaza-cyclopenta[α]inden-3-ylmethyl]-(2-cyclopropyl-ethyl)-(2,2,2-trifluoro-ethyl)-amine, scheme 2: (H)

Prepared as described for the example above. LC/MS: $t_R$=3.07 min, 603.24 (MH$^+$).

EXAMPLE 205

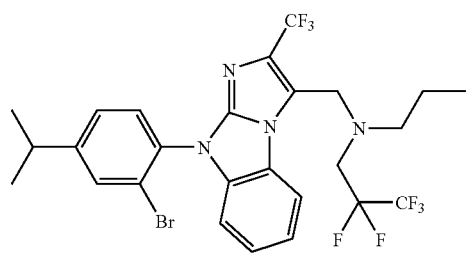

[8-(2-Bromo-4-isopropyl-phenyl)-2-trifluoromethyl-8H-1,3a,8-triaza-cyclopenta[α]inden-3-ylmethyl]-(2,2,3,3,3-pentafluoro-propyl)-propyl-amine, scheme 2: (H)

Prepared as described for the example above. LC/MS: $t_R$=3.06 min, 627.22 (MH$^+$).

EXAMPLE 206

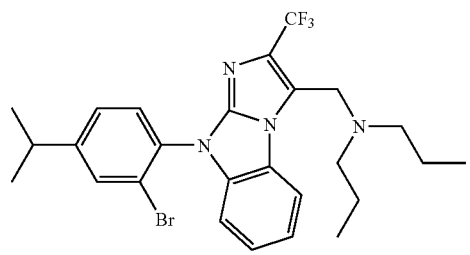

[8-(2-Bromo-4-isopropyl-phenyl)-2-trifluoromethyl-8H-1,3a,8-triaza-cyclopenta[α]inden-3-ylmethyl]-dipropyl-amine, scheme 2: (H)

Prepared as described for the example above. LC/MS: $t_R$=2.36 min, 537.20 (MH$^+$).

EXAMPLE 207

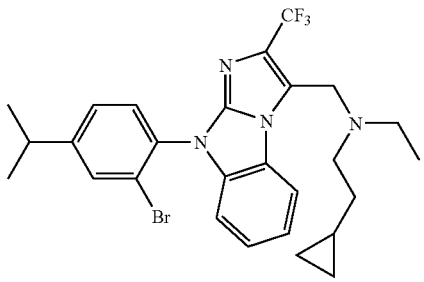

[8-(2-Bromo-4-isopropyl-phenyl)-2-trifluoromethyl-8H-1,3a,8-triaza-cyclopenta[α]inden-3-ylmethyl]-(2-cyclopropyl-ethyl)-ethyl-amine, scheme 2: (H)

Prepared as described for the example above. LC/MS: $t_R$=3.52 min, 549.29 (MH$^+$).

EXAMPLE 208

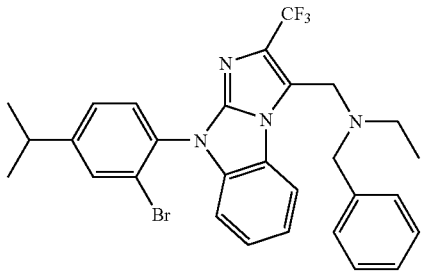

Benzyl-[8-(2-bromo-4-isopropyl-phenyl)-2-trifluoromethyl-8H-1,3a,8-triaza-cyclopenta[α]inden-3-ylmethyl]-ethyl-amine, scheme 2: (H)

Prepared as described for the example above. LC/MS: $t_R$=2.43 min, 571.26 (MH$^+$).

EXAMPLE 209

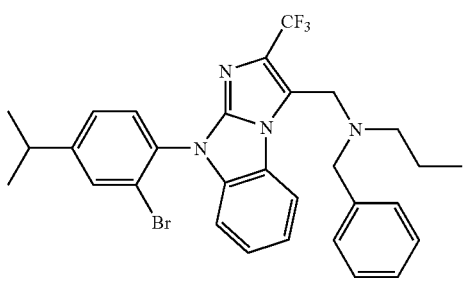

Benzyl-[8-(2-bromo-4-isopropyl-phenyl)-2-trifluoromethyl-8H-1,3a,8-triaza-cyclopenta[α]inden-3-ylmethyl]-propyl-amine, scheme 2: (H)

Prepared as described for the example above. LC/MS: $t_R$=2.47 min, 585.27 (MH$^+$).

EXAMPLE 210

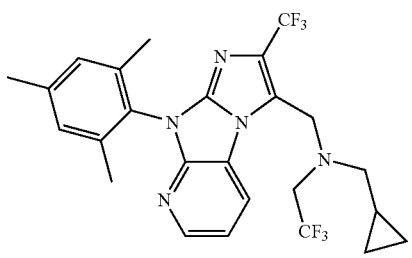

Cyclopropylmethyl-(2,2,2-trifluoro-ethyl)-[2-trifluoromethyl-8-(2,4,6-trimethyl-phenyl)-8H-1,3a,7,8-tetraaza-cyclopenta[α]inden-3-ylmethyl]-amine, scheme 2: (H)

Prepared as described for the example above. LC/MS: $t_R$=2.86 min, 510.23 (MH$^+$).

EXAMPLE 211

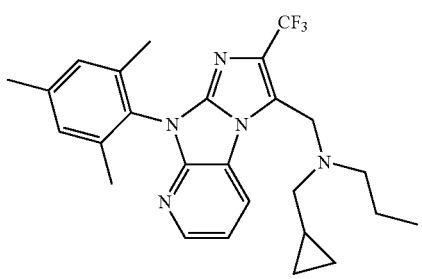

Cyclopropylmethyl-propyl-[2-trifluoromethyl-8-(2,4,6-trimethyl-phenyl)-8H-1,3a,7,8-tetraaza-cyclopenta[a]inden-3-ylmethyl]-amine, scheme 2: (H)

Prepared as described for the example above. LC/MS: $t_R$=2.00 min, 470.26 (MH$^+$).

EXAMPLE 212

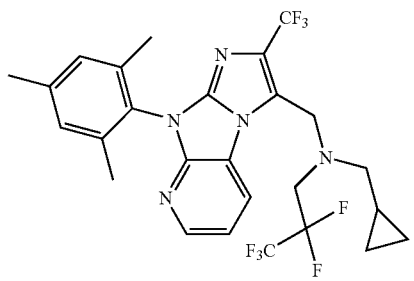

Cyclopropylmethyl-(2,2,3,3,3-pentafluoro-propyl)-[2-trifluoromethyl-8-(2,4,6-trimethyl-phenyl)-8H-1,3a,7,8-tetraaza-cyclopenta[α]inden-3-ylmethyl]-amine, scheme 2: (H)

Prepared as described for the example above. LC/MS: $t_R$=2.94 min, 560.21 (MH$^+$).

EXAMPLE 213

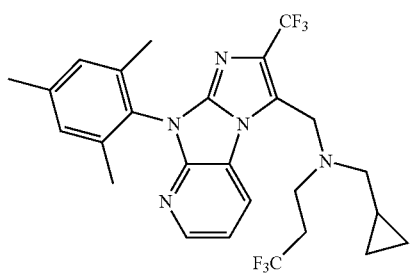

Cyclopropylmethyl-[2-trifluoromethyl-8-(2,4,6-trimethyl-phenyl)-8H-1,3a,7,8-tetraaza-cyclopenta[α]inden-3-ylmethyl]-(3,3,3-trifluoro-propyl)-amine, scheme 2: (H)

Prepared as described for the example above. LC/MS: $t_R$=2.79 min, 524.24 (MH$^+$).

EXAMPLE 214

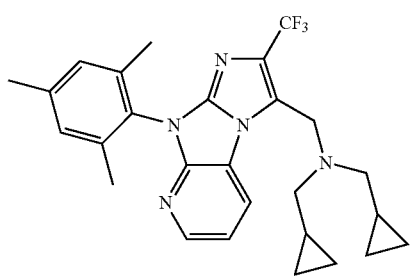

Bis-cyclopropylmethyl-[2-trifluoromethyl-8-(2,4,6-trimethyl-phenyl)-8H-1,3a,7,8-tetraaza-cyclopenta[α]inden-3-ylmethyl]-amine, scheme 2: (H)

Prepared as described for the example above. LC/MS: $t_R$=2.01 min, 482.27 (MH$^+$).

EXAMPLE 215

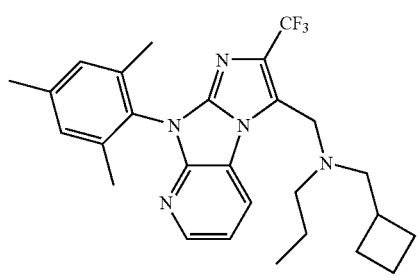

Cyclobutylmethyl-propyl-[2-trifluoromethyl-8-(2,4,6-trimethyl-phenyl)-8H-1,3a,7,8-tetraaza-cyclopenta[α]inden-3-ylmethyl]-amine, scheme 2: (H)

Prepared as described for the example above. LC/MS: $t_R$=2.18 min, 484.28 (MH$^+$).

EXAMPLE 216

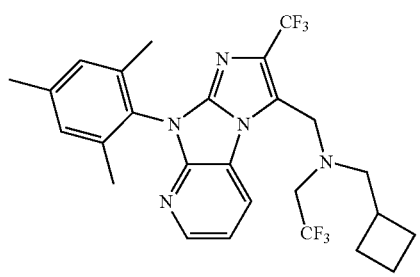

Cyclobutylmethyl-(2,2,2-trifluoro-ethyl)-[2-trifluoromethyl-8-(2,4,6-trimethyl-phenyl)-8H-1,3a,7,8-tetraaza-cyclopenta[α]inden-3-ylmethyl]-amine, scheme 2: (H)

Prepared as described for the example above. LC/MS: $t_R$=2.96 min, 524.24 (MH$^+$).

EXAMPLE 217

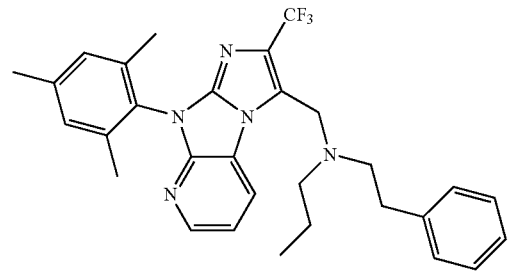

Phenylethyl-propyl-[2-trifluoromethyl-8-(2,4,6-trimethyl-phenyl)-8H-1,3a,7,8-tetraaza-cyclopenta[α]inden-3-ylmethyl]-amine, scheme 2: (H)

Prepared as described for the example above. LC/MS: $t_R$=2.45 min, 520.27 (MH$^+$).

EXAMPLE 218

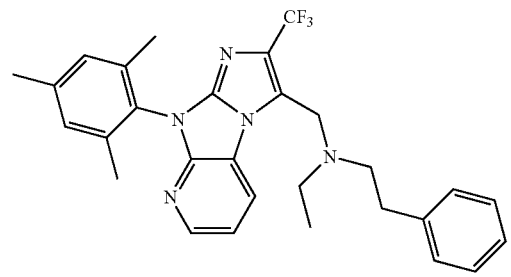

Ethyl-phenethyl-[2-trifluoromethyl-8-(2,4,6-trimethyl-phenyl)-8H-1,3a,7,8-tetraaza-cyclopenta[α]inden-3-ylmethyl]-amine, scheme 2: (H)

Prepared as described for the example above. LC/MS: $t_R$=2.27 min, 506.26 (MH$^+$).

EXAMPLE 219

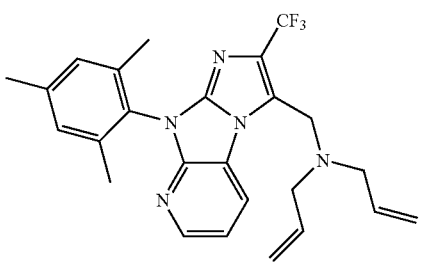

Diallyl-[2-trifluoromethyl-8-(2,4,6-trimethyl-phenyl)-8H-1,3a,7,8-tetraaza-cyclopenta[α]inden-3-ylmethyl]-amine, scheme 2: (H)

Prepared as described for the example above. LC/MS: $t_R$=2.15 min, 454.24 (MH$^+$).

EXAMPLE 220

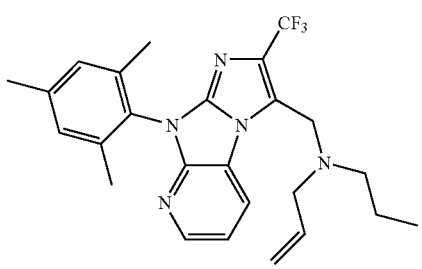

Allyl-propyl-[2-trifluoromethyl-8-(2,4,6-trimethyl-phenyl)-8H-1,3a,7,8-tetraaza-cyclopenta[α]inden-3-ylmethyl]-amine, scheme 2: (H)

Prepared as described for the example above. LC/MS: $t_R$=2.03 min, 456.25 (MH$^+$).

EXAMPLE 221

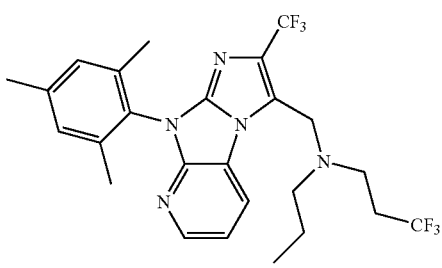

(4) Propyl-[2-trifluoromethyl-8-(2,4,6-trimethyl-phenyl)-8H-1,3a,7,8-tetraaza-cyclopenta[α]inden-3-ylmethyl]-(3,3,3-trifluoro-propyl)-amine, scheme 2: (H)

Prepared as described for the example above. LC/MS: $t_R$=2.79 min, Mass spec.: 512.24 (MH$^+$).

EXAMPLE 222

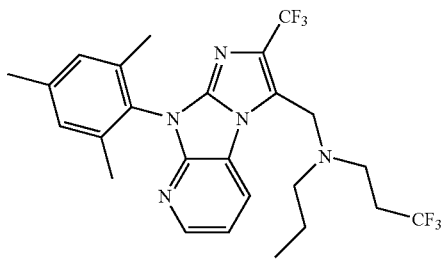

Propyl-(2,2,2-trifluoro-ethyl)-[2-trifluoromethyl-8-(2,4,6-trimethyl-phenyl)-8H-1,3a,7,8-tetraaza-cyclopenta[α]inden-3-ylmethyl]-amine, scheme 2: (H)

Prepared as described for the example above. LC/MS: $t_R$=2.84 min, 498.22 (MH$^+$).

EXAMPLE 223

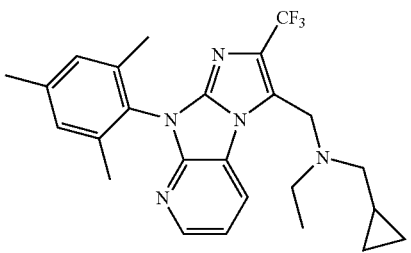

Cyclopropylmethyl-ethyl-[2-trifluoromethyl-8-(2,4,6-trimethyl-phenyl)-8H-1,3a,7,8-tetraaza-cyclopenta[α]inden-3-ylmethyl]-amine, scheme 2: (H)

Prepared as described for the example above. LC/MS: $t_R$=1.90 min, 456.25 (MH$^+$).

EXAMPLE 224

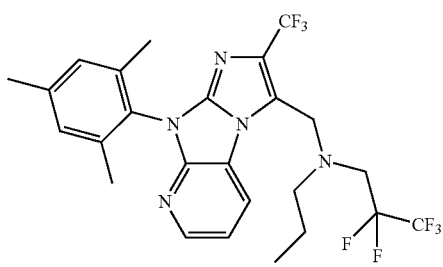

(2,2,3,3,3-Pentafluoro-propyl)-propyl-[2-trifluorom-ethyl-8-(2,4,6-trimethyl-phenyl)-8H-1,3a,7,8-tet-raaza-cyclopenta[α]inden-3-ylmethyl]-amine, scheme 2: (H)

Prepared as described for the example above. LC/MS: $t_R$=2.94 min, 548.21 (MH$^+$).

EXAMPLE 225

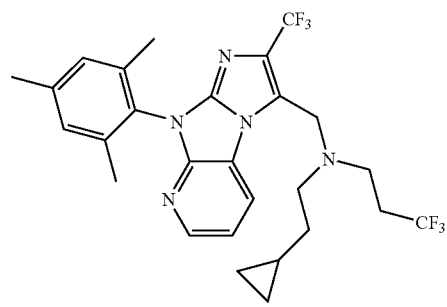

(2-Cyclopropyl-ethyl)-[2-trifluoromethyl-8-(2,4,6-trimethyl-phenyl)-8H-1,3a,7,8-tetraaza-cyclopenta[α]inden-3-ylmethyl]-(3,3,3-trifluoro-propyl)-amine, scheme 2: (H)

Prepared as described for the example above. LC/MS: $t_R$=2.93 min, 538.26 (MH$^+$).

EXAMPLE 226

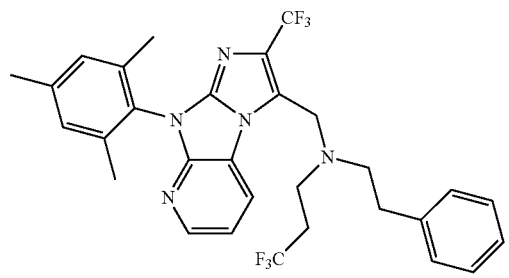

Phenethyl-[2-trifluoromethyl-8-(2,4,6-trimethyl-phenyl)-8H-1,3a,7,8-tetraaza-cyclopenta[a]inden-3-ylmethyl]-(3,3,3-trifluoro-propyl)-amine scheme 2:(H)

Prepared as described for the example above. LC/MS: $t_R$=2.99 min, 574.25 (MH$^+$).

EXAMPLE 227

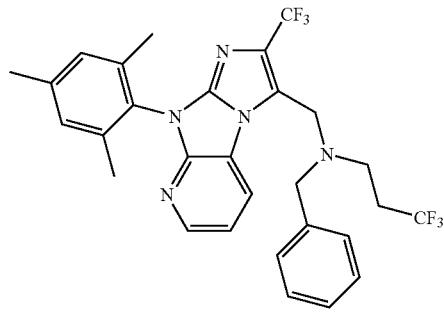

Benzyl-[2-trifluoromethyl-8-(2,4,6-trimethylphenyl)-8H-1,3a,7,8-tetraaza-cyclopenta[α]inden-3-ylm-ethyl]-(3,3,3-trifluoro-propyl)-amine, scheme 2: (H)

Prepared as described for the example above. LC/MS: $t_R$=2.94 min, 560.23 (MH$^+$).

EXAMPLE 228

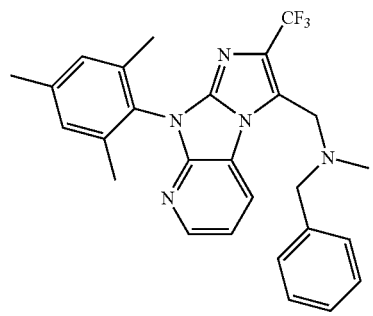

Benzyl-methyl-[2-trifluoromethyl-8-(2,4,6-trim-ethyl-phenyl)-8H-1,3a,7,8-tetraaza-cyclopenta[α]inden-3-ylmethyl]-amine, scheme 2: (H)

Prepared as described for the example above. LC/MS: $t_R$=2.08 min, 478.23 (MH$^+$).

EXAMPLE 229

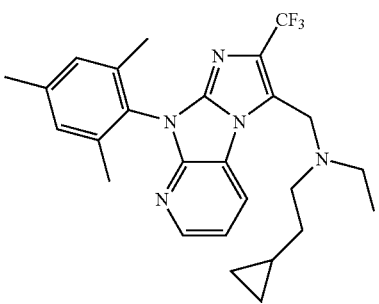

(2-Cyclopropyl-ethyl)-ethyl-[2-trifluoromethyl-8-(2,
4,6-trimethyl-phenyl)-8H-1,3a,7,8-tetraaza-cyclo-
penta[α]inden-3-ylmethyl]-amine, scheme 2: (H)

Prepared as described for the example above. LC/MS: $t_R$=2.06 min, 470.27 (MH$^+$).

EXAMPLE 230

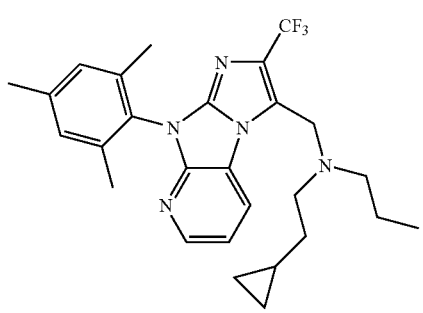

(2-Cyclopropyl-ethyl)-propyl-[2-trifluoromethyl-8-
(2,4,6-trimethyl-phenyl)-8H-1,3a,7,8-tetraaza-cyclo-
penta[α]inden-3-ylmethyl]-amine, scheme 2: (H)

Prepared as described for the example above. LC/MS: $t_R$=2.17 min, 484.28 (MH$^+$).

EXAMPLE 231

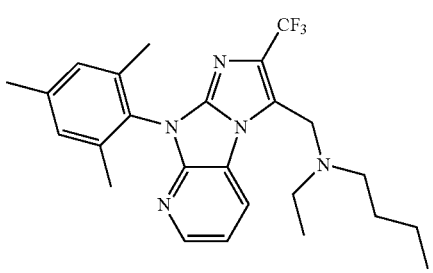

Butyl-ethyl-[2-trifluoromethyl-8-(2,4,6-trimethyl-
phenyl)-8H-1,3a,7,8-tetraaza-cyclopenta[α]inden-3-
ylmethyl]-amine, scheme 2: (H)

Prepared as described for the example above. LC/MS: $t_R$=2.01 min, 458.26 (MH$^+$).

EXAMPLE 232

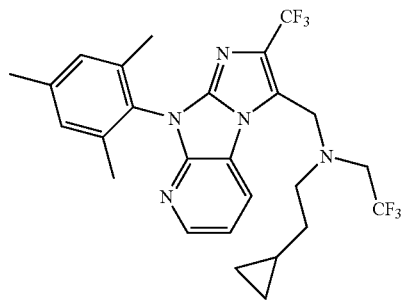

(2-Cyclopropyl-ethyl)-(2,2,2-trifluoro-ethyl)-[2-trif-
luoromethyl-8-(2,4,6-trimethyl-phenyl)-8H-1,3a,7,8-
tetraaza-cyclopenta[α]inden-3-ylmethyl]-amine,
scheme 2: (H)

Prepared as described for the example above. LC/MS: $t_R$=2.94 min, 524.25 (MH$^+$).

EXAMPLE 233

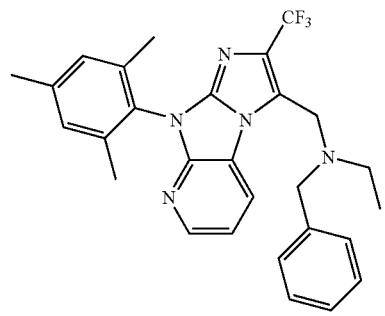

Benzyl-ethyl-[2-trifluoromethyl-8-(2,4,6-trimethyl-
phenyl)-8H-1,3a,7,8-tetraaza-cyclopenta[α]inden-3-
ylmethyl]-amine, scheme 2: (H)

Prepared as described for the example above. LC/MS: $t_R$=2.16 min, 492.25 (MH$^+$).

EXAMPLE 234

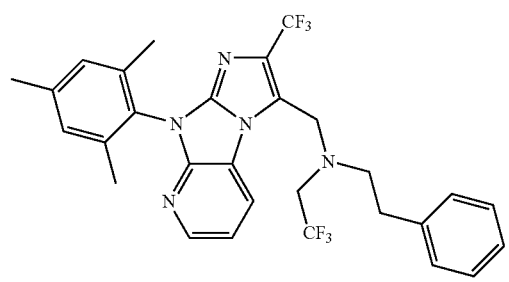

Phenethyl-(2,2,2-trifluoro-ethyl)-[2-trifluoromethyl-8-(2,4,6-trimethyl-phenyl)-8H-1,3a,7,8-tetraaza-cyclopenta[α]inden-3-ylmethyl]-amine, scheme 2: (H)

Prepared as described for the example above. LC/MS: $t_R$=2.96 min, 560.25 (MH$^+$).

EXAMPLE 235

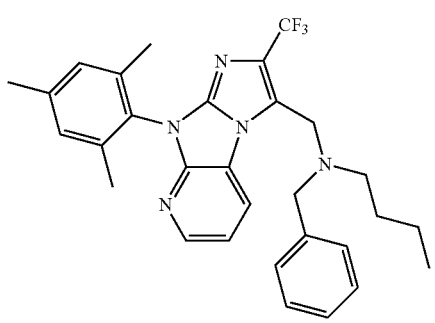

Benzyl-butyl-[2-trifluoromethyl-8-(2,4,6-trimethyl-phenyl)-8H-1,3a,7,8-tetraaza-cyclopenta[α]inden-3-ylmethyl]-amine, scheme 2: (H)

Prepared as described for the example above. LC/MS: $t_R$=2.56 min, 520.27 (MH$^+$).

EXAMPLE 236

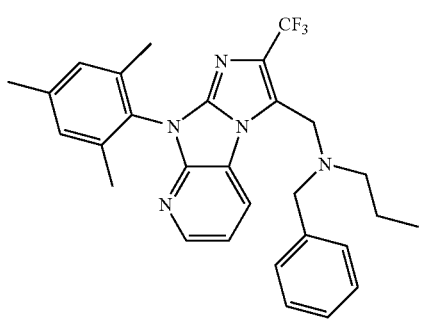

Benzyl-propyl-[2-trifluoromethyl-8-(2,4,6-trimethyl-phenyl)-8H-1,3a,7,8-tetraaza-cyclopenta[α]inden-3-ylmethyl]-amine, scheme 2: (H)

Prepared as described for the example above. LC/MS: $t_R$=2.40 min, 506.26 (MH$^+$).

EXAMPLE 237

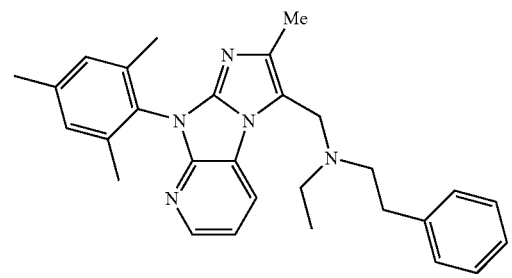

Ethyl-[2-methyl-8-(2,4,6-trimethyl-phenyl)-8H-1,3a,7,8-tetraaza-cyclopenta[α]inden-3-ylmethyl]-phenethyl-amine, scheme 2: (H)

Prepared as described for the example above. LC/MS: $t_R$=1.95 min, 452.28 (MH$^+$).

EXAMPLE 238

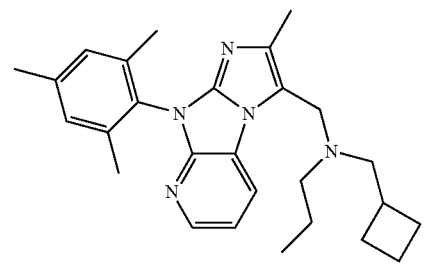

Cyclobutylmethyl-[2-methyl-8-(2,4,6-trimethyl-phenyl)-8H-1,3a,7,8-tetraaza-cyclopenta[α]inden-3-ylmethyl]-propyl-amine, scheme 2: (H)

Prepared as described for the example above. LC/MS: $t_R$=1.84 min, 430.30 (MH$^+$).

EXAMPLE 239

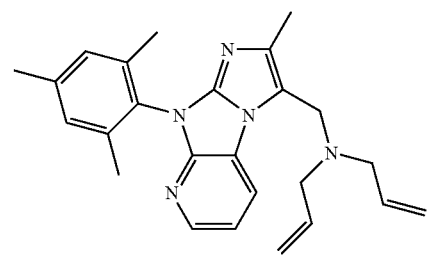

177

Diallyl-[2-methyl-8-(2,4,6-trimethyl-phenyl)-8H-1,
3a,7,8-tetraaza-cyclopenta[α]linden-3-ylmethyl]-
amine, scheme 2: (H)

Prepared as described for the example above. LC/MS: $t_R$=1.66 min, 400.27 (MH⁺).

EXAMPLE 240

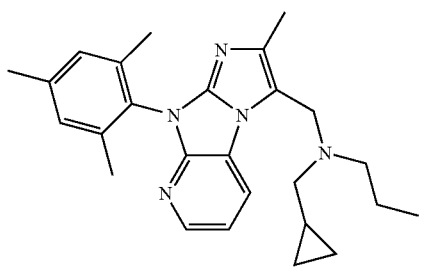

Cyclopropylmethyl-[2-methyl-8-(2,4,6-trimethyl-
phenyl)-8H-1,3a,7,8-tetraaza-cyclopenta[α]inden-3-
ylmethyl]-propyl-amine, scheme 2: (H)

Prepared as described for the example above. LC/MS: $t_R$=1.68 min, 416.29 (MH⁺).

EXAMPLE 241

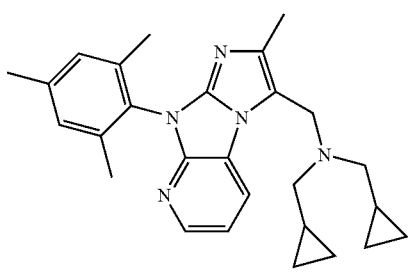

178

Bis-cyclopropylmethyl-[2-methyl-8-(2,4,6-trimethyl-
phenyl)-8H-1,3a,7,8-tetraaza-cyclopenta[α]inden-3-
ylmethyl]-amine, scheme 2: (H)

Prepared as described for the example above. LC/MS: $t_R$=1.84 min, 428.29 (MH⁺).

EXAMPLE 242

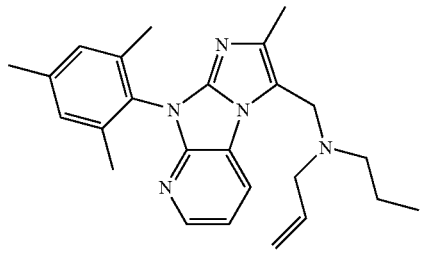

Allyl-[2-methyl-8-(2,4,6-trimethyl-phenyl)-8H-1,3a,
7,8-tetraaza-cyclopenta[α]inden-3-ylmethyl]-propyl-
amine, scheme 2: (H)

Prepared as described for the example above. LC/MS: $t_R$=1.65 min, 402.28 (MH⁺).

EXAMPLE 243

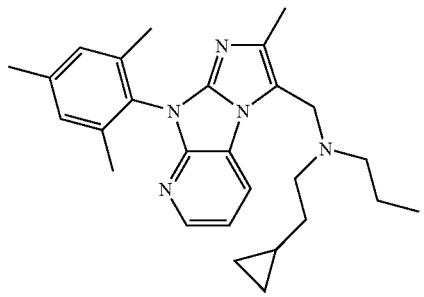

(2-Cyclopropyl-ethyl)-[2-methyl-8-(2,4,6-trimethyl-
phenyl)-8H-1,3a,7,8-tetraaza-cyclopenta[α]inden-3-
ylmethyl]-propyl-amine, scheme 2: (H)

Prepared as described for the example above. LC/MS: $t_R$=1.84 min, 430.31 (MH⁺).

EXAMPLE 244

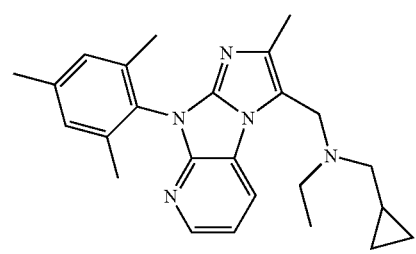

Cyclopropylmethyl-ethyl-[2-methyl-8-(2,4,6-trimethyl-phenyl)-8H-1,3a,7,8-tetraaza-cyclopenta[α]inden-3-ylmethyl]-amine, scheme 2: (H)

Prepared as described for the example above. LC/MS: $t_R$=1.60 min, 402.28 (MH$^+$).

EXAMPLE 245

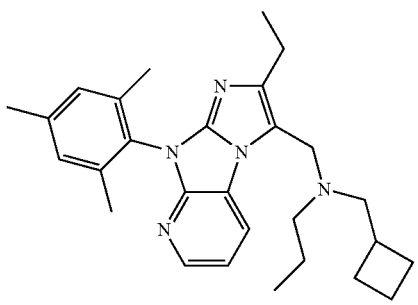

Cyclobutylmethyl-[2-ethyl-8-(2,4,6-trimethyl-phenyl)-8H-1,3a,7,8-tetraaza-cyclopenta[α]inden-3-ylmethyl]-propyl-amine, scheme 2: (H)

Prepared as described for the example above. LC/MS: $t_R$=1.95 min, 444.33 (MH$^+$)

EXAMPLE 246

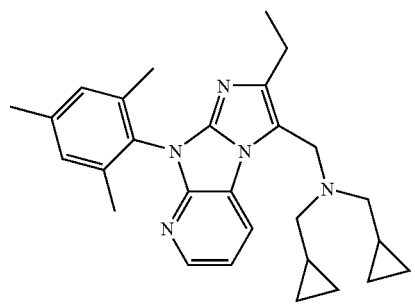

Bis-cyclopropylmethyl-[2-ethyl-8-(2,4,6-trimethyl-phenyl)-8H-1,3a,7,8-tetraaza-cyclopenta[α]inden-3-ylmethyl]-amine, scheme 2: (H)

Prepared as described for the example above. LC/MS: $t_R$=1.82 min, 442.31 (MH$^+$).

EXAMPLE 247

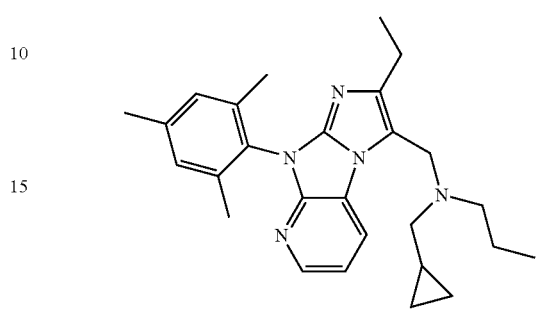

Cyclopropylmethyl-[2-ethyl-8-(2,4,6-trimethyl-phenyl)-8H-1,3a,7,8-tetraaza-cyclopenta[α]inden-3-ylmethyl]-propyl-amine, scheme 2: (H)

Prepared as described for the example above. LC/MS: $t_R$=1.68 min, 430.31 (MH$^+$).

EXAMPLE 248

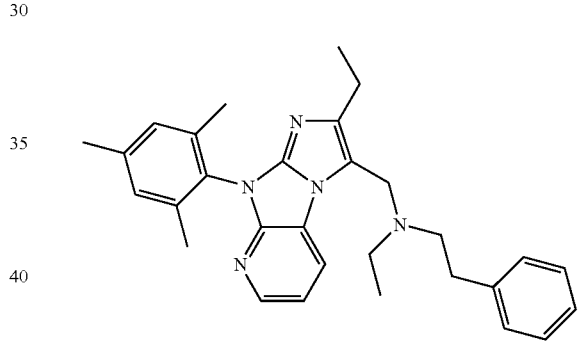

Ethyl-[2-ethyl-8-(2,4,6-trimethyl-phenyl)-8H-1,3a,7,8-tetraaza-cyclopenta[α]inden-3-ylmethyl]-phenethyl-amine, scheme 2: (H)

Prepared as described for the example above. LC/MS: $t_R$=2.05 min, 466.30 (MH$^+$).

EXAMPLE 249

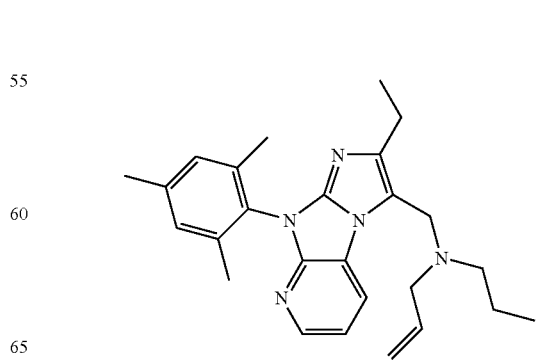

181

Allyl-[2-ethyl-8-(2,4,6-trimethyl-phenyl)-8H-1,3a,7,
8-tetraaza-cyclopenta[α]inden-3-ylmethyl]-propyl-
amine, scheme 2: (H)

Prepared as described for the example above. LC/MS: $t_R$=1.78 min, 416.29 (MH$^+$).

EXAMPLE 250

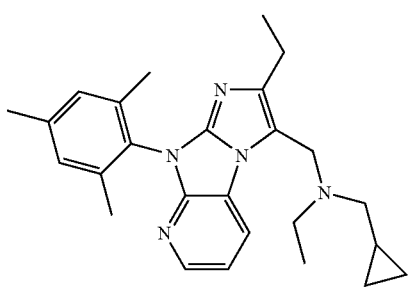

Cyclopropylmethyl-ethyl-[2-ethyl-8-(2,4,6-trim-
ethyl-phenyl)-8H-1,3a,7,8-tetraaza-cyclopenta[α]
inden-3-ylmethyl]-amine, scheme 2: (H)

Prepared as described for the example above. LC/MS: $t_R$=1.70 min, 416.31 (MH$^+$).

EXAMPLE 251

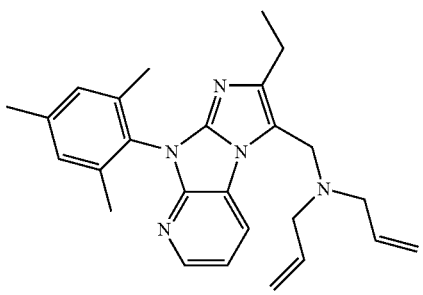

Diallyl-[2-ethyl-8-(2,4,6-trimethyl-phenyl)-8H-1,3a,
7,8-tetraaza-cyclopenta[α]inden-3-ylmethyl]-amine,
scheme 2: (H)

Prepared as described for the example above. LC/MS: $t_R$=1.79 min, 414.28 (MH$^+$).

182

EXAMPLE 252

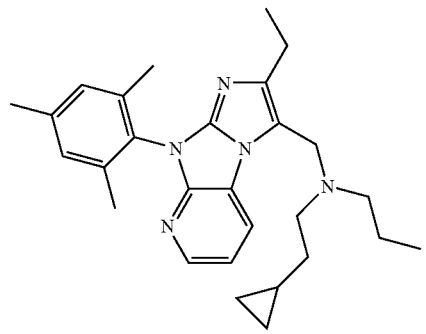

(2-Cyclopropyl-ethyl)-[2-ethyl-8-(2,4,6-trimethyl-
phenyl)-8H-1,3a,7,8-tetraaza-cyclopenta[α]inden-3-
ylmethyl]-propyl-amine, scheme 2: (H)

Prepared as described for the example above. LC/MS: $t_R$=1.95 min, 444.33 (MH$^+$).

For Examples 253-282 LC/MS were run using the following conditions: Column, YMC ODC S7 3.0×50 mm; run time, 3 min.

EXAMPLE 253

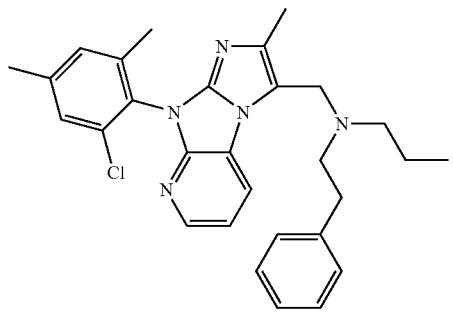

[8-(2-Chloro-4,6-dimethyl-phenyl)-2-methyl-8H-1,
3a,7,8-tetraaza-cyclopenta[a]inden-3-ylmethyl]-
phenethyl-propyl-amine, scheme 2: (H)

Prepared as described for the example above. LC/MS: $t_R$=1.64 min, 486.27 (MH$^+$).

EXAMPLE 254

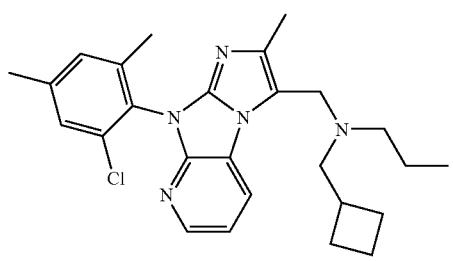

[8-(2-Chloro-4,6-dimethyl-phenyl)-2-methyl-8H-1,
3a,7,8-tetraaza-cyclopenta[α]inden-3-ylmethyl]-
cyclobutylmethyl-propyl-amine, scheme 2: (H)

Prepared as described for the example above. LC/MS: $t_R$=1.54 min, 450.30 (MH$^+$).

EXAMPLE 255

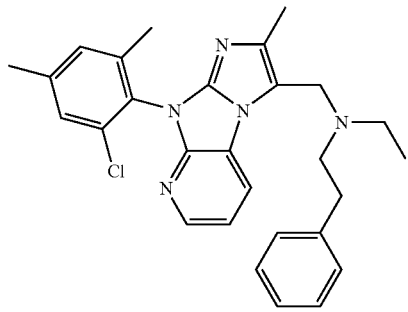

[8-(2-Chloro-4,6-dimethyl-phenyl)-2-methyl-8H-1,
3a,7,8-tetraaza-cyclopenta[a]inden-3-ylmethyl]-
ethyl-phenethyl-amine, scheme 2: (H)

Prepared as described for the example above. LC/MS: $t_R$=1.60 min, 472.24 (MH$^+$).

EXAMPLE 256

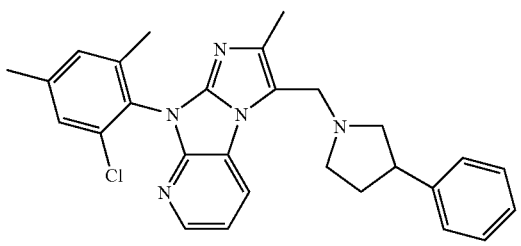

8-(2-Chloro-4,6-dimethyl-phenyl)-2-methyl-3-(3-
phenyl-pyrrolidin-1-ylmethyl)-8H-1,3a,7,8-tetraaza-
cyclopenta[α]indene, scheme 2: (H)

Prepared as described for the example above. LC/MS: $t_R$=1.60 min, 470.20 (MH$^+$).

EXAMPLE 257

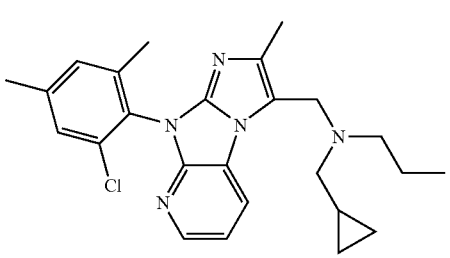

[8-(2-Chloro-4,6-dimethyl-phenyl)-2-methyl-8H-1,
3a,7,8-tetraaza-cyclopenta[α]inden-3-ylmethyl]-
cyclopropylmethyl-propyl-amine, scheme 2: (H)

Prepared as described for the example above. LC/MS: $t_R$=1.47 min, 436.26 (MH$^+$).

EXAMPLE 258

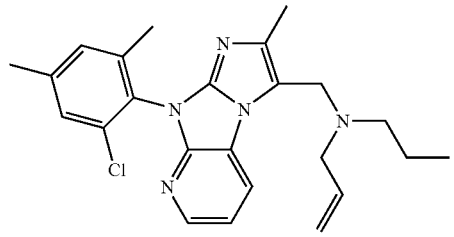

Allyl-[8-(2-chloro-4,6-dimethyl-phenyl)-2-methyl-
8H-1,3a,7,8-tetraaza-cyclopenta[α]inden-3-ylm-
ethyl]-propyl-amine, scheme 2: (H)

Prepared as described for the example above. LC/MS: $t_R$=1.46 min, Mass spec.: 422.30 (MH$^+$).

EXAMPLE 259

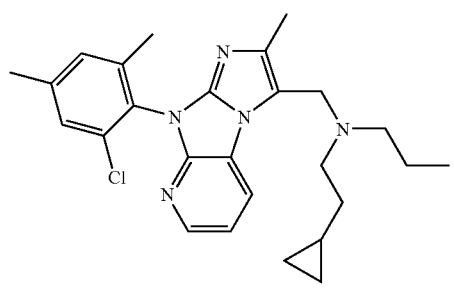

[8-(2-Chloro-4,6-dimethyl-phenyl)-2-methyl-8H-1,
3a,7,8-tetraaza-cyclopenta[α]inden-3-ylmethyl]-(2-
cyclopropyl-ethyl)-propyl-amine, scheme 2: (H)

Prepared as described for the example above. LC/MS: $t_R$=1.55 min, 450.30 (MH$^+$).

EXAMPLE 260

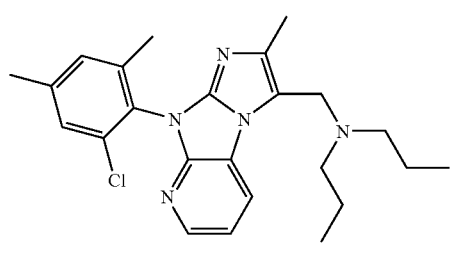

[8-(2-Chloro-4,6-dimethyl-phenyl)-2-methyl-8H-1,
3a,7,8-tetraaza-cyclopenta[α]inden-3-ylmethyl]-
dipropyl-amine, scheme 2: (H)

Prepared as described for the example above. LC/MS: $t_R$=1.45 min, 424.24 (MH$^+$).

EXAMPLE 261

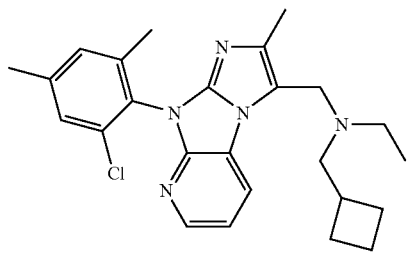

[8-(2-Chloro-4,6-dimethyl-phenyl)-2-methyl-8H-1, 3a,7,8-tetraaza-cyclopenta[α]inden-3-ylmethyl]-cyclobutylmethyl-ethyl-amine, scheme 2: (H)

Prepared as described for the example above. LC/MS: $t_R$=1.51 min, 436.30 (MH$^+$).

EXAMPLE 262

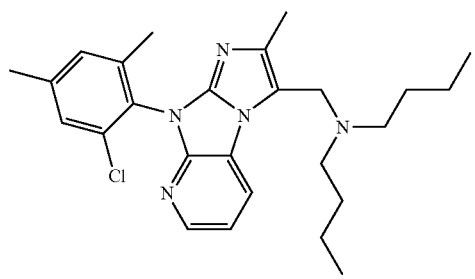

Dibutyl-[8-(2-chloro-4,6-dimethyl-phenyl)-2-methyl-8H-1,3a,7,8-tetraaza-cyclopenta[α]inden-3-ylmethyl]-amine, scheme 2: (H)

Prepared as described for the example above. LC/MS: $t_R$=1.60 min, 452.29 (MH$^+$).

EXAMPLE 263

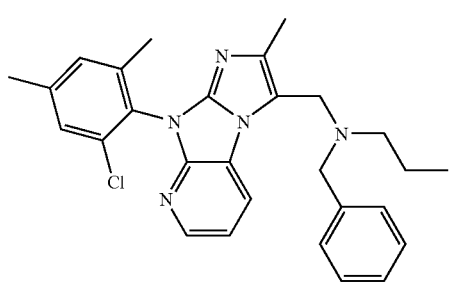

Benzyl-[8-(2-chloro-4,6-dimethyl-phenyl)-2-methyl-8H-1,3a,7,8-tetraaza-cyclopenta[α]inden-3-ylmethyl]-propyl-amine, scheme 2: (H)

Prepared as described for the example above. LC/MS: $t_R$=1.59 min, 472.32 (MH$^+$).

EXAMPLE 264

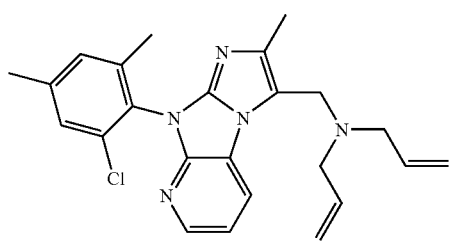

Diallyl-[8-(2-chloro-4,6-dimethyl-phenyl)-2-methyl-8H-1,3a,7,8-tetraaza-cyclopenta[α]inden-3-ylmethyl]-amine, scheme 2: (H)

Prepared as described for the example above. LC/MS: $t_R$=1.45 min, 420.25 (MH$^+$).

EXAMPLE 265

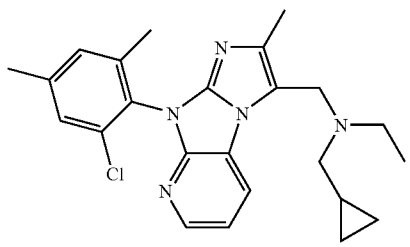

[8-(2-Chloro-4,6-dimethyl-phenyl)-2-methyl-8H-1, 3a,7,8-tetraaza-cyclopenta[α]inden-3-ylmethyl]-cyclopropylmethyl-ethyl-amine, scheme 2: (H)

Prepared as described for the example above. LC/MS: $t_R$=1.43 min, 422.22 (MH$^+$).

EXAMPLE 266

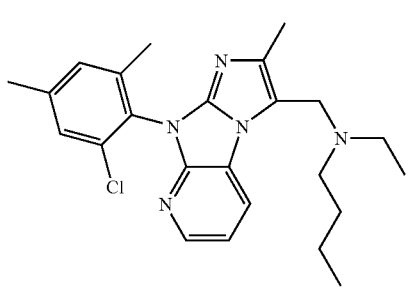

Butyl-[8-(2-chloro-4,6-dimethyl-phenyl)-2-methyl-8H-1,3a,7,8-tetraaza-cyclopenta[α]inden-3-ylmethyl]-ethyl-amine, scheme 2: (H)

Prepared as described for the example above. LC/MS: $t_R$=1.48 min, 424.30 (MH⁺).

EXAMPLE 267

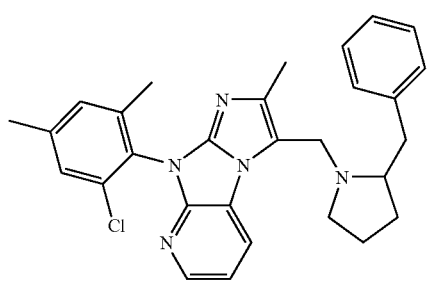

3-(2-Benzyl-pyrrolidin-1-ylmethyl)-8-(2-chloro-4,6-dimethyl-phenyl)-2-methyl-8H-1,3a,7,8-tetraaza-cyclopenta[α]indene, scheme 2: (H)

Prepared as described for the example above. LC/MS: $t_R$=1.62 min, 484.26 (MH⁺).

EXAMPLE 268

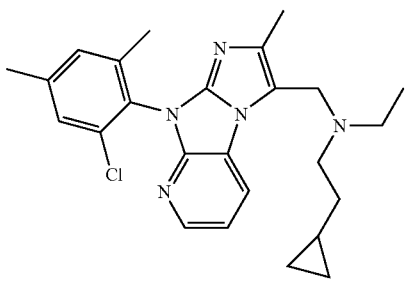

[8-(2-Chloro-4,6-dimethyl-phenyl)-2-methyl-8H-1,3a,7,8-tetraaza-cyclopenta[α]inden-3-ylmethyl]-(2-cyclopropyl-ethyl)-ethyl-amine, scheme 2: (H)

Prepared as described for the example above. LC/MS: $t_R$=1.51 min, 436.32 (MH⁺).

EXAMPLE 269

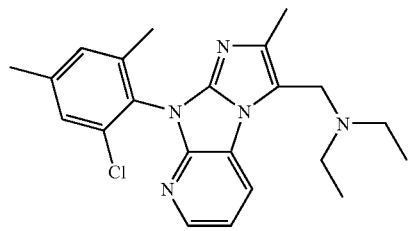

[8-(2-Chloro-4,6-dimethyl-phenyl)-2-methyl-8H-1,3a,7,8-tetraaza-cyclopenta[α]inden-3-ylmethyl]-diethyl-amine, scheme 2: (H)

Prepared as described for the example above. LC/MS: $t_R$=1.36 min, 396.25 (MH⁺).

EXAMPLE 270

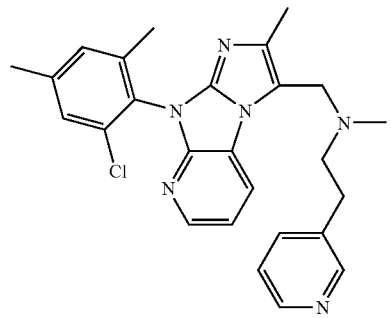

[8-(2-Chloro-4,6-dimethyl-phenyl)-2-methyl-8H-1,3a,7,8-tetraaza-cyclopenta[α]inden-3-ylmethyl]-methyl-(2-pyridin-3-yl-ethyl)-amine, scheme 2: (H)

Prepared as described for the example above. LC/MS: $t_R$=1.31 min, 459.26 (MH⁺).

EXAMPLE 271

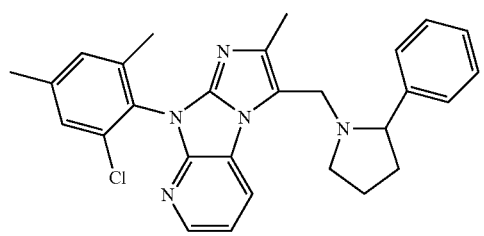

8-(2-Chloro-4,6-dimethyl-phenyl)-2-methyl-3-(2-phenyl-pyrrolidin-1-ylmethyl)-8H-1,3a,7,8-tetraaza-cyclopenta[α]indene, scheme 2: (H)

Prepared as described for the example above. LC/MS: $t_R$=1.57 min, 470.24 (MH⁺).

EXAMPLE 272

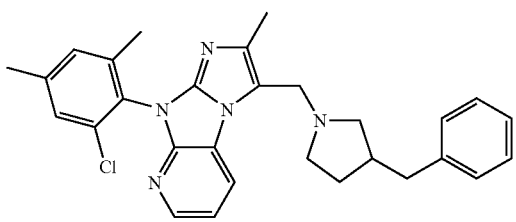

3-(3-Benzyl-pyrrolidin-1-ylmethyl)-8-(2-chloro-4,6-dimethyl-phenyl)-2-methyl-8H-1,3a,7,8-tetraaza-cyclopenta[α]indene, scheme 2: (H)

Prepared as described for the example above. LC/MS: $t_R$=1.64 min, 484.24 (MH⁺).

EXAMPLE 273

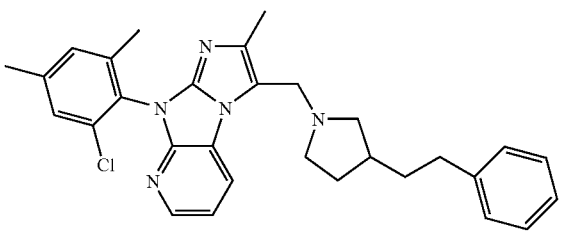

8-(2-Chloro-4,6-dimethyl-phenyl)-2-methyl-3-(3-phenethyl-pyrrolidin-1-ylmethyl)-8H-1,3a,7,8-tetraaza-cyclopenta[α]indene, scheme 2: (H)

Prepared as described for the example above. LC/MS: $t_R$=1.71 min, 498.27 (MH⁺).

EXAMPLE 274

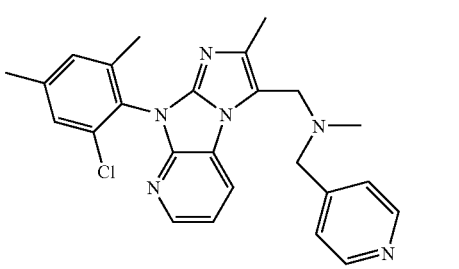

[8-(2-Chloro-4,6-dimethyl-phenyl)-2-methyl-8H-1,3a,7,8-tetraaza-cyclopenta[α]inden-3-ylmethyl]-methyl-pyridin-4-ylmethyl-amine, scheme 2: (H)

Prepared as described for the example above. LC/MS: $t_R$=1.51 min, 445.22 (MH⁺).

EXAMPLE 275

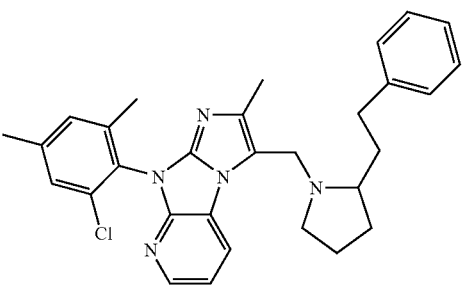

8-(2-Chloro-4,6-dimethyl-phenyl)-2-methyl-3-(2-phenethyl-pyrrolidin-1-ylmethyl)-8H-1,3a,7,8-tetraaza-cyclopenta[α]indene, scheme 2: (H)

Prepared as described for the example above. LC/MS: $t_R$=1.66 min, 498.27 (MH⁺).

EXAMPLE 276

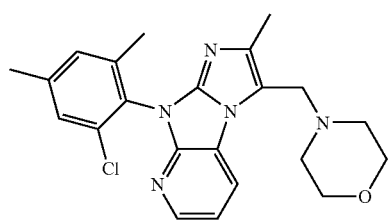

8-(2-Chloro-4,6-dimethyl-phenyl)-2-methyl-3-morpholin-4-ylmethyl-8H-1,3a,7,8-tetraaza-cyclopenta[α]indene, scheme 2: (H)

Prepared as described for the example above. LC/MS: $t_R$=1.35 min, 410.25 (MH⁺).

EXAMPLE 277

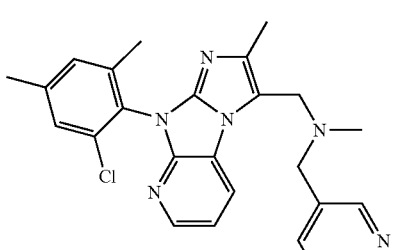

[8-(2-Chloro-4,6-dimethyl-phenyl)-2-methyl-8H-1,
3a,7,8-tetraaza-cyclopenta[α]inden-3-ylmethyl]-
methyl-pyridin-3-ylmethyl-amine, scheme 2: (H)

Prepared as described for the example above. LC/MS: $t_R$=1.34 min, 445.22 (MH$^+$).

EXAMPLE 278

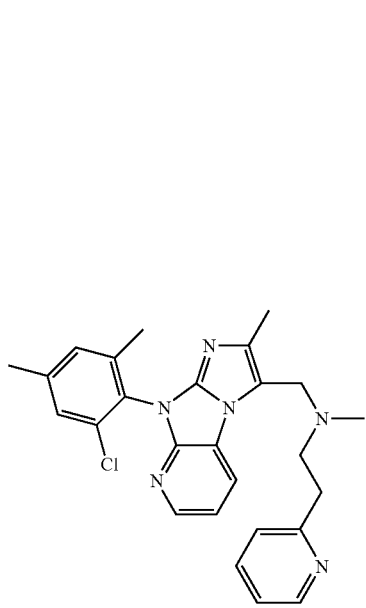

[8-(2-Chloro-4,6-dimethyl-phenyl)-2-methyl-8H-1,
3a,7,8-tetraaza-cyclopenta[α]inden-3-ylmethyl]-
methyl-(2-pyridin-2-yl-ethyl)-amine, scheme 2: (H)

Prepared as described for the example above. LC/MS: $t_R$=1.37 min, 459.20 (MH$^+$).

EXAMPLE 279

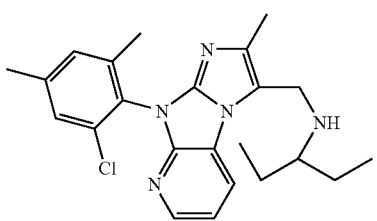

[8-(2-Chloro-4,6-dimethyl-phenyl)-2-methyl-8H-1,
3a,7,8-tetraaza-cyclopenta[α]inden-3-ylmethyl]-(1-
ethyl-propyl)-amine, scheme 2: (H)

Prepared as described for the example above. LC/MS: $t_R$=1.44 min, 410.30 (MH$^+$).

EXAMPLE 280

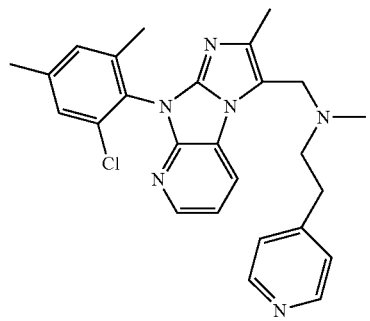

[8-(2-Chloro-4,6-dimethyl-phenyl)-2-methyl-8H-1,
3a,7,8-tetraaza-cyclopenta[α]inden-3-ylmethyl]-
methyl-(2-pyridin-4-yl-ethyl)-amine, scheme 2: (H)

Prepared as described for the example above. LC/MS: $t_R$=1.30 min, 459.26 (MH$^+$).

EXAMPLE 281

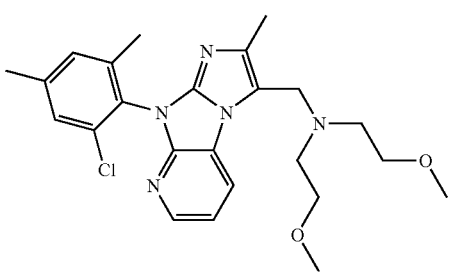

[8-(2-Chloro-4,6-dimethyl-phenyl)-2-methyl-8H-1,
3a,7,8-tetraaza-cyclopenta[α]inden-3-ylmethyl]-bis-
(2-methoxy-ethyl)-amine, scheme 2: (H)

Prepared as described for the example above. LC/MS: $t_R$=1.46 min, 456.27 (MH$^+$).

EXAMPLE 282

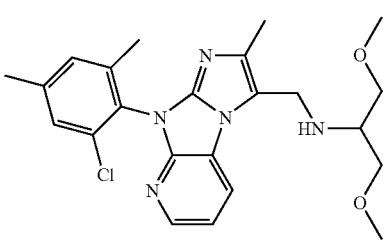

[8-(2-Chloro-4,6-dimethyl-phenyl)-2-methyl-8H-1,3a,7,8-tetraaza-cyclopenta[α]inden-3-ylmethyl]-(2-methoxy-1-methoxymethyl-ethyl)-amine, scheme 2: (H)

Prepared as described for the example above. LC/MS: $t_R$=1.44 min, 442.27 (MH$^+$).

The following Intermediates 95-112 may be used to synthesize Examples 283-300.

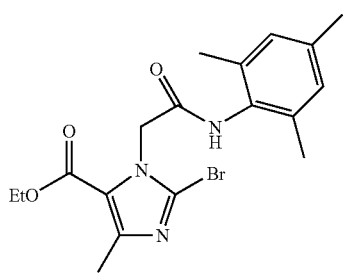

Intermediate 95

2-Bromo-5-methyl-3-[(2,4,6-trimethyl-phenylcarbamoyl)-methyl]-3H-imidazole-4-carboxylic acid ethyl ester, scheme 5 (V)

To a solution of 2-bromo-5-methyl-3H-imidazole-4-carboxylic acid ethyl ester (1.00 g, 4.291 mmol) and 2-bromo-N-(2,4,6-trimethyl-phenyl)-acetamide (1.209 g, 4.720 mmol) in a mixture of toluene (16 mL) and acetone (8 mL) was added diazabicycloundecene (0.71 mL, 4.720 mmol). The resulting solution was stirred at room temperature for 24 h. Methanol (10 mL) was added to dissolve the precipitate formed, followed by the addition of silica gel (25 g). The solvent was removed under reduced pressure to dryness and the residue was applied to a silica gel-packed column. The isolation of the product was achieved by column chromatography (hexanes-ethyl acetate 4:1 to 1:2). Yield—0.736 g (42%). $^1$H NMR (DMSO d-6, 500 MHz) δ 9.52 (s, 1H), 6.86 (s, 2H), 5.15 (br s, 2H), 4.25 (q, J=7.1 Hz, 2H), 2.38 (s, 3H), 2.21 (s, 3H), 2.11 (s, 6H), 1.30 (t, J=7.1 Hz, 3H); LC/MS: $t_R$=1.46 min., MS: [M+H]=408.

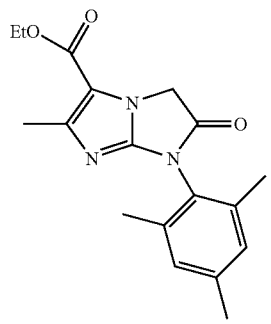

Intermediate 96

2-Methyl-6-oxo-7-(2,4,6-trimethyl-phenyl)-6,7-dihydro-5H-imidazo[1,2-a]imidazole-3-carboxylic acid ethyl ester, scheme 5: (W)

A suspension of 2-bromo-5-methyl-3-[(2,4,6-trimethyl-phenylcarbamoyl)-methyl]-3H-imidazole-4-carboxylic acid ethyl ester (17.4 mg, 0.038 mmol) and silver carbonate (11.6 mg, 0.042 mmol) in sulfolane (0.5 mL) was heated at 150° C. for 4 h. The resulting reaction mixture was cooled to room temperature and filtered through a short pad of celite. The final purification was achieved by a reverse-phase preparative HPLC to give the desired product as white solid. Yield—12.2 mg (73%). $^1$H NMR (DMSO d-6, 500 MHz) δ 7.04 (s, 2H), 4.99 (s, 2H), 4.26 (q, J=7.2 Hz, 2H), 2.34 (s, 3H), 2.30 (s, 3H), 2.06 (s, 6H), 1.31 (t, J=7.2 Hz, 3H); LC/MS: $t_R$=1.75 min., MS: [M+H]=328.

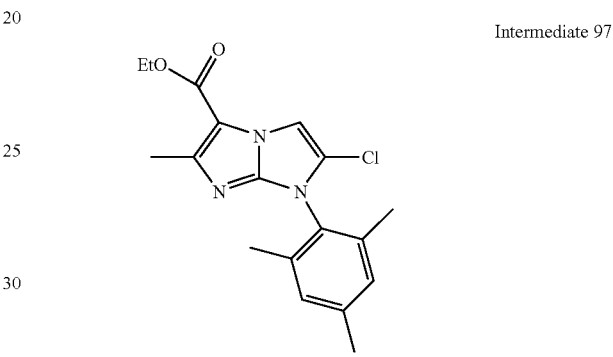

Intermediate 97

6-Chloro-2-methyl-7-(2,4,6-trimethyl-phenyl)-7H-imidazo[1,2-a]imidazole-3-carboxylic acid ethyl ester, scheme 6: (AA)

A solution of 3-ethoxycarbonyl-2-methyl-6-oxo-7-(2,4,6-trimethyl-phenyl)-6,7-dihydro-5H-imidazo[1,2-a]imidazolium trifluoroacetate (22.2 mg, 0.050 mmol) in phosphorus oxychloride (1 mL) was heated at 150° C. for 48 h. The excess of phosphorus oxychloride was removed under reduced pressure, the residue was dissolved in saturated aqueous solution of sodium bicarbonate (20 mL) and extracted with ethyl acetate (5×20 mL). The combined organic extracts were dried with MgSO$_4$. The solvent was removed under reduced pressure and the crude product was dried under pump vacuum overnight. Yield—23.3 mg (99%). LC/MS: $t_R$=1.93 min., MS: [M+H]=346.

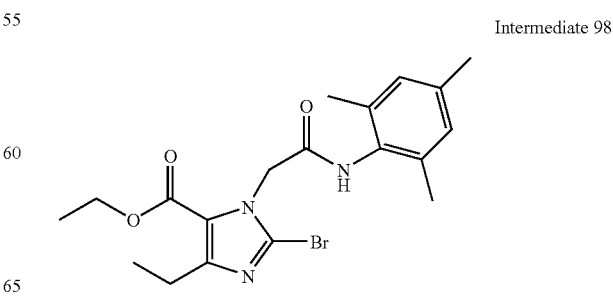

Intermediate 98

2-Bromo-5-ethyl-3-[(2,4,6-trimethylphenylcarbamoyl)methyl]-3H-imidazole-4-carboxylic acid ethyl ester, scheme 5: (V)

Prepared as described above for intermediate 95. MS: m/e 422 (M+H)⁺.

2-Bromo-3-[(2-chloro-4,6-dimethylphenylcarbamoyl)-methyl]-5-ethyl-3H-imidazole-4-carboxylic acid ethyl ester, scheme 5: (V)

Prepared as described above for intermediate 95. MS: m/e 442 (M+H)⁺.

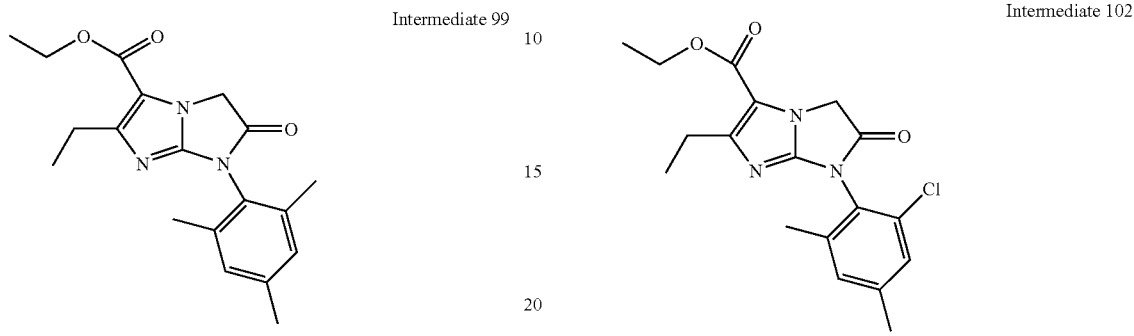

Intermediate 99

Intermediate 102

2-Ethyl-6-oxo-7-(2,4,6-trimethylphenyl)-6,7-dihydro-5H-imidazo[1,2-a]imidazole-3-carboxylic acid ethyl ester, scheme 5: (W)

Prepared as described above for intermediate 96. MS: m/e 342 (M+H)⁺.

7-(2-Chloro-4,6-dimethylphenyl)-2-ethyl-6-oxo-6,7-dihydro-5H-imidazo[1,2-a]imidazole-3-carboxylic acid ethyl ester, scheme 5: (W)

Prepared as described above for intermediate 96. MS: m/e 362 (M+H)⁺.

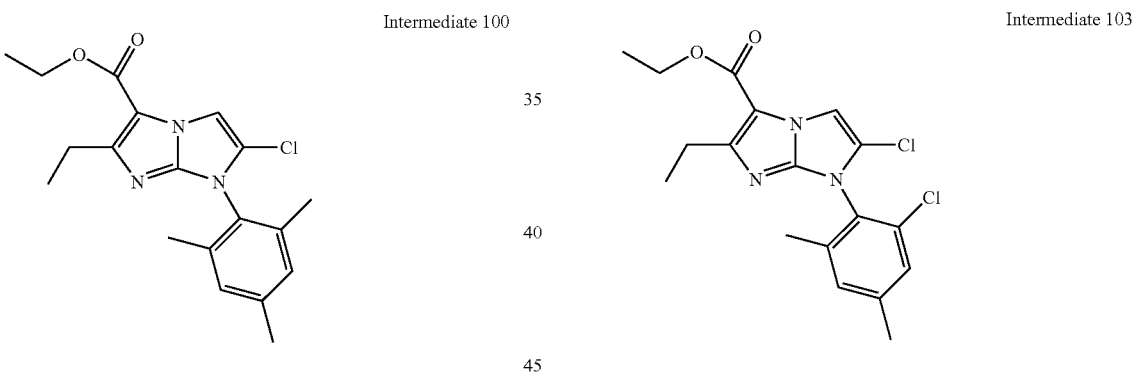

Intermediate 100

Intermediate 103

6-Chloro-2-ethyl-7-(2,4,6-trimethylphenyl)-7H-imidazo[1,2-a]imidazole-3-carboxylic acid ethyl ester, scheme 6: (AA)

Prepared as described above for intermediate 97. MS: m/e 360 (M+H)⁺.

6-Chloro-7-(2-chloro-4,6-dimethylphenyl)-2-ethyl-7H-imidazo[1,2-a]imidazole-3-carboxylic acid ethyl ester, scheme 6: (AA)

Prepared as described above for intermediate 97. MS: m/e 380 (M+H)⁺.

Intermedaite 101

Intermediate 104

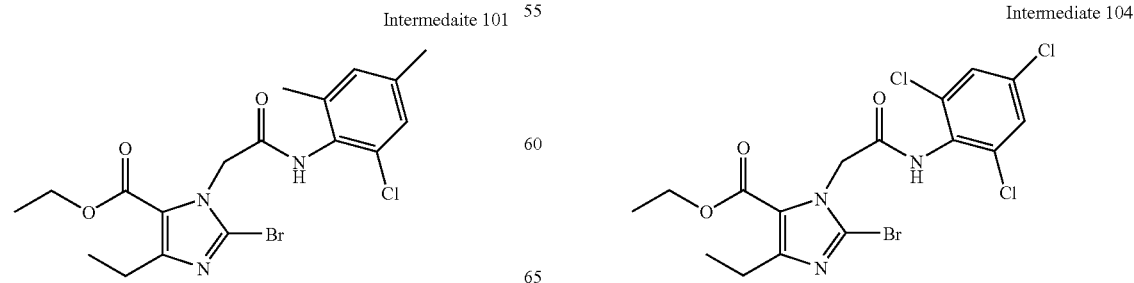

2-Bromo-5-ethyl-3-[(2,4,6-trichlorophenylcarbamoyl)-methyl]-3H-imidazole-4-carboxylic acid ethyl ester, scheme 5: (V)

Prepared as described above for intermediate 95. MS: m/e 482 (M+H)+.

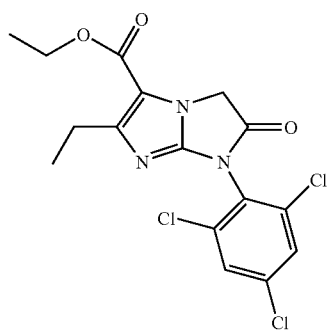

Intermediate 105

2-Ethyl-6-oxo-7-(2,4,6-trichlorophenyl)-6,7-dihydro-5H-imidazo[1,2-a]imidazole-3-carboxylic acid ethyl ester, scheme 5: (W)

Prepared as described above for intermediate 96. MS: m/e 402 (M+H)+.

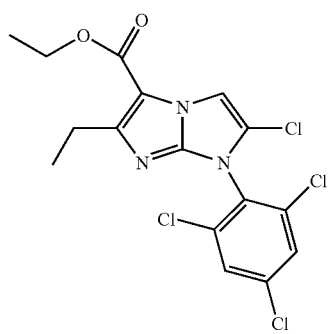

Intermediate 106

6-Chloro-2-ethyl-7-(2,4,6-trichlorophenyl)-7H-imidazo[1,2-a]imidazole-3-carboxylic acid ethyl ester, scheme 6: (AA)

Prepared as described above for intermediate 97. MS: m/e 420 (M+H)+.

Intermediate 107

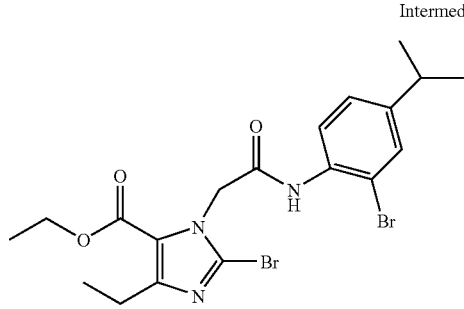

2-Bromo-5-ethyl-3-[(2-bromo-4-isopropylphenylcarbamoyl)-methyl]-3H-imidazole-4-carboxylic acid ethyl ester, scheme 5: (V)

Prepared as described above for intermediate 95. MS: m/e 500 (M+H)+.

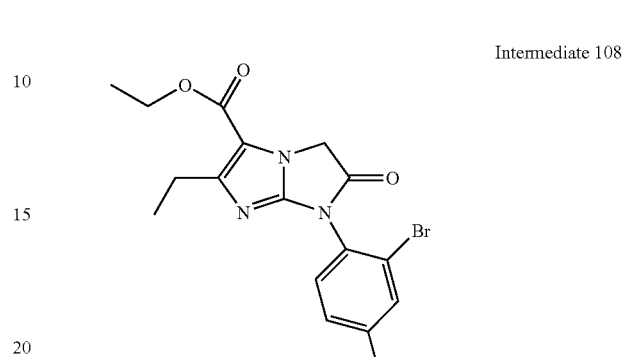

Intermediate 108

2-Ethyl-6-oxo-7-(2-bromo-4-isopropylphenyl)-6,7-dihydro-5H-imidazo[1,2-a]imidazole-3-carboxylic acid ethyl ester, scheme 5: (W)

Prepared as described above for intermediate 96. MS: m/e 420 (M+H)+.

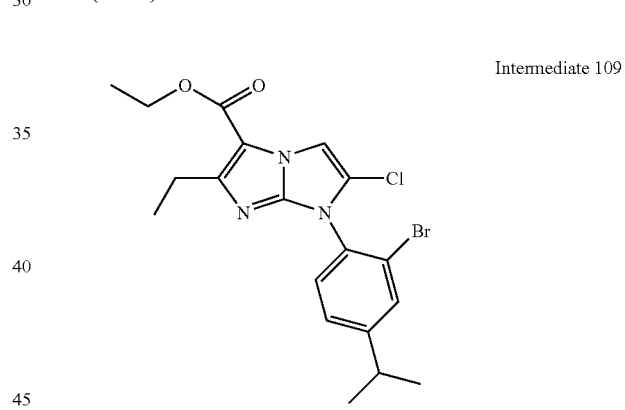

Intermediate 109

6-Chloro-2-ethyl-7-(2-bromo-4-isopropylphenyl)-7H-imidazo[1,2-a]imidazole-3-carboxylic acid ethyl ester, scheme 6: (AA)

Prepared as described above for intermediate 97. MS: m/e 438 (M+H)+.

Intermediate 110

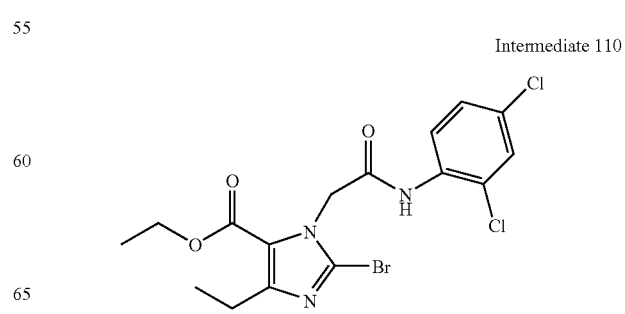

2-Bromo-3-[(2,4-dichlorophenylcarbamoyl)-methyl]-5-ethyl-3H-imidazole-4-carboxylic acid ethyl ester, scheme 5: (V)

Prepared as described above for intermediate 95. MS: m/e 448 (M+H)+.

Intermediate 111

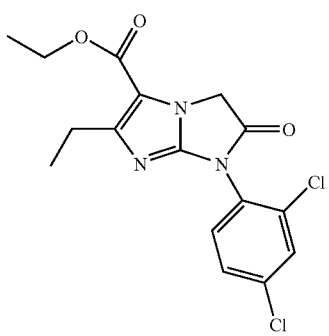

7-(2,4-Dichlorophenyl)-2-ethyl-6-oxo-6,7-dihydro-5H-imidazo[1,2-a]imidazole-3-carboxylic acid ethyl ester, scheme 5: (W)

Prepared as described above for intermediate 96. MS: m/e 368 (M+H)+.

Intermediate 112

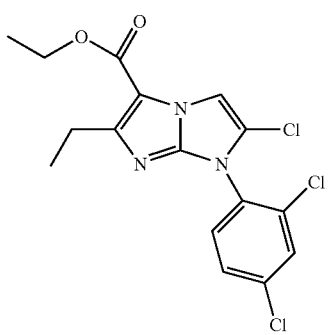

6-Chloro-7-(2,4-dichlorophenyl)-2-ethyl-7H-imidazo[1,2-a]imidazole-3-carboxylic acid ethyl ester, scheme 6: (AA)

Prepared as described above for intermediate 97. MS: m/e 386 (M+H)+.

EXAMPLE 283

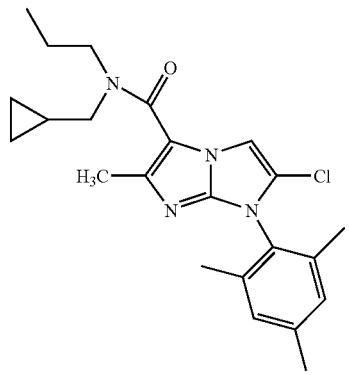

6-Chloro-2-methyl-7-(2,4,6-trimethyl-phenyl)-7H-imidazo[1,2-a]imidazole-3-carboxylic acid cyclopropylmethyl-propyl-amide, scheme 6: (BB)

To a solution of N-cyclopropylmethylpropylamine (0.22 mL, 1.530 mmol) in toluene (1.5 mL) at 0° C. was added 2.0M solution of trimethylaluminum in toluene (0.77 mL, 1.530 mmol). The clear solution was warmed to room temperature and stirred for 1 h. A solution of 6-chloro-2-methyl-7-(2,4,6-trimethyl-phenyl)-7H-imidazo[1,2-a]imidazole-3-carboxylic acid ethyl ester (32.2 mg, 0.098 mmol) in toluene (1.0 mL) was added at 0° C. via cannula. The reaction mixture was heated at 80° C. for 2 h. A solution of Rochelle's salt (2.0 mL) was added carefully at 0° C. and the mixture was vigorously stirred for 30 min. The crude product was extracted with ethylacetate. The combined organic extracts were dried with $MgSO_4$. The solvent was removed under reduced pressure and the crude product was purified by a reverse-phase preparative HPLC. Yield—21.3 mg (42%). $^1$H NMR ($CD_3CN$, 500 MHz) δ 7.69 (s, 1H), 7.16 (s, 2H), 3.59 (t, J=7.3 Hz, 2H), 3.39 (d, J=6.9 Hz, 2H), 2.39 (s, 3H), 2.37 (s, 3H), 2.05 (s, 6H), 1.68 (sextet, J=7.3 Hz, 2H), 1.11 (m, 1H), 0.90 (t, J=7.3 Hz, 3H), 0.60 (m, 2H), 0.23 (m, 2H); LC/MS: $t_R$=1.71 min., MS: [M+H]=413.

EXAMPLE 284

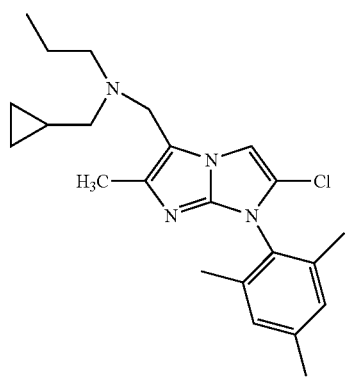

[6-Chloro-2-methyl-7-(2,4,6-trimethyl-phenyl)-7H-imidazo[1,2-a]imidazol-3-ylmethyl]-cyclopropylmethyl-propyl-amine, scheme 6: (DD)

A solution of 3-(cyclopropylmethyl-propyl-carbamoyl)-2-methyl-6-oxo-7-(2,4,6-trimethyl-phenyl)-6,7-dihydro-5H-imidazo[1,2-a]imidazole (31.7 mg, 0.077 mmol) in toluene (3 mL) was added a 65% solution of Red-Al in toluene (0.12 mL, 0.384 mmol). The reaction mixture was stirred at room temperature for 14 h. A solution of Rochelle's salt (2.0 mL) was added carefully at 0° C. and the mixture was vigorously stirred for 30 min. The crude product was extracted with ethylacetate. The combined organic extracts were dried with $Na_2SO_4$. The solvent was removed under reduced pressure and the crude product was purified by a reverse-phase preparative HPLC. Yield—25.2 mg (64%). $^1$H NMR (CD$_3$OD, 500 MHz) δ 8.09 (s, 1H), 7.19 (s, 2H), 4.75 (s, 2H), 3.31 (t, J=6.5 Hz, 2H), 3.24 (d, J=7.2 Hz, 2H), 2.44 (s, 3H), 2.39 (s, 3H), 2.06 (s, 6H), 1.24 (m, 3H), 1.05 (t, J=7.4 Hz, 3H), 0.85-0.82 (m, 2H), 0.50 (m, 2H); LC/MS: $t_R$=1.43 min., MS: [M+H]=399.

EXAMPLE 285

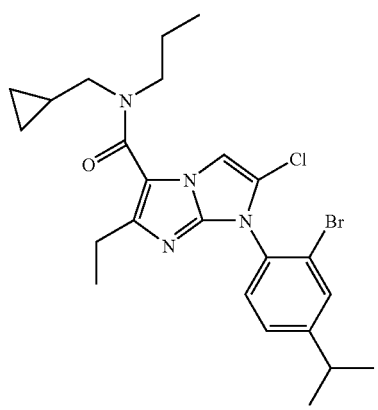

6-Chloro-2-ethyl-7-(2-bromo-4-isopropylphenyl)-7H-imidazo[1,2-a]imidazole-3-carboxylic acid N-cyclopropylmethyl-N-propylamide, scheme 6: (BB)

Prepared as described for Example 283. IR(film): 1615 cm$^{-1}$. $^1$H NMR (CDCl$_3$) δ 7.57 (d, J=2.0 Hz, 1H), 7.36 (d, J=8.1 Hz, 1H), 7.29 (dd, J=8.1, 2.0 Hz, 1H), 7.22 (s, 1H), 3.60 (t, J=7.1 Hz, 2H), 3.39 (d, J=7.1 Hz, 2H), 2.95 (m, 1H), 2.66 (q, J=7.6 Hz, 2H), 1.64 (m, 2H), 1.55 (s, 3H), 1.40 (s, 3H), 1.23 (t, J=7.1 Hz, 3H), 0.88 (t, J=7.1 Hz, 3H), 0.54 (m, 2H), 0.17 (m, 2H). MS: m/e 505(M+H)$^+$.

EXAMPLE 286

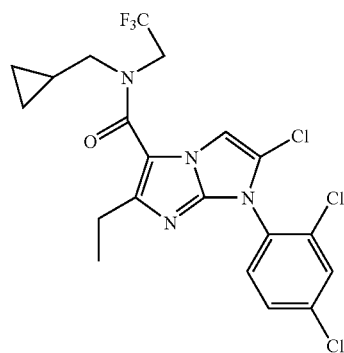

6-Chloro-2-ethyl-7-(2,4-dichlorophenyl)-7H-imidazo[1,2-a]imidazole-3-carboxylic acid N-cyclopropylmethyl-N-(2,2,2-trifluoroethyl)amide, scheme 6: (BB)

Prepared as described for Example 283. IR(film): 1630 cm$^{-1}$. $^1$H NMR (CDCl$_3$) δ 7.60 (m, 1H), 7.42 (m, 2H), 7.27 (s, 1H), 4.41 (q, J=9.1 Hz, 2H), 3.52 (d, J=6.6 Hz, 2H), 2.66 (q, J=7.6 Hz, 2H), 1.23 (t, J=7.6 Hz, 3H), 0.94 (m, 1H), 0.60 (m, 2H), 0.16 (m, 2H). MS: m/e 493 (M+H)$^+$.

EXAMPLE 287

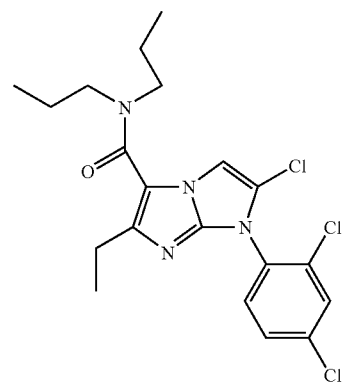

6-Chloro-2-ethyl-7-(2,4-dichlorophenyl)-7H-imidazo[1,2-a]imidazole-3-carboxylic acid N,N-dipropylamide, scheme 6: (BB)

Prepared as described for Example 283. IR(film): 1615 cm$^{-1}$. $^1$H NMR (CDCl$_3$) δ 7.59 (m, 1H), 7.41 (m, 2H), 7.24

(s, 1H), 3.47 (t, J=7.1 Hz, 4H), 2.65 (q, J=7.6 Hz, 2H), 1.62 (m, 4H), 1.24 (t, J=7.6 Hz, 3H), 0.87 (t, J=7.1 Hz, 6H). MS: m/e 441 (M+H)$^+$.

EXAMPLE 288

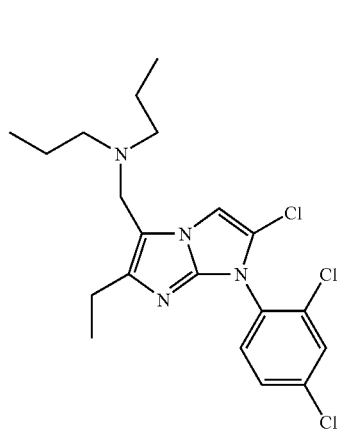

3-[(N,N-Dipropylamino)methyl]-6-chloro-2-ethyl-7-(2,4-diclorophenyl)-7H-imidazo[1,2-a]imidazole, scheme 6: (DD)

Prepared as described for Example 284. $^1$H NMR (DMSO-d$_6$) δ 7.98 (m, 1H), 7.89 (m, 1H), 7.70 (m, 2H), 4.52 (s, 2H), 3.00 (q, J=7.6 Hz, 4H), 2.55 (q, J=7.6 Hz, 2H), 1.68 (m, 4H), 1.12 (t, J=7.6 Hz, 3H), 0.89 (t, J=7.6 Hz, 6H). MS: m/e 427 (M+H)$^+$.

EXAMPLE 289

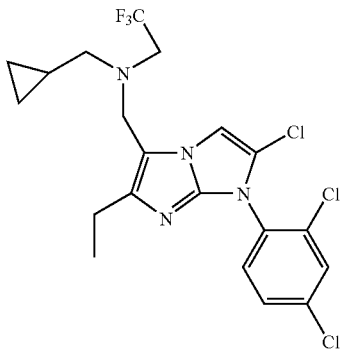

3-[(N-Cyclopropylmethyl-N-(2,2,2-trifluoroethyl)amino)methyl]-6-chloro-2-ethyl-7-(2,4-diclorophenyl)-7H-imidazo[1,2-a]imidazole, scheme 6: (DD)

Prepared as described for Example 284. $^1$H NMR (CDCl$_3$) δ 7.62 (d, J=2.0 Hz, 1H), 7.53 (d, J=8.6 Hz, 1H), 7.47 (dd, J=8.6, 2.0 Hz, 1H), 7.42 (s, 1H), 3.97 (s, 2H), 3.26 (q, J=9.6 Hz, 2H), 2.69 (q, J=7.6 Hz, 2H), 2.57 (q, J=6.6 Hz, 1H), 2.47 (q, J=7.1 Hz, 1H), 1.26 (t, J=7.6 Hz, 3H), 0.86 (m, 1H), 0.59 (m, 2H), 0.12 (m, 2H). MS: m/e 479 (M+H)$^+$.

EXAMPLE 290

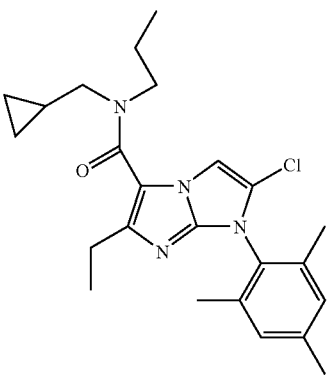

6-Chloro-2-ethyl-7-(2,4,6-trimethylphenyl)-7H-imidazo[1,2-a]imidazole-3-carboxylic acid N-cyclopropylmethyl-N-propylamide, scheme 6: (BB)

Prepared as described for Example 283. $^1$H NMR (CDCl$_3$, 400 MHz) δ 7.26 (s, 1H), 6.98 (s, 2H), 3.60 (t, J=7.1 Hz, 2H), 3.39 (d, J=7.1 Hz, 2H), 2.65 (q, J=7.6 Hz, 2H), 2.32 (s, 3H), 2.01 (s, 6H), 1.64 (m, 3H), 1.22 (t, J=7.6 Hz, 3H), 0.88 (m, 3H), 0.54 (m, 2H), 0.16 (q, J=4.6, 6.1 Hz, 2H). MS: m/e: 427 (M+H)$^+$.

EXAMPLE 291

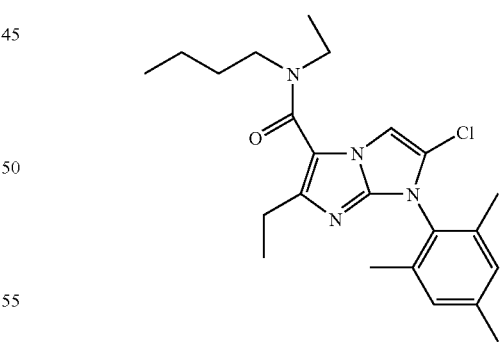

6-Chloro-2-ethyl-7-(2,4,6-trimethylphenyl)-7H-imidazo[1,2-a]imidazole-3-carboxylic acid N-butyl-N-ethylamide, scheme 6: (BB)

Prepared as described for Example 283. $^1$H NMR (CDCl$_3$, 400 MHz) δ 7.26 (s, 1H), 6.98 (s, 2H), 3.53 (m, 4H), 2.65 (q, J=7.1 Hz, 2H), 2.32 (s, 3H), 2.01 (s, 6H), 1.58 (m, 4H), 1.25 (m, 6H), 0.87 (t, J=7.1 Hz, 3H). MS: m/e: 415 (M+H)$^+$.

EXAMPLE 292

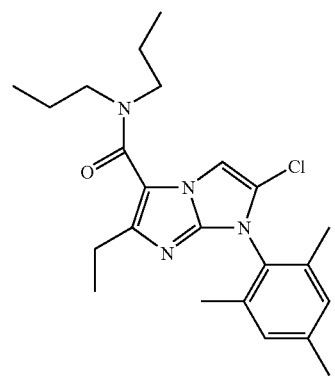

6-Chloro-2-ethyl-7-(2,4,6-trimethylphenyl)-7H-imidazo[1,2-a]imidazole-3-carboxylic acid N,N-dipropylamide, scheme 6: (BB)

Prepared as described for Example 283. $^1$H NMR (CDCl$_3$, 400 MHz) δ 7.29 (s, 1H), 7.02 (s, 2H), 3.50 (t, J=7.1 Hz, 4H), 2.69 (q, J=7.1, 7.6 Hz, 2H), 2.36 (s, 3H), 2.05 (s, 6H), 1.64 (m, 4H), 1.26 (t, J=7.6 Hz, 3H), 0.91 (overlapping d, J=7.1, 7.6 Hz, 6H). MS: m/e: 415 (M+H)$^+$.

EXAMPLE 293

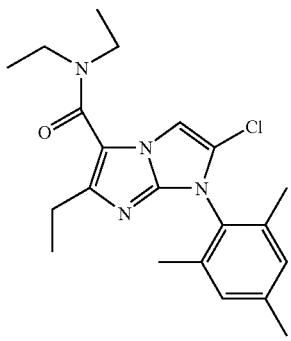

6-Chloro-2-ethyl-7-(2,4,6-trimethylphenyl)-7H-imidazo[1,2-a]imidazole-3-carboxylic acid N,N-diethylamide, scheme 6: (BB)

Prepared as described for Example 283. $^1$H NMR (CDCl$_3$, 400 MHz) δ 7.28 (s, 1H), 6.98 (s, 2H), 3.56 (q, J=7.1 Hz, 4H), 2.65 (q, J=7.6 Hz, 2H), 2.32 (s, 3H), 2.01 (s, 6H), 1.21 (m, 9H). MS: m/e: 387 (M+H)$^+$.

EXAMPLE 294

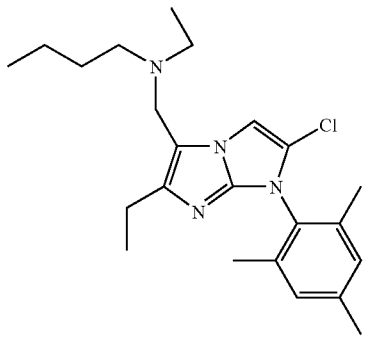

3-[(N-Butyl-N-ethylamino)methyl]-6-chloro-2-ethyl-7-(2,4 6-trimethylphenyl)-7H-imidazo[1,2-a]imidazole, scheme 6: (DD)

Prepared as described for Example 284. $^1$H NMR (CDCl$_3$, 400 MHz) δ 7.99 (s, 1H), 7.11 (s, 2H), 4.54 (d, J=4.6 Hz, 2H), 3.09 (m, 4H), 2.59 (q, J=7.58 Hz, 2H), 2.33 (s, 3H), 1.93 (s, 6H), 1.61 (m, 2H), 1.29 (m, 6H), 1.13 (t, J=7.6 Hz, 3H), 0.89 (dd, J=7.1, 7.6 Hz, 3H). MS: m/e: 401 (M+H)$^+$.

EXAMPLE 295

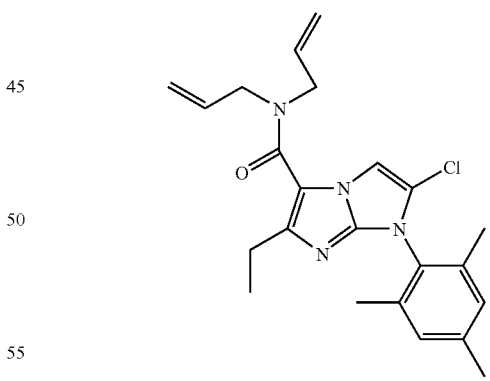

6-Chloro-2-ethyl-7-(2,4,6-trimethylphenyl)-7H-imidazo[1,2-a]imidazole-3-carboxylic acid N,N-diallylamide, scheme 6: (BB)

Prepared as described for Example 283. $^1$H NMR (CDCl$_3$, 400 MHz) δ 7.20 (s, 1H), 6.93 (s, 2H), 5.77 (m, 2H), 5.17 (m, 4H), 4.07 (d, J=6.1 Hz, 4H), 2.62 (dd, J=7.1, 7.6 Hz, 2H), 2.27 (s, 3H), 1.96 (s, 6H), 1.17 (t, J=7.6 Hz, 3H). MS: m/e: 411 (M+H)$^+$.

EXAMPLE 296

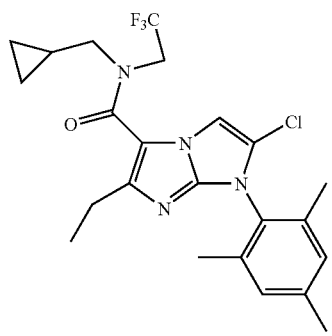

6-Chloro-2-ethyl-7-(2,4,6-trimethylphenyl)-7H-imidazo[1,2-a]imidazole-3-carboxylic acid N-cyclopropylmethyl-N-(2,2,2-trifluoroethyl)amide, scheme 6: (BB)

Prepared as described for Example 283. ¹H NMR (CDCl₃, 400 MHz) δ 7.27 (s, 1H), 6.99 (s, 2H), 4.41 (q, J=9.1 Hz, 2H), 3.53 (d, J=7.1 Hz, 2H), 2.66 (q, J=7.6 Hz, 2H), 2.33 (s, 3H), 2.01 (s, 6H), 1.22 (t, J=7.6 Hz, 3H), 0.93 (m, 1H), 0.59 (m, 2H), 0.15 (dd, J=4.6, 6.1 Hz, 2H). MS: m/e: 467 (M+H)⁺.

EXAMPLE 297

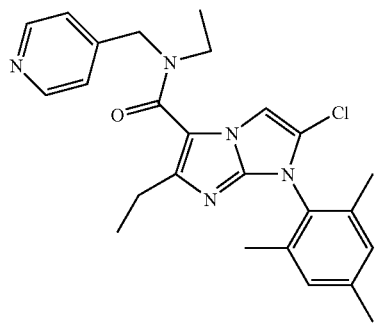

6-Chloro-2-ethyl-7-(2,4,6-trimethylphenyl)-7H-imidazo[1,2-a]imidazole-3-carboxylic acid N-ethyl-N-(pyridin-4-yl)methylamide, scheme 6: (BB)

Prepared as described for Example 283. ¹H NMR (CDCl₃, 400 MHz) δ 8.58 (m, 2H), 7.32 (s, 1H), 7.22 (d, J=6.1 Hz, 2H), 6.98 (s, 2H), 4.74 (s, 2H), 3.54 (dd, J=7.1, 7.6 Hz, 2H), 2.68 (dd, J=7.1, 7.6 Hz, 2H), 2.32 (s, 3H), 2.01 (s, 6H). 1.21 (m, 6H). MS: m/e: 450 (M+H)⁺.

EXAMPLE 298

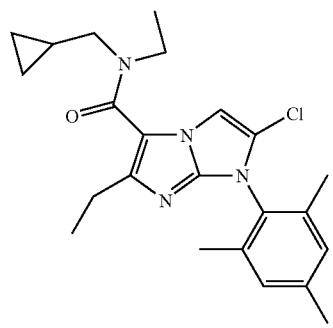

6-Chloro-2-ethyl-7-(2,4,6-trimethylphenyl)-7H-imidazo[1,2-a]imidazole-3-carboxylic acid N-cyclopropylmethyl-N-ethylamide, scheme 6: (BB)

Prepared as described for Example 283. ¹H NMR (CDCl₃, 400 MHz) δ 7.27 (s, 1H), 6.97 (s, 2H), 3.69 (q, J=7.1 Hz, 2H), 3.40 (d, J=6.6 Hz, 2H), 2.65 (dd, J=7.1, 7.6 Hz, 2H), 2.32 (s, 3H), 2.01 (s, 6H), 1.22 (t, J=7.1 Hz, 6H), 1.03 (m, 1H), 0.55 (m, 2H), 0.18 (dd, J=5.1, 5.6 Hz, 2H). MS: m/e: 413 (M+H)⁺.

EXAMPLE 299

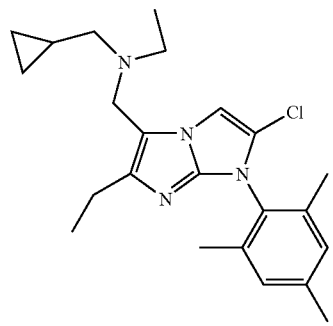

3-[(N-Cyclopropylmethyl-N-ethylamino)methyl]-6-chloro-2-ethyl-7-(2,4,6-trimethylphenyl)-7H-imidazo[1,2-a]imidazole, scheme 6: (DD)

Prepared as described for Example 284. ¹H NMR (CDCl₃, 400 MHz) δ 7.92 (s, 1H), 7.02 (s, 2H), 4.46 (s, 2H), 3.34 (s, 2H), 3.10 (d, J=7.1 Hz, 2H), 2.74 (m, 2H), 2.34 (s, 3H), 1.97 (s, 6H), 1.41 (t, J=7.1 Hz, 3H), 1.29 (t, J=7.1 Hz, 3H), 1.13 (m, 1H), 0.86 (m, 2H), 0.46 (m, 2H). MS: m/e: 399 (M+H)⁺.

EXAMPLE 300

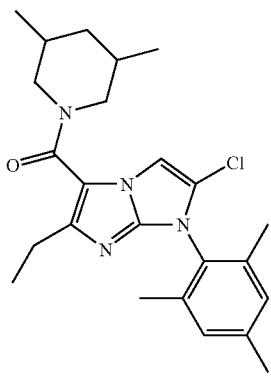

6-Chloro-2-ethyl-7-(2,4,6-trimethylphenyl)-7H-imidazo[1,2-a]imidazole-3-carboxylic acid (3,5-dimethylpiperidin-1-yl)amide, scheme 6: (BB)

Prepared as described for Example 283. $^1$H NMR (CDCl$_3$, 400 MHz) δ 7.18 (s, 1H), 6.90 (s, 2H), 4.12 (m, 2H), 2.57 (q, J=7.6 Hz, 2H), 2.36 (t, J=11.6, 12.6 Hz, 2H), 2.25 (s, 3H), 1.94 (s, 6H), 1.70 (m, 4H), 1.14 (t, J=7.1, 7.6 Hz, 3H), 0.84 (d, J=6.6 Hz, 4H), 0.78 (m, 2H). MS: m/e: 427 (M+H)$^+$.

Intermediates 95 and 96 were used to synthesize Example 301.

EXAMPLE 301

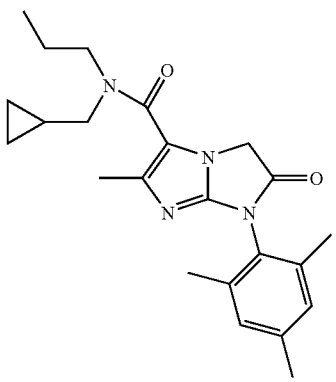

2-Methyl-6-oxo-7-(2,4,6-trimethyl-phenyl)-6,7-dihydro-5H-imidazo[1,2-a]imidazole-3-carboxylic acid cyclopropylmethyl-propyl-amide, scheme 7: (LL)

To a solution of N-cyclopropylmethylpropylamine (0.22 mL, 1.530 mmol) in toluene (1.5 mL) at 0° C. was added 2.0M solution of trimethylaluminum in toluene (0.77 mL, 1.530 mmol). The clear solution was warmed to room temperature and stirred for 1 h. A solution of 6-chloro-2-methyl-7-(2,4,6-trimethyl-phenyl)-7H-imidazo[1,2-a]imidazole-3-carboxylic acid ethyl ester (20.0 mg, 0.058 mmol) in toluene (1.5 mL) was added at 0° C. via cannula. The reaction mixture was heated at 80° C. for 2 h. A solution of Rochelle's salt (2.0 mL) was added carefully at 0° C. and the mixture was vigorously stirred for 30 min. The crude product was extracted with ethyl acetate. The combined organic extracts were dried with MgSO$_4$. The solvent was removed under reduced pressure and the crude product was purified by a reverse-phase preparative HPLC. Yield—3.6 mg (12%). $^1$H NMR (CD$_3$CN, 500 MHz) δ 7.07 (s, 2H), 4.73 (s, 2H), 3.57 (t, J=7.1 Hz, 2H), 3.37 (d, J=6.9 Hz, 2H), 2.35 (s, 3H), 2.19 (s, 3H), 2.14 (s, 6H), 1.65 (sextet, J=7.3 Hz, 2H), 1.08 (m, 1H), 0.90 (t, J=7.4 Hz, 3H), 0.56 (m, 2H), 0.21 (m, 2H); LC/MS: t$_R$=1.67 min., MS: [M+H]=395.

The following Intermediates 113-115 may be used to synthesize Examples 302 and 303.

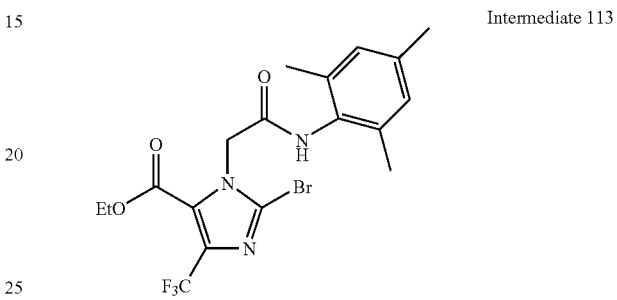

Intermediate 113

2-Bromo-5-trifluoromethyl-3-[(2,4,6-trimethyl-phenylcarbamoyl)-methyl]-3H-imidazole-4-carboxylic acid ethyl ester, scheme 5: (V)

To a solution of 2-bromo-5-trifluoromethyl-3H-imidazole-4-carboxylic acid ethyl ester (3.00 g, 10.45 mmol) and 2-bromo-N-(2,4,6-trimethyl-phenyl)-acetamide (2.94 g, 11.50 mmol) in a mixture of toluene (16 mL) and acetone (8 mL) was added DBU (1.72 mL, 11.50 mmol). The resulting solution was stirred at room temperature for 5 days. Methanol (10 mL) was added to dissolve the precipitate formed, followed by the addition of silica gel (25 g). The solvent was removed under reduced pressure to dryness and the residue was applied to a silica gel-packed column. The isolation of the product was achieved by column chromatography (hexanes-ethyl acetate 4:1). Yield—4.25 g (88%). LC/MS: t$_R$=1.62 min., MS: [M+H]=462.

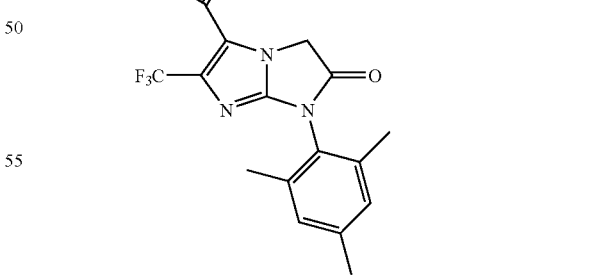

Intermediate 114

2-Bromo-5-trifluoromethyl-3-[(2,4,6-trimethyl-phenylcarbamoyl)-methyl]-3H-imidazole-4-carboxylic acid ethyl ester, Scheme 5: (W)

A suspension of 2-bromo-5-trifluoromethyl-3-[(2,4,6-trimethyl-phenylcarbamoyl)-methyl]-3H-imidazole-4-carboxylic acid ethyl ester (20.12 g, 0.044 mmol) and silver triflate (11.87 g, 0.046 mol) in sulfolane (200 mL) was heated at 150° C. for 6 h. The resulting reaction mixture was cooled to room temperature and filtered through a short pad of celite. The final purification was achieved by a reverse-phase preparative HPLC to give the desired product as yellowish solid. Yield—5.24 g (24%). LC/MS: $t_R$=1.89 min., MS: [M+H]=382.

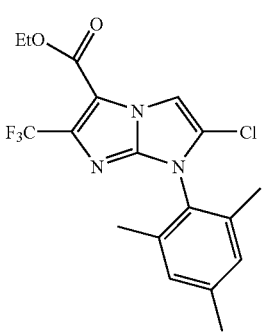

Intermediate 115

6-Chloro-2-trifluoromethyl-7-(2,4,6-trimethyl-phenyl)-7H-imidazo[1,2-a]imidazole-3-carboxylic acid ethyl ester, Scheme 6: (AA)

A solution of 6-oxo-2-trifluoromethyl-7-(2,4,6-trimethyl-phenyl)-6,7-dihydro-5H-imidazo[1,2-a]imidazole-3-carboxylic acid ethyl ester (3.04 g, 6.137 mol) in phosphorus oxychloride (70 mL) was heated at 150° C. for 72 h. The excess of phosphorus oxychloride was removed under reduced pressure, the residue was dissolved in saturated aqueous solution of sodium bicarbonate (100 mL) and extracted with ethyl acetate (5×50 mL). The combined organic extracts were dried with MgSO$_4$. The solvent was removed under reduced pressure and the crude product was dried under pump vacuum overnight. Yield—1.192 g (38%). LC/MS: $t_R$=2.17 min., MS: [M+H]=400.

EXAMPLE 302

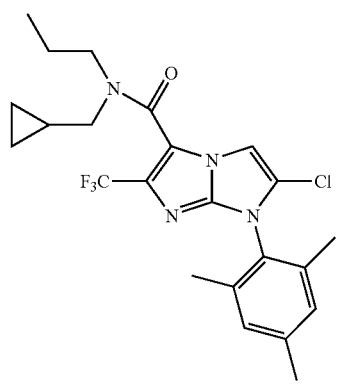

6-Chloro-2-trifluoromethyl-7-(2,4,6-trimethyl-phenyl)-7H-imidazo[1,2-a]imidazole-3-carboxylic acid cyclopropylmethyl-propyl-amide, Scheme 6: (BB)

To a solution of N-cyclopropylmethylpropylamine (0.22 mL, 1.530 mmol) in toluene (1.5 mL) at 0° C. was added 2.0M solution of trimethylaluminum in toluene (0.77 mL, 1.530 mmol). The clear solution was warmed to room temperature and stirred for 1 h. A solution of 6-chloro-2-trifluoromethyl-7-(2,4,6-trimethyl-phenyl)-7H-imidazo[1,2-a]imidazole-3-carboxylic acid ethyl ester (37.7 mg, 0.094 mmol) in toluene (1.0 mL) was added at 0° C. via cannula. The reaction mixture was heated at 80° C. for 2 h. A solution of Rochelle's salt (2.0 mL) was added carefully at 0° C. and the mixture was vigorously stirred for 30 min. The crude product was extracted with ethyl acetate. The combined organic extracts were dried with MgSO$_4$. The solvent was removed under reduced pressure and the crude product was purified by a reverse-phase preparative HPLC. Yield—39.5 mg (90%). LC/MS: $t_R$=1.93 min., MS: [M+H]=467.

EXAMPLE 303

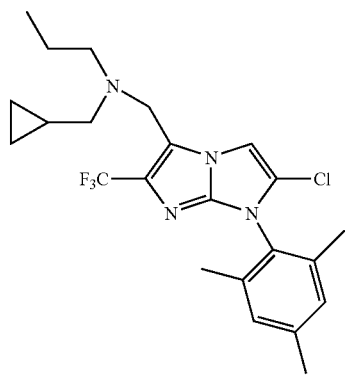

[6-Chloro-2-trifluoromethyl-7-(2,4,6-trimethyl-phenyl)-7H-imidazo[1,2-a]imidazol-3-ylmethyl]-cyclopropylmethyl-propyl-amine, Scheme 6: (DD)

A solution of 6-chloro-2-trifluoromethyl-7-(2,4,6-trimethyl-phenyl)-7H-imidazo[1,2-a]imidazole-3-carboxylic acid cyclopropylmethyl-propyl-amide (27.2 mg, 0.058 mmol) in toluene (3 mL) was added a 65% solution of Red-Al in toluene (0.10 mL, 0.320 mmol). The reaction mixture was stirred at room temperature for 14 h. A solution of Rochelle's salt (2.0 mL) was added carefully at 0° C. and the mixture was vigorously stirred for 30 min. The crude product was extracted with ethyl acetate. The combined organic extracts were dried with Na$_2$SO$_4$. The solvent was removed under reduced pressure and the crude product was purified by a reverse-phase preparative HPLC. Yield—12.8 mg (39%). LC/MS: $t_R$=1.77 min., MS: [M+H]=453.

The following Intermediates 116 and 117 may be used to synthesize Examples 303-347.

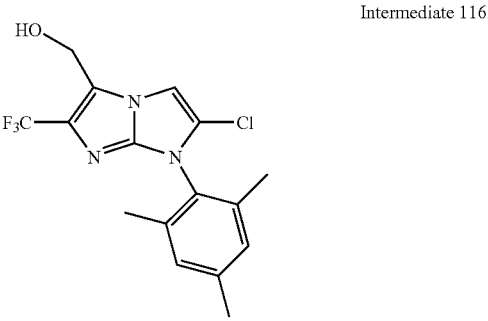

Intermediate 116

[6-Chloro-2-trifluoromethyl-7-(2,4,6-trimethyl-phenyl)-7H-imidazo[1,2-a]imidazol-3-yl]-methanol, Scheme 6: (CC)

To a solution of 6-chloro-2-trifluoromethyl-7-(2,4,6-trimethyl-phenyl)-7H-imidazo[1,2-a]imidazole-3-carboxylic acid ethyl ester (978.3 mg, 1.904 mmol) in tetrahydrofuran (100 mL) at 0° C. was added a 1.0M solution of lithium aluminum hydride in tetrahydrofuran (5.71 mL, 5.71 mmol). The resulting solution was stirred at 0° C. for 10 min. Acetone (5 mL) was added and the solution was aded via cannula to a vigorously stirred ice-cold solution of Rochelle's salt (100 mL). The product was extracted with ethyl acetate (5×50 mL) and the combined organic extracts were dried over anhydrous $Na_2SO_4$. The solvent was removed in vacuo and the crude mixture was chromatographed on short silica gel column (hexanes-ethyl acetate 4:1) to give the desired product (614.8 mg, 90%) which was pure by LC-MS. LC/MS: $t_R$=1.25 min., MS: [M+H]=358.

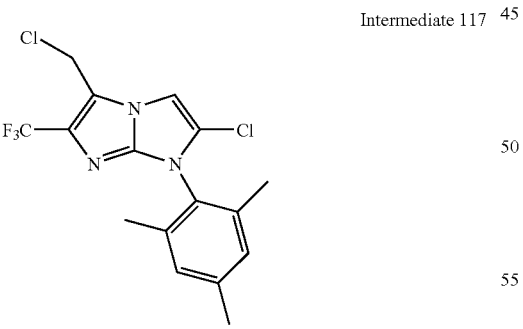

Intermediate 117

2-Chloro-5-chloromethyl-6-trifluoromethyl-1-(2,4,6-trimethyl-phenyl)-1H-imidazo[1,2-a]imidazole A solution of [6-chloro-2-trifluoromethyl-7-(2,4,6-trimethyl-phenyl)-7H-imidazo[1,2-a]imidazol-3-yl]-methanol (614.8 mg, 1.718 mmol) and thionyl chloride (1.25 mL) in dichloromethane was stirred at 0° C. for 15 min. Thionyl chloride and the solvent were removed in vacuo and the residue was dried under high vacuum to yield the desired product as a yellow solid (646.3 mg, 100%). LC/MS: $t_R$=1.46 min., MS: [MH−Cl+OMe]=373.

EXAMPLE 303

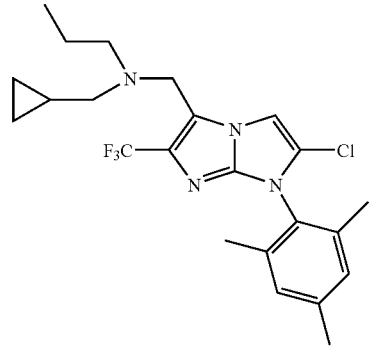

[6-Chloro-2-trifluoromethyl-7-(2,4,6-trimethyl-phenyl)-7H-imidazo[1,2-a]imidazol-3-ylmethyl]-cyclopropylmethyl-propyl-amine, Scheme 6: (DD)

To a solution of amine (6.1 mg, 0.054 mmol) and Hünig's base (0.05 mL) in acetonitrile (0.5 mL) at room temperature was added slowly a solution of 2-chloro-5-chloromethyl-6-trifluoromethyl-1-(2,4,6-trimethyl-phenyl)-1H-imidazo[1,2-a]imidazole (10.0 mg, 0.027 mmol) in acetonitrile (0.5 mL). The reaction mixture was stirred overnight. The final purification was achieved by a reverse-phase preparative HPLC to give the desired product as colorless oil. Yield—9.9 mg (65%). LC/MS: $t_R$=1.77 min., MS: [M+H]=453.

EXAMPLE 304

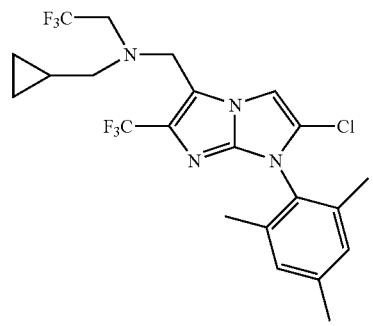

[6-Chloro-2-trifluoromethyl-7-(2,4,6-trimethyl-phenyl)-7H-imidazo[1,2-a]imidazol-3-ylmethyl]-cyclopropylmethyl-(2,2,2-trifluoro-ethyl)-amine, Scheme 6: (DD)

Prepared as described for the example above. LC/MS: $t_R$=2.31 min., MS: [M+H]=494.

EXAMPLE 305

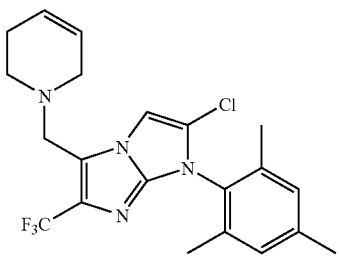

2-Chloro-5-(3,6-dihydro-2H-pyridin-1-ylmethyl)-6-trifluoromethyl-1-(2,4,6-trimethyl-phenyl)-1H-imidazol[1,2-a]imidazole, Scheme 6: (DD)

Prepared as described for the example above. LC/MS: $t_R$=1.59 min., MS: [M+H]=423.

EXAMPLE 306

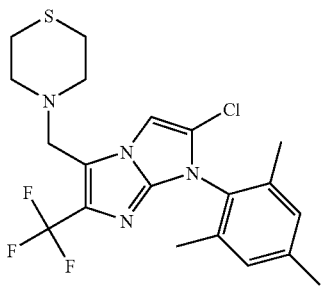

2-Chloro-5-thiomorpholin-4-ylmethyl-6-trifluoromethyl-1-(2,4,6-trimethyl-phenyl)-1H-imidazol[1,2-a]imidazole, Scheme 6: (DD)

Prepared as described for the example above. LC/MS: $t_R$=1.63 min., MS: [M+H]=443.

EXAMPLE 307

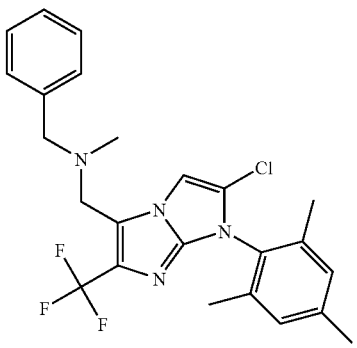

Benzyl-[6-chloro-2-trifluoromethyl-7-(2,4,6-trimethyl-phenyl)-7H-imidazo[1,2-a]imidazol-3-ylmethyl]-methyl-amine, Scheme 6: (DD)

Prepared as described for the example above. LC/MS: $t_R$=1.73 min., MS: [M+H]=461.

EXAMPLE 308

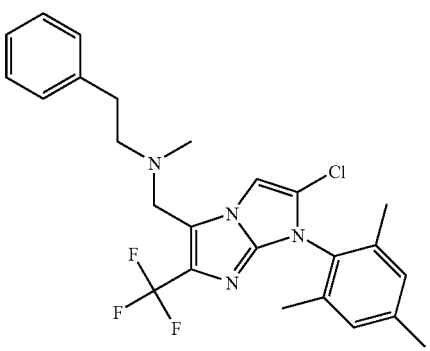

[6-Chloro-2-trifluoromethyl-7-(2,4,6-trimethyl-phenyl)-7H-imidazo[1,2-a]imidazol-3-ylmethyl]-methyl-phenethyl-amine, Scheme 6: (DD)

Prepared as described for the example above. LC/MS: $t_R$=1.76 min., MS: [M+H]=475.

EXAMPLE 309

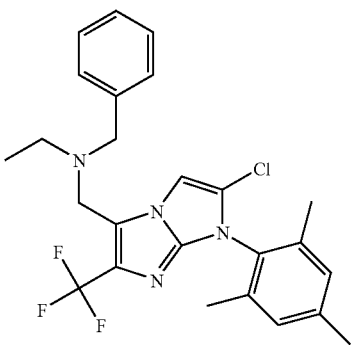

Benzyl-[6-chloro-2-trifluoromethyl-7-(2,4,6-trimethyl-phenyl)-7H-imidazol[1,2-a]imidazol-3-ylmethyl]-ethyl-amine, Scheme 6: (DD)

Prepared as described for the example above. LC/MS: $t_R$=1.77 min., MS: [M+H]=475.

EXAMPLE 310

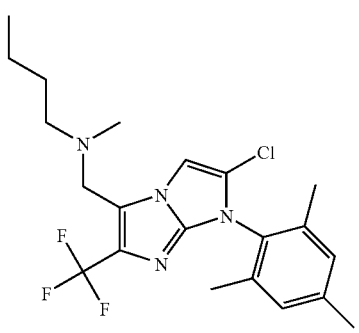

Butyl-[6-chloro-2-trifluoromethyl-7-(2,4,6-trimethyl-phenyl)-7H-imidazo[1,2-a]imidazol-3-ylmethyl]-methyl-amine, Scheme 6: (DD)

Prepared as described for the example above. LC/MS: $t_R$=1.62 min., MS: [M+H]=427.

EXAMPLE 311

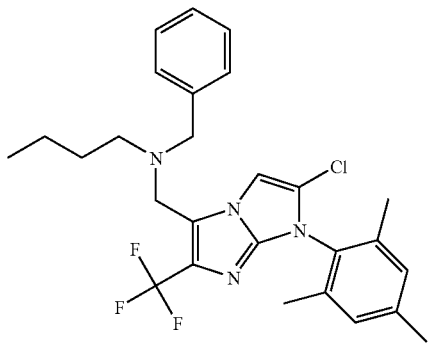

Benzyl-butyl-[6-chloro-2-trifluoromethyl-7-(2,4,6-trimethyl-phenyl)-7H-imidazo[1,2-a]imidazol-3-ylmethyl]-amine, Scheme 6: (DD)

Prepared as described for the example above. LC/MS: $t_R$=1.92 min., MS: [M+H]=503.

EXAMPLE 312

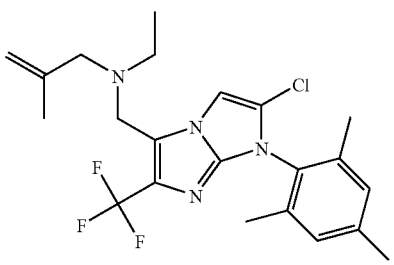

[6-Chloro-2-trifluoromethyl-7-(2,4,6-trimethyl-phenyl)-7H-imidazo[1,2-a]imidazol-3-ylmethyl]-ethyl-(2-methyl-allyl)-amine, Scheme 6: (DD)

Prepared as described for the example above. LC/MS: $t_R$=1.70 min., MS: [M+H]=439.

EXAMPLE 313

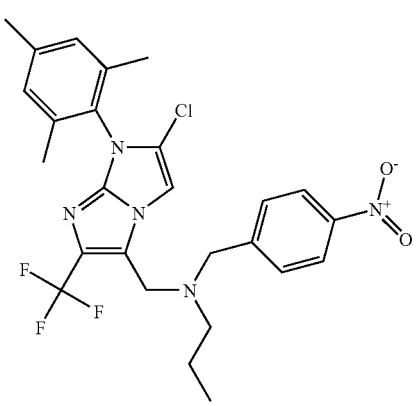

[6-Chloro-2-trifluoromethyl-7-(2,4,6-trimethyl-phenyl)-7H-imidazo[1,2-a]imidazol-3-ylmethyl]-(4-nitro-benzyl)-propyl-amine, Scheme 6: (DD)

Prepared as described for the example above. LC/MS: $t_R$=2.16 min., MS: [M+H]=534.

EXAMPLE 314

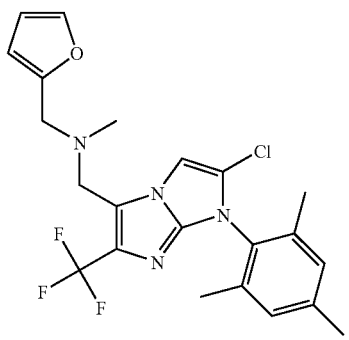

[6-Chloro-2-trifluoromethyl-7-(2,4,6-trimethyl-phenyl)-7H-imidazo[1,2-a]imidazol-3-ylmethyl]-furan-2-ylmethyl-methyl-amine, Scheme 6: (DD)

Prepared as described for the example above. LC/MS: $t_R$=1.67 min., MS: [M+H]=451.

EXAMPLE 315

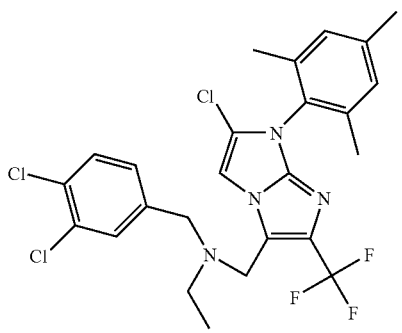

[6-Chloro-2-trifluoromethyl-7-(2,4,6-trimethyl-phenyl)-7H-imidazo[1,2-a]imidazol-3-ylmethyl]-(3,4-dichloro-benzyl)-ethyl-amine, Scheme 6: (DD)

Prepared as described for the example above. LC/MS: $t_R$=2.14 min., MS: [M+H]=543.

EXAMPLE 316

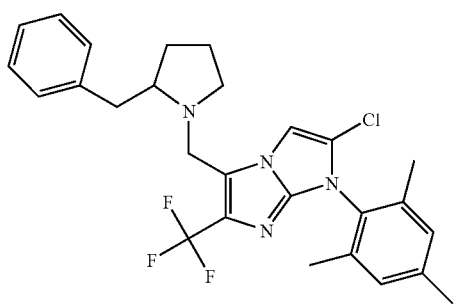

5-(2-Benzyl-pyrrolidin-1-ylmethyl)-2-chloro-6-trifluoromethyl-1-(2,4,6-trimethyl-phenyl)-1H-imidazo[1,2-a]imidazole, Scheme 6: (DD)

Prepared as described for the example above. LC/MS: $t_R$=1.80 min., MS: [M+H]=501.

EXAMPLE 317

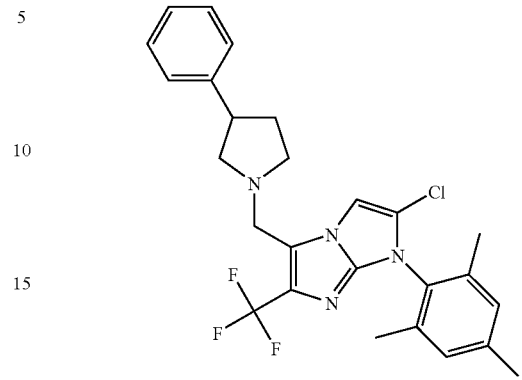

2-Chloro-5-(3-phenyl-pyrrolidin-1-ylmethyl)-6-trifluoromethyl-1-(2,4,6-trimethyl-phenyl)-1H-imidazo[1,2-a]imidazole, Scheme 6: (DD)

Prepared as described for the example above. LC/MS: $t_R$=1.78 min., MS: [M+H]=487.

EXAMPLE 318

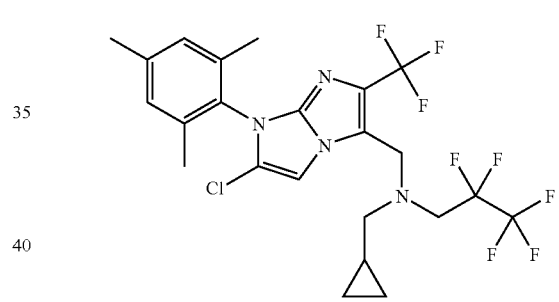

6-Chloro-2-trifluoromethyl-7-(2,4,6-trimethyl-phenyl)-7H-imidazo[1,2-a]imidazol-3-ylmethyl]-cyclopropylmethyl-(2,2,3,3,3-pentafluoro-propyl)-amine, Scheme 6: (DD)

Prepared as described for the example above. LC/MS: $t_R$=2.38 min., MS: [M+H]=543.

EXAMPLE 319

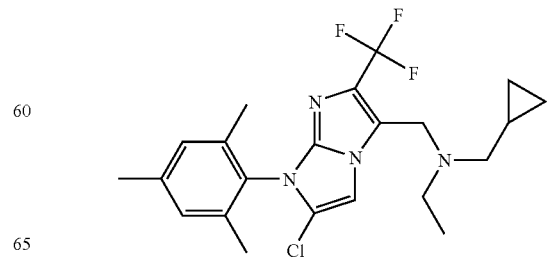

[6-Chloro-2-trifluoromethyl-7-(2,4,6-trimethyl-phenyl)-7H-imidazo[1,2-a]imidazol-3-ylmethyl]-cyclopropylmethyl-ethyl-amine, Scheme 6: (DD)

Prepared as described for the example above. LC/MS: $t_R$=1.64 min., MS: [M+H]=439.

EXAMPLE 320

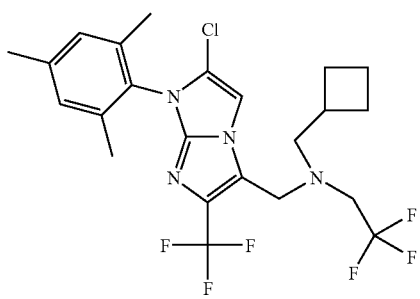

[6-Chloro-2-trifluoromethyl-7-(2,4,6-trimethyl-phenyl)-7H-imidazo[1,2-a]imidazol-3-ylmethyl]-cyclobutylmethyl-(2,2,2-trifluoro-ethyl)-amine, Scheme 6: (DD)

Prepared as described for the example above. LC/MS: $t_R$=2.40 min., MS: [M+H]=507.

EXAMPLE 321

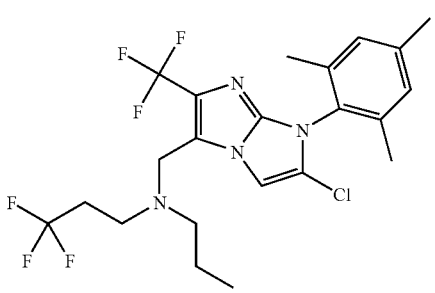

[6-Chloro-2-trifluoromethyl-7-(2,4,6-trimethyl-phenyl)-7H-imidazo[1,2-a]imidazol-3-ylmethyl]-propyl-(3,3,3-trifluoro-propyl)-amine, Scheme 6: (DD)

Prepared as described for the example above. LC/MS: $t_R$=2.02 min., MS: [M+H]=495.

EXAMPLE 322

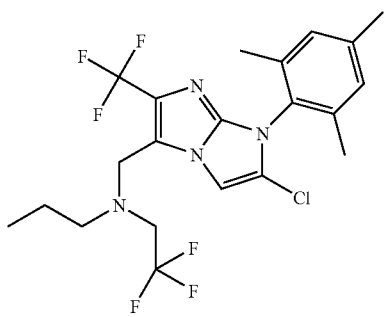

[6-Chloro-2-trifluoromethyl-7-(2,4,6-trimethyl-phenyl)-7H-imidazo[1,2-a]imidazol-3-ylmethyl]-propyl-(2,2,2-trifluoro-ethyl)-amine, Scheme 6: (DD)

Prepared as described for the example above. LC/MS: $t_R$=2.29 min., MS: [M+H]=481.

EXAMPLE 323

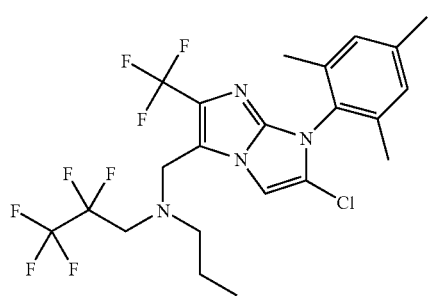

[6-Chloro-2-trifluoromethyl-7-(2,4,6-trimethyl-phenyl)-7H-imidazo[1,2-a]imidazol-3-ylmethyl]-(2,2,3,3,3-pentafluoro-propyl)-propyl-amine, Scheme 6: (DD)

Prepared as described for the example above. LC/MS: $t_R$=2.38 min., MS: [M+H]=531.

EXAMPLE 324

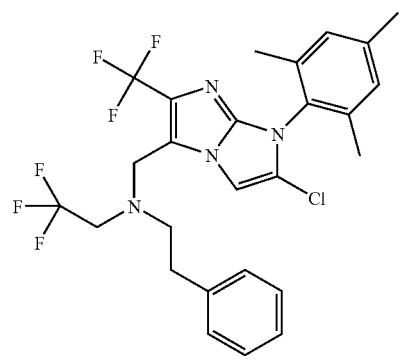

[6-Chloro-2-trifluoromethyl-7-(2,4,6-trimethyl-phenyl)-7H-imidazo[1,2-a]imidazol-3-ylmethyl]-phenethyl-(2,2,2-trifluoro-ethyl)-amine, Scheme 6: (DD)

Prepared as described for the example above. LC/MS: $t_R$=2.32 min., MS: [M+H]=543.

EXAMPLE 325

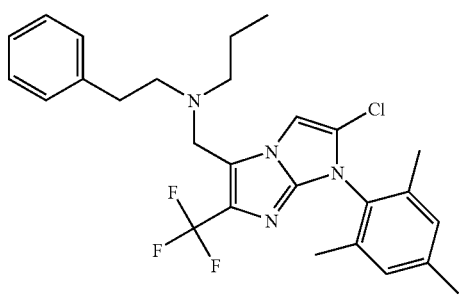

[6-Chloro-2-trifluoromethyl-7-(2,4,6-trimethyl-phenyl)-7H-imidazo[1,2-a]imidazol-3-ylmethyl]-phenethyl-propyl-amine, Scheme 6: (DD)

Prepared as described for the example above. LC/MS: $t_R$=1.85 min., MS: [M+H]=503.

EXAMPLE 326

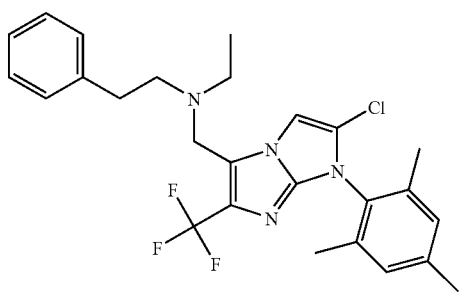

[6-Chloro-2-trifluoromethyl-7-(2,4,6-trimethyl-phenyl)-7H-imidazo[1,2-a]imidazol-3-ylmethyl]-ethyl-phenethyl-amine, Scheme 6: (DD)

Prepared as described for the example above. LC/MS: $t_R$=1.79 min., MS: [M+H]=489.

EXAMPLE 327

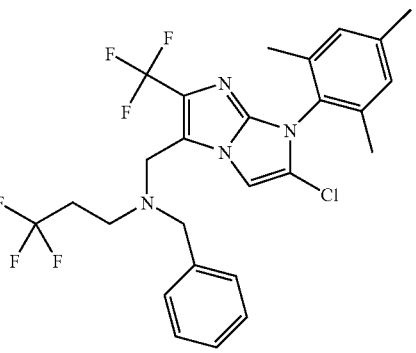

Benzyl-[6-chloro-2-trifluoromethyl-7-(2,4,6-trimethyl-phenyl)-7H-imidazo[1,2-a]imidazol-3-ylmethyl]-(3,3,3-trifluoro-propyl)-amine, Scheme 6: (DD)

Prepared as described for the example above. LC/MS: $t_R$=2.34 min., MS: [M+H]=543.

EXAMPLE 328

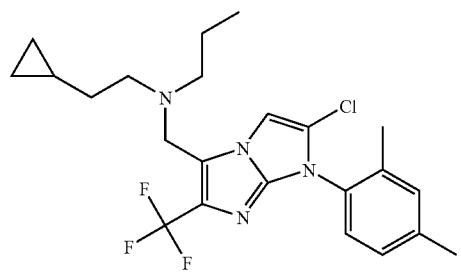

[6-Chloro-2-trifluoromethyl-7-(2,4,6-trimethyl-phenyl)-7H-imidazo[1,2-a]imidazol-3-ylmethyl]-(2-cyclopropyl-ethyl)-propyl-amine, Scheme 6: (DD)

Prepared as described for the example above. LC/MS: $t_R$=1.76 min., MS: [M+H]=467.

EXAMPLE 329

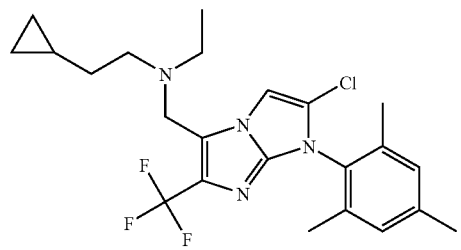

[6-Chloro-2-trifluoromethyl-7-(2,4,6-trimethyl-phenyl)-7H-imidazo[1,2-a]imidazol-3-ylmethyl]-(2-cyclopropyl-ethyl)-ethyl-amine, Scheme 6: (DD)

Prepared as described for the example above. LC/MS: $t_R$=1.71 min., MS: [M+H]=453.

EXAMPLE 330

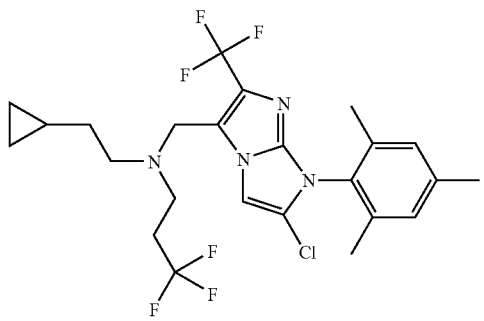

[6-Chloro-2-trifluoromethyl-7-(2,4,6-trimethyl-phenyl)-7H-imidazo[1,2-a]imidazol-3-ylmethyl]-(2-cyclopropyl-ethyl)-(3,3,3-trifluoro-propyl)-amine, Scheme 6: (DD)

Prepared as described for the example above. LC/MS: $t_R$=2.15 min., MS: [M+H]=521.

EXAMPLE 331

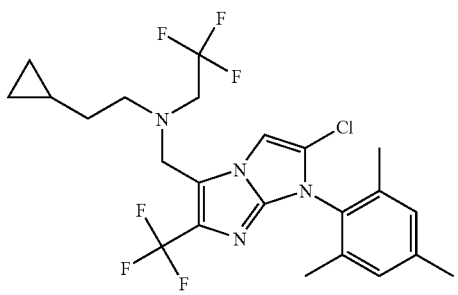

[6-Chloro-2-trifluoromethyl-7-(2,4,6-trimethyl-phenyl)-7H-imidazo[1,2-a]imidazol-3-ylmethyl]-(2-cyclopropyl-ethyl)-(2,2,2-trifluoro-ethyl)-amine, Scheme 6: (DD)

Prepared as described for the example above. LC/MS: $t_R$=2.01 min., MS: [M+H]=507.

EXAMPLE 332

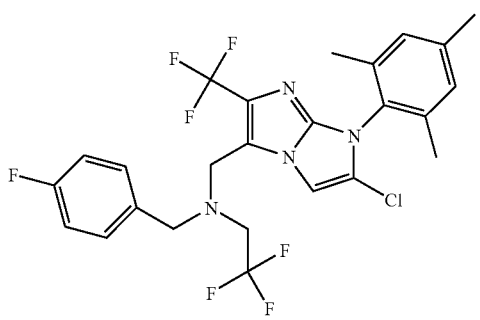

[6-Chloro-2-trifluoromethyl-7-(2,4,6-trimethyl-phenyl)-7H-imidazo[1,2-a]imidazol-3-ylmethyl]-(4-fluoro-benzyl)-(2,2,2-trifluoro-ethyl)-amine, Scheme 6: (DD)

Prepared as described for the example above. LC/MS: $t_R$=2.33 min., MS: [M+H]=547.

EXAMPLE 333

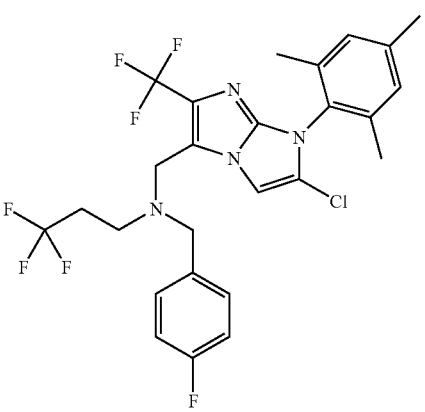

-Chloro-2-trifluoromethyl-7-(2,4,6-trimethyl-phenyl)-7H-imidazo[1,2-a]imidazol-3-ylmethyl]-(4-fluoro-benzyl)-(3,3,3-trifluoro-propyl)-amine, Scheme 6: (DD).

Prepared as described for the example above. LC/MS: $t_R$=2.33 min., MS: [M+H]=561.

EXAMPLE 334

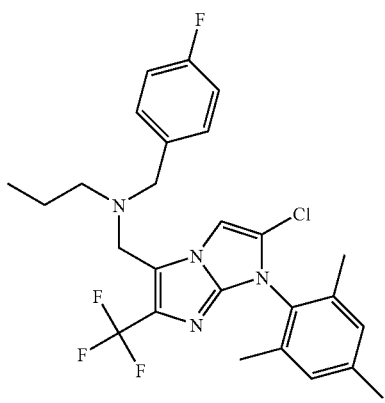

[6-Chloro-2-trifluoromethyl-7-(2,4,6-trimethyl-phenyl)-7H-imidazo[1,2-a]imidazol-3-ylmethyl]-(4-fluoro-benzyl)-propyl-amine, Scheme 6: (DD)

Prepared as described for the example above. LC/MS: $t_R$=1.91 min., MS: [M+H]=507.

EXAMPLE 335

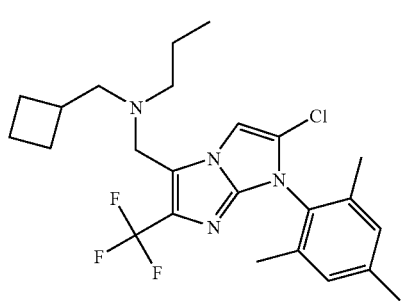

[6-Chloro-2-trifluoromethyl-7-(2,4,6-trimethyl-phenyl)-7H-imidazo[1,2-a]imidazol-3-ylmethyl]-cyclobutylmethyl-propyl-amine, Scheme 6: (DD)

Prepared as described for the example above. LC/MS: $t_R$=1.75 min., MS: [M+H]=467.

EXAMPLE 336

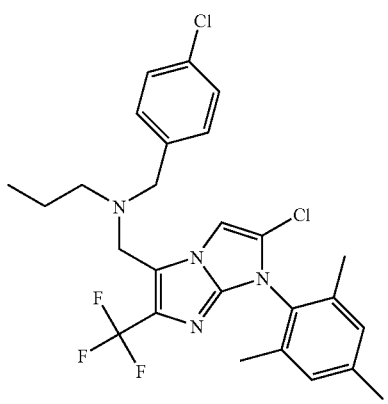

(4-Chloro-benzyl)-[6-chloro-2-trifluoromethyl-7-(2,4,6-trimethyl-phenyl)-7H-imidazo[1,2-a]imidazol-3-ylmethyl]-(3,3,3-trifluoro-propyl)-amine, Scheme 6: (DD)

Prepared as described for the example above. LC/MS: $t_R$=2.42 min., MS: [M+H]=577.

EXAMPLE 337

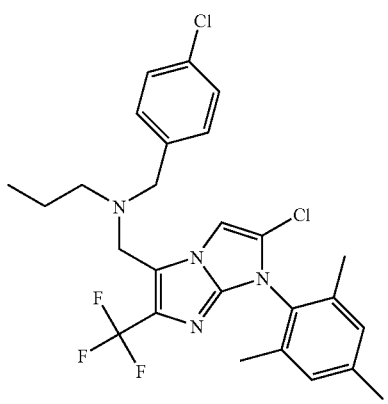

(4-Chloro-benzyl)-[6-chloro-2-trifluoromethyl-7-(2,4,6-trimethyl-phenyl)-7H-imidazo[1,2-a]imidazol-3-ylmethyl]-propyl-amine, Scheme 6: (DD)

Prepared as described for the example above. LC/MS: $t_R$=2.05 min., MS: [M+H]=523.

EXAMPLE 338

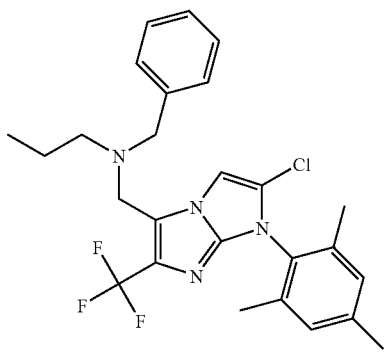

Benzyl-[6-chloro-2-trifluoromethyl-7-(2,4,6-trimethyl-phenyl)-7H-imidazo[1,2-a]imidazol-3-ylmethyl]-propyl-amine, Scheme 6: (DD)

Prepared as described for the example above. LC/MS: $t_R$=1.86 min., MS: [M+H]=489.

EXAMPLE 339

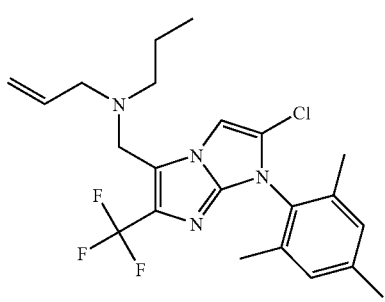

Allyl-[6-chloro-2-trifluoromethyl-7-(2,4,6-trimethyl-phenyl)-7H-imidazol[1,2-a]imidazol-3-ylmethyl]-propyl-amine, Scheme 6: (DD)

Prepared as described for the example above. LC/MS: $t_R$=1.67 min., MS: [M+H]=539.

EXAMPLE 340

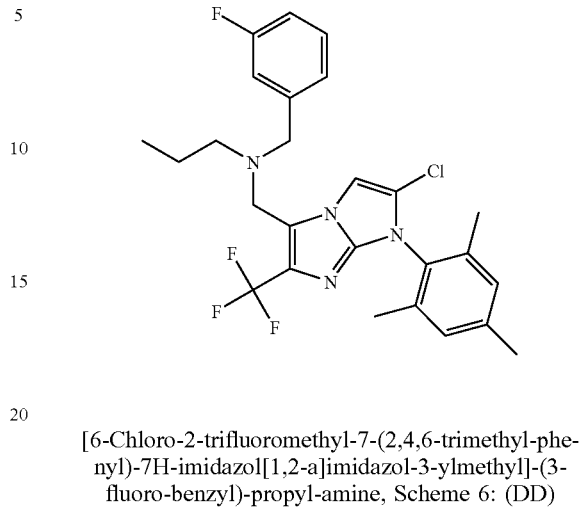

[6-Chloro-2-trifluoromethyl-7-(2,4,6-trimethyl-phenyl)-7H-imidazol[1,2-a]imidazol-3-ylmethyl]-(3-fluoro-benzyl)-propyl-amine, Scheme 6: (DD)

Prepared as described for the example above. LC/MS: $t_R$=1.99 min., MS: [M+H]=507.

EXAMPLE 341

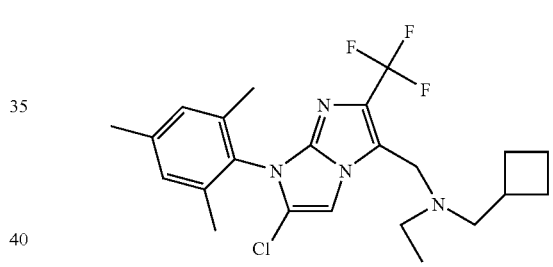

[6-Chloro-2-trifluoromethyl-7-(2,4,6-trimethyl-phenyl)-7H-imidazo[1,2-a]imidazol-3-ylmethyl]-cyclobutylmethyl-ethyl-amine, Scheme 6: (DD)

Prepared as described for the example above. LC/MS: $t_R$=1.72 min., MS: [M+H]=453.

EXAMPLE 342

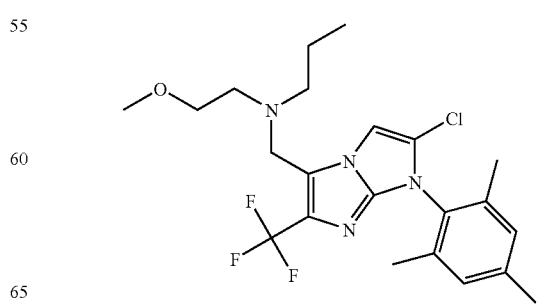

[6-Chloro-2-trifluoromethyl-7-(2,4,6-trimethyl-phenyl)-7H-imidazo[1,2-a]imidazol-3-ylmethyl]-(2-methoxy-ethyl)-propyl-amine, Scheme 6: (DD)

Prepared as described for the example above. LC/MS: $t_R$=1.68 min., MS: [M+H]=457.

EXAMPLE 343

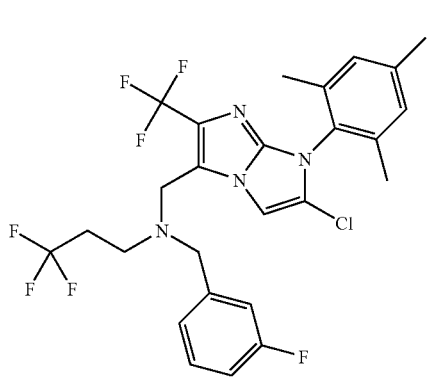

[6-Chloro-2-trifluoromethyl-7-(2,4,6-trimethyl-phenyl)-7H-imidazo[1,2-a]imidazol-3-ylmethyl]-(3-fluoro-benzyl)-(3,3,3-trifluoro-propyl)-amine, Scheme 6: (DD)

Prepared as described for the example above. LC/MS: $t_R$=2.32 min., MS: [M+H]=561.

EXAMPLE 344

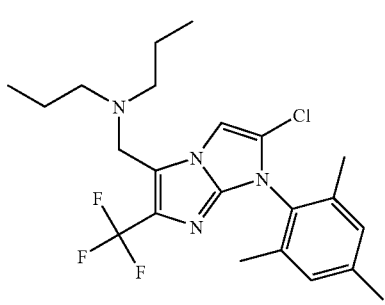

[6-Chloro-2-trifluoromethyl-7-(2,4,6-trimethyl-phenyl)-7H-imidazo[1,2-a]imidazol-3-ylmethyl]-dipropyl-amine, Scheme 6: (DD)

Prepared as described for the example above. LC/MS: $t_R$=1.68 min., MS: [M+H]=441.

EXAMPLE 345

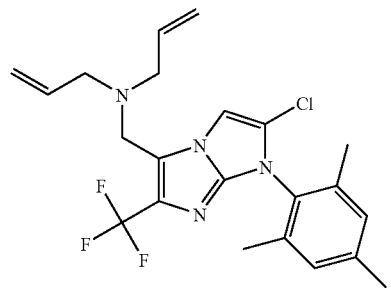

Diallyl-[6-chloro-2-trifluoromethyl-7-(2,4,6-trimethyl-phenyl)-7H-imidazo[1,2-a]imidazol-3-ylmethyl]-amine, Scheme 6: (DD)

Prepared as described for the example above. LC/MS: $t_R$=1.70 min., MS: [M+H]=437.

EXAMPLE 346

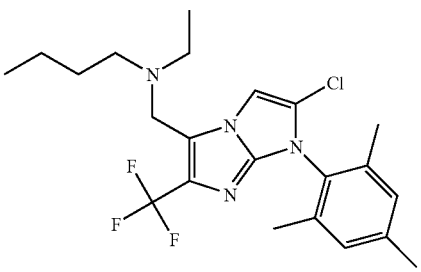

Butyl-[6-chloro-2-trifluoromethyl-7-(2,4,6-trimethyl-phenyl)-7H-imidazo[1,2-a]imidazol-3-ylmethyl]-ethyl-amine, Scheme 6: (DD)

Prepared as described for the example above. LC/MS: $t_R$=1.71 min., MS: [M+H]=441.

EXAMPLE 347

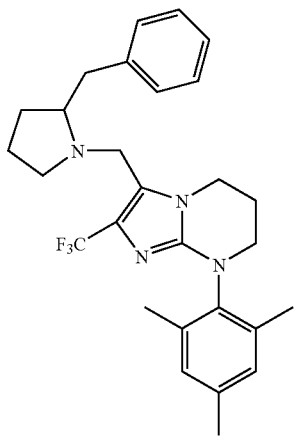

3-(2-Benzyl-pyrrolidin-1-ylmethyl)-2-trifluoromethyl-8-(2,4,6-trimethyl-phenyl)-5,6,7,8-tetrahydroimidazo[1,2-a]pyrimidine, Scheme 7: (KK)

LC/MS: $t_R$=1.7 min., MS: [M+H]=483.

The following amine hydrochloride salts are intermediates that were used in many of the above examples:

INTERMEDIATE 118

2-Cyclopropylethylamine hydrochloride

A 1M solution of borane in tetrahydrofuran (250 mL, 2 equiv.) that had been cooled to 0° C. was added to cyclopropylacetonitrile (10.00 g, 123.3 mmoles) at 0° C. under nitrogen. The stirred mixture was heated at reflux for 12 hours, cooled to 0° C., and then carefully quenched with methanol (50 mL). The mixture was heated at reflux for 2 hours and then, upon re-cooling to 0° C., treated with a solution of t-butylpyrocarbonate (37.67 g, 1.4 equiv.) in methylene chloride (25 mL). The resulting mixture was stirred at room temperature overnight and then evaporated. the residue was partitioned between ethyl acetate and water. The organic was washed with water, brine, dried over magnesium sulfate, and evaporated to give the crude Boc-protected amine. This was dissolved in methylene chloride (25 mL) and treated with 4M hydrogen chloride in dioxane (77 mL, 2.5 equiv.). The mixture was stirred at room temperature overnight and then evaporated. The resulting white solid was triturated with ether and the product was collected by filtration, washed with ether, and dried in vacuo (12.72 g, 85%). $^1$H-NMR δ (CDCl$_3$) 0.14 (m, 2H), 0.52 (m, 2H), 0.75 (m, 1H), 1.66 (q, 2H), 3.09 (m, 2H), 8.27 (br, 3H).

INTERMEDIATE 119

3,3,3-Trifluoroacetic acid N-hydroxysuccinimide active ester, Scheme 8: (MM)

A stirred solution of 3,3,3-trifluoroacetic acid (9.7 mL, 110 mmoles) and N-hydroxysuccinimide (13.92 g, 1.1 equiv.) in methylene chloride (100 mL) at 0° C. was treated with EDC hydrochloride (21.08 g, 1 equiv.). The mixture was allowed to warm to room temperature. After stirring overnight, the solvent was evaporated and the residue partitioned between ethyl acetate and water. The organic phase was washed with brine, dried over magnesium sulfate, and evaporated to give the crude active ester which was used without further purification (22.78 g, 92%). $^1$H-NMR δ (CDCl$_3$) 2.86 (s, 4H), 3.51 (q, 2H).

INTERMEDIATE 120

Cyclopropylmethyl-3,3,3-trifluoropropyl-amine hydrochloride, Scheme 8: (OO)

A stirred solution of 3,3,3-trifluoroacetic acid N-hydroxysuccinimide active ester (12.98 g, 57.65 mmoles) in methylene chloride (80 mL) at 0° C. was treated with cyclopropylmethylamine (5.0 mL, 1 equiv.). The mixture was stirred at room temperature for 14 hours and then evaporated. The residue was partitioned between ethyl acetate and water. The organic phase was washed with water, brine, dried over magnesium sulfate, and evaporated to give the crude amide. This was dried under high vacuum for several hours and then, under a nitrogen atmosphere at 0° C., it was carefully treated with a 1M solution of borane in tetrahydrofuran (173 mL, 3 equiv.). The mixture was heated at reflux for 14 hours and then re-cooled to 0° C. Methanol (50 mL) was added very carefully to avoid excess foaming, and the mixture was heated at reflux for 5 hours. Upon re-cooling to 0° C., a solution of t-butylpyrocarbonate (17.62 g, 1.4 equiv.) in methylene chloride (25 mL) was added. The resulting mixture was stirred at room temperature overnight and then evaporated. the residue was partitioned between ethyl acetate and water. The organic was washed with water, brine, dried over magnesium sulfate, and evaporated to give the crude Boc-protected amine. This was dissolved in methylene chloride (25 mL) and treated with 4M hydrogen chloride in dioxane (36 mL, 2.5 equiv.). The mixture was stirred at room temperature overnight and then evaporated. The resulting white solid was triturated with ether and the product was collected by filtration, washed with ether, and dried in vacuo (10.10 g, 86%). $^1$H-NMR δ (D$_2$O) 0.36 (m, 2H), 0.67 (m, 2H), 1.07 (m, 1H), 2.72 (m, 2H), 2.99 (d, 2H), 3.89 (t, 2H).

Similarly Prepared:

INTERMEDIATE 121

2-Cyclopropylethyl-3,3,3-trifluoropropyl-amine hydrochloride, scheme 8: (OO)

$^1$H-NMR δ (D$_2$O) 0.14 (m, 2H), 0.52 (m, 2H), 0.74 (m, 1H), 1.61 (m, 2H), 2.73 (m, 2H), 3.20 (t, 2H), 3.38 (t, 2H).

INTERMEDIATE 122 n-Propyl-3,3,3-trifluoropropyl-amine hydrochloride, scheme 8: (OO)

$^1$H-NMR δ (D$_2$O) 0.98 (t, 3H), 1.71 (q, 2H), 2.72 (m, 2H), 3.06 (t, 2H), 3.36 (t, 2H).

INTERMEDIATE 123

Benzyl-3,3,3-trifluoropropyl-amine hydrochloride, scheme 8: (OO)

$^1$H-NMR δ (D$_2$O) 2.73 (m, 2H), 3.40 (t, 2H), 4.31 (s, 2H), 7.51 (brs, 5H).

INTERMEDIATE 124 p-Fluoro-benzyl-3,3,3-trifluoropropyl-amine hydrochloride, scheme 8: (OO)

$^1$H-NMR δ (D$_2$O) 2.73 (m, 2H), 3.38 (t, 2H), 4.28 (s, 2H), 7.23 (ABq, 2H), 7.51 (ABq, 2H).

INTERMEDIATE 125 p-Chloro-benzyl-3,3,3-trifluoropropyl-amine hydrochloride, scheme 8: (OO)

$^1$H-NMR δ (D$_2$O) 2.72 (m, 2H), 3.39 (t, 2H), 4.29 (s, 2H), 7.49 (q, 4H).

INTERMEDIATE 126 m-Fluoro-benzyl-3,3,3-trifluoropropyl-amine hydrochloride, scheme 8: (OO)

$^1$H-NMR δ (D$_2$O) 2.73 (m, 2H), 3.41 (t, 2H), 4.39 (s, 2H), 7.30 (m, 3H), 7.66 (m, 1H).

INTERMEDIATE 127

2-Phenylethyl-3,3,3-trifluoropropyl-amine hydrochloride, scheme 8: (OO)

$^1$H-NMR δ (D$_2$O) 2.73 (m, 2H), 3.07 (t, 2H), 3.40 (m, 4H), 7.42 (m, 5H).

INTERMEDIATE 128

Benzyl-2,2,2-trifluoroethyl-amine hydrochloride, scheme 8: (OO)

A stirred solution of benzylamine (5.0 mL, 45.77 mmoles) and triethylamine (6.4 mL, 1 equiv.) in methylene chloride (50 mL) at 0° C. was treated with trifluoroacetic anhydride (6.5 mL, 1 equiv.), dropwise over 10 minutes. After 2 hours, the solvents were evaporated and the residue partitioned between ethyl acetate and 2% phosphoric acid. The organic phase was washed with water and brine, dried over magnesium sulfate, and evaporated. The crude amide was cooled to 0° C. under nitrogen and treated with ice-cold 1M borane-tetrahydrofuran complex (137 mL, 3 equiv.). The reaction mixture was heated at reflux for 14 hours and then cooled to 0° C. Methanol (50 mL) was carefully added and, when bubbling had largely ceased, the mixture was heated at reflux for 5 hours. Upon cooling to room temperature, the stirred mixture was treated with a solution of t-butylpyrocarbonate (14.00 g, 1.4 equiv.) in methylene chloride (25 mL). After continued stirring overnight at room temperature, the mixture was evaporated and the residue partitioned between ethyl acetate and water. The organic phase was washed with more water and brine, dried over magnesium sulfate, and evaporated. The residue in methylene chloride (25 mL) was treated with 4M hydrogen chloride in dioxane (69 mL, 1.5 equiv.) and the reaction was stirred at room temperature overnight. Evaporation gave a semi-solid that was triturated with ether. The resulting white solid product was collected by filtration, washed with ether, and dried in vacuo (9.28 g, 90%). $^1$H-NMR δ (D$_2$O) 3.97 (q, 2H), 4.07 (s, 2H), 7.52 (s, 5H).

Similarly Prepared:

INTERMEDIATE 129

Cyclopropylmethyl-2,2,2-trifluoroethyl-amine hydrochloride, scheme 8: (OO)

$^1$H-NMR δ (D$_2$O) 0.39 (m, 2H), 0.72 (q, 2H), 1.08 (m, 1H), 3.11 (d, 2H), 4.00 (q, 2H).

INTERMEDIATE 130

Cyclobutylmethyl-2,2,2-trifluoroethyl-amine hydrochloride, scheme 8: (OO)

$^1$H-NMR δ (D$_2$O) 1.75-2.02 (m, 4H), 2.12 (m, 2H), 2.71 (m, 1H), 3.24 (d, 2H), 3.93 (q, 2H).

INTERMEDIATE 131

2-Cyclopropylethyl-2,2,2-trifluoroethyl-amine hydrochloride, scheme 8: (OO)

$^1$H-NMR δ (D$_2$O) 0.14 (m, 2H), 0.53 (m, 2H), 0.76 (m, 1H), 1.64 (q, 2H), 3.30 (t, 2H), 3.98 (q, 2H).

INTERMEDIATE 132 n-Propyl-2,2,2-trifluoroethyl-amine hydrochloride, scheme 8: (OO)

$^1$H-NMR δ (D$_2$O) 1.00 (t, 3H), 1.76 (m, 2H), 3.17 (t, 2H), 3.97 (q, 2H).

INTERMEDIATE 133 p-Fluorobenzyl-2,2,2-trifluoroethyl-amine hydrochloride, scheme 8: (OO)

$^1$H-NMR δ (D$_2$O) 3.98 (q, 2H), 4.40 (s, 2H), 7.24 (t, 2H), 7.53 (m, 2H).

INTERMEDIATE 134 m-Fluorobenzyl-2,2,2-trifluoroethyl-amine hydrochloride, scheme 8: (OO)

$^1$H-NMR δ (D$_2$O) 3.97 (q, 2H), 4.39 (s, 2H), 7.30 (m, 3H), 7.66 (m, 1H).

INTERMEDIATE 135 p-Chlorobenzyl-2,2,2-trifluoroethyl-amine hydrochloride, scheme 8: (OO)

$^1$H-NMR δ (D$_2$O) 3.98 (q, 2H), 4.39 (s, 2H), 7.50 (m, 4H).

INTERMEDIATE 136

2-Phenylethyl-2,2,2-trifluoroethyl-amine hydrochloride, Scheme 8: (OO)

$^1$H-NMR δ (D$_2$O) 3.10 (t, 2H), 3.49 (t, 2H), 4.00 (q, 2H), 7.41 (m, 5H).

INTERMEDIATE 137

Cyclopropylmethyl-2,2,3,3,3-pentafluoropropyl-amine hydrochloride, scheme 8: (OO)

$^1$H-NMR δ (D$_2$O) 0.41 (m, 2H), 0.72 (m, 2H), 1.21 (m, 1H), 3.14 (d, 2H), 4.06 (t, 2H).

INTERMEDIATE 138 n-Propyl-2,2,3,3,3-pentafluoropropyl-amine hydrochloride, scheme 8: (OO)

$^1$H-NMR δ (D$_2$O) 1.00 (t, 3H), 1.78 (m, 2H), 3.20 (t, 2H), 4.05 (t, 2H).

INTERMEDIATE 139 bis-Cyclopropylmethyl-amine hydrochloride, scheme 8: (OO)

$^1$H-NMR δ (D$_2$O) 0.35 (m, 2H), 0.68 (m, 2H), 1.07 (m, 1H), 2.95 (d, 2H).

INTERMEDIATE 140

Cyclopropylmethyl-ethyl-amine hydrochloride, scheme 8: (OO)

$^1$H-NMR δ (D$_2$O) 0.34 (m, 2H), 0.67 (m, 2H), 1.04 (m, 1H), 1.27 (t, 3H), 2.90 (d, 2H), 3.08 (q, 2H).

INTERMEDIATE 141

2-Cyclopropylethyl-ethyl-amine hydrochloride, scheme 8: (OO)

$^1$H-NMR δ (D$_2$O) 0.12 (m, 2H), 0.51 (m, 2H), 0.73 (m, 1H), 1.28 (t, 3H), 1.60 (m, 2H), 3.12 (m, 4H).

INTERMEDIATE 142

2-Cyclopropylethyl-propyl-amine hydrochloride, scheme 8: (OO)

$^1$H-NMR δ (D$_2$O) 0.13 (m, 2H), 0.51 (m, 2H), 0.72 (m, 1H), 0.97 (t, 3H), 1.58 (q, 2H), 1.66 (m, 2H), 3.00 (t, 2H), 3.13 (t, 2H).

INTERMEDIATE 143

Cyclobutylmethyl-propyl-amine hydrochloride, scheme 8: (OO)

$^1$H-NMR δ (D$_2$O) 0.95 (t, 3H), 1.60-2.05 (m, 6H), 2.10 (m, 2H), 2.62 (m, 1H), 2.96 (t, 2H), 3.06 (t, 2H).

INTERMEDIATE 144

Benzyl-propyl-amine hydrochloride, scheme 8: (OO)

$^1$H-NMR δ (D$_2$O) 0.96 (t, 3H), 1.71 (m, 2H), 3.04 (t, 2H), 4.23 (s, 2H), 7.50 (m, 5H).

INTERMEDIATE 145

3-Pyridylmethyl-propyl-amine hydrochloride, scheme 8: (OO)

$^1$H-NMR δ (D$_2$O) 0.99 (t, 3H), 1.73 (m, 2H), 3.13 (t, 2H), 4.51 (s, 2H), 8.11 (t, 1H), 8.67 (d, 1H), 8.87 (d, 1H), 8.95 (s, 1H).

INTERMEDIATE 146

2-Pyridylmethyl-propyl-amine hydrochloride, scheme 8: (OO)

$^1$H-NMR δ (D$_2$O) 0.97 (t, 3H), 1.71 (m, 2H), 3.14 (t, 2H), 4.50 (s, 2H), 7.81 (m, 2H), 8.30 (m, 1H), 8.56 (d, 1H).

INTERMEDIATE 147

4-Pyridylmethyl-propyl-amine hydrochloride, scheme 8: (OO)

$^1$H-NMR δ (D$_2$O) 1.00 (t, 3H), 1.77 (m, 2H), 3.21 (t, 2H), 4.61 (s, 2H), 8.18 (d, 2H), 8.91 (d, 2H).

INTERMEDIATE 148 p-Fluorobenzyl-propyl-amine hydrochloride, scheme 8: (OO)

$^1$H-NMR δ (D$_2$O) 0.96 (t, 3H), 1.73 (m, 2H), 3.03 (t, 2H), 4.22 (s, 2H), 7.22 (t, 2H), 7.51 (m, 2H).

INTERMEDIATE 149 m-Fluorobenzyl-propyl-amine hydrochloride, scheme 8: (OO)

$^1$H-NMR δ (D$_2$O) 0.98 (t, 3H), 1.73 (m, 2H), 3.14 (t, 2H), 4.39 (s, 2H), 7.30 (m, 3H), 7.65 (m, 1H).

INTERMEDIATE 150 p-Chlorobenzyl-propyl-amine hydrochloride, scheme 8: (OO)

$^1$H-NMR δ (D$_2$O) 0.96 (t, 3H), 1.71 (m, 2H), 3.03 (t, 2H), 4.22 (s, 2H), 7.47 (q, 4H).

INTERMEDIATE 151

2-Phenylethyl-propyl-amine hydrochloride, scheme 8: (OO)

$^1$H-NMR δ (D$_2$O) 0.95 (t, 3H), 1.69 (m, 2H), 3.05 (m, 4H), 3.32 (t, 2H), 7.37 (m, 5H).

INTERMEDIATE 152

2-Phenylethyl-ethyl-amine hydrochloride, scheme 8: (OO)

$^1$H-NMR δ (D$_2$O) 1.26 (t, 3H), 3.11 (m, 4H), 3.32 (t, 2H), 7.41 (m, 5H).

INTERMEDIATE 153

Allyl-propylamine hydrochloride, scheme 8: (OO)

A stirred solution of allylamine (10.0 mL, 133.3 mmoles) in methylene chloride (80 mL) at 0° C. was treated with propionic anhydride (8.54 mL, 0.5 equi.v), dropwise over 10 minutes. After 2 hours, the solvents were evaporated and the residue partitioned between ethyl acetate and 2% phosphoric acid. The organic phase was washed with brine, dried over magnesium sulfate, and evaporated.

The crude amide in toluene (10 mL) was cooled to 0° C. under nitrogen and treated with a 3.33M solution of Red-Al in toluene (7.1 mL, 2.5 equiv.). After stirring at room temperature for 14 hours, the mixture was cooled to 0° C. and carefully quenched with acetone (12 mL). The reaction was allowed to warm to room temperature and then was treated with methanol (3 mL) and, after a further 1 hour at room temperature, a solution of t-butylpyrocarbonate (2.87 g, 1.4 equiv.) in methylene chloride (5 mL). After 14 hours at room temperature, the solvents were evaporated and the residue partitioned between ethyl acetate and 10% aqueous citric acid. The organic phase was washed with more water and brine, dried over magnesium sulfate, and evaporated. The residue in methylene chloride (5 mL) was treated with 4M hydrogen chloride in dioxane (6 mL, 2.5 equiv.) and the reaction was stirred at room temperature overnight. Evaporation gave a semi-solid that was triturated with ether. the resulting white solid product was collected by filtration, washed with ether, and dried in vacuo (0.760 g, 60%). $^1$H-NMR δ ($D_2O$) 0.97 (t, 3H), 1.70 (m, 2H), 3.01 (t, 2H), 3.66 (d, 2H), 5.50 (t, 2H), 5.91 (m, 1H).

REFERENCES

1. Kulagowski, J. J.; Moody, C. J.; Rees, C. W. *Journal of Chemical Society Perkin Transaction I* 1985, 2725-2733.
2. Zhou, J.; Oh, L. M.; Bakthavatchalay, R.; PCT WO 98/42706, p16.
3. Scherz, M. W.; Fialeix, M.; Fischer, J. B.; Reddy, N. L.; Server, A. C.; Sonders, M. S.; Tester, B. C.; Weber, E.; Wong, S.; Keana, J. F. W. *Journal of Medcinal Chemistry* 1990, 33, 2421-2429.
4. Anisimova, V. A.; Kuzmenko, T. A.; Spasov, A. A.; Bocharova, I. A.; Orobinskaya, T. A. *Pharmaceutical Chemistry Journal* 1999, 33, 361-365.
5. Weijnen, J. G.; Koudijs, A.; Schellekens, G.; Engbersen, J. F.; *Journal of Chemical Society Perkin Transaction II* 1992, 829-834.
6. Cieplik, J.; Machon, Z.; *Farmaco*, 1995, 50, 131-136.
7. Basha, A.; Lipton, M.; Weinreb, S. M.; *Tetrahedron Letters*, 1977, 4171.
8. Bazant, V.; Capka, M.; Cerny, M.; Chvalousky, V.; Kochloefl, K.; Kraus, M.; Malek, J.; *Tetrahedron Letters*, 1968, 3303.

$CRF_1$ Receptor Binding Protocol $CRF_1$ receptor antagonists, by occupying the same receptors, blocks the accessibility of the receptors to CRF, a hypothalamic factor mediating body's responses to physiological and psychological stress. The following radioligand binding assay examines the ability of the antagonists to bind the $CRF_1$ receptors by assessing their ability to compete with binding of CRF to the receptors in cell membrane. Compounds of the present invention exemplified in examples 1-15 all showed $K_i$ values less than 75 micromolar. See Table I.

Tissue culture and membrane preparation. IMR-32 cells were grown at 37° C. in 5% $CO_2$ as a monolayer in medium consisting of MEM supplemented with 10% heat-inactivated fetal bovine serum, 0.1 mM nonessential amino acids, 1 mM sodium pyruvate and 2 mM L-glutamine. Cells were transformed by exposure to 2.5 μM 5'-bromo-2'-deoxyuridine for 10 days. After transformation, cells were rinsed twice with phosphate-buffered saline, and incubated for 10-15 min. at 4° C. in homogenization buffer consisting of 50 mM Tris (pH 7.2), 10 mM $MgCl_2$ and 2 mM EGTA. Cells were transferred from plates to polypropylene tubes (16×100 mm), homogenized and centrifuged at 32,000×g for 15 min. Pellets were resuspended by homogenization in buffer and centrifuged at 32,000×g for 15 min. Pellets were resuspended in homogenization buffer then stored at −80° C. until needed.

Radioligand binding assays. Membranes (150 μg/well) were incubated with [$^{125}$I]-oCRF (100 pM) and increasing concentrations of test compound for 100 minutes at 25° C. in a total volume of 200 μl. The assay buffer consisted of 50 mM Tris (pH 7.2), 10 mM $MgCl_2$, 0.5% BSA, 0.005% Triton X-100, 10 μg/mL aprotinin and 10 μg/mL leupeptin. Assays were stopped by addition of ice-cold wash buffer (50 mM Tris, pH 7.4 and 0.2% BSA). Filtration over glass fiber filters (Whatman GF/B) previously soaked in 50 mM Tris, pH 7.2 and 1% BSA was carried out using a Brandel cell harvester. Filters were washed with 10 mL of ice-cold wash buffer. Non-specific binding was defined with 10 μM oCRF. $IC_{50}$ values for oCRF and test compounds were calculated by nonlinear regression using a one-site binding curve (GraphPad Prism).

TABLE I

| Key A < 10 nM, B < 100 nM, C < 1,000 nM D < 10,000 nM | |
|---|---|
| Example number | $K_i$ (CRF-1R), nM |
| 1 | C |
| 2 | B |
| 5 | B |
| 6 | B |
| 7 | B |
| 8 | B |
| 9 | B |
| 10 | B |
| 11 | C |
| 12 | C |
| 13 | C |
| 14 | C |
| 15 | C |
| 16 | C |
| 17 | C |
| 18 | C |
| 19 | C |
| 20 | C |
| 21 | D |
| 22 | D |
| 23 | D |
| 24 | D |
| 25 | D |
| 26 | D |
| 27 | B |
| 28 | B |
| 29 | C |
| 30 | B |
| 31 | B |
| 32 | B |
| 33 | B |
| 34 | C |
| 35 | D |
| 36 | C |
| 37 | C |
| 38 | D |

TABLE I-continued

Key A < 10 nM, B < 100 nM, C < 1,000 nM D < 10,000 nM

| Example number | $K_i$ (CRF-1R), nM |
|---|---|
| 39 | D |
| 40 | D |
| 41 | C |
| 42 | C |
| 43 | C |
| 44 | B |
| 45 | C |
| 46 | D |
| 47 | C |
| 48 | B |
| 49 | C |
| 50 | B |
| 54 | D |
| 55 | D |
| 56 | D |
| 57 | D |
| 58 | D |
| 59 | B |
| 60 | C |
| 61 | C |
| 62 | C |
| 63 | C |
| 64 | C |
| 65 | C |
| 66 | C |
| 67 | B |
| 68 | C |
| 69 | C |
| 70 | C |
| 71 | B |
| 72 | C |
| 73 | A |
| 74 | B |
| 75 | B |
| 76 | B |
| 77 | B |
| 78 | C |
| 79 | B |
| 80 | C |
| 81 | C |
| 82 | B |
| 83 | B |
| 84 | C |
| 85 | D |
| 86 | C |
| 87 | C |
| 88 | C |
| 89 | C |
| 90 | C |
| 91 | C |
| 92 | C |
| 93 | B |
| 94 | C |
| 95 | B |
| 96 | B |
| 97 | C |
| 98 | C |
| 99 | C |
| 100 | C |
| 101 | C |
| 102 | C |
| 103 | B |
| 104 | C |
| 105 | C |
| 106 | C |
| 107 | C |
| 108 | C |
| 109 | C |
| 110 | C |
| 111 | C |
| 112 | B |
| 113 | B |
| 114 | C |
| 115 | B |
| 116 | C |

TABLE I-continued

Key A < 10 nM, B < 100 nM, C < 1,000 nM D < 10,000 nM

| Example number | $K_i$ (CRF-1R), nM |
|---|---|
| 117 | C |
| 118 | C |
| 119 | C |
| 120 | C |
| 121 | C |
| 122 | C |
| 123 | C |
| 124 | C |
| 125 | C |
| 126 | C |
| 127 | C |
| 128 | C |
| 129 | C |
| 130 | C |
| 131 | B |
| 132 | C |
| 133 | C |
| 134 | C |
| 135 | B |
| 136 | C |
| 137 | C |
| 138 | B |
| 139 | D |
| 140 | C |
| 141 | C |
| 142 | D |
| 143 | D |
| 144 | B |
| 145 | B |
| 146 | B |
| 147 | B |
| 148 | B |
| 149 | C |
| 150 | B |
| 151 | B |
| 152 | B |
| 153 | B |
| 154 | B |
| 155 | B |
| 156 | B |
| 157 | B |
| 158 | B |
| 159 | B |
| 160 | C |
| 161 | C |
| 162 | C |
| 163 | C |
| 164 | C |
| 165 | C |
| 166 | C |
| 167 | C |
| 168 | C |
| 169 | C |
| 170 | C |
| 171 | C |
| 172 | D |
| 173 | D |
| 174 | D |
| 175 | D |
| 176 | D |
| 177 | C |
| 178 | C |
| 179 | C |
| 180 | D |
| 181 | D |
| 182 | D |
| 183 | D |
| 184 | D |
| 185 | D |
| 186 | D |
| 187 | B |
| 188 | B |
| 189 | C |
| 190 | C |
| 191 | C |

TABLE I-continued

Key A < 10 nM, B < 100 nM, C < 1,000 nM D < 10,000 nM

| Example number | $K_i$ (CRF-1R), nM |
| --- | --- |
| 192 | C |
| 193 | C |
| 194 | C |
| 195 | C |
| 196 | C |
| 197 | C |
| 198 | C |
| 199 | D |
| 200 | D |
| 201 | D |
| 202 | D |
| 203 | D |
| 204 | D |
| 205 | D |
| 206 | D |
| 207 | D |
| 208 | D |
| 209 | D |
| 210 | B |
| 211 | B |
| 212 | B |
| 213 | B |
| 214 | B |
| 215 | B |
| 216 | B |
| 217 | B |
| 218 | C |
| 219 | C |
| 220 | C |
| 221 | C |
| 222 | C |
| 223 | C |
| 224 | C |
| 225 | C |
| 226 | C |
| 227 | C |
| 228 | C |
| 229 | C |
| 230 | C |
| 231 | C |
| 232 | C |
| 233 | D |
| 234 | D |
| 235 | D |
| 236 | D |
| 237 | A |
| 238 | A |
| 239 | B |
| 240 | B |
| 241 | B |
| 242 | B |
| 243 | B |
| 244 | B |
| 245 | B |
| 246 | B |
| 247 | B |
| 248 | B |
| 249 | B |
| 250 | C |
| 251 | C |
| 252 | C |
| 253 | A |
| 254 | A |
| 255 | A |
| 256 | A |
| 257 | B |
| 258 | B |
| 259 | B |
| 260 | B |
| 261 | B |
| 262 | B |
| 263 | B |
| 264 | B |
| 265 | B |
| 266 | B |
| 267 | B |
| 268 | B |
| 269 | C |
| 270 | C |
| 271 | C |
| 272 | C |
| 273 | C |
| 274 | D |
| 275 | D |
| 276 | D |
| 277 | D |
| 278 | D |
| 279 | D |
| 280 | D |
| 281 | D |
| 282 | D |
| 283 | B |
| 284 | B |
| 285 | C |
| 286 | A |
| 287 | A |
| 288 | B |
| 289 | B |
| 290 | B |
| 291 | B |
| 292 | B |
| 293 | C |
| 294 | C |
| 295 | C |
| 296 | A |
| 297 | C |
| 298 | A |
| 299 | B |
| 300 | B |
| 301 | C |
| 302 | B |
| 303 | A |
| 304 | A |
| 305 | C |
| 306 | C |
| 307 | C |
| 308 | C |
| 309 | C |
| 310 | C |
| 311 | C |
| 312 | B |
| 313 | C |
| 314 | C |
| 315 | C |
| 316 | C |
| 317 | C |
| 318 | A |
| 319 | A |
| 320 | A |
| 321 | A |
| 322 | A |
| 323 | C |
| 324 | C |
| 325 | B |
| 326 | A |
| 327 | B |
| 328 | B |
| 329 | B |
| 330 | A |
| 331 | A |
| 332 | C |
| 333 | B |
| 334 | B |
| 335 | A |
| 336 | A |
| 337 | B |
| 338 | C |
| 339 | A |
| 340 | C |
| 341 | A |

TABLE I-continued

| Example number | $K_i$ (CRF-1R), nM |
|---|---|
| 342 | B |
| 343 | B |
| 344 | B |
| 345 | A |
| 346 | B |
| 347 | A |

Key A < 10 nM, B < 100 nM, C < 1,000 nM D < 10,000 nM

What is claimed is:

1. A compound of Formula (I)

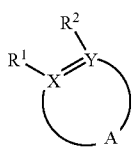

(I)

or a pharmaceutically acceptable salt or hydrate thereof wherein
  $R^1$ is H, $C_{1-6}$alkyl, $C_{1-6}$haloalkyl, $C_{1-6}$alkoxy, $C_{1-6}$thioalkyl, cyano, halo, $C_{3-7}$cycloalkyl, —$C_{1-6}$alkylene-$C_{3-7}$cycloalkyl, $C_{2-6}$alkenyl or $C_{3-6}$alkynyl;
  $R^2$ is $C(D)NR^3R^4$, $D'$-$D''(R^3)(R^4)$ or $CH_2N R^3R^4$
  $D'$ is $CH_2$ or a bond;
  $D''$ is C, C—OH or CH
    wherein
      said C is attached to $R^3$ by a single or double bond;
      said C is attached to $R^4$ by a single or double bond;
      provided that
        C is not attached to both $R^3$ and $R^4$ by double bonds;
      said CH is attached to $R^3$ and $R^4$ by single bonds;
      said C of C—OH is attached to $R^3$ and $R^4$ by single bonds;
  D is O or S;
  $R^3$ and $R^4$ are each independently selected from the group consisting of H, $C_{1-6}$alkyl, $C_{1-6}$haloalkyl, —$C_{1-6}$hydroxyalkyl, —$C_{1-4}$alkylene-O—$C_{1-4}$alkyl, —$C_{1-3}$alkylene-$C_{1-6}$thioalkyl, —$C_{2-6}$alkylidene-$(C_{1-4}$ alkoxy$)_2$, $C_{3-7}$cycloalkyl, —$C_{1-6}$alkylene-$C_{3-7}$cycloalkyl, $C_{2-6}$alkenyl, $C_{3-6}$alkynyl, —$C_{1-6}$alkylene-CN, —$C_{1-6}$alkylene-heterocyclo and —$C_{1-6}$alkylene-aryl;
    wherein said aryl of said —$C_{1-6}$alkylene-aryl is optionally substituted with one to three of the same or different substituents selected from the group consisting of fluoro, chloro, bromo, cyano, nitro, $C_{1-4}$alkyl and $C_{1-3}$alkoxy;
  or
  $R^3$ and $R^4$ together with the nitrogen to which they are attached form a five or six-membered heterocycle,
    said heterocycle optionally containing one additional heteroatom selected from the group consisting of N, S and O; and
    said heterocycle optionally substituted with one or more groups selected from the group consisting of $C_{1-6}$alkyl, $C_{1-6}$alkoxy, aryl, —$C_{1-4}$alkylene-aryl, pyridyl and halogen;
    wherein said aryl of said —$C_{1-4}$alkylene-aryl is optionally substituted with one to three of the same or different substituents selected from the group consisting of fluoro, chloro, bromo, cyano, nitro and $C_{1-3}$alkoxy;
  X is C;
  Y is C;
  A is

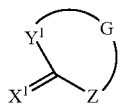

wherein
  $X^1$ is N and is attached to X;
  $Y^1$ is N and is attached to Y;
  G is

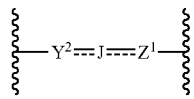

wherein
  $Y^2$ is $CE^1$ and is attached to $Y^1$;
  J is a bond;
  $Z^1$ is $CE^3$ and is attached to Z;
    wherein
      $E^1$ and $E^3$ together form $C_4$-alk(en)lyene; optionally substituted with halogen, —CN, $C_1$-$C_4$alkyl, $C_3$-$C_6$cycloalkyl, substituted or unsubstituted phenyl, hydroxy, $C_1$-$C_4$alkoxy, SH, $C_1$-$C_4$thioalkyl, $NH_2$, $NH(C_1$-$C_4$alkyl) or $N(C_1$-$C_4$alkyl$)_2$;
  Z is N—V, wherein V is phenyl, 2-pyridyl or 3-pyridyl substituted with two to three of the same or different substituents selected from the group consisting of $C_{1-4}$alkyl, $C_{1-4}$alkoxy, $C_{1-6}$thioalkyl, $C_{1-4}$haloalkyl, halogen, $N(C_1$-$C_4$alkyl$)_2$ and CN.

2. A compound according to claim 1 wherein V is phenyl or 3-pyridyl and is substituted with two to three of the same or different substituents selected from the group consisting of $C_{1-4}$alkyl, $C_{1-4}$alkoxy, $C_{1-6}$thioalkyl, $C_{1-4}$haloalkyl, halogen, $N(C_1$-$C_4$alkyl$)_2$ and CN; said substituents attached at the 2, 4 or 6-positions of said phenyl or said 3-pyridyl.

3. A compound according to claim 1 wherein V is 2-pyridyl and is substituted with two of the same or different substituents selected from the group consisting of $C_{1-4}$alkyl, $C_{1-4}$alkoxy, $C_{1-6}$thioalkyl, $C_{1-4}$haloalkyl, halogen, $N(C_1$-$C_4$alkyl$)_2$ and CN; said substituents attached at the 3 and 5-positions of said 2-pyridyl.

4. A compound according to claim 1 wherein $R^1$ is $C_{1-6}$alkyl or $C_{1-6}$haloalkyl.

5. A compound according to claim 1 wherein $R^1$ is methyl or trifluoromethyl.

6. A compound according to claim 1 wherein $R^2$ C(D)$NR^3R^4$ and D is O.

7. A compound according to claim 1 wherein $R^2$ $CH_2N R^3R^4$.

8. A compound according to claim 1 wherein $R^2$ $D'$-$D''(R^3)(R^4)$, $D'$ is a bond and $D''$ is C—OH.

9. A compound according to claim 1 wherein $R^2$ is $D'$-$D''(R^3)(R^4)$, $D'$ is a bond and $D''$ is C or CH.

10. A compound according to claim 1 wherein $R^3$ and $R^4$ are each independently selected from the group consisting of H, $C_{1-6}$alkyl, $C_{1-6}$haloalkyl, —$C_{1-6}$hydroxyalkyl, —$C_{1-4}$alkylene-O—$C_{1-4}$alkyl, —$C_{1-3}$alkylene-$C_{1-6}$thioalkyl, —$C_{2-6}$alkylidene-($C_{1-4}$alkoxy)$_2$, $C_{3-7}$cycloalkyl, —$C_{1-6}$alkylene-$C_{3-7}$cycloalkyl, $C_{2-6}$alkenyl, $C_{3-6}$alkynyl and —$C_{1-6}$ alkylene-CN.

11. A compound according to claim 1 wherein $R^3$ and $R^4$ together with the nitrogen to which they are attached form a five or six-membered heterocycle.

12. A compound according to claim 1 wherein V is 2, 4, 6-trimethylphenyl.

13. A compound according to claim 1 wherein V is 2,4-dichlorophenyl.

14. A compound according to claim 1 wherein $E^1$ and $E^3$ together form $C_4$-alk(en)lyene optionally substituted with halogen.

15. A compound or pharmaceutically acceptable salt or hydrate thereof selected from the group consisting of Cyclopropylmethyl-(2,2,2-trifluoro-ethyl)-[2-trifluoromethyl-8-(2,4,6-trimethylphenyl-8H-1,3a,8-triaza-cyclopenta[a]inden-3-ylmethyl]-amine;

5-Fluoro-2-methyl-8-(2,4,6-trimethyl-phenyl)-8H-1,3a,8-triaza-cyclopenta[a]indene-3-carboxylic acid ethyl ester;

2-Ethyl-5-fluoro-8-(2,4,6-trimethyl-phenyl)-8H-1,3a,8-triaza-cyclopenta[a]indene-3-carboxylic acid ethyl ester;

2-Ethyl-8-(2,4,6-trimethyl-phenyl)-8H-1,3a,8-triaza-cyclopenta[a]indene-3-carboxylic acid ethyl ester;

2-Trifluoromethyl-8-(2,4,6-trimethyl-phenyl)-8H-1,3a,8-triaza-cyclopenta[a]indene-3-carboxylic acid ethyl ester;

8-(2,4-Dichloro-phenyl)-2-methyl-8H-1,3a,8-triaza-cyclopenta[a]indene-3-carboxylic acid ethyl ester;

[2-Trifluoromethyl-8-(2,4,6-trimethylphenyl)-8H-1,3a,8-triaza-cyclopenta[a]inden-3-yl]-methanol;

[8-(2,4-Dichlorophenyl)-2-trifluoromethyl-8H-1,3a,8-triaza-cyclopenta[a]inden-3-yl]-methanol;

3-Chloromethyl-2-trifluoromethyl-8-(2,4,6-trimethyl-phenyl)-8H-1,3a,8-triaza-cyclopenta[a]indene;

5-Fluoro-2-methyl-8-(2,4,6-trimethyl-phenyl)-8H-1,3a,8-triaza-cyclopenta[a]indene-3-carboxylic acid cyclopropylmethyl-propyl-amide;

2-Methyl-8-(2,4,6-trimethyl-phenyl)-8H-1,3a,8-triaza-cyclopenta[a]indene-3-carboxylic acid cyclopropylmethyl-propyl-amide;

2-Ethyl-8-(2,4,6-trimethyl-phenyl)-8H-1,3a,8-triaza-cyclopenta[a]indene-3-carboxylic acid cyclopropylmethyl-propyl-amide;

2-trifluoromethyl-8-(2,4,6-trimethylphenyl)-8H-1,3a,8-triaza-cyclopenta[a]indene-3-carboxylic acid cyclopropylmethyl-propyl-amide;

8-(2,4-Dichloro-phenyl)-2-methyl-8H-1,3a,8-triaza-cyclopenta[a]indene-3-carboxylic acid cyclopropylmethyl-propyl-amide;

2-Ethy-5-fluoro-8-(2,4,6-trimethyl-phenyl)-8H-1,3a,8-triaza-cyclopenta[a]indene-3-carboxylic acid cyclopropylmethyl-propyl-amide;

Cyclopropylmethyl-[5-fluoro-2-methyl-8-(2,4,6-trimethyl-phenyl)-8H-1,3a,8-triaza-cyclopenta[a]inden-3-ylmethyl]-propyl-amine;

Cyclopropylmethyl-[2-ethyl-8-(2,4,6-trimethyl-phenyl)-8H-1,3a,8-triaza-cyclopenta[a]inden-3-ylmethyl]-propyl-amine;

Cyclopropylmethyl-propyl-(trifluoromethyl-trimethylphenyl-8H-1,3a,8-triaza-cyclopenta[a]inden-3-ylmethyl)-amine;

Cyclopropylmethyl-[2-ethyl-5-fluoro-8-(2,4,6-trimethylphenyl)-8H-1,3a,8-triaza-cyclopenta[a]inden-3-ylmethyl]-propyl-amine; and Cyclopropylmethyl-(2,2,2-trifluoro-ethyl)-[2-trifluoromethyl-8-(2,4,6-trimethylphenyl-8H-1,3 a,8-triaza-cyclopenta[a]inden-3-ylmethyl]-amine.

16. A method of treating depression and anxiety comprising the administration of an effective amount of a pharmaceutical composition comprising a compound according to claim 1.

* * * * *